(12) United States Patent
Anderson et al.

(10) Patent No.: US 9,725,515 B2
(45) Date of Patent: Aug. 8, 2017

(54) PROLACTIN RECEPTOR BINDING PROTEINS AND USES THEREOF

(71) Applicant: AbbVie Inc., North Chicago, IL (US)

(72) Inventors: Mark Anderson, Grayslake, IL (US); Jieyi Wang, Belmont, CA (US); Archana Thakur, Pleasanton, CA (US); Debra Chao, Fremont, CA (US); Chung-Ming Hsieh, Newton, MA (US); Qian Zhang, Gurnee, IL (US); Edward B. Reilly, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/138,906

(22) Filed: Dec. 23, 2013

(65) Prior Publication Data

US 2014/0227294 A1 Aug. 14, 2014

Related U.S. Application Data

(60) Provisional application No. 61/745,707, filed on Dec. 24, 2012.

(51) Int. Cl.
*A61K 39/395* (2006.01)
*C07K 16/28* (2006.01)
*A61K 45/06* (2006.01)
*A61K 39/00* (2006.01)

(52) U.S. Cl.
CPC ...... *C07K 16/2869* (2013.01); *A61K 39/3955* (2013.01); *A61K 45/06* (2013.01); *A61K 2039/505* (2013.01); *C07K 2317/24* (2013.01); *C07K 2317/34* (2013.01); *C07K 2317/55* (2013.01); *C07K 2317/567* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,867,187 | B2 | 3/2005 | Clevenger et al. |
| 7,422,899 | B2 | 9/2008 | Elenbaas et al. |
| 7,507,716 | B2 | 3/2009 | Diogenes et al. |
| 7,867,493 | B2 | 1/2011 | Damiano et al. |
| 8,648,046 | B2 | 2/2014 | Chen |
| 8,754,035 | B2 | 6/2014 | Chen |
| 2007/0269438 | A1 | 11/2007 | Elenbaas et al. |
| 2011/0150760 | A1 | 6/2011 | Damiano et al. |
| 2012/0315276 | A1 | 12/2012 | Otto et al. |
| 2012/0321632 | A1 | 12/2012 | Otto et al. |
| 2013/0022606 | A1 | 1/2013 | Otto et al. |
| 2013/0129739 | A1 | 5/2013 | Ottto et al. |
| 2013/0171147 | A1 | 7/2013 | Otto et al. |
| 2013/0272968 | A1 | 10/2013 | Otto et al. |

FOREIGN PATENT DOCUMENTS

| | | |
|---|---|---|
| WO | WO-2008/022295 A2 | 2/2008 |
| WO | WO-2011/069795 A1 | 6/2011 |
| WO | WO-2011/151405 A1 | 12/2011 |
| WO | WO-2012/136519 A1 | 10/2012 |
| WO | WO-2012/163932 A1 | 12/2012 |

OTHER PUBLICATIONS

Arden et al., "The Genes Encoding the Receptors for Prolactin and Growth Hormone Map to Human Chromosome 5", *Am J Hum Genet* 45 Suppl A129, 1989.
Arden et al., "The receptors for prolactin and growth hormone are localized in the same region of human chromosome 5", *Cytogenet Cell Genet*, 53:161-165, 1990.
Boutin et al., "Identification of a cDNA Encoding a Long Form of Prolactin Receptor in Human Hepatoma and Breast Cancer Cells", *Molec. Endocrinol.*, 3(9):1455-1461, 1989.
"Competitive inhibition", Internet Citation, Sep. 13, 2011, pp. 1-5, XP002660444, Retrieved from the Internet: URL:http://en.wikipedia.org/wiki/ Competitive inhibition.
Damiano et al., "Neutralization of Prolactin Receptor Function by Monoclonal Antibody LFA102, a Novel Potential Therapeutic for the Treatment of Breast Cancer", *Molec. Cancer Therapeutics*, 12(3):295-305, 2013.
Gill et al., "Expression of prolactin receptors in normal, benign, and malignant breast tissue: an immunohistological study", *J Clin Pathol.*, 54:956-960, 2001.
Leav et al., "Prolactin Receptor Expression in the Developing Human Prostate and in Hyperplastic, Dysplastic, and Neoplastic Lesions", *American Journal of Pathology*, 154(3):863-870, 1999.
Li et al., "Activation of Signal Transducer and Activator of Transcription 5 in Human Prostate Cancer Is Associated with High Histological Grade", *Cancer Res.*, 64:4774-4782, 2004.
Sissom et al., "Anti-Growth Action on Mouse Mammary and Prostate Glands of a Monoclonal Antibody to Prolactin Receptor", *Am. J. Pathol.*, 133:589-595, 1988.
Touraine et al., "Increased Expression of Prolactin Receptor Gene Assessed by Quantitative Polymerase Chain Reaction in Human Breast Tumors Versus Normal Breast Tissues", *J Clin Endocrinol Metab.*, 83(2):667-674, 1998.
Tworoger et al., "Plasma Prolactin Concentrations and Risk of Postmenopausal Breast Cancer", *Cancer Res.*, 64:6814-6819, 2004.
Tworoger et al., "Association between Plasma Prolactin Concentrations and Risk of Breast Cancer among Predominately Premenopausal Women", *Cancer Res.*, 66(4):2476-2482, 2006.

(Continued)

*Primary Examiner* — Michael Pak
(74) *Attorney, Agent, or Firm* — McCarter & English, LLP; Cristin H. Cowles

(57) ABSTRACT

The present invention encompasses PRLR binding proteins. Specifically, the invention relates to antibodies that are chimeric, CDR grafted and humanized antibodies. Preferred antibodies have high affinity for hPRLR and neutralize hPRLR activity in vitro and in vivo. An antibody of the invention can be a full-length antibody or an antigen-binding portion thereof. Methods of making and methods of using the antibodies of the invention are also provided. The antibodies, or antibody portions, of the invention are useful for detecting hPRLR and for inhibiting hPRLR activity, e.g., in a human subject suffering from a disorder in which hPRLR activity is detrimental. Also included in the invention are anti-PRLR antibody drug conjugates (ADCs).

50 Claims, 11 Drawing Sheets

(56) References Cited

OTHER PUBLICATIONS

Van Agthoven et al., "Structural Characterization of the Stem—Stem Dimerization Interface between Prolactin Receptor Chains Complexed with the Natural Hormone", *J. Mol. Biol.*, 404:112-126, 2010.

Wennbo et al., "Activation of the Prolactin Receptor but Not the Growth Hormone Receptor is Important for Induction of Mammary Tumors in Transgenic Mice", *J Clin Invest.*, 100:2744-2751, 1997.

Wennbo et al., "Transgenic Mice Overexpressing the Prolactin Gene Develop Dramatic Enlargement of the Prostate Gland", *Endocrinology*, 138(10):4410-4415, 1997.

Xu et al., "A Molecular Mimic of Phosphorylated Prolactin Markedly Reduced Tumor Incidence and Size When DU145 Human Prostate Cancer Cells Were Grown in Nude Mice", *Cancer Res.*, 61:6098-6104, 2001.

International Search Report and Written Opinion for PCT/US2013/077452 dated May 8, 2014.

International Preliminary Report on Patentability for PCT/US2013/077452 dated Mar. 31, 2015.

Bauernhofer et al., "Prolactin receptor is a negative prognostic factor in patients with squamous cell carcinoma of the head and neck," *British Journal of Cancer*, 104:1641-1648, 2011.

Harbaum et al., Clinicopathological significance of prolactin receptor expression in colorectal carcinoma and corresponding metastases, *Modern Pathology*, 23:961-971, 2010.

Levine et al., "Biological Significance of Prolactin in Gynecologic Cancers", *Cancer Research*, 69(12):5226-5233, 2009.

Figure 1

PRLR VH alignment

```
              FR1                                              CDR1              FR2                    CDR2
          ----------------------------------------           ---------    ---------------------    ----------------------
                    1         2         3                         a                4         5               6
          1234567890123456789012345678901234567890           12345a       6789012345678 9       012a345678 9012345
Ab5  VH   QVQLQQPGAELVRPGTSVKLSCKASGYTFT                     SFWMH-       WVKQRPGQGLEWIG           VIDPSDTYTNYNQKFKG
Ab13 VH   QVQLQQPGAELVRPGTSVKLSCKASGYTFT                     SFWMH-       WVKQRPGQGLEWIG           VIDPSDSHTNYNQKFKG
Ab7  VH   QVQLQQPGAELVMPGTSVKLSCKASGYTFT                     SYWIH-       WVKQRPGQGLEWIG           EIDPSDSYTNYNQKFKG
Ab6  VH   QVQLQQPGAELVMPGSSVKLSCKASGYTFT                     SYWIH-       WVKQRPGQGLEWIG           EIDPSDSYSNYNQKFKD
Ab8  VH   EVQLQQSGPELVKPGASVKISCKASGYTFT                     TYWMH-       WVKQSHGKSLEWIG           YIYPNNDGTGYNQKFKS
Ab9  VH   EVQLQQSGPELVRPGASVKISCKASGYTFT                     DYNIH-       WVKQSHGKSLEWIG           YIYPYNGGAGYNQKFKS
Ab10 VH   EVQLHQSGPELVKPGASVKISCKASGYSFT                     DYNMH-       WVKQSHGKSLEWIG           YFYPYNGGTGYNQKFKS
Ab11 VH   EVKLVESGGGLVQPGGSLKLSCAASGFTFS                     DYYMF-       WMKQSHGKSLEWIG           YISNGGGSTYYPDTVKG
Ab12 VH   DVQLQESGPGLVKPSQSLSLTCTVTGYSIT                     SDYAWN       WIRQFPGNKLEWMG           YIG-YSGRTSFNPSLKS

FR3                                         CDR3               FR4
          ----------------------------------------    ---------------     ------------
                  7         8         9                                         1
          67890123456789012abc3456789012 34           567890abcde12       34567890123
Ab5  VH   KATLTVDTSSSTAYMQLSSLTSEDSAVYYCAR             GDYSNWF------TY      WGQGTLVTVSA   (IGHJ3*01)
Ab13 VH   KATLTVNTSSSTAYMHLSSLTSEDSAVYYCAR             GDYSNWF------TY      WGQGTLVTVSA   (IGHJ3*01)
Ab7  VH   KATLTVDRSSSTAYMQLSSLTSEDSAVYYCGR             SFFTNWF------AY      WGQGTLVTVSA   (IGHJ3*01)
Ab6  VH   KATLTVDKSSSTAYMQLSSLTSEDSAVYYCAR             NGGLGPAWF----SY      WGQGTLVTVSA   (IGHJ3*01)
Ab8  VH   KATLTVDNSSSTAYMEVRSLTSEDSAVYYCAR             GDGNYVGDM----DY      WGQGTSVTVSS   (IGHJ4*01)
Ab9  VH   KATMNVGISSSTAYMELRSLTSEDSAVYYCAR             GDGNYVGDM----DY      WGQGTSVTVSS   (IGHJ4*01)
Ab10 VH   KATLTVDISSSTAYMELRRLTSEDSAVYYCAR             GGWGIYYAM----DY      WGQGTSVTVSS   (IGHJ4*01)
Ab11 VH   RFTISRDNAKNTLYLQMSRLKSEDTAMYYCSR             QLFYYGSRGAMGY        WGQGTSVTVSS   (IGHJ4*01)
Ab12 VH   RISITRDTSKNQFFLQNSVTTEDTATYYCAR              GGFAM--------DY      WGQGTSVTVSS   (IGHJ4*01)
```

PRLR VL alignment

```
              FR1                          CDR1                    FR2                CDR2
       ----------------------       -------------------     -------------------     -------
                1         2                   3                 4         5              5
       1234567890123456789012 3    4567abcde89012 34   5678901234567 89      0123456
Ab5  VL  DVVMTQTPLSLPVSLGDQASISC    RSSQRLVHSNGNTYLH     WYLQKPGQSPKLLIY    KVSNRFS
Ab13 VL  DVVMTQTPFSLPVSLGDQASISC    RSSQSLVHSNGNTYLH     WYLQKPGQSPKLLIY    KVSNRFS
Ab7  VL  DVVMTQTPLSLPVSLGDQASISC    RSSQSLVHSNGNTYLH     WYLQKPGQSPKLLIY    KVSNRFS
Ab11 VL  DVLMTQTPLSLPVSLGDQASISC    RSSQSIVHSNGNTYLE     WYLQKPGQSPKLLIY    KVSNRFS
Ab8  VL  DIQMTQSPASLSASVGETVTITC    RASE------NIYSYLA    WYQQKQGKSPQLLVY    NAKTLAE
Ab9  VL  DIQMTQSPASLSASVGETVTITC    RASE------NIYSYLA    WYQQKQGKSPQLLVY    NAKTLAE
Ab10 VL  DIQMTQSPASLSASVGETVTITC    RASE------NIYSYLT    WYQQKQGKSPQLLVY    NAKTLAE
Ab6  VL  DIVMTQSQKFMSTTVGDRVSITC    KASQ------YVGTAVA    WYQQKPGQSPKLLIY    SASNRYT
Ab12 VL  QIVLTQSPGIMSASPGEKVTMTC    SASS------SVTYMY     WYQQKPRSSPKPWIY    LTSNLAS FR3                          CDR3               FR4
       --------------------------       ---------          -----------
              6         7         8              9              1
       7890123456789012345678901234567 8    901234 5a67    890 1234567
Ab5  VL  GVPDRFSGSGSGTDFTLKISRVEAEDLGVYFC    SQSTHVP-WT    FGGGTKLEIK    (IGKJ1*01)
Ab13 VL  GVPDRFSGSGSGTDFTLKISRVEAEDLELYFC    SQSTHVP-WT    FGGGTKLEIK    (IGKJ1*01)
Ab7  VL  GVPDRFSGSGSGTDFTLKINRVEAEDLGVYFC    SQSTHVP-FT    FGSGTKLEIK    (IGKJ4*01)
Ab11 VL  GVPDRFSGSGSGTDFTLKISRVEAEDLGVYYC    FQGSHVP-FT    FGSGTKLEIK    (IGKJ4*01)
Ab8  VL  GVPSRFSGGGSGTQFSLKINSLQPEDFGSYYC    QHHYATP-FT    FGSGTKLEIK    (IGKJ4*01)
Ab9  VL  GVPSRFSGSGSGTQFSLKINSLQPEDFGSYYC    QHHSGTP-FT    FGSGTKLEIK    (IGKJ4*01)
Ab10 VL  GVPSRFSGSGSGTQFSLKINSLQPEDFGSYHC    QHHSVTP-LT    FGAGTKLELK    (IGKJ5*01)
Ab6  VL  GVPDRFTDSGSGTDFTLTISNLQSEDLADYFC    QQYSSYP-WT    FGGGTKLEIK    (IGKJ1*01)
Ab12 VL  GVPARFSGSGSGTSYSLTISSMEAEDGATYYC    QQWSSTPPLT    FGGGTKLELN    (IGKJ1/5*01)
```

Figure 2

|          |                                                                                                                                                                                                                                                     |
|----------|-----------------------------------------------------------------------------------------------------------------------------------------------------------------------------------------------------------------------------------------------------------------------|
|          | 1         2         3         4         5         6         7         8         9         0         1         |
|          | 1234567890123456789012345678901234567890abc345678901234567890abc123 |
| Ab5 VH   | QVQLQQPGAELVRPGTSVKLSCKASGYTFTSFWMHWVKQRPGQGLEWIGVIDPSDTYTNYNQKFKGKATLTVDTSSSTAYMQLSSLTSEDSAVYYCARGDYSNWF---TYWGQGTLVTVSA |
| Ab2 VH.1z | QVQLVQSGSEVKKPGSSVKVSCKASGYTFTSFWMHWVRQAPGQGLEWMGVIDPSDTYTNYNQKFKGRVTITADESTSTAYMELSSLRSEDTAVYYCARGDYSNWF---TYWGQGTLVTVSS |
| Ab2 VH.1  | EVQLVQSGAEVKKPGSSVKVSCKASGYTFTSFWMHWVRQAPGQGLEWMGVIDPSDTYTNYNQKFKGRVTITADESTSTAYMELSSLRSEDTAVYYCARGDYSNWF---TYWGQGTLVTVSS |
| Ab2 VH.1a | EVQLVQSGAEVKKPGSSVKVSCKASGYTFTSFWMHWVRQAPGQGLEWIGVIDPSDTYTNYNQKFKGRATLTVDESSTAYMELSSLRSEDTAVYYCARGDYSNWF---TYWGQGTLVTVSS |
| Ab2 VH.1b | EVQLVQSGAEVKKPGSSVKVSCKASGGYTFTSFWMHWVRQAPGQGLEWIGVIDPSDTYTNYAQKFQGRVTITVDESTSTAYMELSSLRSEDTAVYYCARGDYSNWF---TYWGQGTLVTVSS |
| Ab7 VH   | QVQLQQPGAELVMPGSVKLSCKASGYTFTSYWIHWVKQRPGQGLEWIGEIDPSDTYNEYNQKFKGKATLTDRSSSTAYMELSSLRSEDTAVYYCGRSFFTNWF---AYWGQGTLVTVSA |
| Ab4 VH.1z | QVQLVQSGSEVKKPGSSVKVSCKASGYTFTSYWIHWVRQAPGQGLEWMGEIDPSDTYNEYNQKFKGRVTITADKSTSTAYMELSSLRSEDTAVYYCARSFFTNWF---AYWGQGTLVTVSS |
| Ab4 VH.1  | EVQLVQSGAEVKKPGSSVKVSCKASGYTFTSYWIHWVRQAPGQGLEWMGEIDPSDTYNEYNQKFKGRVTITADKSTSTAYMELSSLRSEDTAVYYCARSFFTNWF---AYWGQGTLVTVSS |
| Ab4 VH.1a | EVQLVQSGAEVKKPGSSVKVSCKASGYTFTSYWIHWVRQAPGQGLEWIGEIDPSDTYNEYNQKFKGRATLTVDKSTSTAYMELSSLRSEDTAVYYCARSFFTNWF---AYWGQGTLVTVSS |
| Ab4 VH.1a.2 | EVQLVQSGAEVKKPGSSVKVSCKASGYTFTSYWIHWVRQAPGQGLEWIGEIDPSDTYNEYNQKFKGRATLTVDKSTSTAYMELSSLRSEDTAVYYCGRSFFTNWF---AYWGQGTLVTVSS |
| Ab4 VH.1a.3 | EVQLVQSGAEVKKPGSSVKVSCKASGYTFTSYWIHWVRQAPGQGLEWIGEIDPSDTYNEYNQKFKGRATLTVDKSTSTAYMELSSLRSEDTAVYYCGRSFFTNWF---AYWGQGTLVTVSS |
| Ab4 VH.1b | EVQLVQSGAEVKKPGSSVKVSCKASGGYTFTSFWMHWVRQAPGQGLEWIGEIDPSDTYNYAQKFQGRVTITVDKSTSTAYMELSSLRSEDTAVYYCARSFFTNWF---AYWGQGTLVTVSS |
| Ab4 VH.1b.2 | EVQLVQSGAEVKKPGSSVKVSCKASGYTFTSYWIHWVRQAPGQGLEWIGEIDPSDTYNYAQKFQGRVTITVDKSTSTAYMELSSLRSEDTAVYYCARSFFTNWF---AYWGQGTLVTVSS |
| Ab6 VH   | QVQLQQPGAELVMPGSVKLSCKASGYTFTDYYMHWVKQRPGQGLEWIGEIDPSDSYSNYNQKFKDKATLTVDKSSSTAYMELSSLTSEDSAVYYCARNGGLGPAMFSYWGQGTLVTVSA |
| Ab1 VH.1z | QVQLVQSGSEVKKPGSSVKVSCKASGYTFTDYYMHWVRQAPGQGLEWMGEIDPSDSYSNYNQKFKDRVTITADKSTSTAYMELSSLRSEDTAVYYCARNGGLGPAMFSYWGQGTLVTVSS |
| Ab1 VH.1  | EVQLVQSGAEVKKPGSSVKVSCKASGYTFTDYYMHWVRQAPGQGLEWMGEIDPSDSYSNYNQKFKDRVTITADKSTSTAYMELSSLRSEDTAVYYCARNGGLGPAMFSYWGQGTLVTVSS |
| Ab1 VH.1a | EVQLVQSGAEVKKPGSSVKVSCKASGYTFTDYYMHWVRQAPGQGLEWIGEIDPSDSYSNYNQKFQGRVTITADKSTSTAYMELSSLRSEDTAVYYCARNGGLGPAMFSYWGQGTLVTVSS |
| Ab1 VH.1b | EVQLVQSGAEVKKPGSSVKVSCKASGGYTFTDYYMHWVRQAPGQGLEWIGEIDPSDSYSNYAQKFQGRVTITVDKSTSTAYMELSSLRSEDTAVYYCARNGGLGPAMFSYWGQGTLVTVSS |
| Ab8 VH   | QVQLQQSGPELVKPGASVKLSCKASGYTFTDYNIEWVKQSHGKSLEWIGYIIPNNDGTGYNQKFKSKATLTVDMSSSTAYMEVRSLTSEDSAVYYCARGDGNYVGDMDYWGQGTSVTVSS |
| Ab3 VH.1z | QVQLVQSGSEIVKPGASVKVSCKASGYTFTDYNIEWVRQAPGQGLEWMGYIIPNNDGTGYNQKFKSSVTMTDTSTSTAYMELRSLRSDDTAVYYCARGDGNYVGDMDYWGQGTTVTVSS |
| Ab3 VH.1  | EVQLVQSGAEVKKPGASVKVSCKASGYTFTDYNIEWVRQAPGQGLEWMGYIIPNNDGTGYNQKFKSRVTMTDTSTSTAYMELRSLRSDDTAVYYCARGDGNYVGDMDYWGQGTTVTVSS |
| Ab3 VH.1a | EVQLVQSGAEVKKPGASVKVSCKASGYTFTDYNIEWVRQAPGQGLEWIGYIIPNNDGTGYAQKLQGRVTMTDTSTSTAYMELRSLRSDDNSTAVYYCARGDGNYVGDMDYWGQGTTVTVSS |
| Ab3 VH.1b | EVQLVQSGAEVKKPGASVKVSCKASGGYTFTDYNIEWVRQAPGQGLEWIGYIIPNNDGTGYAQKLQGRVTMTDTSTSTAYMELRSLRSDDTAVYYCARGDGNYVGDMDYWGQGTTVTVSS |

```
                    1         2          3           4         5         6         7         8         9         1         1
          1234567890123456789012345678901234567abcde6789012345678901234567890123456789012345678901234567890123456789012345 6a
Ab5  VL   DVVMTQTPLSLPVSLGDQASISCRSSQRLVHSNGNTYLHWYLQKPGQSPKLLIYKVSNRFSGVPDRFSGSGSGTDFTLKISRVEAEDLGVYFCSQSTHVPWTFGGGTKLEIK
Ab2  VL.1 DIVMTQTPLSLSVTPGQPASISCRSSQRLVHSNGNTYLHWYLQKPGQSPQLLIYKVSNRFSGVPDRFSGSGSGTDFTLKISRVEAEDVGVYYCSQSTHVPWTFGGGTKVEIK
Ab2  VL.1a DVVMTQTPLSLSVTPGQPASISCRSSQRLVHSNGNTYLHWYLQKPGQSPQLLIYKVSNRFSGVPDRFSGSGSGTDFTLKISRVEAEDVGVYYCSQSTHVPWTFGGGTKVEIK
Ab2  VL.1b DVVMTQTPLSLSVTPGQPASISCRSSQRLVHSNGNTYLHWYLQKPGQSPQLLIYKVSNRFSGVPDRFSGSGSGTDFTLKISRVEAEDVGVYYCSQSTHVPWTFGGGTKVEIK
Ab7  VL   DVVMTQTPLSLPVSLGDQASISCRSSQSLVHSNGNTYLHWYLQKPGQSPKLLIYKVSNRFSGVPDRFSGSGSGTDFTLKINRVEAEDLGVYFCSQSTHVPFTFGGGTKVEIK
Ab4  VL.1 DIVMTQTPLSLSVTPGQPASISCRSSQSLVHSNGNTYLHWYLQKPGQSPQLLIYKVSNRFSGVPDRFSGSGSGTDFTLKISRVEAEDVGVYYCSQSTHVPFTFGGGTKVEIK
Ab4  VL.1a DVVMTQTPLSLSVTPGQPASISCRSSQSLVHSNGNTYLHWYLQKPGQSP-LLIYKVSNRFSGVPDRFSGSGSGTDFTLKISRVEAEDVGVYYCSQSTHVPFTFGGGTKVEIK
Ab4  VL.1b DVVMTQTPLSLSVTPGQPASISCRSSQSLVHSNGNTYLHWYLQKPGQSPQLLIYKVSNRFSGVPDRFSGSGSGTDFTLKISRVEAEDVGVYYCSQSTHVPFTFGGGTKVEIK
Ab6  VL   DIVMTQSQKFMSTTVGDRVSITCKASQ------YVGTAVAWYQQKPGQSPKLLIYSASNRYTGVPDRFTDSGSGSGTDFTLTISNLQSEDLADYFCQQYSSYPWTFGGGTKVEIK
Ab1  VL.1 DIQMTQSPSSVSASVGDRVTITCKASQ------YVGTAVAWYQQKPGKAPKLLIYSASNRYTGVPSRFSGSGSGTDFTLTISSLQPEDFATYYCQQYSSYPWTFGGGTKVEIK
Ab1  VL.1a DIQMTQSPSSVSASVGDRVTITCKASQ------YVGTAVAWYQQKPGKAPKLLIYSASNRYTGVPSRFSGSGSGTDFTLTISSLQPEDFATYFCQQYSSYPWTFGGGTKVEIK
Ab1  VL.1b DIQMTQSPSSLSASVGDRVTITCKASQ------YVGTAVAWYQQKPGKAPKLLIYSASNRYTGVPSRFSDSGSGTDFTLTISSLQPEDFATYFCQQYSSYPWTFGGGTKVEIK
Ab1  VL.2  EIVMTQSPATLSVSPGERATLSCKASQ------YVGTAVAWYQQKPGQAPRLLIYSASNRYTGIPARFSGSGSGTEFTLTISSLQSEDFAVYFCQQYSSYPWTFGGGTKVEIK
Ab1  VL.2a EIVMTQSPATLSVSPGERATLSCKASQ------YVGTAVAWYQQKPGQSPRLLIYSASNRYTGVPARFSDSGSGTEFTLTISSLQSEDFAVYFCQQYSSYPWTFGGGTKVEIK
Ab8  VL   DIQMTQSPASLSASVGETVTITCRASE------NIYSYLAWYQQKQGKQPPQLLVYNAKTLAEGVPSRFSGGGSGTQFSLKINSLQPEDFGSYYCQHHYATPFTFGGGTKLEIK
Ab3  VL.1 DIQMTQSPSSLSASVGDRVTITCRASE------NIYSYLAWYQQKPGKAPKLLIYNAKTLAEGVPSRFSGSGSGTDFTLTISSLQPEDFATYYCQHHYATPFTFGGGTKLEIK
Ab3  VL.1a DIQMTQSPSSLSASVGDRVTITCRASE------NIYSYLAWYQQKPGKPPKLLVYNAKTLAEGVPSRFSGSGSGTDFTLTISSLQPEDFATYYCQHHYATPFTFGGGTKLEIK
Ab3  VL.1b DIQMTQSPSSLSASVGDRVTITCRASE------NIYSYLAWYQQKPGKAPKLLVYNAKTLAEGVPSRFSGSGSGTDFTLTISSLQPEDFATYYCQHHYATPFTFGGGTKLEIK
``` simultaneous binding assay results solution mAb#

| surface mAb | | 01 | 02 | 03 | 04 | 05 | 06 | 07 | 08 | 09 | 10 | 11 | 12 |
|---|---|---|---|---|---|---|---|---|---|---|---|---|---|
| | 01 - chAb7 | 0 | -1 | 1 | 0 | 0 | -1 | 0 | 0 | 0 | 0 | 0 | 39 |
| | 02 - Ab39 | -2 | -2 | -2 | -2 | -2 | -2 | -2 | -2 | -2 | -2 | -2 | 36 |
| | 03 - Ab40 | -2 | -2 | -2 | -2 | -2 | -2 | -2 | -2 | -2 | -2 | -3 | 40 |
| | 04 - chAb5 | -1 | 0 | 0 | 0 | 0 | 0 | 0 | -1 | 0 | 0 | 0 | 32 |
| | 05 - Ab30 | -1 | 0 | -1 | -1 | -1 | -1 | -1 | -1 | -1 | -1 | -1 | 35 |
| | 06 - chAb6 | -1 | 0 | -1 | -1 | -1 | -1 | 0 | -1 | -1 | -2 | -2 | 26 |
| | 07 - Ab19 | -1 | -1 | -1 | 0 | -1 | -1 | -1 | -1 | -1 | -1 | -1 | 19 |
| | 08 - Ab21 | -1 | -1 | -1 | -1 | -1 | -1 | -1 | -1 | -1 | -1 | -1 | 21 |
| | 09 - chAb8 | 2 | 1 | 0 | 7 | 6 | 0 | 0 | 0 | -1 | -1 | -1 | 1 |
| | 10 - Ab48 | 1 | 2 | 0 | 8 | 6 | 0 | 0 | 1 | -1 | -1 | 0 | -1 |
| | 11 - Ab49 | 2 | 2 | 0 | 7 | 6 | 0 | 1 | 0 | -1 | -2 | -1 | 1 |
| | 12 - LFA102 | 48 | 92 | 35 | 102 | 103 | 90 | 122 | 104 | -2 | -2 | -2 | -2 |

Values shown are solution mAb binding magnitudes expressed as the percentage of the respective PRLR binding magnitudes.

▓ simultaneous binding (different epitopes)
▨ no simultaneous binding (overlapping epitopes)
☐ small non-reciprocal simultaneous binding

Figure 7

PROLACTIN RECEPTOR BINDING PROTEINS AND USES THEREOF

RELATED APPLICATIONS

The present invention claims priority to U.S. Provisional Application No. 61/745,707, filed Dec. 24, 2012, the entire contents of which is hereby incorporated by reference herein.

SEQUENCE LISTING

The instant application contains a Sequence Listing which has been submitted electronically in ASCII format and is hereby incorporated by reference in its entirety. Said ASCII copy, created on Feb. 26, 2014, is named 117813-10302_SL.txt and is 205,903 bytes in size.

FIELD OF THE INVENTION

The present invention relates to prolactin receptor (PRLR) binding proteins and their use in the prevention and/or treatment of various diseases including cancer.

BACKGROUND OF THE INVENTION

The prolactin receptor (PRLR) is a transmembrane receptor that interacts with prolactin (PRL), a peptide hormone. PRLR contains a single transmembrane domain and is homologous to receptors for cytokines, such as IL2, IL3, IL4, IL6, IL7, erythropoietin, and GM-CSF. PRLR is present in mammary glands, ovaries, pituitary glands, heart, lung, thymus, spleen, liver, pancreas, kidney, adrenal gland, uterus, skeletal muscle, skin, and areas of the central nervous system (Mancini, et al., *Endocrinol Metab Clin North Am,* 2008, 37(1):67-99). Upon activation by prolactin, PRLR dimerizes, resulting in activation of Janus kinase 2, a tyrosine kinase that initiates the JAK-STAT pathway and also results in the activation of mitogen-activated protein kinases and Src kinase. Growth hormone also binds to PRLR and activates the receptor.

PRLR is involved in multiple biological functions, including cell growth, differentiation, development, lactation and reproduction. The human PRLR cDNA was originally isolated from hepatoma and breast cancer libraries (Boutin et al., *Molec. Endocr.* 3: 1455-1461, 1989). The nucleotide sequence predicted a mature protein of 598 amino acids with a much longer cytoplasmic domain than the rat liver PRLR. The PRLR gene resides in the same chromosomal region as the growth hormone receptor gene, which has been mapped to 5p13-p14 (Arden, et al., *Cytogenet. Cell Gene* 53: 161-165, 1990).

The genomic organization of the human PRLR gene has been determined (Hu, Z.-Z. et al., *J. Clin. Endocr. Metab.* 84: 1153-1156, 1999). The 5-prime-untranslated region of the PRLR gene contains 2 alternative first exons: E13, the human counterpart of the rat and mouse E13, and a novel human type of alternative first exon termed E1N. The 5-prime-untranslated region also contains a common noncoding exon 2 and part of exon 3, which contains the translation initiation codon. The E13 and E1N exons are within 800 base pairs of each other. These 2 exons are expressed in human breast tissue, breast cancer cells, gonads, and liver. Overall, the transcript containing E13 is prevalent in most tissues. The PRLR gene product is encoded by exons 3-10, of which exon 10 encodes most of the intracellular domain. The E13 and E1N exons are transcribed from alternative promoters PIII and PN, respectively. The PIII promoter contains Sp1 and C/EBP elements that are identical to those in the rodent promoter and is 81% similar to the region −480/−106 in the rat and mouse. The PN promoter contains putative binding sites for ETS family proteins and a half-site for nuclear receptors.

PRLR exists in a number of different isoforms that differ in the length of their cytoplasmic domains. Four PRLR mRNA isoforms (L, I, S1a, and S1b) have been found in human subcutaneous abdominal adipose tissue and breast adipose tissue (Ling, C. et al., *J. Clin. Endocr. Metab.* 88: 1804-1808, 2003). In addition, expression of both L-PRLR and I-PRLR has been detected in human subcutaneous abdominal adipose tissue and breast adipose tissue using immunoblot analysis. Recent reports have suggested that PRLR is expressed and activated in human breast cancer and prostate cancer tissues (Li et al., *Cancer Res.,* 64:4774-4782, 2004; Gill et al., *J Clin Pathol.,* 54:956-960, 2001; Touraine et al., *J Clin Endocrinol Metab.,* 83:667-674, 1998). It was reported that Stat5 activation and PRLR expression is associated with high histological grade in 54% of prostate cancer specimens (Li et al., supra). Other reports have suggested that primary breast cancer specimens are responsive to PRL in colony formation assays and that plasma PRL concentrations correlate with breast cancer risk (Tworoger et al., *Cancer Res.,* 64:6814-6819, 2004; Tworoger et al., *Cancer Res.,* 66:2476-2482, 2006). Another report indicated that PRL transgenic mice develop malignant mammary carcinomas or prostate hyperplasia (Wennbo et al., *J Clin Invest.,* 100:2744-2751, 1997; Wennbo et al., Endocrinology, 138: 4410-4415, 1997).

A PRLR monoclonal antibody has been shown to diminish the incidence of mammary tumors in mice (Sissom et al., *Am. J. Pathol.* 133:589-595, 1988). In addition, a PRL antagonist (S179D mutant PRL) has been shown to inhibit proliferation of a human prostate carcinoma cell line, DU-145, in vitro and DU-145 induced tumors in vivo (Xu et al., *Cancer Res.,* 61:6098-6104, 2001).

Accordingly, there remains a need for PRLR binding proteins that can be used for therapeutic purposes for treating cancer.

SUMMARY OF THE INVENTION

This invention pertains to PRLR binding proteins and conjugates thereof. Binding proteins of the inventions include, but are not limited to antibodies, antigen binding portions, and other antigen binding proteins capable of binding the human PRLR. Further, the invention provides methods of making and using PRLR binding proteins and conjugates thereof.

In one aspect, the present invention is directed to a binding protein, e.g., antibody, or antigen binding fragment thereof, comprising an antigen binding domain, said binding protein capable of binding prolactin receptor (PRLR), said antigen binding domain comprising at least one CDR comprising an amino acid sequence selected from the group consisting of SEQ ID Nos:97, 98, 99, 100, 101, 102, 151 and 152. In one embodiment, the at least one CDR comprises an amino acid sequence selected from the group consisting of SEQ ID Nos:40-42, 46, 47, 49-51, 56-58, 62, 63, 65-67, 71-73, 77, 79-81, 85-87, 92-94, 149 and 150. In another embodiment, the binding protein e.g., antibody, or antigen binding fragment thereof, comprises at least 3 CDRs. In yet another embodiment, the 3 CDRs are a heavy chain variable domain CDR set (CDR1, CDR2, and CDR3) selected from the group consisting of SEQ ID NOs: 40, 41, and 42; SEQ ID NOs: 46, 47, and 42; SEQ ID NOs: 56, 57, and 58; SEQ ID NOs: 62, 63, and 58; SEQ ID NOs: 71, 72, and 73; SEQ ID NOs: 71, 77, and 73; SEQ ID NOs: 85, 86, and 87; SEQ ID NOs: 149, 150, and 87. Alternatively or in combination, 3 CDRs are a light chain variable domain CDR set (CDR1, CDR2, and CDR3) selected from the group consisting of SEQ ID NOs: 49, 50, and 51; SEQ ID NOs: 65, 66, and 67; SEQ ID NOs: 79, 80, and 81; and SEQ ID NOs: 92, 93, and 94.

In another embodiment, the binding protein, e.g., antibody, or antigen binding fragment thereof, comprises at least one heavy chain variable domain CDR set and at least one light chain variable domain CDR set. In some embodiments, the at least two variable domain CDR sets are selected from a group consisting of:

1) either of the heavy chain variable domain CDR sets SEQ ID Nos:40, 41 and 42 or SEQ ID Nos:46, 47 and 42, and the light chain variable domain CDR set SEQ ID Nos:49, 50 and 51;

(2) either of the heavy chain variable domain CDR sets SEQ ID Nos:56, 57 and 58 or SEQ ID Nos: 62, 63 and 58, and the light chain variable domain CDR set SEQ ID Nos 65, 66 and 67;

(3) either of the heavy chain variable domain CDR sets SEQ ID Nos: 71, 72 and 73 or SEQ ID Nos: 71, 77 and 73, and the light chain variable domain CDR set SEQ ID Nos: 79, 80 and 81; and (4) either of the heavy chain variable domain CDR sets SEQ ID Nos:85, 86 and 87 or SEQ ID Nos: 149, 150 and 87, and the light chain variable domain CDR set SEQ ID Nos: 92, 93 and 94.

In other embodiments, the binding protein, e.g., antibody, or antigen binding fragment thereof, further comprises a human acceptor framework. In some embodiments, the human acceptor framework comprises an amino acid sequence selected from the group consisting of SEQ ID Nos:14-38 or 158. In yet other embodiments, the human acceptor framework comprises at least one Framework Region amino acid substitution, wherein the amino acid sequence of the framework is at least 65% identical to the sequence of said human acceptor framework and comprises at least 70 amino acid residues identical to said human acceptor framework. Alternatively, the human acceptor framework comprises at least one Framework Region amino acid substitution at a key residue, said key residue selected from the group consisting of:
  a residue adjacent to a CDR;
  a glycosylation site residue;
  a rare residue;
  a residue capable of interacting with human PRLR;
  a residue capable of interacting with a CDR;
  a canonical residue;
  a contact residue between heavy chain variable region and light chain variable region;
  a residue within a Vernier zone; and
  a residue in a region that overlaps between a Chothia-defined variable heavy chain CDR1 and a Kabat-defined first heavy chain framework.

In other embodiments, the key residue is selected from the group consisting of 2L, 43L, 48L, 58L, 64L, 87L, 27H, 48H, 60H, 63H, 64H, 65H, 67H, 69H, 71H, 73H, 75H, 93H. In another embodiment, the binding protein, e.g., antibody, or antigen binding fragment thereof, is a consensus human variable domain.

In one embodiment, the binding protein, e.g., antibody, or antigen binding fragment thereof, comprises at least one variable domain having an amino acid sequence selected from the group consisting of SEQ ID NO: 39; SEQ ID NO: 43; SEQ ID NO: 44; SEQ ID NO: 45; SEQ ID NO: 55; SEQ ID NO: 59; SEQ ID NO: 60; SEQ ID NO: 61; SEQ ID NO: 70; SEQ ID NO: 74; SEQ ID NO: 75; SEQ ID NO: 76; SEQ ID NO: 84; SEQ ID NO: 88; SEQ ID NO: 89; SEQ ID NO: 90; SEQ ID NO: 121; SEQ ID NO: 122 and SEQ ID NO: 123. In some embodiments, the binding protein, e.g., antibody, or antigen binding fragment thereof, comprises two variable domains, wherein said two variable domains have amino acid sequences selected from the group consisting of:

(1) one of SEQ ID NO: 39; SEQ ID NO: 43; SEQ ID NO: 44 or SEQ ID NO: 45; and one of SEQ ID NO:48, SEQ ID NO:52, SEQ ID NO: 53 or SEQ ID NO:54;

(2) one of SEQ ID NO: 55; SEQ ID NO: 59; SEQ ID NO: 60 or SEQ ID NO: 61; and one of SEQ ID NO:64, SEQ ID NO:68 or SEQ ID NO: 69;

(3) one of SEQ ID NO: 70; SEQ ID NO: 74; SEQ ID NO: 75 or SEQ ID NO: 76; and one of SEQ ID NO:78, SEQ ID NO:82 or SEQ ID NO: 83; and (4) one of SEQ ID NO: 84; SEQ ID NO: 88; SEQ ID NO: 89; SEQ ID NO: 90; SEQ ID NO: 121; SEQ ID NO: 122 or SEQ ID NO: 123; and one of SEQ ID NO:91, SEQ ID NO:95 or SEQ ID NO:96.

In one embodiment, the binding protein, e.g., antibody, or antigen binding fragment thereof, comprises at least one variable domain having an amino acid sequence selected from the group consisting of SEQ ID NO: 48; SEQ ID NO: 52; SEQ ID NO: 53; SEQ ID NO: 54; SEQ ID NO: 64; SEQ ID NO: 68; SEQ ID NO: 69; SEQ ID NO: 78; SEQ ID NO: 82; SEQ ID NO: 83; SEQ ID NO: 91; SEQ ID NO: 95; and SEQ ID NO: 96.

In a particular embodiment, the binding protein comprises a heavy chain sequence and a light chain sequence selected from the group consisting of: (a) a heavy chain having the amino acid sequence of SEQ ID NO: 124; and a light chain having the amino acid sequence of SEQ ID NO: 125; (b) a heavy chain having the amino acid sequence of SEQ ID NO: 124; and a light chain having the amino acid sequence of SEQ ID NO: 126; (c) a heavy chain having the amino acid sequence of SEQ ID NO: 124; and a light chain having the amino acid sequence of SEQ ID NO: 127; (d) a heavy chain having the amino acid sequence of SEQ ID NO: 124; and a light chain having the amino acid sequence of SEQ ID NO: 128; (e) a heavy chain having the amino acid sequence of SEQ ID NO: 129; and a light chain having the amino acid sequence of SEQ ID NO: 125; (f) a heavy chain having the amino acid sequence of SEQ ID NO: 129; and a light chain having the amino acid sequence of SEQ ID NO: 126; (g) a heavy chain having the amino acid sequence of SEQ ID NO: 129; and a light chain having the amino acid sequence of SEQ ID NO: 127; (h) a heavy chain having the amino acid sequence of SEQ ID NO: 129; and a light chain having the amino acid sequence of SEQ ID NO: 128; (i) a heavy chain having the amino acid sequence of SEQ ID NO: 130; and a light chain having the amino acid sequence of SEQ ID NO: 125; (j) a heavy chain having the amino acid sequence of SEQ ID NO: 130; and a light chain having the amino acid sequence of SEQ ID NO: 126; (k) a heavy chain having the amino acid sequence of SEQ ID NO: 130; and a light chain having the amino acid sequence of SEQ ID NO: 127; (l) a heavy chain having the amino acid sequence of SEQ ID NO: 130; and a light chain having the amino acid sequence of SEQ ID NO: 128; (m) a heavy chain having the amino acid sequence of SEQ ID NO: 131; and a light chain having the amino acid sequence of SEQ ID NO: 132; (n) a heavy chain having the amino acid sequence of SEQ ID NO: 131; and a light chain having the amino acid sequence of SEQ ID NO:

133; (o) a heavy chain having the amino acid sequence of SEQ ID NO: 131; and a light chain having the amino acid sequence of SEQ ID NO: 134; (p) a heavy chain having the amino acid sequence of SEQ ID NO: 135; and a light chain having the amino acid sequence of SEQ ID NO: 132; (q) a heavy chain having the amino acid sequence of SEQ ID NO: 135; and a light chain having the amino acid sequence of SEQ ID NO: 133; (r) a heavy chain having the amino acid sequence of SEQ ID NO: 135; and a light chain having the amino acid sequence of SEQ ID NO: 134; (s) a heavy chain having the amino acid sequence of SEQ ID NO: 136; and a light chain having the amino acid sequence of SEQ ID NO: 132; (t) a heavy chain having the amino acid sequence of SEQ ID NO: 136; and a light chain having the amino acid sequence of SEQ ID NO: 133; (u) a heavy chain having the amino acid sequence of SEQ ID NO: 136; and a light chain having the amino acid sequence of SEQ ID NO: 134; (v) a heavy chain having the amino acid sequence of SEQ ID NO: 137; and a light chain having the amino acid sequence of SEQ ID NO: 138; (w) a heavy chain having the amino acid sequence of SEQ ID NO: 137; and a light chain having the amino acid sequence of SEQ ID NO: 139; (x) a heavy chain having the amino acid sequence of SEQ ID NO: 137; and a light chain having the amino acid sequence of SEQ ID NO: 140; (y) a heavy chain having the amino acid sequence of SEQ ID NO: 141; and a light chain having the amino acid sequence of SEQ ID NO: 138; (z) a heavy chain having the amino acid sequence of SEQ ID NO: 141; and a light chain having the amino acid sequence of SEQ ID NO: 139; (aa) a heavy chain having the amino acid sequence of SEQ ID NO: 141; and a light chain having the amino acid sequence of SEQ ID NO: 140; (bb) a heavy chain having the amino acid sequence of SEQ ID NO: 142; and a light chain having the amino acid sequence of SEQ ID NO: 138; (cc) a heavy chain having the amino acid sequence of SEQ ID NO: 142; and a light chain having the amino acid sequence of SEQ ID NO: 139; (dd) a heavy chain having the amino acid sequence of SEQ ID NO: 142; and a light chain having the amino acid sequence of SEQ ID NO: 140; (ee) a heavy chain having the amino acid sequence of SEQ ID NO: 143; and a light chain having the amino acid sequence of SEQ ID NO: 144; (ff) a heavy chain having the amino acid sequence of SEQ ID NO: 143; and a light chain having the amino acid sequence of SEQ ID NO: 145; (gg) a heavy chain having the amino acid sequence of SEQ ID NO: 143; and a light chain having the amino acid sequence of SEQ ID NO: 146; (hh) a heavy chain having the amino acid sequence of SEQ ID NO: 147; and a light chain having the amino acid sequence of SEQ ID NO: 144; (ii) a heavy chain having the amino acid sequence of SEQ ID NO: 147; and a light chain having the amino acid sequence of SEQ ID NO: 145; (jj) a heavy chain having the amino acid sequence of SEQ ID NO: 147; and a light chain having the amino acid sequence of SEQ ID NO: 146; (kk) a heavy chain having the amino acid sequence of SEQ ID NO: 148; and a light chain having the amino acid sequence of SEQ ID NO: 144; (ll) a heavy chain having the amino acid sequence of SEQ ID NO: 148; and a light chain having the amino acid sequence of SEQ ID NO: 145; (mm) a heavy chain having the amino acid sequence of SEQ ID NO: 148; and a light chain having the amino acid sequence of SEQ ID NO: 146; (nn) a heavy chain having the amino acid sequence of SEQ ID NO: 153; and a light chain having the amino acid sequence of SEQ ID NO: 139; (oo) a heavy chain having the amino acid sequence of SEQ ID NO: 154; and a light chain having the amino acid sequence of SEQ ID NO: 139; and (pp) a heavy chain having the amino acid sequence of SEQ ID NO: 155; and a light chain having the amino acid sequence of SEQ ID NO: 139.

In one embodiment, the binding protein, e.g., antibody, or antigen binding fragment thereof, binds PRLR. In some embodiments, the binding protein, e.g., antibody, or antigen binding fragment thereof, is capable of modulating a biological function of PRLR. In other embodiments, the binding protein, e.g., antibody, or antigen binding fragment thereof, is capable of neutralizing PRLR. In yet other embodiments, the binding protein, e.g., antibody, or antigen binding fragment thereof, has an on rate constant ($K_{on}$) to PRLR selected from the group consisting of: at least about $10^2 M^{-1}s^{-1}$; at least about $10^3 M^{-1}s^{-1}$; at least about $10^4 M^{-1}s^{-1}$; at least about $10^5 M^{-1}s^{-1}$; and at least about $10^6 M^{-1}s^{-1}$; as measured by surface plasmon resonance. In other embodiments, the binding protein, e.g., antibody, or antigen binding fragment thereof, has an off rate constant ($K_{off}$) to PRLR selected from the group consisting of: at most about $10^{-3}$ s$^{-1}$; at most about $10^{-4}$ s$^{-1}$; at most about $10^{-5}$ s$^{-1}$; and at most about $10^{-6}$ s$^{-1}$, as measured by surface plasmon resonance. In another embodiment, the binding protein, e.g., antibody, or antigen binding fragment thereof, has a dissociation constant ($K_D$) to PRLR selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

In another aspect, the invention pertains to a binding protein, e.g., antibody, or antigen binding fragment thereof, capable of binding PRLR that competes with an antibody. In one embodiment, a binding protein, e.g., antibody, or antigen binding fragment thereof, competes with an antibody comprising a heavy chain variable domain and a light chain variable domain selected from the group consisting of:

(1) a variable heavy chain having an amino acid sequence selected from the group consisting of SEQ ID NO: 39; SEQ ID NO: 43; SEQ ID NO: 44 and SEQ ID NO: 45; and a variable light chain having an amino acid sequence selected from the group consisting of SEQ ID NO:48, SEQ ID NO:52, SEQ ID NO: 53 and SEQ ID NO:54;

(2) a variable heavy chain having an amino acid sequence selected from the group consisting of SEQ ID NO: 55; SEQ ID NO: 59; SEQ ID NO: 60 and SEQ ID NO: 61; and a variable light chain having an amino acid sequence selected from the group consisting of SEQ ID NO:64, SEQ ID NO:68 and SEQ ID NO: 69;

(3) a variable heavy chain having an amino acid sequence selected from the group consisting of SEQ ID NO: 84; SEQ ID NO: 88; SEQ ID NO: 89; SEQ ID NO: 90; SEQ ID NO: 121; SEQ ID NO: 122; and SEQ ID NO: 123; and a variable light chain having an amino acid sequence selected from the group consisting of SEQ ID NO:91, SEQ ID NO:95 and SEQ ID NO:96;

(4) the variable heavy chain amino acid sequence set forth in SEQ ID NO:112 and the variable light chain amino acid sequence set forth in SEQ ID NO:103;

(5) the variable heavy chain amino acid sequence set forth in SEQ ID NO:113 and the variable light chain amino acid sequence set forth in SEQ ID NO:104;

(6) the variable heavy chain amino acid sequence set forth in SEQ ID NO:114 and the variable light chain amino acid sequence set forth in SEQ ID NO:105;

(7) the variable heavy chain amino acid sequence set forth in SEQ ID NO:116 and the variable light chain amino acid sequence set forth in SEQ ID NO:107;

(8) the variable heavy chain amino acid sequence set forth in SEQ ID NO:117 and the variable light chain amino acid sequence set forth in SEQ ID NO:108;

(9) the variable heavy chain amino acid sequence set forth in SEQ ID NO:118 and the variable light chain amino acid sequence set forth in SEQ ID NO:109;

(10) the variable heavy chain amino acid sequence set forth in SEQ ID NO:119 and the variable light chain amino acid sequence set forth in SEQ ID NO:110; and

(11) the variable heavy chain amino acid sequence set forth in SEQ ID NO:120 and the variable light chain amino acid sequence set forth in SEQ ID NO:111.

In another embodiment, the binding protein, e.g., antibody, or antigen binding fragment thereof, competes with an antibody comprising a heavy chain variable domain and a light chain variable domain selected from the group consisting of:

(1) a variable heavy chain having an amino acid sequence selected from the group consisting of SEQ ID NO: 39; SEQ ID NO: 43; SEQ ID NO: 44 and SEQ ID NO: 45; and a variable light chain having an amino acid sequence selected from the group consisting of SEQ ID NO:48, SEQ ID NO:52, SEQ ID NO: 53 and SEQ ID NO:54;

(2) a variable heavy chain having an amino acid sequence selected from the group consisting of SEQ ID NO: 55; SEQ ID NO: 59; SEQ ID NO: 60 and SEQ ID NO: 61; and a variable light chain having an amino acid sequence selected from the group consisting of SEQ ID NO:64, SEQ ID NO:68 and SEQ ID NO: 69;

(3) a variable heavy chain having an amino acid sequence selected from the group consisting of SEQ ID NO: 84; SEQ ID NO: 88; SEQ ID NO: 89; SEQ ID NO: 90; SEQ ID NO: 121; SEQ ID NO: 122; and SEQ ID NO: 123; and a variable light chain having an amino acid sequence selected from the group consisting of SEQ ID NO:91, SEQ ID NO:95 and SEQ ID NO:96;

(4) the variable heavy chain amino acid sequence set forth in SEQ ID NO:112 and the variable light chain amino acid sequence set forth in SEQ ID NO:103;

(5) the variable heavy chain amino acid sequence set forth in SEQ ID NO:113 and the variable light chain amino acid sequence set forth in SEQ ID NO:104;

(6) the variable heavy chain amino acid sequence set forth in SEQ ID NO:114 and the variable light chain amino acid sequence set forth in SEQ ID NO:105; and (7) the variable heavy chain amino acid sequence set forth in SEQ ID NO:120 and the variable light chain amino acid sequence set forth in SEQ ID NO:111.

In another embodiment, the binding protein, e.g., antibody, or antigen binding fragment thereof, competes with an antibody comprising the variable heavy chain amino acid sequence set forth in SEQ ID NO:119 and the variable light chain amino acid sequence set forth in SEQ ID NO:110.

In another embodiment, the binding protein, e.g., antibody, or antigen binding fragment thereof, competes with an antibody comprising a heavy chain variable domain and a light chain variable domain selected from the group consisting of:

(1) the variable heavy chain amino acid sequence set forth in SEQ ID NO:115 and the variable light chain amino acid sequence set forth in SEQ ID NO:106;

(2) the variable heavy chain amino acid sequence set forth in SEQ ID NO:116 and the variable light chain amino acid sequence set forth in SEQ ID NO:107; and (3) the variable heavy chain amino acid sequence set forth in SEQ ID NO:117 and the variable light chain amino acid sequence set forth in SEQ ID NO:108.

In another embodiment, the binding protein, e.g., antibody, or antigen binding fragment thereof, competes with an antibody comprising a variable heavy chain having an amino acid sequence selected from the group consisting of SEQ ID NO: 39; SEQ ID NO: 43; SEQ ID NO: 44 and SEQ ID NO: 45; and a variable light chain having an amino acid sequence selected from the group consisting of SEQ ID NO:48, SEQ ID NO:52, SEQ ID NO: 53 and SEQ ID NO:54. In other embodiments, the binding protein, e.g., antibody, or antigen binding fragment thereof, competes with an antibody comprising a variable heavy chain having an amino acid sequence selected from the group consisting of SEQ ID NO: 84; SEQ ID NO: 88; SEQ ID NO: 89; SEQ ID NO: 90; SEQ ID NO: 121; SEQ ID NO: 122; and SEQ ID NO: 123; and a variable light chain having an amino acid sequence selected from the group consisting of SEQ ID NO:91, SEQ ID NO:95 and SEQ ID NO:96.

In another aspect, the invention is directed to a binding protein capable of binding PRLR that competes with an antibody comprising a heavy chain sequence and a light chain sequence selected from the group consisting of (a) a heavy chain having the amino acid sequence of SEQ ID NO: 124; and a light chain having the amino acid sequence of SEQ ID NO: 125; (b) a heavy chain having the amino acid sequence of SEQ ID NO: 124; and a light chain having the amino acid sequence of SEQ ID NO: 126; (c) a heavy chain having the amino acid sequence of SEQ ID NO: 124; and a light chain having the amino acid sequence of SEQ ID NO: 127; (d) a heavy chain having the amino acid sequence of SEQ ID NO: 124; and a light chain having the amino acid sequence of SEQ ID NO: 128; (e) a heavy chain having the amino acid sequence of SEQ ID NO: 129; and a light chain having the amino acid sequence of SEQ ID NO: 125; (f) a heavy chain having the amino acid sequence of SEQ ID NO: 129; and a light chain having the amino acid sequence of SEQ ID NO: 126; (g) a heavy chain having the amino acid sequence of SEQ ID NO: 129; and a light chain having the amino acid sequence of SEQ ID NO: 127; (h) a heavy chain having the amino acid sequence of SEQ ID NO: 129; and a light chain having the amino acid sequence of SEQ ID NO: 128; (i) a heavy chain having the amino acid sequence of SEQ ID NO: 130; and a light chain having the amino acid sequence of SEQ ID NO: 125; (j) a heavy chain having the amino acid sequence of SEQ ID NO: 130; and a light chain having the amino acid sequence of SEQ ID NO: 126; (k) a heavy chain having the amino acid sequence of SEQ ID NO: 130; and a light chain having the amino acid sequence of SEQ ID NO: 127; (l) a heavy chain having the amino acid sequence of SEQ ID NO: 130; and a light chain having the amino acid sequence of SEQ ID NO: 128; (m) a heavy chain having the amino acid sequence of SEQ ID NO: 131; and a light chain having the amino acid sequence of SEQ ID NO: 132; (n) a heavy chain having the amino acid sequence of SEQ ID NO: 131; and a light chain having the amino acid sequence of SEQ ID NO: 133; (u) a heavy chain having the amino acid sequence of SEQ ID NO: 131; and a light chain having the amino acid sequence of SEQ ID NO: 134; (p) a heavy chain having the amino acid sequence of SEQ ID NO: 135; and a light chain having the amino acid sequence of SEQ ID NO: 132; (q) a heavy chain having the amino acid sequence of SEQ ID NO: 135; and a light chain having the amino acid sequence of SEQ ID NO: 133; (r) a heavy chain having the amino acid sequence of SEQ ID NO: 135; and a light chain having the amino acid sequence of SEQ ID NO: 134; (s) a heavy chain having the amino acid sequence of SEQ ID NO: 136; and a light chain having the amino acid sequence of SEQ ID NO: 132; (t) a heavy chain having the amino acid sequence of SEQ ID NO: 136; and a light chain having the amino acid sequence of SEQ ID NO: 133; (u) a heavy chain having the amino acid sequence of SEQ ID NO:

136; and a light chain having the amino acid sequence of SEQ ID NO: 134; (v) a heavy chain having the amino acid sequence of SEQ ID NO: 137; and a light chain having the amino acid sequence of SEQ ID NO: 138; (w) a heavy chain having the amino acid sequence of SEQ ID NO: 137; and a light chain having the amino acid sequence of SEQ ID NO: 139; (x) a heavy chain having the amino acid sequence of SEQ ID NO: 137; and a light chain having the amino acid sequence of SEQ ID NO: 140; (y) a heavy chain having the amino acid sequence of SEQ ID NO: 141; and a light chain having the amino acid sequence of SEQ ID NO: 138; (z) a heavy chain having the amino acid sequence of SEQ ID NO: 141; and a light chain having the amino acid sequence of SEQ ID NO: 139; (aa) a heavy chain having the amino acid sequence of SEQ ID NO: 141; and a light chain having the amino acid sequence of SEQ ID NO: 140; (bb) a heavy chain having the amino acid sequence of SEQ ID NO: 142; and a light chain having the amino acid sequence of SEQ ID NO: 138; (cc) a heavy chain having the amino acid sequence of SEQ ID NO: 142; and a light chain having the amino acid sequence of SEQ ID NO: 139; (dd) a heavy chain having the amino acid sequence of SEQ ID NO: 142; and a light chain having the amino acid sequence of SEQ ID NO: 140; (ee) a heavy chain having the amino acid sequence of SEQ ID NO: 143; and a light chain having the amino acid sequence of SEQ ID NO: 144; (ff) a heavy chain having the amino acid sequence of SEQ ID NO: 143; and a light chain having the amino acid sequence of SEQ ID NO: 145; (gg) a heavy chain having the amino acid sequence of SEQ ID NO: 143; and a light chain having the amino acid sequence of SEQ ID NO: 146; (hh) a heavy chain having the amino acid sequence of SEQ ID NO: 147; and a light chain having the amino acid sequence of SEQ ID NO: 144; (ii) a heavy chain having the amino acid sequence of SEQ ID NO: 147; and a light chain having the amino acid sequence of SEQ ID NO: 145; (jj) a heavy chain having the amino acid sequence of SEQ ID NO: 147; and a light chain having the amino acid sequence of SEQ ID NO: 146; (kk) a heavy chain having the amino acid sequence of SEQ ID NO: 148; and a light chain having the amino acid sequence of SEQ ID NO: 144; (ll) a heavy chain having the amino acid sequence of SEQ ID NO: 148; and a light chain having the amino acid sequence of SEQ ID NO: 145; (mm) a heavy chain having the amino acid sequence of SEQ ID NO: 148; and a light chain having the amino acid sequence of SEQ ID NO: 146; (nn) a heavy chain having the amino acid sequence of SEQ ID NO: 153; and a light chain having the amino acid sequence of SEQ ID NO: 139; (oo) a heavy chain having the amino acid sequence of SEQ ID NO: 154; and a light chain having the amino acid sequence of SEQ ID NO: 139; and (pp) a heavy chain having the amino acid sequence of SEQ ID NO: 155; and a light chain having the amino acid sequence of SEQ ID NO: 139.

In another aspect, the invention pertains to a binding protein, e.g., antibody, or antigen binding fragment thereof, capable of binding PRLR that binds to an epitope in PRLR comprising three, four, five, six, seven, eight, nine or all of the amino acid residues E8, F10, C12, R25, E43, G44, I76, D91, E92, L93, Y94, V95, D96, Y99, I100, E145, F160, K185, D187, H188, Y190 and W191 of SEQ ID NO:2. In one embodiment, the binding protein, e.g., antibody, or antigen binding fragment thereof, capable of binding PRLR, binds to an epitope, wherein the epitope comprises at least five of the amino acid residues. In another embodiment, the binding protein, e.g., antibody, or antigen binding fragment thereof, capable of binding PRLR, binds to an epitope, wherein the epitope comprises all of amino acid residues E8, F10, C12, R25, E43, G44, I76, D91, E92, L93, Y94, V95, D96, Y99, I100, E145, F160, K185, D187, H188, Y190 and W191 of SEQ ID NO:2. In a particular embodiment, the binding protein is an antibody, or antigen binding portion thereof, selected from the group consisting of Ab1, Ab6, chAb6, and Ab14-Ab25.

In another aspect, the invention pertains to a binding protein, e.g., antibody, or antigen binding fragment thereof, capable of binding PRLR that binds to an epitope in PRLR comprising three, four, five, six, seven, eight, nine or all of the amino acid residues E8, I9, F10, K11, C12, R25, E43, G44, W72, T74, I76, D91, E92, L93, Y94, V95, D96, T98, Y99, I100, W139, L143, E145, F160, K185, D187, H188, Y190 and W191 of SEQ ID NO:2. In one embodiment, the binding protein, e.g., antibody, or antigen binding fragment thereof, capable of binding PRLR, binds to an epitope, wherein the epitope comprises at least five of the amino acid residues. In another embodiment, the binding protein, e.g., antibody, or antigen binding fragment thereof, capable of binding PRLR, binds to an epitope, wherein the epitope comprises all of amino acid residues E8, I9, F10, K11, C12, R25, E43, G44, W72, T74, I76, D91, E92, L93, Y94, V95, D96, T98, Y99, I100, W139, L143, E145, F160, K185, D187, H188, Y190 and W191 of SEQ ID NO:2. In a particular embodiment, the binding protein is an antibody, or antigen binding portion thereof, selected from the group consisting of Ab4, Ab7, chAb7, Ab35-Ab43 and Ab53-Ab55.

In another aspect, the invention pertains to a binding protein, e.g., antibody, or antigen binding fragment thereof, capable of binding PRLR that binds to an epitope in PRLR comprising 13, 14, 15, 16, 17, 18, 19, 20, 21 or all of the amino acid residues R25, T141, L143, E145, R147, E155, W156, E157, I158, H159, F160, A161, G162, Q163, Q164, F167, S171, R183, K185, D187, H188, W191, and W194 of SEQ ID NO:2. In one embodiment, the binding protein, e.g., antibody, or antigen binding fragment thereof, capable of binding PRLR, binds to an epitope, wherein the epitope comprises at least 15 of the amino acid residues. In some embodiments, the binding protein, e.g., antibody, or antigen binding fragment thereof, capable of binding PRLR, binds to an epitope, wherein the epitope comprises all of amino acid residues R25, T141, L143, E145, R147, E155, W156, E157, I158, H159, F160, A161, G162, Q163, Q164, F167, S171, R183, K185, D187, H188, W191, and W194 of SEQ ID NO:2. In a particular embodiment, the binding protein is an antibody, or antigen binding portion thereof, selected from the group consisting of Ab3, Ab8, chAb8 and Ab44-Ab52.

In another aspect, the invention pertains to a binding protein, e.g., antibody, or antigen binding fragment thereof, capable of binding PRLR that binds to an epitope in PRLR comprising at least one, two, three, four or all of the amino acid residues R25, K185, D187, H188 or W191 of SEQ ID NO:2. In some embodiments, the binding protein, e.g., antibody, or antigen binding fragment thereof, capable of binding PRLR, binds to an epitope, wherein the epitope comprises all of amino acid residues R25, K185, D187, H188 or W191 of SEQ ID NO:2. In a particular embodiment, the binding protein is an antibody, or antigen binding portion thereof, selected from the group consisting of Ab1, Ab3, Ab4, Ab6-Ab8, chAb6, chAb7, chAb8, Ab14-Ab25 and Ab35-Ab55.

In another aspect, the invention pertains to a binding protein, e.g., antibody, or antigen binding fragment thereof, capable of binding PRLR that binds to an epitope in PRLR comprising amino acids 91-96 of SEQ ID NO:2. In a particular embodiment, the binding protein is an antibody, or antigen binding portion thereof, selected from the group consisting of Ab1, Ab4, Ab6, Ab7, chAb6, chAb7, Ab14-Ab25, Ab35-Ab43 and Ab53-Ab55.

In another aspect, the invention pertains to a binding protein, e.g., antibody, or antigen binding fragment thereof, capable of binding PRLR that binds to an epitope having residues within at least amino acids 8-100, 185-191, 8-143, or 183-194 of SEQ ID NO:2. In a particular embodiment, the binding protein is an antibody, or antigen binding portion thereof, selected from the group consisting of Ab1, Ab3, Ab4, Ab6-Ab8, chAb6, chAb7, chAb8, Ab14-Ab25 and Ab35-Ab55.

In another aspect, the invention pertains to a binding protein, e.g., antibody, or antigen binding fragment thereof, capable of binding PRLR and having the same epitopic specificity as an antibody, or antigen-binding portion thereof, selected from the group consisting of Ab1, Ab2, Ab3, Ab4, Ab5, chAb5, Ab6, chAb6, Ab7, chAb7, Ab8, chAb8, Ab9, chAb9, Ab10, chAb10, Ab11, chAb11, Ab12, chAb12, Ab13, chAb13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 and Ab55.

In various embodiments of the foregoing aspects, the binding protein, e.g., antibody, or antigen binding fragment thereof, is capable of modulating a biological function of PRLR. In other embodiments of the foregoing aspects, the binding protein, e.g., antibody, or antigen binding fragment thereof, binds the ligand binding D1 domain of PRLR. In other embodiments of the foregoing aspects, the binding protein, e.g., antibody, or antigen binding fragment thereof, binds an epitope of PRLR which does not inhibit dimerization of PRLR. In further embodiments of the foregoing aspects, the binding protein, e.g., antibody, or antigen binding fragment thereof, does not bind the D2 domain of PRLR. In further embodiments of the foregoing aspects, the binding protein, e.g., antibody, or antigen binding fragment thereof, binds the ligand binding region of the D1 domain of PRLR. In additional embodiments of the foregoing aspects, the binding protein, e.g., antibody, or antigen binding fragment thereof, does not compete with antibody LFA102 for binding of PRLR. In additional embodiments of the foregoing aspects, the binding protein, e.g., antibody, or antigen binding fragment thereof, blocks binding of prolactin to PRLR.

In particular embodiments of any of the foregoing embodiments of the invention, the binding protein is an antibody, or an antigen binding portion thereof. In particular embodiments of any of the foregoing embodiments of the invention, the binding protein is a human antibody, or an antigen binding portion thereof.

In another aspect, the binding protein of any of the foregoing embodiments of the invention is a crystallized binding protein, e.g., antibody, or antigen binding fragment thereof.

In another aspect, the invention pertains to an antibody construct comprising a binding protein wherein said antibody construct further comprises a linker polypeptide or an immunoglobulin constant domain. In one embodiment, the binding protein of said antibody construct is selected from the group consisting of an immunoglobulin molecule, a disulfide linked Fv, a monoclonal antibody, a scFv, a chimeric antibody, a single domain antibody, a CDR-grafted antibody, a diabody, a humanized antibody, a multispecific antibody, a Fab, a dual specific antibody, a Fab', a bispecific antibody, a F(ab')2, and a Fv.

Alternatively, or in addition, the binding protein of said antibody construct may comprise a heavy chain immunoglobulin constant domain selected from the group consisting of a human IgM constant domain, a human IgG4 constant domain, a human IgG1 constant domain, a human IgE constant domain, a human IgG2 constant domain, and a human IgG3 constant domain, a human IgA constant domain.

In other embodiments, the antibody construct comprises an immunoglobulin constant domain having an amino acid sequence selected from the group consisting of SEQ ID Nos:10-13.

In another aspect, the invention pertains to an antibody conjugate comprising an antibody construct as described previously, wherein said antibody conjugate further comprises an agent selected from the group consisting of: an immunoadhension molecule, an imaging agent, a therapeutic agent, and a cytotoxic agent. In one embodiment, the antibody conjugate comprises an imaging agent selected from the group consisting of a radiolabel, an enzyme, a fluorescent label, a luminescent label, a bioluminescent label, a magnetic label, and biotin. In another embodiment, the antibody conjugate comprises a radiolabel selected from the group consisting of: $^{3}H$, $^{14}C$, $^{35}S$, $^{90}Y$, $^{99}Tc$, $^{111}In$, $^{125}I$, $^{177}Lu$, $^{166}Ho$, and $^{153}Sm$. In other embodiments, the antibody conjugate comprises a therapeutic or cytotoxic agent selected from the group consisting of: an anti-metabolite, an alkylating agent, an antibiotic, a growth factor, a cytokine, an antiangiogenic agent, an anti-mitotic agent, an anthracycline, toxin, and an apoptotic agent. For example, the anti-mitotic agent may be selected from the group consisting of a dolastatin, an auristatin, a maytansinoid, a plant alkaloid, a taxane, and a vinca alkaloid. In some embodiments, the binding protein of said antibody construct possesses a human glycosylation pattern.

In certain embodiments, the antibody construct is a crystallized antibody construct. In some embodiments, the crystallized antibody construct is a carrier-free pharmaceutical controlled release crystallized antibody construct. In another embodiment, the antibody construct has a greater half life in vivo than the soluble counterpart of said antibody construct. In some embodiments, the antibody construct retains biological activity.

In another aspect, the invention pertains to an isolated nucleic acid encoding a binding protein, e.g., antibody, or antigen binding fragment thereof, amino acid sequence. In another aspect, the invention pertains to an isolated nucleic acid encoding an antibody construct amino acid sequence, as described herein, wherein said antibody construct further comprises a linker polypeptide or an immunoglobulin constant domain.

In another aspect, the invention provides a vector comprising said isolated nucleic acid. In another embodiment, said vector is selected from the group consisting of pcDNA, pTT, pTT3, pEFBOS, pBV, pJV, and pBJ.

In another aspect, the invention provides a host cell comprising said vector. In another embodiment, said host cell is a prokaryotic cell, while in yet other embodiments, said host cell is *E. Coli*. In other embodiments, said host cell is a eukaryotic cell. In some embodiments, said eukaryotic cell is selected from the group consisting of a protist cell, an animal cell, a plant cell and a fungal cell. In still other embodiments, the eukaryotic cell is an animal cell selected from the group consisting of: a mammalian cell, an avian cell, and an insect cell, while in other embodiments, the host cell is a CHO cell. In another embodiment, the host cell is COS, while in other embodiments, the host cell is a yeast cell. In some embodiments, said yeast cell is *Saccharomyces cerevisiae*. In other embodiments, the host cell is an insect Sf9 cell.

In another aspect, the invention pertains to a method of producing a protein capable of binding PRLR, comprising culturing a host cell as described above, for example, comprising a vector comprising an isolated nucleic acid encoding an antibody construct amino acid sequence as described above, in culture medium under conditions sufficient to produce a binding protein capable of binding PRLR. In one embodiment, the invention pertains to a protein produced according to said method.

In another aspect, the invention pertains to a composition for the release of a binding protein, e.g., antibody, or antigen binding fragment thereof, said composition comprising: (a) a formulation, wherein said formulation comprises a crystallized binding protein, as described herein, and an ingredient; and (b) at least one polymeric carrier. In one embodiment, the polymeric carrier is a polymer selected from one or more of the group consisting of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(b-hydroxybutryate), poly(caprolactone), poly(dioxanone); poly(ethylene glycol), poly((hydroxypropyl)methacrylamide, poly[(organo)phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. In another embodiment, said ingredient is selected from the group consisting of albumin, sucrose, trehalose, lactitol, gelatin, hydroxypropyl-β-cyclodextrin, methoxypolyethylene glycol and polyethylene glycol. In another embodiment, the invention pertains to a method for treating a mammal comprising the step of administering to the mammal an effective amount of said composition.

In another aspect, the invention pertains to a pharmaceutical composition comprising a binding protein, e.g., antibody, or antigen binding fragment thereof, as described herein, and a pharmaceutically acceptable carrier. In one embodiment, said pharmaceutically acceptable carrier functions as adjuvant useful to increase the absorption, or dispersion of the binding protein, e.g., antibody, or antigen binding fragment thereof. In another embodiment, said adjuvant is hyaluronidase.

In another aspect, the pharmaceutical composition further comprises at least one additional therapeutic agent for treating a disorder in which PRLR activity is detrimental. For example, the additional agent may be selected from the group consisting of: therapeutic agent, imaging agent, cytotoxic agent, angiogenesis inhibitors; kinase inhibitors; co-stimulation molecule blockers; adhesion molecule blockers; anti-cytokine antibody or functional fragment thereof; methotrexate; cyclosporin; rapamycin; FK506; detectable label or reporter; a TNF antagonist; an anti-rheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

In another aspect, the invention provides a method for reducing human PRLR activity by contacting human PRLR with a binding protein of the invention, e.g., antibody, or antigen binding fragment thereof, such that human PRLR activity is reduced.

In another aspect, the invention provides a method for reducing human PRLR activity in a human subject suffering from a disorder in which PRLR activity is detrimental, by administering to the human subject a binding protein of the invention, e.g., antibody, or antigen binding fragment thereof, such that human PRLR activity in the human subject is reduced.

In another aspect, the invention provides a method for treating a subject for a disease or a disorder in which PRLR activity is detrimental by administering to the subject a binding protein of the invention, e.g., antibody, or antigen binding fragment thereof, such that treatment is achieved. In one embodiment, the disorder is a cancer. In another embodiment, the cancer is selected from the group consisting of melanoma, endometrial cancer, lymphoma, breast cancer, ovarian cancer, renal carcinoma, gastrointestinal cancer, colon cancer, lung cancer, pancreatic cancer, and prostate cancer. In yet another embodiment, the cancer is breast cancer. In one embodiment, the binding protein, e.g., antibody, or antigen binding fragment thereof, is administered to the subject by at least one mode selected from the group consisting of parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In another aspect, the invention provides an anti-PRLR antibody, or antigen binding fragment thereof, that specifically competes with an anti-PRLR binding protein as described herein, wherein said competition can be detected in a competitive binding assay using said antibody, the human PRLR polypeptide, and the anti-PRLR binding protein.

In another aspect, the invention pertains to an anti-PRLR Antibody Drug Conjugate (ADC) comprising an anti-PRLR antibody, or antigen-binding fragment thereof, and at least one drug, wherein the antibody, or antigen-binding portion thereof, comprises at least 3 CDRs For example, the invention provides an anti-PRLR Antibody Drug Conjugate (ADC) wherein the antibody, or antigen-binding portion thereof, comprises at least 3 CDRs selected from a heavy chain variable domain CDR set (CDR1, CDR2, and CDR3) consisting of SEQ ID NOs: 40, 41, and 42; SEQ ID NOs: 46, 47, and 42; SEQ ID NOs: 56, 57, and 58; SEQ ID NOs: 62, 63, and 58; SEQ ID NOs: 71, 72, and 73; SEQ ID NOs: 71, 77, and 73; SEQ ID NOs: 85, 86, and 87; SEQ ID NOs: 149, 150, and 87. Alternatively or in combination, the invention provides an anti-PRLR Antibody Drug Conjugate (ADC) wherein the antibody, or antigen-binding portion thereof, comprises at least 3 CDRs selected from a light chain variable domain CDR set (CDR1, CDR2, and CDR3) consisting of SEQ ID NOs: 49, 50, and 51; SEQ ID NOs: 65, 66, and 67; SEQ ID NOs: 79, 80, and 81; and SEQ ID NOs: 92, 93, and 94.

In another embodiment of the ADC set forth above, the drug is selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, and a radiosensitizer. In another embodiment, the invention features an ADC, wherein the drug is selected from the group consisting of Ixempra, dolastatin 10, dolastin 15, auristatin E, auristatin PE, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), 5-benzoylvaleric acid-AE ester (AEVB), methotrexate, daunorubicin, vincristine, maytansine, maytansinol, C-3 esters of maytansinol, ansamitocin P1, ansamitocin P2, ansamitocin P3, ansamitocin P4, docetaxel, paclitaxel, nanoparticle paclitaxel, vindesine sulfate, vincristine, vinblastine, vinorelbine, actinomycines, pyrrolo[2,1-c][1,4]benzodiazepines, pyrrolobenzodiazepines (PBD) dimers, actinomycin D, anthramycin, chicamycin A, DC-18, DC-81, mazethramycin, neothramycin A, neothramycin B, porothramycin, prothracarcin B, SG2285, sibanomicin, sibiromycin, tomaymycin, anthracyclines, daunorubicin, doxorubicin, epirubicin, idarubicin, calicheamicins, $\gamma_1^I$, $\alpha_2^I$, $\alpha_3^I$, N-acetyl-$\gamma_1^I$, PSAG, $\theta^I_1$, duocarmycins, adozelesin, bizelesin, and carzelesin, bleomycin, mitomycin, plicamycin, *bacillus* calmette-guerin (BCG), levamisole, cancer vaccines, recombinant bivalent human papillomavirus (HPV) vaccine types 16 and 18 vaccine, recombinant quadrivalent human papillomavirus (HPV) types 6, 11, 16, and 18 vaccine, sipuleucel-T, cytokines, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH), hepatic growth factor; fibroblast growth factor, prolactin, placental lactogen, tumor necrosis factor, mullerian-inhibiting substance, mouse gonadotropin-associated peptide, inhibin, activin, vascular endothelial growth factor, integrin, thrombopoietin (TPO), nerve growth factors such as NGF, platelet-growth factor, transforming growth factors (TGFs), insulin-like growth factor-I and -II, erythropoietin (EPO), osteoinductive factors, interferons such as interferon α, β, and γ, colony stimulating factors (CSFs), granulocyte-macrophage-C-SF (GM-CSF), and granulocyte-CSF (G-CSF), interleukins (ILs) such as IL-1, IL-1α, IL-2, IL-3, IL-4, IL-5, IL-6, IL-7, IL-8, IL-9, IL-11, IL-12, tumor necrosis factor and other polypeptide factors including LIF and kit ligand (KL), colony-stimulating factors, erythropoietin (epoetin), filgrastim, sargramostim, promegapoietin, Oprelvekin, immunomodulating gene therapeutics, nucleic acid encoding a functional, therapeutic gene that is used to replace a mutated or otherwise dysfunctional (e.g. truncated) gene associated with cancer, nucleic acid that encodes for or otherwise provides for the production of a therapeutic protein to treat cancer, alkyl sulfonates, busulfan, nitrogen mustards, chlorambucil, cyclophosphamide, estramustine, ifosfamide, mechlorethamine, and melphalan, nitrosoureas, carmustine, fotemustine, lomustine, nimustine, streptozocin, triazines and hydrazines, dacarbazine, procarbazine, temozolomide, ethylenimines, thiopeta, diaziquone, mitomycin C, methylamine derivatives, epoxides, altretamine, dianhydrogalactitol, dibromodulcitol, angiostatin, ABX EFG, C1-1033, PKI-166, EGF vaccine, EKB-569, GW2016, ICR-62, EMD 55900, CP358, PD153035, AG1478, IMC-C225, OSI-774, Erlotinib, angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme, IMC-1C11, Neovastat, marimstat, prinomastat, BMS-275291, COL-3, MM1270, SU101, SU6668, 5U11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus, and temsirolimus), tyrosine kinase inhibitors (e.g., imatinib, gefitinib, dasatinib, sunitinib, nilotinib, lapatinib, sorafenib, phosphoinositide 3-kinases (PI3K), folic acid antagonists, methotrexate, 4-amino-folic acid, lometrexol, pemetrexed, trimetrexate, a pyrimidine antagonists, azacitidine, capecitabine, cytarabine, decitabine, 5-fluorouracil, 5-fluoro-2'-deoxyuridine 5'-phosphate, 5-fluorouridine triphosphate, gemcitabine, foxuridine, a purine antagonist azathioprine, cladribine, mercaptopurine, fludarabine, pentostatin, 6-thioguanine, adenosine deaminase inhibitors, Cladribine, Fludarabine, Nelarabine, Pentostatin, borophycin, bortezomib, chemoprotective agents, amifostine, dexrazoxane, mesna, androgens, estrogens, medroxyprogesterone acetate, progestins, aminoglutethimide, anastrozole, bicalutamide, chlorotrianises, cyproterone acetate, degarelix, exemestane, flutamide, fulvestrant, goserelin, letrozole, leuprolide, lupron, medroxyprogesterone acetate, Megestrol acetate, tamoxifen, triptorelin, asparaginase, dacarbazine, hydroxyurea, levamisole, mitotane, procarbazane, tretinoin, glucocorticoids, prednisone, chromagens, dyes, antisense oligonucleotides whether naturally occurring or synthesized using standard and/or non-standard nucleotides (including RNA interference (RNAi)), double-stranded RNA (dsRNA), small interfering RNA (siRNA), microRNA (miRNA), aptamers, CpG oligonucleotides, ribozymes, angiozyme, $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{211}$Pb, Co-58, Ga-67, Br-80m, Tc-99m, Rh-103m, Pt-109, In-111 1, Sb-119, I-125, Ho-161, Os-189m, Ir-192, Dy-152, At-211, Bi-212, Ra-223, Rn-219, Po-215, Bi-21 1, Ac-225, Fr-221, At-217, Bi-213, Fm-255, $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, taxane, cisplatin, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, camptothecins, irinotecan, topotecan, amsacrine, daunorubicin, doxotrubicin, epipodophyllotoxins, ellipticines, epirubicin, etoposide, razoxane, teniposide, Axitinib, Bosutinib, Cediranib, Dasatinib, Erlotinib, Gefitinib, Imatinib, Lapatinib, Lestaurtinib, Nilotinib, Semaxanib, Sunitinib, Vandetanib, abrin, abrin A chain, alpha toxin, *Aleurites fordii* proteins, amatoxin, crotin, curcin, dianthin proteins, diptheria toxin, diphtheria A chain, nonbinding active fragments of diphtheria toxin, deoxyribonuclease (Dnase), gelonin, mitogellin, modeccin A chain, *momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin, exotoxin A chain from *Pseudomonas aeruginosa*, restrictocin, ricin, ricin A chain, ribonuclease (Rnase), sapaonaria officinalis inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors, PS-341, HDAC inhibitors, vorinostat, belinostat, entinostat, mocetinostat, panobinostat, COX-2 inhibitors, substituted ureas, heat shock protein inhibitors, Geldanamycin, adrenocortical suppressants, tricothecenes, A12, 19D12, Cp751-871, H7C10, alphaIR3, ScFV/FC, EM/164, Matuzumab, Erbitux, Vectibix, mAb 806, Nimotuxumab, AVEO, AMG102, 5D5 (OA-5d5), H244G11, Ab #14 (MM 121-14), Herceptin, 1B4C3; 2D1D12, NVP-AEW541-A, BMS-536,924H-benzoimidazol-2-yl)-1H-pyridin-2-one), BMS-554,417, Cycloligan, TAE226, PQ401, Iressa, CI-1033 (PD 183805), Lapatinib (GW-572016), Tykerb, Tarceva, PKI-166, PD-158780, EKB-569, Tyrphostin AG 1478 (4-(3-Chloroanillino)-6,7-dimethoxyquinazoline), PHA665752, ARQ 197, Capecitabine, 5-Trifluoromethyl-2'-deoxyuridine, Methotrexate sodium, Raltitrexed, Pemetrexed, Tegafur, Cytosine Arabinoside (Cytarabine), 5-azacytidine, 6-mercaptopurine (Mercaptopurine, 6-MP), Azathioprine, 6-thioguanine, Pentostatin, Fludarabine phosphate, Cladribine (2-CdA, 2-chlorodeoxyadenosine), Ribonucleotide Reductase Inhibitor, Cyclophosphamide, Neosar, ifosfamide, Thiotepa, BCNU→1,3-bis(2-chloroethyl)-1-nitosourea, CCNU→1, -(2-chloroethyl)-3-cyclohexyl-1-nitrosourea (methyl CCNU), Hexamethylmelamine, busulfan, Procarbazine HCL, Dacarbazine (DTIC), chlorambucil, melphalan, carboplatin, oxaliplatin, doxorubicin HCL, daunorubicin citrate, mitoxantrone HCL, actinomycin D, etoposide, topotecan HCl, teniposide, irinotecan HCL (CPT-11), vincristine, vinblastine sulfate, vinorelbine tartrate, vindesine sulphate, paclitaxel, docetaxel, abraxane, ixabepilone, imatinib mesylate, sunitinib malate, sorafenib toslate, nilotinib hydrochloride monohydrate, L-asparaginase, alpha interferon, Avastin, IL-2, Aldesleukin, Proleukin, IL-12, Toremifene citrate, Fulvestrant, raloxifene HCL, anastrazole, letrozole, Fadrozole (CGS 16949A), exemestane, leuprolide acetate, Lupron, goserelin acetate, triptorelin pamoate, buserelin, Nafarelin, cetrorelix, bicalutamide, nilutamide, megestrol acetate, somatostatin Analogs, prendinsolone, dexamethasone, ketoconazole, sirolimus, temsirolimus (CCI-779), deforolimus (AP23573), and everolimus (RAD00I).

In another aspect, the invention pertains to a pharmaceutical composition comprising an ADC as described above.

In yet another aspect, the invention pertains to a method of treating cancer in a subject in need thereof, said method comprising administering an ADC as described above, such that the subject is treated.

In another aspect, the invention pertains to a method of treating cancer in a subject in need thereof, said method comprising administering an ADC as described above, such that the subject is treated, wherein the cancer is selected from the group consisting of melanoma, endometrial cancer, lymphoma, breast cancer, ovarian cancer, renal carcinoma, gastrointestinal cancer, colon cancer, lung cancer, pancreatic cancer, and prostate cancer. In other embodiments, the invention pertains to a method of treating cancer in a subject in need thereof, said method comprising administering an ADC as described above, such that the subject is treated, wherein the cancer is breast cancer. In other embodiments, the invention pertains to a method of treating cancer in a subject in need thereof, said method comprising administering an ADC as described above, such that the subject is treated, wherein the ADC is administered to the subject by a mode selected from the group consisting of parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

BRIEF DESCRIPTION OF THE DRAWINGS

FIG. 1. Alignment of variable heavy chain sequences for murine antibodies Ab5 (SEQ ID NO:112), Ab6 (SEQ ID NO:113), Ab7 (SEQ ID NO:114), Ab8 (SEQ ID NO:115), Ab9 (SEQ ID NO:116), Ab10 (SEQ ID NO:117), Ab11 (SEQ ID NO:118), Ab12 (SEQ ID NO:119) and Ab13 (SEQ ID NO:120).

FIG. 2. Alignment of variable light chain sequences for murine antibodies Ab5 (SEQ ID NO:103), Ab6 (SEQ ID NO:104), Ab7 (SEQ ID NO:105), Ab8 (SEQ ID NO:106), Ab9 (SEQ ID NO:107), Ab10 (SEQ ID NO:108), Ab11 (SEQ ID NO:109), Ab12 (SEQ ID NO:110) and Ab13 (SEQ ID NO:111).

FIG. 3. Alignment of variable heavy chain sequences for murine antibodies Ab5 (SEQ ID NO:112), Ab6 (SEQ ID NO:113), Ab7 (SEQ ID NO:114) and Ab8 (SEQ ID NO:115); and humanized variable heavy chain sequences derived therefrom, i.e., Ab1 VH.1z (SEQ ID NO:39), Ab1 VH.1 (SEQ ID NO:43), Ab1 VH.1a (SEQ ID NO:44), Ab1 VH.1b (SEQ ID NO:45), Ab2 VH.1z (SEQ ID NO:55), Ab2 VH.1 (SEQ ID NO:59), Ab2 VH.1a (SEQ ID NO:60), Ab2 VH.1b (SEQ ID NO:61), Ab3 VH.1z (SEQ ID NO:70), Ab3 VH.1 (SEQ ID NO:74), Ab3 VH.1a (SEQ ID NO:75), Ab3 VH.1b (SEQ ID NO:76), Ab4 VH.1z (SEQ ID NO:84), Ab4 VH.1 (SEQ ID NO:88), Ab4 VH.1a (SEQ ID NO:89), Ab4 VH.1a.2 (SEQ ID NO:121), Ab4 VH.1a.3 (SEQ ID NO:122), Ab4 VH.1b (SEQ ID NO:123), and Ab4 VH.1b.2 (SEQ ID NO:90).

FIG. 4. Alignment of variable light chain sequences for murine antibodies Ab5 (SEQ ID NO:103), Ab6 (SEQ ID NO:104), Ab7 (SEQ ID NO:105) and Ab8 (SEQ ID NO:106); and humanized variable heavy chain sequences derived therefrom, i.e., Ab1 VL.1 (SEQ ID NO:48), Ab1 VL.1a (SEQ ID NO:52), Ab1 VL.2 (SEQ ID NO:53), Ab1 VL.2a (SEQ ID NO:54), Ab2 VL.1 (SEQ ID NO:64), Ab2 VL.1a (SEQ ID NO:68), Ab2 VL.1b (SEQ ID NO:69), Ab3 VL.1 (SEQ ID NO:78), Ab3 VL.1a (SEQ ID NO:82), Ab3 VL.1b (SEQ ID NO:83), Ab4 VL.1 (SEQ ID NO:91), Ab4 VL.1a (SEQ ID NO:95) and Ab4 VL.1b (SEQ ID NO:96).

FIG. 7. Simultaneous binding assay results for chimeric and humanized antibodies chAb7, Ab39, Ab40, chAb5, Ab30, chAb6, Ab19, Ab21, chAb8, Ab48 and Ab49, and for the LFA102 antibody demonstrate that the humanization of chimeric antibodies did not significantly change the core epitope for each root antibody (see Example 4).

DETAILED DESCRIPTION OF THE INVENTION

Figure 5:
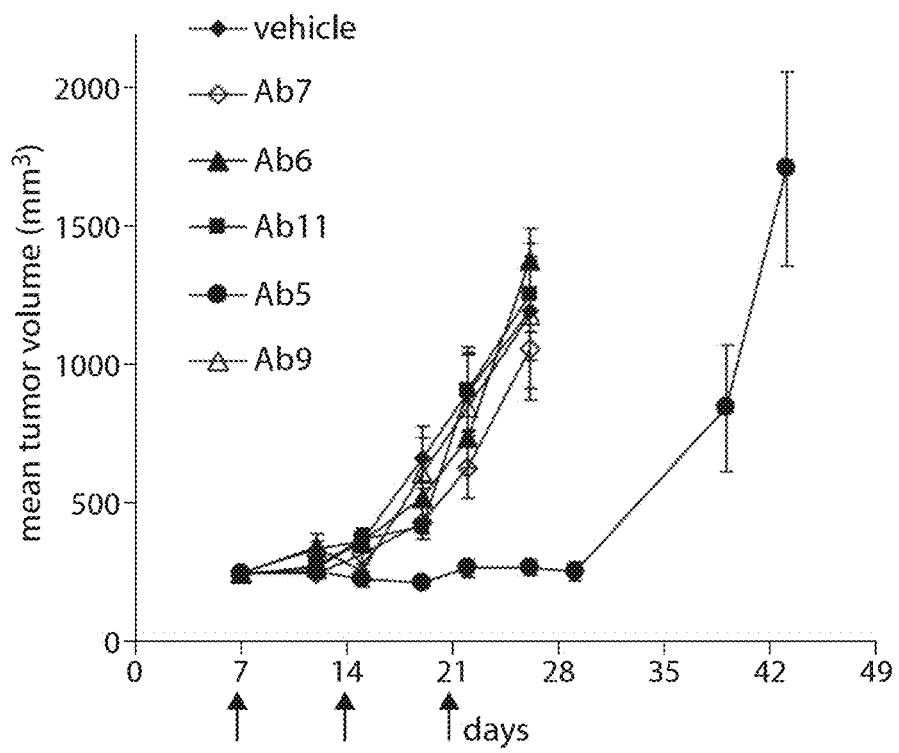
FIG. 5. Effect of anti-PRLR antibodies on the growth of Nb2-11 cells implanted in SCID-beige mice. Antibodies were dosed on the indicated study day (day 7, 14 and 21). Error bars indicate the standard error of the mean (see Example 3).

This invention pertains to human PRLR binding proteins, particularly anti-PRLR antibodies, or antigen-binding portions thereof, that bind PRLR, and uses thereof. Various aspects of the invention relate to antibodies and antibody fragments, conjugates thereof and pharmaceutical compositions thereof, as well as nucleic acids, recombinant expression vectors and host cells for making such antibodies and fragments. Methods of using the antibodies of the invention to detect human PRLR, to inhibit human PRLR activity, either in vitro or in vivo; and to prevent or treat disorders such as breast cancer are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "human PRLR" and "human PRLR wild type" (abbreviated herein as hPRLR, hPRLRwt), as used herein, refers to a single membrane spanning class 1 cytokine receptor. Human PRLR includes an extracellular region that binds prolactin, a transmembrane region, and a cytoplasmic region. The term human PRLR is intended to include recombinant human PRLR (rhPRLR), which can be prepared by standard recombinant expression methods. Table 1 provides the amino acid sequence of human PRLR (i.e., SEQ ID NO. 1), and the extracellular domain thereof (i.e., SEQ ID NO:2), which are known in the art. In addition, various isoforms of hPRLR are known in the art and are set forth in Table 1 below.

TABLE 1

Sequence of human PRLR

| Protein | Sequence Identifier | Sequence 123456789012345678901234567890212 |
|---|---|---|
| Human PRLR | SEQ ID NO.: 1 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV ALKGYSMVTCIFPPVPGPKIKGFDAHLLEKGK SEELLSALGCQDFPPTSDYEDLLVEYLEVDDS EDQHLMSVHSKEHPSQGMKPTYLDPDTDSGRG SCDSPSLLSEKCEEPQANPSTFYDPEVIEKPE NPETTHTWDPQCISMEGKIPYFHAGGSKCSTW PLPQPSQHNPRSSYHNITDVCELAVGPAGAPA TLLNEAGKDALKSSQTIKSREEGKATQQREVE SFHSETDQDTPWLLPQEKTPFGSAKPLDYVEI HKVNKDGALSLLPKQRENSGKPKKPGTPENNK EYAKVSGVMDNNILVLVPDPHAKNVACFEESA KEAPPSLEQNQAEKALANFTATSSKCRLQLGG LDYLDPACFTHSFH |
| Human PRLR | SEQ ID NO: 2 | QLPPGKPEIFKCRSPNKETFTCWWRPGTDGGL PTNYSLTYHREGETLMHECPDYITGGPNSCHF |

TABLE 1-continued

Sequence of human PRLR

| Protein | Sequence Identifier | Sequence 123456789012345678901234567890123456789012 |
|---|---|---|
| Extracellular Domain | | GKQYTSMWRTYIMMVNATNQMGSSFSDELYVD VTYIVQPDPPLELAVEVKQPEDRKPYLWIKWS PPTLIDLKTGWFTLLYEIRLKPEKAAEWEIHF AGQQTEFKILSLHPGQKYLVQVRCKPDHGYWS AWSPATFIQIPSDFTMN |
| Human PRLR Isoform 2 | SEQ ID NO: 3 | MKENVASATVFTLLLFLNTCLLNVQPDPPLEL AVEVKQPEDRKPYLWIKWSPPPTLIDLKTGWFT LLYEIRLKPEKAAEWEIHFAGQQTEFKILSLH PGQKYLVQVRCKPDHGYWSAWSPATFIQIPSD FTMNDTTVWISVAVLSAVICLIIVWAVALKGY SMVTCIFPPVPGPKIKGFDAHLLEKGKSEELL SALGCQDFPPTSDYEDLLVEYLEVDDSEDQHL MSVHSKEHPSQGMKPTYLDPDTDSGRGSCDSP SLLSEKCEEPQANPSTFYDPEVIEKPENPETT HTWDPQCISMEGKIPYFHAGGSKCSTWPLPQP SQHNPRSSYHNITDVCELAVGPAGAPATLLNE AGKDALKSSQTIKSREEGKATQQREVESFHSE TDQDTPWLLPQEKTPFGSAKPLDYVEIHKVNK DGALSLLPKQRENSGKPKKPGTPENNKEYAKV SGVMDNNILVLVPDPHAKNVACFEESAKEAPP SLEQNQAEKALANFTATSSKCRLQLGGLDYLD PACFTHSFH |
| Human PRLR Isoform 3 | SEQ ID NO: 4 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSAW |
| Human PRLR Isoform 4 | SEQ ID NO: 5 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV ALKGYSMVTCIFPPVPGPKIKGFDAHLLEKGK SEELLSALGCQDFPPTSDYEDLLVEYLEVDDS EDQHLMSVHSKEHPSQGDPLMLGASHYKNLKS YRPRKISSQGRLAVFTKATLTTVQ |
| Human PRLR Isoform 5 | SEQ ID NO: 6 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV ALKGYSMVTCIFPPVPGPKIKGFDAHLLEKGK SEELLSALGCQDFPPTSDYEDLLVEYLEVDDS EDQHLMSVHSKEHPSQEREQRQAQEARDS |
| Human PRLR Isoform 6 | SEQ ID NO: 7 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV ALKGYSMVTCIFPPVPGPKIKGFDAHLLEVTP |
| Human PRLR Isoform 7 | SEQ ID NO: 8 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSGDPLMLGASHYKNLKSYRPRKISSQGRL AVFTKATLTTVQ |
| Human PRLR Isoform 8 | SEQ ID NO: 9 | MHECPDYITGGPNSCHFGKQYTSMWRTYIMMV NATNQMGSSFSDELYVDVTYIVQPDPPLELAV EVKQPEDRKPYLWIKWSPPPTLIDLKTGWFTLL YEIRLKPEKAAEWEIHFAGQQTEFKILSLHPG QKYLVQVRCKPDHGYWSAWSPATFIQIPSDFT MNDTTVWISVAVLSAVICLIIVWAVALKGYSM VTCIFPPVPGPKIKGFDAHLLEVTP |

"Biological activity" as used herein, refers to all inherent biological properties of the prolactin receptor. Biological properties of PRLR include but are not limited to binding prolactin, binding growth hormone, binding placental lactogen, activation of JAK2 kinase activity, activation of transmembrane receptor protein tyrosine kinase activity, anti-apoptotic activity, cell surface receptor signaling, cytokine mediated signaling, involvement in embryo implantation, JAK-STAT cascade activity, JAK STAT cascade activity involved in growth hormone signaling, involvement in lactation, involvement in mammary gland alveolus development, involvement in mammary gland epithelial cell differentiation, involvement in mammary gland epithelium development, involvement in prostate gland growth, regulation of cell adhesion, regulation of epithelial cell differentiation, steroid biosynthetic activity, and T cell activation.

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., hPRLR). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art and represented in Table 2.

TABLE 2

Sequence of human IgG heavy chain constant domain and light chain constant domain

| Protein | Sequence Identifier | Sequence 1234567890123456789012345678901 2 |
|---|---|---|
| Ig gamma-1 constant region | SEQ ID NO.: 10 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO.: 11 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KFEDTLMISRTFEVTCVVVDVSHEDFEVKFNW YVDGVEVHNAKTKFREEQYNSTYRVVSVLTVL HQDWLNGKEYKCKVSNKALPAPIEKTISKAKG QFREFQVYTLFFSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO.: 12 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | SEQ ID NO.: 13 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal poly-histidine tag to make bivalent and biotinylated scFv molecules (Kipriyanov, S. M., et al. (1994) *Mol. Immunol.* 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hPRLR is substantially free of antibodies that specifically bind antigens other than hPRLR). An isolated antibody that specifically binds hPRLR may, however, have cross-reactivity to other antigens, such as PRLR molecules from other species. Moreover, an isolated antibody may be substantially free of other cellular material and/or chemicals.

The term "human antibody", as used herein, is intended to include antibodies having variable and constant regions derived from human germline immunoglobulin sequences.

The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human PRLR which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The terms "Kabat numbering", "Kabat definitions and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., *J. Mol. Biol.* 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

Heavy Chain Acceptor Sequences

| SEQ ID No. | Protein region | Sequence 123456789012345678901234567890ABC |
|---|---|---|
| 14 | VH1-18 & JH6 FR1 | QVQLVQSGAEVKKPGASVKVSCKASGYTFT |
| 15 | VH1-18 & JH6 FR2 | WVRQAPGQGLEWMG |
| 16 | VH1-18 & JH6 FR3 | RVTMTTDTSTSTAYMELRSLRSDDTAVYYCAR |
| 17 | VH1-18 & JH6 FR4 | WGQGTTVTVSS |
| 14 | 21/28 & JH4 FR1 | QVQLVQSGAEVKKPGASVKVSCKASGYTFT |

TABLE 3-continued

Heavy Chain Acceptor Sequences

| SEQ ID No. | Protein region | Sequence 123456789012345678901234567890ABC |
|---|---|---|
| 18 | 21/28 & JH4 FR2 | WVRQAPGQRLEWMG |
| 19 | 21/28 & JH4 FR3 | RVTITRDTSASTAYMELSSLRSEDTAVYYCAR |
| 20 | 21/28 & JH4 FR4 | WGQGTLVTVSS |
| 21 | VH2-26 & JH6 FR1 | QVTLKESGPVLVKPTETLTLTCTVSGFSLS |
| 22 | VH2-26 & JH6 FR2 | WIRQPPGKALEWLAH |
| 23 | VH2-26 & JH6 FR3 | RLTISKDTSKSQVVLTMTNMDPVDTATYYCAR |
| 17 | VH2-26 & JH6 FR4 | WGQGTTVTVSS |
| 24 | M60 & JH4 FR1 | QVTLRESGPALVKPTQTLTLTCTLYGFSLS |
| 25 | M60 & JH4 FR2 | WIRQPPGKALEWLA |
| 26 | M60 & JH4 FR3 | RLTISKDTSKNQVVLTMTNMDPVDTATYYCAR |
| 20 | M60 & JH4 FR4 | WGQGTLVTVSS |
| 14 | VH1-46 & JH6 FR1 | QVQLVQSGAEVKKPGASVKVSCKASGYTFT |
| 15 | VH1-46 & JH6 FR2 | WVRQAFGQGLEWMG |
| 27 | VH1-46 & JH6 FR3 | RVTMTRDTSTSTVYMELSSLRSEGTAVYYCAR |
| 17 | VH1-46 & JH6 FR4 | WGQGTTVTVSS |

TABLE 4

Light Chain Acceptor Sequences

| SEQ ID No. | Protein region | Sequence 123456789012345678901234567890ABC |
|---|---|---|
| 28 | A20 & JK4 FR1 | DIQMTQSPSSLSASVGDRVTITC |
| 29 | A20 & JK4 FR2 | WYQQKPGKVPKLLIY |
| 30 | A20 & JK4 FR3 | GVPSRFSGSGSGTDFTLTISSLQPEDVATYYC |
| 31 | A20 & JK4 FR4 | FGGGTKVEIKR |
| 28 | III-3R & JK4 FR1 | DIQMTQSPSSLSASVGDRVTITC |
| 158 | III-3R & JK4 FR2 | WYQQKPGKAPKLLIY |
| 32 | III-3R & JK4 FR3 | GVPSRISGSGSGTDFTFTISSLQPEDIATYYC |

TABLE 4-continued

Light Chain Acceptor Sequences

| SEQ ID No. | Protein region | Sequence 12345678901234567890123456789012 |
|---|---|---|
| 31 | III-3R & JK4 FR4 | FGGGTKVEIKR |
| 33 | A1 & JK4 FR1 | DVVMTQSPLSLPVTLGQPASISC |
| 34 | A1 & JK4 FR2 | WFQQRPGQSPRRLIY |
| 35 | A1 & JK4 FR3 | GVPDRFSGSGSGTDFTLKISRVEAEDVGVYYC |
| 31 | A1 & JK4 FR4 | FGGGTKVEIKR |
| 36 | O1 & JK2 FR1 | DIVMTQTPLSLPVTPGEPASISC |
| 37 | O1 & JK2 FR2 | WYLQKPGQSPQLLIY |
| 35 | O1 & JK2 FR3 | GVPDRFSGSGSGTDFTLKISRVEAEDVGVYYC |
| 38 | O1 & JK2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CHL hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig.

Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of a cytokine receptor when a binding protein specifically binds the cytokine receptor. Preferably, a neutralizing binding protein is a neutralizing antibody whose binding to hPRLR results in inhibition of a biological activity of hPRLR. Preferably the neutralizing binding protein binds hPRLR and reduces a biologically activity of hPRLR by at least about 20%, 40%, 60%, 80%, 85% or more Inhibition of a biological activity of hPRLR by a neutralizing binding protein can be assessed by measuring one or more indicators of hPRLR biological activity well known in the art. For example, inhibition of phosphorylation of PRLR, pSTAT5 or ERK1/2 in a PRLR expressing cell line, e.g., the human breast carcinoma cell line T47D, can be measured. Alternatively, inhibition of proliferation of PRLR expressing cell lines, e.g., Baf3 pro-B lymphoid cells transfected with human PRLR, Nb2-11 rat lymphoma cells, MDA-MB-231-PRLR human breast carcinoma cells transfected with PRLR or BT474 human breast cancer cells, can be measured.

The term "activity" includes activities such as the binding specificity/affinity of an antibody for an antigen, for example, an anti-hPRLR antibody that binds to an hPRLR antigen and/or the neutralizing potency of an antibody, for example, an anti-hPRLR antibody whose binding to hPRLR inhibits the biological activity of hPRLR, e.g., inhibition of phosphorylation of PRLR, pSTAT5 or ERK1/2 in a PRLR expressing cell line, e.g., the human breast carcinoma cell line T47D, or inhibition of proliferation of PRLR expressing cell lines, e.g., Baf3 pro-B lymphoid cells transfected with human PRLR, Nb2-11 rat lymphoma cells, MDA-MB-231-PRLR human breast carcinoma cells transfected with PRLR or BT474 human breast cancer cells.

The term "epitope" includes any polypeptide determinant capable of specific binding to a binding protein, e.g., an antibody or antigen binding portion thereof. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In various embodiments, an epitope may be a linear or sequential epitope, i.e., a linear sequence of amino acids, of the primary structure of the antigen, i.e., PRLR. Alternatively, in other embodiments, an epitope may be a conformational epitope having a specific three-dimensional shape when the antigen assumes its secondary structure. For example, the conformational epitope may comprise non-linear, i.e., non-sequential, amino acids of the antigen.

In a particular embodiment, an epitope is a region of an antigen that is bound by a binding protein, e.g., antibody or antigen binding portion thereof. In certain embodiments, a binding protein, e.g., antibody or antigen binding portion thereof, is said to specifically bind an antigen when it preferentially recognizes its target antigen in a complex mixture of proteins and/or macromolecules. In a particular embodiment, an epitope of the antigen, i.e., PRLR, includes those amino acid residues within 4 angstroms (Å) of the binding protein, e.g., antibody or antigen binding portion thereof, when the binding protein is bound to the antigen.

The term "surface plasmon resonance", as used herein, refers to an optical phenomenon that allows for the analysis of real-time bio specific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody drug conjugate" or "ADC" refers to a binding protein, such as an antibody or antigen binding fragment thereof, chemically linked to one or more chemical agent(s) that may optionally be therapeutic or cytotoxic agents. Examples of agents that may be used in the ADCs of the invention include, but are not limited to, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The term "agent" or "drug" is used herein to denote a chemical compound, a mixture of chemical compounds, a biological macromolecule, or an extract made from biological materials.

The term "cytotoxin" or "cytotoxic agent" includes any agent that is detrimental to (e.g., kills) cells. In one embodiment of the invention, an antibody described herein is conjugated to a cytotoxic agent.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as used herein refers to a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., WO 2007/014162 incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The term "regulate" and "modulate" are used interchangeably, and, as used herein, refers to a change or an alteration in the activity of a molecule of interest (e.g., the biological activity of hPRLR). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hPRLR). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, hPRLR polypeptides or polypeptides, nucleic acids, carbohydrates, or any other molecules that bind to hPRLR.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of hPRLR. Antagonists and inhibitors of hPRLR may include, but are not limited to, proteins, nucleic acids, carbohydrates, or any other molecules, which bind to hPRLR.

The term "inhibit binding to prolactin" refers to the ability of the binding protein to prevent the binding of prolactin ("PRL") to hPRLR. Such inhibition of binding to prolactin would result in diminishing or abolishing the biological activity mediated by binding of prolactin to hPRLR.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

As used herein, the term "LFA102" refers to an anti-PRLR humanized antibody of the IgG1 kappa subtype described in WO 2008022295 A2 (Novartis) and comprising the heavy chain set forth in SEQ ID NO:156 and the light chain set forth in SEQ ID NO:157. LFA102 binds to the putative dimerization region of PRLR in a non-ligand competitive manner and inhibits PRL-induced signaling. LFA102 binds to the membrane proximal D2 domain of PRLR, which is believed to contain the dimerization interface of the receptor. PRLR does not bind to the D1 domain (see, e.g., Damiano et al., 2013, *Molec. Cancer. Therapeutics,* 12:295-305). As such, while LFA102 is capable of inhibiting PRLR dimerization, because LFA102 does not exhibit direct contact with the D1 domain of PRLR which contains the majority of the ligand-binding pocket, LFA102 appears to allow simultaneous binding of prolactin to PRLR (see, e.g., Damiano et al., 2013, *Molec. Cancer. Therapeutics,* 12:295-305 and van et al., 2010, *J. Mol. Biol.,* 404: 112-26).

I. Antibodies that Bind Human hPRLR

One aspect of the present invention provides isolated murine monoclonal antibodies, or antigen-binding portions thereof, that bind to PRLR with high affinity, a slow off rate and high neutralizing capacity. A second aspect of the invention provides chimeric antibodies that bind PRLR. A third aspect of the invention provides humanized antibodies, or antigen-binding portions thereof, that bind PRLR. Preferably, the antibodies, or portions thereof, are isolated antibodies. Preferably, the antibodies of the invention are neutralizing human anti-PRLR antibodies.

A. Method of Making Anti-PRLR Antibodies

Antibodies of the present invention may be made by any of a number of techniques known in the art.

1. Anti-PRLR Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1). Briefly, mice can be immunized with a PRLR antigen. In a preferred embodiment, the PRLR antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a PRLR antigen, antibodies and/or antibody-producing cells may be obtained from the animal. An anti-PRLR antibody-containing serum is obtained from the animal by bleeding or sacrificing the animal. The serum may be used as it is obtained from the animal, an immunoglobulin fraction may be obtained from the serum, or the anti-PRLR antibodies may be purified from the serum. Serum or immunoglobulins obtained in this manner are polyclonal, thus having a heterogeneous array of properties.

Once an immune response is detected, e.g., antibodies specific for the antigen PRLR are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding PRLR. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using PRLR, or a portion thereof, or a cell expressing PRLR. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-PRLR antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-PRLR antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

2. Anti-PRLR Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the antigen PRLR, a subunit of PRLR, or a fragment thereof, is coupled to sheep red blood cells using a linker, such as biotin, and used to identify single cells that secrete antibodies with specificity for PRLR. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to PRLR. The amplified immunoglobulin sequences further can be manipulated in vitro, such as by in vitro affinity maturation methods such as those described in PCT Publication WO 97/29131 and PCT Publication WO 00/56772.

3. Anti-PRLR Monoclonal Antibodies Using Transgenic Animals

In another embodiment of the instant invention, antibodies are produced by immunizing a non-human animal comprising some, or all, of the human immunoglobulin locus with a PRLR antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and κ light chain loci. See Mendez et al., *Nature Genetics*

15:146-156 (1997), Green and Jakobovits *J. Exp. Med.* 188:483-495 (1998), the disclosures of which are hereby incorporated by reference.

4. Anti-PRLR Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with PRLR, or a portion of PRLR, such as the extracellular domain. Alternatively, the recombinant antibody library may be from a naïve subject, i.e., one who has not been immunized with PRLR, such as a human antibody library from a human subject who has not been immunized with human PRLR. Antibodies of the invention are selected by screening the recombinant antibody library with the peptide comprising human PRLR to thereby select those antibodies that recognize PRLR. Methods for conducting such screening and selection are well known in the art, such as described in the references in the preceding paragraph. To select antibodies of the invention having particular binding affinities for hPRLR, such as those that dissociate from human PRLR with a particular $k_{off}$ rate constant, the art-known method of surface plasmon resonance can be used to select antibodies having the desired $k_{off}$ rate constant. To select antibodies of the invention having a particular neutralizing activity for hPRLR, such as those with a particular an $IC_{50}$, standard methods known in the art for assessing the inhibition of hPRLR activity may be used.

In one aspect, the invention pertains to an isolated antibody, or an antigen-binding portion thereof, that binds human PRLR. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in Wittrup et al. (U.S. Pat. No. 6,699,658) incorporated herein by reference.

B. Production of Recombinant PRLR Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Humanized Anti PRLR Antibodies

Table 5 is a list of amino acid sequences of VH and VL regions of preferred humanized anti-hPRLR antibodies of the invention.

TABLE 5

List of Amino Acid Sequences of VH and VL regions

| SEQ ID No. | Protein region | | Sequence 12345678901234567890123456789 |
|---|---|---|---|
| 39 | VH1.z Ab1 | | QVQLVQSGAEVKKPGSSVKVSCKASGYTFT TYWMHWVRQAPGQGLEWMGEIDPSDSYSNY NQKFKDRVTITADSKTSTAYMELSSLRSED TAVYYCARNGGLGPAWFSYWGQGTLVTVSS |
| 40 | VH.1z Ab1 CDR-H1 | Residues 26-35 of SEQ ID No.: 39 | GYTFTTYWMH |
| 41 | VH.1z Ab1 CDR-H2 | Residues 50-66 of SEQ ID No.: 39 | EIDPSDSYSNYNQKFKD |
| 42 | VH.1z Ab1 CDR-H3 | Residues 99-109 of SEQ ID No.: 39 | NGGLGPAWFSY |
| 43 | VH.1 Ab1 | | EVQLVQSGAEVKKPGSSVKVSCKASGYTFT TYWMHWVRQAPGQGLEWMGEIDPSDSYSNY NQKFKDRVTITADKSTSTAYMELSSLRSED TAVYYCARNGGLGPAWFSYWGQGTLVTVSS |

TABLE 5-continued

List of Amino Acid Sequences of VH and VL regions

| SEQ ID No. | Protein region | | Sequence 12345678901234567890123456789 0 |
|---|---|---|---|
| 40 | VH.1 Ab1 CDR-H1 | Residues 26-35 of SEQ ID No.: 43 | GYTFTTYWMH |
| 41 | VH.1 Ab1 CDR-H2 | Residues 50-66 of SEQ ID No.: 43 | EIDPSDSYSNYNQKFKD |
| 42 | VH.1 Ab1 CDR-H3 | Residues 99-109 of SEQ ID No.: 43 | NGGLGPAWFSY |
| 44 | VH.1a Ab1 | | EVQLVQSGAEVKKPGSSVKVSCKASGYTFT TYWMHWVRQAPGQGLEWIGEIDPSDSYSNY NQKFKDRATLTVDKSTSTAYMELSSLRSED TAVYYCARNGGLGPAWFSYWGQGLTVTVSS |
| 40 | VH.1a Ab1 CDR-H1 | Residues 26-35 of SEQ ID No.: 44 | GYTFTTYWMH |
| 41 | VH.1a Ab1 CDR-H2 | Residues 50-66 of SEQ ID No.: 44 | EIDPSDSYSNYNQKFKD |
| 42 | VH.1a Ab1 CDR-H3 | Residues 99-109 of SEQ ID No.: 44 | NGGLGPAWFSY |
| 45 | VH.1b Ab1 | | EVQLVQSGAEVKKPGSSVKVSCKASGGTFT TYWMHWVRQAPGQGLEWIGEIDPSDSYSNY AQKFQGRVTITVDKSTSTAYMELSSLRSED TAVYYCARNGGLGPAWFSYWGQGTLVTVSS |
| 46 | VH.1b Ab1 CDR-H1 | Residues 26-35 of SEQ ID No.: 45 | GGTFTTYWMH |
| 47 | VH.1b Ab1 CDR-H2 | Residues 50-64 of SEQ ID No.: 45 | EIDPSDSYSNYAQKF |
| 42 | VH.1b Ab1 CDR-H3 | Residues 99-109 of SEQ ID No.: 45 | NGGLGPAWFSY |
| 48 | VL.1 Ab1 | | DIQMTQSPSSVSASVGDRVTITCKASQYVG TAVAWYQQKPGKAPKLLIYSASNRYTGVPS RFSGSGSGTDFTLTISSLQPEDFATYYCQQ YSSYPWTFGGGTKVEIK |
| 49 | VL.1 Ab1 CDR-L1 | Residues 24-34 of SEQ ID No.: 48 | KASQYVGTAVA |
| 50 | VL.1 Ab1 CDR-L2 | Residues 50-56 of SEQ ID No.: 48 | SASNRYT |
| 51 | VL.1 Ab1 CDR-L3 | Residues 89-97 of SEQ ID No.: 48 | QQYSSYPWT |
| 52 | VL.1a Ab1 | | DIQMTQSPSSVSASVGDRVTITCKASQYVG TAVAWYQQKPGK<u>S</u>PKLLIYSASNRYTGVPS RF<u>D</u>SGSGTDFTLTISSLQPEDFATY<u>F</u>CQQ YSSYPWTFGGGTKVEIK |
| 49 | VL.1a Ab1 CDR-L1 | Residues 24-34 of SEQ ID No.: 52 | KASWYVGTAVA |
| 50 | VL.1a Ab1 CDR-L2 | Residues 50-56 of SEQ ID No.: 52 | SASNRYT |
| 51 | VL.1a Ab1 CDR-L3 | Residues 89-97 of SEQ ID No.: 52 | QQYSSYPWT |
| 53 | VL.2 Ab1 | | EIVMTQSPATLSVSPGERATLSCKASQYVG TAVAWYQQKPGQAPRLLIYSASNRYTGIPA RFSGSGSGTEFTLTISSLQSEDFAVYYCQQ YSSYPWTFGGGTKVEIK |
| 49 | VL.2 Ab1 CDR-L1 | Residues 24-34 of SEQ ID No.: 53 | KASQYVGTAVA |
| 50 | VL.2 Ab1 CDR-L2 | Residues 50-56 of SEQ ID No.: 53 | SASNRYT |

TABLE 5-continued

List of Amino Acid Sequences of VH and VL regions

| SEQ ID No. | Protein region | | Sequence 12345678901234567890123456789 0 |
|---|---|---|---|
| 51 | VL.2 Ab1 CDR-L3 | Residues 89-97 of SEQ ID No.: 53 | QQYSSYPWT |
| 54 | VL.2a Ab1 | | EIVMTQSPATLSVSPGERATLSCKASQYVG TAVAWYQQKPGQSPRLLIYSASNRYTGVPA RFSDSGSGTEFTLTISSLQSEDFAVYFCQQ YSSYPWTFGGGTKVEIK |
| 49 | VL.2a Ab1 CDR-L1 | Residues 24-34 of SEQ ID No.: 54 | KASQYVGTAVA |
| 50 | VL.2a Ab1 CDR-L2 | Residues 50-56 of SEQ ID No.: 54 | SASNRYT |
| 51 | VL.2a Ab1 CDR-L3 | Residues 89-97 of SEQ ID No.: 54 | QQYSSYPWT |
| 55 | VH.1z Ab2 | | QVLQVQSGAEVKKPGSSVKVSCKASGYTFT SFWMHWVRQAPGQGLEWMGVIDPSDTYTNY NQKFKGRVTITADESTSTAYMELSSLRSED TAVYYCARGDYSNWFTYWGQGLTVTVSS |
| 56 | VH.1z Ab2 CDR-H1 | Residues 26-35 of SEQ ID No.: 55 | GYTFTSFWMH |
| 57 | VH.1z Ab2 CDR-H2 | Residues 50-66 of SEQ ID No.: 55 | VIDPSDTYTNYNQKFKG |
| 58 | VH.1z Ab2 CDR-H3 | Residues 99-107 of SEQ ID No.: 55 | GDYSNWFTY |
| 59 | VH.1 Ab2 | | EVQLVQSGAEVKKPGSSVKVSCKASGYTFT SFWMHWVRQAPGQGLEWMGVIDPSDTYTNY NQKFKGRVTITADESTSTAYMELSSLRSED TAVYYCARGDYSNWFTYWGQGTLVTVSS |
| 56 | VH.1 Ab2 CDR-H1 | Residues 26-35 of SEQ ID No.: 59 | GYTFTSFWMH |
| 57 | VH.1 Ab2 CDR-H2 | Residues 50-66 of SEQ ID No.: 59 | VIDPSDTYTNYNQKFKG |
| 58 | VH.1 Ab2 CDR-H3 | Residues 99-107 of SEQ ID No.: 59 | GDYSNWFTY |
| 60 | VH.1a Ab2 | | EVLQVQSGAEVKKPGSSVKVSCKASGYTFT SFWMHWVRQAPGQGLEWIGVIDPSDTYTNY NQKFKGRATLTVDESSSTAYMELSSLRSED TAVYYCARGDYSNWFTYWGQGTLVTVSS |
| 56 | VH.1a Ab2 CDR-H1 | Residues 26-35 of SEQ ID No.: 60 | GYTFTSFWMH |
| 57 | VH.1a Ab2 CDR-H2 | Residues 50-66 of SEQ ID No.: 60 | VIDPSDTYTNYNQKFKG |
| 58 | VH.1a Ab2 CDR-H3 | Residues 99-107 of SEQ ID No.: 60 | GDYSNWFTY |
| 61 | VH.1b Ab2 | | EVQLVQSGAEVKKPGSSVKVSCKASGGTFT SFWMHWVRQAPGQGLEWIGVIDPSDTYTNY AQKFQGRVTITVDESTSTAYMELSSLRSED TAVYYCARGDYSNWFTYWGQGTLVTVSS |
| 62 | VH.1b Ab2 CDR-H1 | Residues 26-35 of SEQ ID No.: 61 | GGTFTSFWMH |
| 63 | VH.1b Ab2 CDR-H2 | Residues 50-66 of SEQ ID No.: 61 | VIDPSDTYTNYAQKFQG |
| 58 | VH.1b Ab2 CDR-H3 | Residues 99-107 of SEQ ID No.: 61 | GDYSNWFTY |

TABLE 5-continued

List of Amino Acid Sequences of VH and VL regions

| SEQ ID No. | Protein region | | Sequence 12345678901234567890123456789 0 |
|---|---|---|---|
| 64 | VL.1 Ab2 | | DIVMTQTPLSLSVTPGQPASISCRSSQRLV HSNGNTYLHWYLQKPGQSPQLLIYKVSNRF SGVPDRFSGSGSGTDFTLKISRVEAEDVGV YYCSQSTHVPWTFGGGTKVEIK |
| 65 | VL.1 Ab2 CDR-L1 | Residues 24-39 of SEQ ID No.: 64 | RSSQRLVHSNGNTYLH |
| 66 | VL.1 Ab2 CDR-L2 | Residues 55-61 of SEQ ID No.: 64 | KVSNRFS |
| 67 | VL.1 Ab2 CDR-L3 | Residues 94-102 of SEQ ID No.: 64 | SQSTHVPWT |
| 68 | VL.1a Ab2 | | DVVMTQTPLSLSVTPGQPASISCRSSQRLV HSNGNTYLHWYLQKPGQSPQLLIYKVSNRF SGVPDRFSGSGSGTDFTLKISRVEAEDVGV YFCSQSTHVPWTFGGGTKVRIK |
| 65 | VL.1a Ab2 CDR-L1 | Residues 24-39 of SEQ ID No.: 64 | RSSQRLVHSNGNTYLH |
| 66 | VL.1a Ab2 CDR-L2 | Residues 55-61 of SEQ ID No.: 64 | KVSNRFS |
| 67 | VL.1a Ab2 CDR-L3 | Residues 94-102 of SEQ ID No.: 64 | SQSTHVPWT |
| 69 | VL.1b Ab2 | | DVVMTQTPLSLSVTPGQPASISCRSSQRLV HSNGNTYLHWYLQKPGQSPQLLIYKVSNRF SGVPDRFSGSGSGTDFTLKISRVEAEDVGV YYCSQSTHVPWTFGGGTKVEIK |
| 65 | VL.1b Ab2 CDR-L1 | Residues 24-39 of SEQ ID No.: 69 | RSSQRLVHSNGNTYLH |
| 66 | VL.1b Ab2 CDR-L2 | Residues 55-61 of SEQ ID No.: 69 | KVSNRFS |
| 67 | VL.1b Ab2 CDR-L3 | Residues 94-102 of SEQ ID No.: 69 | SQSTHVPWT |
| 70 | VH.1z Ab3 | | QVQLVQSGAEVKKPGASVKVSCKASGYTFT NYNIHWVRQAPGQGLEWMGYIYPNNDGTGY NQKFKSRVTMTTDTSTAYMELRSLRSDD TAVYYCARGDGNYVGDMDYWGQGTTVTSS |
| 71 | VH.1z Ab3 CDR-H1 | Residues 26-35 of SEQ ID No.: 70 | GYTFTDYNIH |
| 72 | VH.1z Ab3 CDR-H2 | Residues 50-66 of SEQ ID No.: 70 | YIYPNNDGTYNQKFKS |
| 73 | VH.1z Ab3 CDR-H3 | Residues 99-109 of SEQ ID No.: 70 | GDGNYVGDMDY |
| 74 | VH.1 Ab3 | | EVQLVQSGAEVKKPGASVKVSCKASGYTFT DYNIHWVRQAPGQGLEWMGYIYPNNDGTGY NQKFKSRVTMTTDTSTAYMELRSLRSDD YAVYYCARGDGNYVGDMDYWGQGTTVTSS |
| 71 | VH.1 Ab3 CDR-H1 | Residues 26-35 of SEQ ID No.: 74 | GYTFTDYNIH |
| 72 | VH.1 Ab3 CDR-H2 | Residues 50-66 of SEQ ID No.: 74 | YIYPNNDGTYNQKFKS |
| 73 | VH.1 Ab3 CDR-H3 | Residues 99-109 of SEQ ID No.: 74 | GDGNYVGDMDY |
| 75 | VH.1a Ab3 | | EVQLVQSGAEVKKPGASVKVSCKASGYTFT DYNIHWVRQAPGQGLEWIGYIYPNNDGTGY NQKFKSRATLTVDNSTATAYMELRSLRSDD TAVYYCARGDGNYVGDMDYWGQGTTVTSS |

TABLE 5-continued

List of Amino Acid Sequences of VH and VL regions

| SEQ ID No. | Protein region | | Sequence 12345678901234567890123456 7890 |
|---|---|---|---|
| 71 | VH.1a Ab3 CDR-H1 | Residues 26-35 of SEQ ID No.: 75 | GYTFTDYNIH |
| 72 | VH.1a Ab3 CDR-H2 | Residues 50-66 of SEQ ID No.: 75 | YIYPNNDGTGYNQKFKS |
| 73 | VH.1a Ab3 CDR-H3 | Residues 99-109 of SEQ ID No.: 75 | GDGNYVGDMDY |
| 76 | VH.1b Ab3 | | EVQLVQSGAEVKKPGASVKVSCKASGYTFT DYNIHWVRQAPGQGLEWIGYIYPNNDGTGY AQKLQGRVTMTVDTSTSTAYMELRSLRSDD TAVYYCARGDGNYVGDMDYWGQGTTVTVSS |
| 71 | VH.1b Ab3 CDR-H1 | Residues 26-35 of SEQ ID No.: 76 | GYTFTDYNIH |
| 77 | VH.1b Ab3 CDR-H2 | Residues 50-66 of SEQ ID No.: 76 | YIYPNNDGTGYAQKLQG |
| 73 | VH.1b Ab3 CDR-H3 | Residues 99-109 of SEQ ID No.: 76 | GDGNYVGDMDY |
| 78 | VL.1 Ab3 | | DIQMTQSPSSLSASVGDRVTITCRASENIY SYLAWYQQKPGKAPKLLIYNAKTLAEGVPS RFSGSGSGTDFTLTISSLQPEDFATYYCQH HYATPFTFGQGTKLEIK |
| 79 | VL.1 Ab3 CDR-L1 | Residues 24-34 of SEQ ID No.: 78 | RASENIYSYLA |
| 80 | VL.1 Ab3 CDR-L2 | Residues 50-56 of SEQ ID No.: 78 | NAKTLAE |
| 81 | VL.1 Ab3 CDR-L3 | Residues 99-107 of SEQ ID No.: 78 | QHHYATPFT |
| 82 | VL.1a Ab3 | | DIQMTQSPSSLSASVGDRVTITCRASENIY SYLAWYQQKPGKPPKLLVYNAKTLAEGVPS RFSGSGSGTDFTLTISSLQPEDFATYYCQH HYATPFTFGQGTKLEIK |
| 79 | VL.1a Ab3 CDR-L1 | Residues 24-34 of SEQ ID No.: 82 | RASENIYSYLA |
| 80 | VL.1a Ab3 CDR-L2 | Residues 50-56 of SEQ ID No.: 82 | NAKTLAE |
| 81 | VL.1a Ab3 CDR-L3 | Residues 99-107 of SEQ ID No.: 82 | QHHYATPFT |
| 83 | VL.1b Ab3 | | DIQMTQSPSSLSASVGDRVTITCRASENIY SYLAWYQQKPGKAPKLLVYNAKTLAEGVPS RFSGSGSGTDFTLTISSLQPEDFATYYCQH HYATPFTFGQGTKLEIK |
| 79 | VL.1b Ab3 CDR-L1 | Residues 24-34 of SEQ ID No.: 83 | RASENIYSYLA |
| 80 | VL.1b Ab3 CDR-L2 | Residues 50-56 of SEQ ID No.: 83 | NAKTLAE |
| 81 | VL.1b Ab3 CDR-L3 | Residues 99-107 of SEQ ID No.: 83 | QHHYATPFT |
| 84 | VH.1z Ab4 | | QVQLVQSGAEVKKPGSSVKVSCKASGYTFT SYWIHWVRQAPGQGLEWMGEIDPSDSYTNY NQKFKGRVTITADKSTSTAYMELSSLRSED TAVYYCARSFFTNWFAYWGQGTLVTVSS |
| 85 | VH.1z Ab4 CDR-H1 | Residues 26-35 of SEQ ID No.: 84 | GYTFTSYWIH |

TABLE 5-continued

List of Amino Acid Sequences of VH and VL regions

| SEQ ID No. | Protein region | | Sequence<br>12345678901234567890123456789 0 |
|---|---|---|---|
| 86 | VH.1z Ab4 CDR-H2 | Residues 50-66 of SEQ ID No.: 84 | EIDPSDSYTNYNQKFKG |
| 87 | VH.1z Ab4 CDR-H3 | Residues 99-107 of SEQ ID No.: 84 | SFFTNWFAY |
| 88 | VH.1 Ab4 | | EVQLVQSGAEVKKPGSSVKVSCKASGYTFT SYWIHWVRQAPGQGLEWMGEIDPSDSYTNY NQKFKGRVTITADKSTSTAYMELSSLRSED TAVYYCARSFFTNWFAYWGQGTLVTVSS |
| 85 | VH.1 Ab4 CDR-H1 | Residues 26-35 of SEQ ID No.: 88 | GYTFTSYWIH |
| 86 | VH.1 Ab4 CDR-H2 | Residues 50-66 of SEQ ID No.: 88 | EIDPSDSYTNYNQKFKG |
| 87 | VH.1 Ab4 CDR-H3 | Residues 99-107 of SEQ ID No.: 88 | SFFTNWFAY |
| 89 | VH.1a Ab4 | | EVQLVQSGAEVKKPGSSVKVSCKASGYTFT WYWIHWVRQAPGQGLEWIGEIDPSDSYTNY NQKFKGRATLTVDKSSSTAYMELSSLRSED TAVYYCARSFFTNWFAYWGQGTLVTVSS |
| 85 | VH.1a Ab4 CDR-H1 | Residues 26-35 of SEQ ID No.: 89 | GYTFTSYWIH |
| 86 | VH.1a Ab4 CDR-H2 | Residues 50-66 of SEQ ID No.: 89 | EIDPSDSYTNYNQKFKG |
| 87 | VH.1a Ab4 CDR-H3 | Residues 99-107 of SEQ ID No.: 89 | SFFTNWFAY |
| 121 | VH.1a.2 Ab4 | | EVQLVQSGAEVKKPGSSVKVSCKASGYTFT SYWIHWVRQAPGQGLEWIGEIDPSDSYTNY NQKFKGRATLTVDRSSSTAYMELSSLRSED TAVYYCGRSFFTNWFAYWGQGTLVTVSS |
| 85 | VH.1a.2 Ab4 CDR-H1 | Residues 26-35 of SEQ ID No.: 121 | GYTFTSYWIH |
| 86 | VH.1a.2 Ab4 CDR-H2 | Residues 50-66 of SEQ ID No.: 121 | EIDPSDSYTNYNQKFKG |
| 87 | VH.1a.2 Ab4 CDR-H3 | Residues 99-107 of SEQ ID No.: 121 | SFFTNWFAY |
| 122 | VH.1a.3 Ab4 | | EVQLVQSGAEVKKPGSSVKVSCKASGYTFT SYWIHWVRQAPGQGLEWIGEIDPSDSYTNY NQKFKGRATLTVDKSSSTAYMELSSLRSED TAVYYCGRSFFTNWFAYWGQGTLVTVSS |
| 85 | VH.1a.3 Ab4 CDR-H1 | Residues 26-35 of SEQ ID No.: 122 | GYFTFSYWIH |
| 86 | VH.1a.3 Ab4 CDR-H2 | Residues 50-66 of SEQ ID No.: 122 | EIDPSDSYTNYNQKFKG |
| 87 | VH.1a.3 Ab4 CDR-H3 | Residues 99-107 of SEQ ID No.: 122 | SFFTNWFAY |
| 123 | VH.1b Ab4 | | EVQLVQSGAEVKKPGSSVKVSCKASGGTFT SYWIHWVRQAPGQGLEWIGEIDPSDSYTNY AQKFKGRVTITVDKSTSTAYMELSSLRSED TAVYYCARSFFTNWFAYWGQGTLVTVSS |
| 149 | VH.1b Ab4 CDR-H1 | Residues 26-35 of SEQ ID No.: 123 | GGTFTSYWIH |
| 159 | VH.1b Ab4 CDR-H2 | Residues 50-66 of SEQ ID No.: 123 | EIDPSDSYTNYAQKFQG |
| 87 | VH.1b Ab4 CDR-H3 | Residues 99-107 of SEQ ID No.: 123 | SFFTNWFAY |

TABLE 5-continued

List of Amino Acid Sequences of VH and VL regions

| SEQ ID No. | Protein region | | Sequence 123456789012345678901234567890 |
|---|---|---|---|
| 90 | VH.1b.2 Ab4 | | EVQLVQSGAEVKKPGSSVKVSCKASGYTFT SYWIHWVRQAPGQGLEWIGEIDPSDSYTNY NQKFKGRVTITVDKSTSTAYMWLSSLRSED TAVYYCARSFFTNWFAYWGQGTLVTVSS |
| 85 | VH.1b.2 Ab4 CDR-H1 | Residues 26-35 of SEQ ID No.: 90 | GYTFTSYWIH |
| 86 | VH.1b.2 Ab4 CDR-H2 | Residues 50-66 of SEQ ID No.: 90 | EIDPSDSYTNYNQKFKG |
| 87 | VH.1b.2 Ab4 CDR-H3 | Residues 99-107 of SEQ ID No.: 90 | SFFTNWFAY |
| 91 | VL.1 Ab4 | | DIVMTQTPLSLSVTPGQPASISCRSSQSLV HSNGNTYLHWYLQKPGQSPQLLIYKVSNRF SGVPDRFSGSGSGTDFTLKISRVEAEDVGV YYCSQSTHVPFTFGGGTKVEIK |
| 92 | VL.1 Ab4 CDR-H1 | Residues 24-39 of SEQ ID No.: 91 | RSSQSLVHSNGNTYLH |
| 93 | VL.1 Ab4 CDR-H2 | Residues 50-61 of SEQ ID No.: 91 | KVSNRFS |
| 94 | VL.1 Ab4 CDR-H3 | Residues 94-102 of SEQ ID No.: 91 | SQSTHVPFT |
| 95 | VL.1a Ab4 | | DVVMTQTPLSLSVTPGQPASISCRSSQSLV HSNGNTYLHWYLQKPGQSPQLLIYKVSNRF SGVPDRFSGSGSGTDFTLKISRVEAEDVGV YFCSQSTHVPFTFGGGTKVEIK |
| 92 | VL.1a Ab4 CDR-H1 | Residues 24-39 of SEQ ID No.: 95 | RSSQSLVHSNGNTYLH |
| 93 | VL.1a Ab4 CDR-H2 | Residues 55-61 of SEQ ID No.: 95 | KVSNRFS |
| 94 | VL.1a Ab4 CDR-H3 | Residues 94-102 of SEQ ID No.: 95 | SQSTHVPFT |
| 96 | VL.1b Ab4 | | DVVMTQTPLSLSVTPGQPASISCRSSQSLV HSNGNTYLHWYLQKPGQSPQLLIYKVSNRF SGVPDRFSGSGSGTDFTLKISRVEAEDVGV YYCSQSTHVPFTFGGGTKVEIK |
| 92 | VL.1b Ab4 CDR-H1 | Residues 24-39 of SEQ ID No.: 96 | RSSQSLVHSNGNTYLH |
| 93 | VL.1b Ab4 CDR-H1 | Residues 24-39 of SEQ ID No.: 96 | KVSNRFS |
| 94 | VL.1b Ab4 CDR-H1 | Residues 24-39 of SEQ ID No.: 96 | SQSTHVPFT |

As used herein, the term "Ab1" refers to an antibody comprising (i) one variable heavy chain having an amino acid sequence selected from the group consisting of SEQ ID NO: 39; SEQ ID NO: 43; SEQ ID NO: 44 and SEQ ID NO: 45; and (ii) one variable light chain having an amino acid sequence selected from the group consisting of SEQ ID NO:48, SEQ ID NO:52, SEQ ID NO: 53 and SEQ ID NO:54.

As used herein, the term "Ab2" refers to an antibody comprising (i) one variable heavy chain having an amino acid sequence selected from the group consisting of SEQ ID NO: 55; SEQ ID NO: 59; SEQ ID NO: 60 and SEQ ID NO: 61; and (ii) one variable light chain having an amino acid sequence selected from the group consisting of SEQ ID NO:64, SEQ ID NO:68 and SEQ ID NO: 69.

As used herein, the term "Ab3" refers to an antibody comprising (i) one variable heavy chain having an amino acid sequence selected from the group consisting of SEQ ID NO: 70; SEQ ID NO: 74; SEQ ID NO: 75 and SEQ ID NO: 76; and (ii) one variable light chain having an amino acid sequence selected from the group consisting of SEQ ID NO:78, SEQ ID NO:82 and SEQ ID NO: 83.

As used herein, the term "Ab4" refers to an antibody comprising (i) one variable heavy chain having an amino acid sequence selected from the group consisting of SEQ ID NO: 84; SEQ ID NO: 88; SEQ ID NO: 89, SEQ ID NO: 90, SEQ ID NO:121, SEQ ID NO:122 and SEQ ID NO:123; and (ii) one variable light chain having an amino acid sequence selected from the group consisting of SEQ ID NO:91, SEQ ID NO:95 and SEQ ID NO:96.

In particular embodiments, the present invention provides humanized antibodies Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 and Ab55 having heavy chain and light chain sequences as set forth in Table 6 below:

TABLE 6

Humanized PRLR Antibodies and Sequences Thereof

| Ab | Heavy Chain Sequence | HC SEQ ID NO: | Light Chain Sequence | LC SEQ ID NO: | Variable Sequences |
|---|---|---|---|---|---|
| Ab14 | EVQLVQSGAEVKKPGSSVKVSCKASGYTFT TYWMHWVRQAPGQGLEWMGEIDPSDSYSNY NQKFKDRVTITADKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 124 | DIQMTQSPSSVSASVGDRVTITCKASQYVG TAVAWYQQKPGKAPKLLIYSASNRYTGVPS RFSGSGSGTDFTLTISSLQPEDFATYYCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 125 | Ab1 HC.1 & Ab1 LC.1 |
| Ab15 | EVQLVQSGAEVKKPGSSVKVSCKASGYTFT TYWMHWVRQAPGQGLEWMGEIDPSDSYSNY NQKFKDRVTITADKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 124 | DIQMTQSPSSVSASVGDRVTITCKASQYVG TAVAWYQQKPGKSPKLLIYSASNRYTGVPS RFSDSGSGTDFTLTISSLQPEDFATYFCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 126 | Ab1 HC.1 and Ab1 LC.1a |
| Ab16 | EVQLVQSGAEVKKPGSSVKVSCKASGYTFT TYWMHWVRQAPGQGLEWMGEIDPSDSYSNY NQKFKDRVTITADKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 124 | EIVMTQSPATLSVSPGERATLSCKASQYVG TAVAWYQQKPGQAPRLLIYSASNRYTGIPA RFSGSGSGTEFTLTISSLQSEDFAVYYCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 127 | Ab1 HC.1 and Ab1 LC.2 |
| Ab17 | EVQLVQSGAEVKKPGSSVKVSCKASGYTFT TYWMHWVRQAPGQGLEWMGEIDPSDSYSNY NQKFKDRVTITADKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 124 | EIVMTQSPATLSVSPGERATLSCKASQYVG TAVAWYQQKPGQSPRLLIYSASNRYTGVPA RFSDSGSGTEFTLTISSLQSEDFAVYFCQQ YSSYPWTFGGGTKVEIKRTVAAPSVFIFPP SDEQLKSGTASVVCLLNNFYPREAKVQWKV DNALQSGNSQESVTEQDSKDSIYSLSSTLT LSKADYEKHKVYACEVTHQGLSSPVTKSFN RGEC | 128 | Ab1 HC.1 and Ab1 LC.2a |
| Ab18 | EVQLVQSGAEVKKPGSSVKVSCKASGYTFT TYWMHWVRQAPGQGLEWIGEIDPSDSYSNY NQKFKDRATLTVDKSTSTAYMELSSLRSED | 129 | DIQMTQSPSSVSASVGDRVTITCKASQYVG TAVAWYQQKPGKAPKLLIYSASNRYTGVPS RFSGSGSGTDFTLTISSLQPEDFATYYCQQ | 125 | Ab1 HC.1a and Ab1 LC.1 |

TABLE 6 -continued

Humanized PRLR Antibodies and Sequences Thereof

| Ab | Heavy Chain Sequence | HC SEQ ID NO: | Light Chain Sequence | LC SEQ ID NO: | Variable Sequences |
|---|---|---|---|---|---|
| | TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | | YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | | |
| Ab19 | EVQLVQSGAEVKKPGSSVKVSCKASGYTFT TYWMHWVRQAPGQGLEWIGEIDPSDSYSNY NQKFKDRATLTVDKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 129 | DIQMTQSPSSVSASVGDRVTITCKASQYVG TAVAWYQQKPGKSPKLLIYSASNRYTGVPS RFSDSGSGTDFTLTISSLQPEDFATYFCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 126 | Ab1 HC.1a and Ab1 LC.1a |
| Ab20 | EVQLVQSGAEVKKPGSSVKVSCKASGYTFT TYWMHWVRQAPGQGLEWIGEIDPSDSYSNY NQKFKDRATLTVDKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 129 | EIVMTQSPATLSVSPGERATLSCKASQYVG TAVAWYQQKPGQAPRLLIYSASNRYTGIPA RFSGSGSGTEFTLTISSLQSEDFAVYYCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 127 | Ab1 HC.1a and Ab1 LC.2 |
| Ab21 | EVQLVQSGAEVKKPGSSVKVSCKASGYTFT TYWMHWVRQAPGQGLEWIGEIDPSDSYSNY NQKFKDRATLTVDKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK | 129 | EIVMTQSPATLSVSPGERATLSCKASQYVG TAVAWYQQKPGQSPRLLIYSASNRYTGVPA RFSDSGSGTEFTLTISSLQSEDFAVYFCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 128 | Ab1 HC.1a and Ab1 LC.2a |
| Ab22 | EVQLVQSGAEVKKPGSSVKVSCKASGGTFT TYWMHWVRQAPGQGLEWIGEIDPSDSYSNY AQKFQGRVTITVDKSTSTAYMELSSLRSED TAVYYCARNGGLGPAWFSYWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP | 130 | DIQMTQSPSSVSASVGDRVTITCKASQYVG TAVAWYQQKPGKAPKLLIYSASNRYTGVPS RFSGSGSGTDFTLTISSLQPEDFATYYCQQ YSSYPWTFGGGTKVEIKRTVAAPSVFIFPP SDEQLKSGTASVVCLLNNFYPREAKVQWKV DNALQSGNSQESVTEQDSKDSTYSLSSTLT LSKADYEKHKVYACEVTHQGLSSPVTKSFN RGEC | 125 | Ab1 HC.1b and Ab1 LC.1 |

TABLE 6 -continued

Humanized PRLR Antibodies and Sequences Thereof

| Ab | Heavy Chain Sequence<br>12345678901234567890123456 7890 | HC SEQ<br>ID NO: | Light Chain Sequence<br>12345678901234567890123456 7890 | LC SEQ<br>ID NO: | Variable<br>Sequences |
|---|---|---|---|---|---|
|  | ENNYKTTPPVLDSDGSFFLYSKLTVDKSRW<br>QQGNVFSCSVMHEALHNHYTQKSLSLSPGK |  |  |  |  |
| Ab23 | EVQLVQSGAEVKKPGSSVKVSCKASGGTFT<br>TYWMHWVRQAPGQGLEWIGEIDPSDSYSNY<br>AQKFQGRVTITVDKSTSTAYMELSSLRSED<br>TAVYYCARNGGLGPAWFSYWGQGTLVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 130 | DIQMTQSPSSVSASVGDRVTITCKASQYVG<br>TAVAWYQQKPGKSPKLLIYSASNRYTGVPS<br>RFSDSGSGTDFTLTISSLQPEDFATYFCQQ<br>YSSYPWTFGGGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 126 | Ab1 HC.1b<br>and Ab1<br>LC.1a |
| Ab24 | EVQLVQSGAEVKKPGSSVKVSCKASGGTFT<br>TYWMHWVRQAPGQGLEWIGEIDPSDSYSNY<br>AQKFQGRVTITVDKSTSTAYMELSSLRSED<br>TAVYYCARNGGLGPAWFSYWGQGTLVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 130 | EIVMTQSPATLSVSPGERATLSCKASQYVG<br>TAVAWYQQKPGQAPRLLIYSASNRYTGIPA<br>RFSGSGSGTEFTLTISSLQSEDFAVYYCQQ<br>YSSYPWTFGGGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 127 | Ab1 HC.1b<br>and Ab1<br>LC.2 |
| Ab25 | EVQLVQSGAEVKKPGSSVKVSCKASGGTFT<br>TYWMHWVRQAPGQGLEWIGEIDPSDSYSNY<br>AQKFQGRVTITVDKSTSTAYMELSSLRSED<br>TAVYYCARNGGLGPAWFSYWGQGTLVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 130 | EIVMTQSPATLSVSPGERATLSCKASQYVG<br>TAVAWYQQKPGQSPRLLIYSASNRYTGVPA<br>RFSDSGSGTEFTLTISSLQSEDFAVYFCQQ<br>YSSYPWTFGGGTKVEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 128 | Ab1 HC.1b<br>and Ab1<br>LC.2a |
| Ab26 | EVQLVQSGAEVKKPGSSVKVSCKASGYTFT<br>SFWMHWVRQAPGQGLEWMGVIDPSDTYTNY<br>NQKFKGRVTITADESTSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 131 | DIVMTQTPLSLSVTPGQPASISCRSSQRLV<br>HSNGNTYLHWYLQKPGQSPQLLIYKVSNRF<br>SGVPDRFSGSGSGTDFTLKISRVEAEDVGV<br>YYCSQSTHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 132 | Ab2 HC.1<br>and Ab2<br>LC.1 |
| Ab27 | EVQLVQSGAEVKKPGSSVKVSCKASGYTFT<br>SFWMHWVRQAPGQGLEWMGVIDPSDTYTNY<br>NQKFKGRVTITADESTSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS | 131 | DVVMTQTPLSLSVTPGQPASTSCRSSQRLV<br>HSNGNTYLHWYLQKPGQSPQLLIYKVSNRF<br>SGVPDRFSGSGSGTDFTLKISRVEAEDVGV<br>YFCSQSTHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 133 | Ab2 HC.1<br>and Ab2<br>LC.1a |

TABLE 6 -continued

Humanized PRLR Antibodies and Sequences Thereof

| Ab | Heavy Chain Sequence<br>12345678901234567890123456 7890 | HC SEQ<br>ID NO: | Light Chain Sequence<br>12345678901234567890123456 7890 | LC SEQ<br>ID NO: | Variable<br>Sequences |
|---|---|---|---|---|---|
| | VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | | | | |
| Ab28 | EVQLVQSGAEVKKPGSSVKVSCKASGYTFT<br>SFWMHWVRQAPGQGLEWMGVIDPSDTYTNY<br>NQKFKGRVTITADESTSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNI<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 131 | DVVMTQTPLSLSVTPGQPASISCRSSQRLV<br>HSNGNTYLHWYLQKPGQSPQLLIYKVSNRF<br>SGVPDRFSGSGSGTDFTLKISRVEAEDVGV<br>YYCSQSTHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 134 | Ab2 HC.1<br>and Ab2<br>LC.1b |
| Ab29 | EVQLVQSGAEVKKPGSSVKVSCKASGYTFT<br>SFWMHWVRQAPGQGLEWIGVIDPSDTYTNY<br>NQKFKGRATLTVDESSSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 135 | DIVMTQTPLSLSVTPGQPASISCRSSQRLV<br>HSNGNTYLHWYLQKPGQSPQLLIYKVSNRF<br>SGVPDRFSGSGSGTDFTLKISRVEAEDVGV<br>YYCSQSTHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 132 | Ab2 HC.1a<br>and Ab2<br>LC.1 |
| Ab30 | EVQLVQSGAEVKKPGSSVKVSCKASGYTFT<br>SFWMHWVRQAPGQGLEWIGVIDPSDTYTNY<br>NQKFKGRATLTVDESSSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 135 | DVVMTQTPLSLSVTPGQPASISCRSSQRLV<br>HSNGNTYLHWYLQKPGQSPQLLIYKVSNRF<br>SGVPDRFSGSGSGTDFTLKISRVEAEDVGV<br>YFCSQSIHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 133 | Ab2 HC.1a<br>and Ab2<br>LC.1a |
| Ab31 | EVQLVQSGAEVKKPGSSVKVSCKASGYTFT<br>SFWMHWVRQAPGQGLEWIGVIDPSDTYTNY<br>NQKFKGRATLTVDESSSTAYMELSSLRSED<br>TAVYYCARGDYSNWFTYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 135 | DVVMTQTPLSLSVTPGQPASTSCRSSQRLV<br>HSNGNTYLHWYLQKPGQSPQLLIYKVSNRF<br>SGVPDRFSGSGSGTDFTLKISRVEAEDVGV<br>YYCSQSTHVPWTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 134 | Ab2 HC.1a<br>and Ab2<br>LC.1b |
| Ab32 | EVQLVQSGAEVKKPGSSVKVSCKASGGTFT<br>SFWMHWVRQAPGQGLEWIGVIDPSDTYTNY<br>AQKFQGRVTITVDESTSTAYMELSSLRSED | 136 | DIVMTQTPLSLSVTPGQPASTSCRSSQRLV<br>HSNGNTYLHWYLQKPGQSPQLLIYKVSNRF<br>SGVPDRFSGSGSGTDFTLKISRVEAEDVGV | 132 | Ab2 HC.1b<br>and Ab2<br>LC.1 |

TABLE 6 -continued

Humanized PRLR Antibodies and Sequences Thereof

| Ab | Heavy Chain Sequence | HC SEQ ID NO: | Light Chain Sequence | LC SEQ ID NO: | Variable Sequences |
|---|---|---|---|---|---|
| | TAVYYCARGDYSNWFTYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK | | YYCSQSTHVPWTFGGGTKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC | | |
| Ab33 | EVQLVQSGAEVKKPGSSVKVSCKASGGTFT SFWMHWVRQAPGQGLEWIGVIDPSDIYINY AQKFQGRVTITVDESTSTAYMELSSLRSED TAVYYCARGDYSNWFTYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNI KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK | 136 | DVVMTQTPLSLSVTPGQPASISCRSSQRLV HSNGNTYLHWYLQKPGQSPQLLIYKVSNRF SGVPDRFSGSGSGTDFTLKISRVEAEDVGV YFCSQSTHVPWTFGGGTKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC | 133 | Ab2 HC.1b and Ab2 LC.1a |
| Ab34 | EVQLVQSGAEVKKPGSSVKVSCKASGGTFT SFWMHWVRQAPGQGLEWIGVIDPSDTYTNY AQKFQGRVTITVDESTSTAYMELSSLRSED TAVYYCARGDYSNWFTYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK | 136 | DVVMTQTPLSLSVTPGQPASTSCRSSQRLV HSNGNTYLHWYLQKPGQSPQLLIYKVSNRF SGVPDRFSGSGSGTDFTLKISRVEAEDVGV YYCSQSTHVPWTFGGGTKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC | 134 | Ab2 HC.1b and Ab2 LC.1b |
| Ab35 | EVQLVQSGAEVKKPGSSVKVSCKASGYTFT SYWIHWVRQAPGQGLEWMGEIDPSDSYTNY NQKFKGRVTITADKSTSTAYMELSSLRSED TAVYYCARSFFTNWFAYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNT KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN NYKTTPPVLDSDGSFFLYSKLTVDKSRWQQ GNVFSCSVMHEALHNHYTQKSLSLSPGK | 137 | DIVMTQTPLSLSVTPGQPASTSCRSSQSLV HSNGNTYLHWYLQKPGQSPQLLIYKVSNRF SGVPDRFSGSGSGTDFTLKISRVEAEDVGV YYCSQSIHVPFTFGGGIKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC | 138 | Ab4 HC.1 and Ab4 LC.1 |
| Ab36 | EVQLVQSGAEVKKPGSSVKVSCKASGYTFT SYWIHWVRQAPGQGLEWMGEIDPSDSYTNY NQKFKGRVTITADKSTSTAYMELSSLRSED TAVYYCARSFFTNWFAYWGQGTLVTVSSAS TKGPSVFPLAPSSKSTSGGTAALGCLVKDY FPEPVTVSWNSGALTSGVHTFPAVLQSSGL YSLSSVVTVPSSSLGTQTYICNVNHKPSNI KVDKKVEPKSCDKTHTCPPCPAPELLGGPS VFLFPPKPKDTLMISRTPEVTCVVVDVSHE DPEVKFNWYVDGVEVHNAKTKPREEQYNST YRVVSVLTVLHQDWLNGKEYKCKVSNKALP APIEKTISKAKGQPREPQVYTLPPSREEMT KNQVSLTCLVKGFYPSDIAVEWESNGQPEN | 137 | DVVMTQTPLSLSVTPGQPASISCRSSQSLV HSNGNTYLHWYLQKPGQSPQLLIYKVSNRF SGVPDRFSGSGSGTDFTLKISRVEAEDVGV YFCSQSTHVPFTFGGGTKVEIKRTVAAPSV FIFPPSDEQLKSGTASVVCLLNNFYPREAK VQWKVDNALQSGNSQESVTEQDSKDSTYSL SSTLTLSKADYEKHKVYACEVTHQGLSSPV TKSFNRGEC | 139 | Ab4 HC.1 and Ab4 LC.1a |

TABLE 6 -continued

Humanized PRLR Antibodies and Sequences Thereof

| Ab | Heavy Chain Sequence<br>12345678901234567890 1234567890 | HC SEQ<br>ID NO: | Light Chain Sequence<br>12345678901234567890 1234567890 | LC SEQ<br>ID NO: | Variable<br>Sequences |
|---|---|---|---|---|---|
| | NYKTTPPVLDSDGSFFLYSKLTVDKSRWQQ<br>GNVFSCSVMHEALHNHYTQKSLSLSPGK | | | | |
| Ab37 | EVQLVQSGAEVKKPGSSVKVSCKASGYTFT<br>SYWIHWVRQAPGQGLEWMGEIDPSDSYTNY<br>NQKFKGRVTITADKSTSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 137 | DVVMTQIPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YYCSQSTHVPFTGGGTKVEIKRTVAAPSV<br>FIFPPSDEQLKSGTASVVCLLNNFYPREAK<br>VQWKVDNALQSGNSQESVTEQDSKDSIYSL<br>SSTLTLSKADYEKHKVYACEVTHQGLSSPV<br>TKSFNRGEC | 140 | Ab4 HC.1<br>and Ab4<br>LC.1b |
| Ab38 | EVQLVQSGAEVKKPGSSVKVSCKASGYTFT<br>SYWIHWVRQAPGQGLEWIGEIDPSDSYTNY<br>NQKFKGRATLTVDKSSSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNI<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 141 | DIVMTQTPLSLSVTPGQPASISCRSSQSLV<br>HSNGNTYLHWYLQKPGQSPQLLIYKVSNRF<br>SGVPDRFSGSGSGTDFITKISRVEAEDVGV<br>YYCSQSIHVPFTGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 138 | Ab4 HC.1a<br>and Ab4<br>LC.1 |
| Ab39 | EVQLVQSGAEVKKPGSSVKVSCKASGYTFT<br>SYWIHWVRQAPGQGLEWIGEIDPSDSYTNY<br>NQKFKGRATLTVDKSSSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 141 | DVVMTQTPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YFCSQSTHVPFTGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 139 | Ab4 HC.1a<br>and Ab4<br>LC.1a |
| Ab40 | EVQLVQSGAEVKKPGSSVKVSCKASGYTFT<br>SYWIHWVRQAPGQGLEWIGEIDPSDSYTNY<br>NQKFKGRATLTVDKSSSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 141 | DVVMTQTPLSLSVTPGQPASISCRSSQSLV<br>HSNGNTYLHWYLQKPGQSPQLLIYKVSNRF<br>SGVPDRFSGSGSGTDFTLKISRVEAEDVGV<br>YYCSQSTHVPFTGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 140 | Ab4 HC.1a<br>and Ab4<br>LC.1b |
| Ab41 | EVQLVQSGAEVKKPGSSVKVSCKASGGTFT<br>SYWIHWVRQAPGQGLEWIGEIDPSDSYTNY<br>AQKFQGRVTITLRSEDKSTSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS | 142 | DIVMTQTPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YYCSQSTHVPFTGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 138 | Ab4 HC.1b<br>and Ab4<br>LC.1 |

TABLE 6 -continued

Humanized PRLR Antibodies and Sequences Thereof

| Ab | Heavy Chain Sequence<br>123456789012345678901234567890 | HC SEQ<br>ID NO: | Light Chain Sequence<br>12345678901234567890123456789 | LC SEQ<br>ID NO: | Variable<br>Sequences |
|---|---|---|---|---|---|
|  | VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK |  |  |  |  |
| Ab42 | EVQLVQSGAEVKKPGSSVKVSCKASGGTFT<br>SYWIHWVRQAPGQGLEWIGEIDPSDSYTNY<br>AQKFQGRVTITVDKSTSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 142 | DVVMTQTPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YFCSQSTHVPFTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 139 | Ab4 HC.1b<br>and Ab4<br>LC.1a |
| Ab43 | EVQLVQSGAEVKKPGSSVKVSCKASGGTFT<br>SYWIHWVRQAPGQGLEWIGEIDPSDSYTNY<br>AQKFQGRVTITVDKSTSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNI<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 142 | DVVMTQTPLSLSVTPGQPASISCRSSQSLV<br>HSNGNTYLHWYLQKPGQSPQLLIYKVSNRF<br>SGVPDRFSGSGSGTDFTLKISRVEAEDVGV<br>YYCSQSTHVPFIFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 140 | Ab4 HC.1b<br>and Ab4<br>LC.1b |
| Ab44 | EVQLVQSGAEVKKPGASVKVSCKASGYTFT<br>DYNIHWVRQAPGQGLEWMGYIYPNNDGTGY<br>NQKFKSRVTMTTDTSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 143 | DIQMTQSPSSLSASVGDRVTITCRASENIY<br>SYLAWYQQKPGKAPKLLIYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 144 | Ab3 HC.1<br>and Ab3<br>LC.1 |
| Ab45 | EVQLVQSGAEVKKPGASVKVSCKASGYTFT<br>DYNIHWVRQAPGQGLEWMGYIYPNNDGTGY<br>NQKFKSRVTMTTDTSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 143 | DIQMTQSPSSLSASVGDRVTITCRASENIY<br>SYLAWYQQKPGKPPKLLVYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 145 | Ab3 HC.1<br>and Ab3<br>LC.1a |
| Ab46 | EVQLVQSGAEVKKPGASVKVSCKASGYTFT<br>DYNIHWVRQAPGQGLEWMGYIYPNNDGITGY<br>NQKFKSRVTMTTDTSTSTAYMELRSLRSDD | 143 | DIQMTQSPSSLSASVGDRVTITCRASENIY<br>SYLAWYQQKPGKAPKLLVYNAKTLAEGVPS<br>RFSGSGSGTDFTLTISSLQPEDFATYYCQH | 146 | Ab3 HC.1<br>and Ab3<br>LC.1b |

TABLE 6 -continued

Humanized PRLR Antibodies and Sequences Thereof

| Ab | Heavy Chain Sequence<br>1234567890123456789012345 67890 | HC SEQ<br>ID NO: | Light Chain Sequence<br>1234567890123456789012345 67890 | LC SEQ<br>ID NO: | Variable<br>Sequences |
|---|---|---|---|---|---|
| | TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | | HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | | |
| Ab47 | EVQLVQSGAEVKKPGASVKVSCKASGYTFT<br>DYNIHWVRQAPGQGLEWIGYIYPNNDGTGY<br>NQKFKSRATLTVDNSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 147 | DIQMTQSPSSLSASVGDRVTITCRASENIY<br>SYLAWYQQKPGKAPKLLIYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 144 | Ab3 HC.1a<br>and Ab3<br>LC.1 |
| Ab48 | EVQLVQSGAEVKKPGASVKVSCKASGYTFT<br>DYNIHWVRQAPGQGLEWIGYIYPNNDGTGY<br>NQKFKSRATLTVDNSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 147 | DIQMTQSPSSLSASVGDRVTITCRASENIY<br>SYLAWYQQKPGKPPKLLVYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 145 | Ab3 HC.1a<br>and Ab3<br>LC.1a |
| Ab49 | EVQLVQSGAEVKKPGASVKVSCKASGYTFT<br>DYNIHWVRQAPGQGLEWIGYIYPNNDGTGY<br>NQKFKSRATLTVDNSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 147 | DIQMTQSPSSLSASVGDRVTITCRASENIY<br>SYLAWYQQKPGKAPKLLVYNAKTLAEGVPS<br>RFSGSGSGTDFTLTISSLQPEDFATYYCQH<br>HYATPFTFGQGIKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 146 | Ab3 HC.1a<br>and Ab3<br>LC.1b |
| Ab50 | EVQLVQSGAEVKKPGASVKVSCKASGYTFT<br>DYNIHWVRQAPGQGLEWIGYIYPNNDGTGY<br>AQKLQGRVTMTVDTSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP | 148 | DIQMTQSPSSLSASVGDRVTITCRASENIY<br>SYLAWYQQKPGKAPKLLIYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 144 | Ab3 HC.1b<br>and Ab3<br>LC.1 |

TABLE 6 -continued

Humanized PRLR Antibodies and Sequences Thereof

| Ab | Heavy Chain Sequence<br>12345678901234567890123456 7890 | HC SEQ<br>ID NO: | Light Chain Sequence<br>12345678901234567890123456 7890 | LC SEQ<br>ID NO: | Variable<br>Sequences |
|---|---|---|---|---|---|
| | ENNYKTTPPVLDSDGSFFLYSKLTVDKSRW<br>QQGNVFSCSVMHEALHNHYTQKSLSLSPGK | | | | |
| Ab51 | EVQLVQSGAEVKKPGASVKVSCKASGYTFT<br>DYNIHWVRQAPGQGLEWIGYIYPNNDGTGY<br>AQKLQGRVTMTVDISTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 148 | DIQMTQSPSSLSASVGDRVTITCRASENIY<br>SYLAWYQQKPGKPPKLLVYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 145 | Ab3 HC.1b<br>and Ab3<br>LC.1a |
| Ab52 | EVQLVQSGAEVKKPGASVKVSCKASGYTFT<br>DYNIHWVRQAPGQGLEWIGYIYPNNDGTGY<br>AQKLQGRVTMTVDTSTSTAYMELRSLRSDD<br>TAVYYCARGDGNYVGDMDYWGQGTTVTVSS<br>ASTKGPSVFPLAPSSKSTSGGTAALGCLVK<br>DYFPEPVTVSWNSGALTSGVHTFPAVLQSS<br>GLYSLSSVVTVPSSSLGTQTYICNVNHKPS<br>NTKVDKKVEPKSCDKTHTCPPCPAPELLGG<br>PSVFLFPPKPKDTLMISRTPEVTCVVVDVS<br>HEDPEVKFNWYVDGVEVHNAKTKPREEQYN<br>STYRVVSVLTVLHQDWLNGKEYKCKVSNKA<br>LPAPIEKTISKAKGQPREPQVYTLPPSREE<br>MTKNQVSLTCLVKGFYPSDIAVEWESNGQP<br>ENNYKTTPPVLDSDGSFFLYSKLTVDKSRW<br>QQGNVFSCSVMHEALHNHYTQKSLSLSPGK | 148 | DIQMTQSPSSLSASVGDRVTITCRASENIY<br>SYLAWYQQKPGKAPKLLVYNAKTLAEGVPS<br>RFSGSGSGTDFTLTISSLQPEDFATYYCQH<br>HYATPFTFGQGTKLEIKRTVAAPSVFIFPP<br>SDEQLKSGTASVVCLLNNFYPREAKVQWKV<br>DNALQSGNSQESVTEQDSKDSTYSLSSTLT<br>LSKADYEKHKVYACEVTHQGLSSPVTKSFN<br>RGEC | 146 | Ab3 HC.1b<br>and Ab3<br>LC.1b |
| Ab53 | EVQLVQSGAEVKKPGSSVKVSCKASGYTFT<br>SYWIHWVRQAPGQGLEWIGEIDPSDSYTNY<br>NQKFKGRVTITVDKSTSTAYMELSSLRSED<br>TAVYYCARSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 153 | DVVMTQTPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YFCSQSTHVPFTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 139 | Ab4<br>HC.1b.2<br>and Ab4<br>LC.1a |
| Ab54 | EVQLVQSGAEVKKPGSSVKVSCKASGYTFT<br>SYWIHWVRQAPGQGLEWIGEIDPSDSYTNY<br>NQKFKGRATLTVDKSSSTAYMELSSLRSED<br>TAVYYCGRSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNT<br>KVDKKVEPKSCDKTHTCPPCPAPELLGGPS<br>VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | 154 | DVVMTQTPLSLSVTPGQPASISCRSSQSLV<br>HSNGNTYLHWYLQKPGQSPQLLIYKVSNRF<br>SGVPDRFSGSGSGTDFTLKISRVEAEDVGV<br>YFCSQSTHVPFTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 139 | Ab4<br>HC.1a.3<br>and Ab4<br>LC.1a |
| Ab55 | EVQLVQSGAEVKKPGSSVKVSCKASGYTFT<br>SYWIHWVRQAPGQGLEWIGEIDPSDSYTNY<br>NQKFKGRATLTVDRSSSTAYMELSSLRSED<br>TAVYYCGRSFFTNWFAYWGQGTLVTVSSAS<br>TKGPSVFPLAPSSKSTSGGTAALGCLVKDY<br>FPEPVTVSWNSGALTSGVHTFPAVLQSSGL<br>YSLSSVVTVPSSSLGTQTYICNVNHKPSNI<br>KVDKKVEPKSCDKTHTCPPCPAPELLGGPS | 155 | DVVMTQTPLSLSVTPGQPASTSCRSSQSLV<br>HSNGNTYLHWYLQKPGQSPQLLIYKVSNRF<br>SGVPDRFSGSGSGTDFTLKISRVEAEDVGV<br>YFCSQSTHVPFTFGGGTKVEIKRTVAAPSV<br>FIFPPSDEQLKSGTASVVCLLNNFYPREAK<br>VQWKVDNALQSGNSQESVTEQDSKDSTYSL<br>SSTLTLSKADYEKHKVYACEVTHQGLSSPV<br>TKSFNRGEC | 139 | Ab4<br>HC.1a.2<br>and Ab4<br>LC.1a |

TABLE 6 -continued

Humanized PRLR Antibodies and Sequences Thereof

| Ab | Heavy Chain Sequence<br>12345678901234567890123456 7890 | HC SEQ<br>ID NO: | Light Chain Sequence<br>12345678901234567890123456 7890 | LC SEQ<br>ID NO: | Variable<br>Sequences |
|---|---|---|---|---|---|
| | VFLFPPKPKDTLMISRTPEVTCVVVDVSHE<br>DPEVKFNWYVDGVEVHNAKTKPREEQYNST<br>YRVVSVLTVLHQDWLNGKEYKCKVSNKALP<br>APIEKTISKAKGQPREPQVYTLPPSREEMT<br>KNQVSLTCLVKGFYPSDIAVEWESNGQPEN<br>NYKTTPPVLDSDGSFFLYSKLTVDKSRWQQ<br>GNVFSCSVMHEALHNHYTQKSLSLSPGK | | | | |

In one embodiment, the present invention is directed to antibody Ab14 comprising a heavy chain having the amino acid sequence of SEQ ID NO: 124; and a light chain having the amino acid sequence of SEQ ID NO: 125.

In one embodiment, the present invention is directed to antibody Ab15 comprising a heavy chain having the amino acid sequence of SEQ ID NO: 124; and a light chain having the amino acid sequence of SEQ ID NO: 126.

In one embodiment, the present invention is directed to antibody Ab16 comprising a heavy chain having the amino acid sequence of SEQ ID NO: 124; and a light chain having the amino acid sequence of SEQ ID NO: 127.

In one embodiment, the present invention is directed to antibody Ab17 comprising a heavy chain having the amino acid sequence of SEQ ID NO: 124; and a light chain having the amino acid sequence of SEQ ID NO: 128.

In one embodiment, the present invention is directed to antibody Ab18 comprising a heavy chain having the amino acid sequence of SEQ ID NO: 129; and a light chain having the amino acid sequence of SEQ ID NO: 125.

In one embodiment, the present invention is directed to antibody Ab19 comprising a heavy chain having the amino acid sequence of SEQ ID NO: 129; and a light chain having the amino acid sequence of SEQ ID NO: 126.

In one embodiment, the present invention is directed to antibody Ab20 comprising a heavy chain having the amino acid sequence of SEQ ID NO: 129; and a light chain having the amino acid sequence of SEQ ID NO: 127.

In one embodiment, the present invention is directed to antibody Ab21 comprising a heavy chain having the amino acid sequence of SEQ ID NO: 129; and a light chain having the amino acid sequence of SEQ ID NO: 128.

In one embodiment, the present invention is directed to antibody Ab22 comprising a heavy chain having the amino acid sequence of SEQ ID NO: 130; and a light chain having the amino acid sequence of SEQ ID NO: 125.

In one embodiment, the present invention is directed to antibody Ab23 comprising a heavy chain having the amino acid sequence of SEQ ID NO: 130; and a light chain having the amino acid sequence of SEQ ID NO: 126.

In one embodiment, the present invention is directed to antibody Ab24 comprising a heavy chain having the amino acid sequence of SEQ ID NO: 130; and a light chain having the amino acid sequence of SEQ ID NO: 127.

In one embodiment, the present invention is directed to antibody Ab25 comprising a heavy chain having the amino acid sequence of SEQ ID NO: 130; and a light chain having the amino acid sequence of SEQ ID NO: 128.

In one embodiment, the present invention is directed to antibody Ab26 comprising a heavy chain having the amino acid sequence of SEQ ID NO: 131; and a light chain having the amino acid sequence of SEQ ID NO: 132.

In one embodiment, the present invention is directed to antibody Ab27 comprising a heavy chain having the amino acid sequence of SEQ ID NO: 131; and a light chain having the amino acid sequence of SEQ ID NO: 133.

In one embodiment, the present invention is directed to antibody Ab28 comprising a heavy chain having the amino acid sequence of SEQ ID NO: 131; and a light chain having the amino acid sequence of SEQ ID NO: 134.

In one embodiment, the present invention is directed to antibody Ab29 comprising a heavy chain having the amino acid sequence of SEQ ID NO: 135; and a light chain having the amino acid sequence of SEQ ID NO: 132.

In one embodiment, the present invention is directed to antibody Ab30 comprising a heavy chain having the amino acid sequence of SEQ ID NO: 135; and a light chain having the amino acid sequence of SEQ ID NO: 133.

In one embodiment, the present invention is directed to antibody Ab31 comprising a heavy chain having the amino acid sequence of SEQ ID NO: 135; and a light chain having the amino acid sequence of SEQ ID NO: 134.

In one embodiment, the present invention is directed to antibody Ab32 comprising a heavy chain having the amino acid sequence of SEQ ID NO: 136; and a light chain having the amino acid sequence of SEQ ID NO: 132.

In one embodiment, the present invention is directed to antibody Ab33 comprising a heavy chain having the amino acid sequence of SEQ ID NO: 136; and a light chain having the amino acid sequence of SEQ ID NO: 133.

In one embodiment, the present invention is directed to antibody Ab34 comprising a heavy chain having the amino acid sequence of SEQ ID NO: 136; and a light chain having the amino acid sequence of SEQ ID NO: 134.

In one embodiment, the present invention is directed to antibody Ab35 comprising a heavy chain having the amino acid sequence of SEQ ID NO: 137; and a light chain having the amino acid sequence of SEQ ID NO: 138.

In one embodiment, the present invention is directed to antibody Ab36 comprising a heavy chain having the amino acid sequence of SEQ ID NO: 137; and a light chain having the amino acid sequence of SEQ ID NO: 139.

In one embodiment, the present invention is directed to antibody Ab37 comprising a heavy chain having the amino acid sequence of SEQ ID NO: 137; and a light chain having the amino acid sequence of SEQ ID NO: 140.

In one embodiment, the present invention is directed to antibody Ab38 comprising a heavy chain having the amino acid sequence of SEQ ID NO: 141; and a light chain having the amino acid sequence of SEQ ID NO: 138.

In one embodiment, the present invention is directed to antibody Ab39 comprising a heavy chain having the amino acid sequence of SEQ ID NO: 141; and a light chain having the amino acid sequence of SEQ ID NO: 139.

In one embodiment, the present invention is directed to antibody Ab40 comprising a heavy chain having the amino acid sequence of SEQ ID NO: 141; and a light chain having the amino acid sequence of SEQ ID NO: 140.

In one embodiment, the present invention is directed to antibody Ab41 comprising a heavy chain having the amino acid sequence of SEQ ID NO: 142; and a light chain having the amino acid sequence of SEQ ID NO: 138.

In one embodiment, the present invention is directed to antibody Ab42 comprising a heavy chain having the amino acid sequence of SEQ ID NO: 142; and a light chain having the amino acid sequence of SEQ ID NO: 139.

In one embodiment, the present invention is directed to antibody Ab43 comprising a heavy chain having the amino acid sequence of SEQ ID NO: 142; and a light chain having the amino acid sequence of SEQ ID NO: 140.

In one embodiment, the present invention is directed to antibody Ab44 comprising a heavy chain having the amino acid sequence of SEQ ID NO: 143; and a light chain having the amino acid sequence of SEQ ID NO: 144.

In one embodiment, the present invention is directed to antibody Ab45 comprising a heavy chain having the amino acid sequence of SEQ ID NO: 143; and a light chain having the amino acid sequence of SEQ ID NO: 145.

In one embodiment, the present invention is directed to antibody Ab46 comprising a heavy chain having the amino acid sequence of SEQ ID NO: 143; and a light chain having the amino acid sequence of SEQ ID NO: 146.

In one embodiment, the present invention is directed to antibody Ab47 comprising a heavy chain having the amino acid sequence of SEQ ID NO: 147; and a light chain having the amino acid sequence of SEQ ID NO: 144.

In one embodiment, the present invention is directed to antibody Ab48 comprising a heavy chain having the amino acid sequence of SEQ ID NO: 147; and a light chain having the amino acid sequence of SEQ ID NO: 145.

In one embodiment, the present invention is directed to antibody Ab49 comprising a heavy chain having the amino acid sequence of SEQ ID NO: 147; and a light chain having the amino acid sequence of SEQ ID NO: 146.

In one embodiment, the present invention is directed to antibody Ab50 comprising a heavy chain having the amino acid sequence of SEQ ID NO: 148; and a light chain having the amino acid sequence of SEQ ID NO: 144.

In one embodiment, the present invention is directed to antibody Ab51 comprising a heavy chain having the amino acid sequence of SEQ ID NO: 148; and a light chain having the amino acid sequence of SEQ ID NO: 145.

In one embodiment, the present invention is directed to antibody Ab52 comprising a heavy chain having the amino acid sequence of SEQ ID NO: 148; and a light chain having the amino acid sequence of SEQ ID NO: 146.

In one embodiment, the present invention is directed to antibody Ab53 comprising a heavy chain having the amino acid sequence of SEQ ID NO: 153; and a light chain having the amino acid sequence of SEQ ID NO: 139.

In one embodiment, the present invention is directed to antibody Ab54 comprising a heavy chain having the amino acid sequence of SEQ ID NO: 154; and a light chain having the amino acid sequence of SEQ ID NO: 139.

In one embodiment, the present invention is directed to antibody Ab55 comprising a heavy chain having the amino acid sequence of SEQ ID NO: 155; and a light chain having the amino acid sequence of SEQ ID NO: 139.

The foregoing isolated anti-PRLR antibody CDR sequences establish a novel family of PRLR binding proteins, isolated in accordance with this invention, and comprising polypeptides that include the CDR sequences listed in Table 7a or 7b below. To generate and to select CDRs of the invention having preferred PRLR binding and/or neutralizing activity with respect to hPRLR, standard methods known in the art for generating binding proteins of the present invention and assessing the PRLR binding and/or neutralizing characteristics of those binding protein may be used, including but not limited to those specifically described herein.

TABLE 7a

Consensus PRLR CDR affinity ligands based on murine antibodies
(alternative residues are listed below each amino acid position;
— indicates residue may be absent).

| CDR region | Sequence Identifier | Consensus Sequence |
|---|---|---|
| CDR-H1 | SEQ ID NO.: 97 | 26 $X_1$ G F | 27 $X_2$ Y S | 28 $X_3$ T | 29 $X_4$ F I | 30 $X_5$ T S | 31 $X_6$ S D T | 32 $X_7$ Y F D | 33 $X_8$ W N Y | 34 $X_9$ M I A | 35 $X_{10}$ H F W | 35a $X_{11}$ — N |
| CDR-H2 | SEQ ID NO.: 98 | 50 $X_1$ Y V E | 51 $X_2$ I F | 52 $X_3$ D Y S G | 52a $X_4$ N — | 53 $X_5$ S Y N G | 54 $X_6$ D N G S | 55 $X_7$ G S D T | 56 $X_8$ Y G H S R | 57 $X_9$ T S A | 58 $X_{10}$ N G Y S | 59 $X_{11}$ Y F | 60 $X_{12}$ N P | 61 $X_{13}$ Q D P | 62 $X_{14}$ K E T S | 63 $X_{15}$ F L V | 64 $X_{16}$ K | 65 $X_{17}$ G S D N |
| CDR-H3 | SEQ ID NO.: 99 | 95 $X_1$ G S N Q | 96 $X_2$ D F G L | 97 $X_3$ G F Y W | 98 $X_4$ S N T L | 99 $X_5$ Y N G I G Y A | 100 $X_6$ W V P G M — — | 100a $X_7$ F G A Y S — — | 100b $X_8$ — D W A R | 100c $X_9$ — M F G | 100d $X_{10}$ — A | 100e $X_{11}$ — M | 101 $X_{12}$ D T A S G | 102 $X_{13}$ Y |

TABLE 7a -continued

Consensus PRLR CDR affinity ligands based on murine antibodies (alternative residues are listed below each amino acid position; — indicates residue may be absent).

| CDR region | Sequence Identifier | | | | | | | | | | | | | | | | |
|---|---|---|---|---|---|---|---|---|---|---|---|---|---|---|---|---|---|
| | | | | | | | | Consensus Sequence | | | | | | | | | |
| CDR-L1 | SEQ ID NO.: 100 | 24 $X_1$ R K S | 25 $X_2$ A S | 26 $X_3$ S | 27 $X_4$ Q E S | 27a $X_5$ — S R | 27b $X_6$ — L I | 27c $X_7$ — V | 27d $X_8$ — H | 27e $X_9$ — S | 28 $X_{10}$ N Y — S | 29 $X_{11}$ G I V V | 30 $X_{12}$ N Y G | 31 $X_{13}$ T S | 32 $X_{14}$ Y A | 33 $X_{15}$ L V M | 34 $X_{16}$ H A T E |
| CDR-L2 | SEQ ID NO.: 101 | 50 $X_1$ K N S L | 51 $X_2$ A V T | 52 $X_3$ S K | 53 $X_4$ N T | 54 $X_5$ R L | 55 $X_6$ F A Y | 56 $X_7$ S E T S | | | | | | | | | |
| CDR-L3 | SEQ ID NO.: 102 | 89 $X_1$ Q S F | 90 $X_2$ Q H | 91 $X_3$ S H G Y W | 92 $X_4$ S T Y | 93 $X_5$ H S A G V | 94 $X_6$ V T Y | 95 $X_7$ P | 95a $X_8$ — P | 96 $X_9$ F W L | 97 $X_{10}$ T | | | | | | |

Note:
Except for CDR-H1, the CDR and residue position are defined by Kabat et al (1991) Sequences of Proteins of Immunological Interest, Fifth Edition. NIH Publication No. 91-3242. For CDR-H1 residues 26 to 30 are included.

TABLE 7b

Consensus PRLR CDR affinity ligands based on murine and humanized antibodies (alternative residues are listed below each amino acid position; — indicates residue may be absent).

| CDR region | Sequence Identifier | | | | | | | | | | | | | | | | | |
|---|---|---|---|---|---|---|---|---|---|---|---|---|---|---|---|---|---|---|
| | | | | | | | | | Consensus Sequence | | | | | | | | | |
| CDR-H1 | SEQ ID NO.: 151 | 26 $X_1$ G | 27 $X_2$ Y F G | 28 $X_3$ T S | 29 $X_4$ F I | 30 $X_5$ T S D | 31 $X_6$ S D | 32 $X_7$ Y F T D | 33 $X_8$ W N D Y | 34 $X_9$ M I Y A | 35 $X_{10}$ H F W | 35a $X_{11}$ — N | | | | | | | |
| CDR-H2 | SEQ ID NO.: 152 | 50 $X_1$ Y V E | 51 $X_2$ I F | 52 $X_3$ D Y S G | 52a $X_4$ P N — | 53 $X_5$ S Y Y N G | 54 $X_6$ D N G D T | 55 $X_7$ G S S | 56 $X_8$ Y G H S R | 57 $X_9$ T S A | 58 $X_{10}$ N N G Y S | 59 $X_{11}$ Y F | 60 $X_{12}$ N P A P | 61 $X_{13}$ Q D P | 62 $X_{14}$ K E T S | 63 $X_{15}$ F L V | 64 $X_{16}$ K Q | 65 $X_{17}$ G S D N | |
| CDR-H3 | SEQ ID NO.: 99 | 95 $X_1$ G S N Q | 96 $X_2$ D F G L | 97 $X_3$ G F Y W | 98 $X_4$ S N T L G Y A | 99 $X_5$ Y N G I G Y A | 100 $X_6$ W V P G M Y — | 100a $X_7$ F G A Y S — | 100b $X_8$ — D M W A R | 100c $X_9$ — M F A G | 100d $X_{10}$ — A | 100e $X_{11}$ — M | 101 $X_{12}$ D T A S G | 102 $X_{13}$ Y | | | | | | |
| CDR-L1 | SEQ ID NO.: 100 | 24 $X_1$ R K S | 25 $X_2$ A S | 26 $X_3$ S | 27 $X_4$ Q E S | 27a $X_5$ — S R | 27b $X_6$ — L I | 27c $X_7$ — V | 27d $X_8$ — H | 27e $X_9$ — S | 28 $X_{10}$ N Y — S | 29 $X_{11}$ G I V V | 30 $X_{12}$ N Y G | 31 $X_{13}$ T S | 32 $X_{14}$ Y A | 33 $X_{15}$ L V M | 34 $X_{16}$ H A T E | | |
| CDR-L2 | SEQ ID NO.: 101 | 50 $X_1$ K N S L | 51 $X_2$ A V T | 52 $X_3$ S K | 53 $X_4$ N T | 54 $X_5$ R L | 55 $X_6$ F A Y | 56 $X_7$ S E T S | | | | | | | | | | | |

TABLE 7b -continued

Consensus PRLR CDR affinity ligands based on murine and humanized antibodies (alternative residues are listed below each amino acid position; — indicates residue may be absent).

| CDR region | Sequence Identifier | Consensus Sequence |
|---|---|---|
| CDR-L3 | SEQ ID NO.: 102 | 89 90 91 92 93 94 95 95a 96 97<br>$X_1$ $X_2$ $X_3$ $X_4$ $X_5$ $X_6$ $X_7$ $X_8$ $X_9$ $X_{10}$<br>Q Q S S H V P — F T<br>S H H T S T    P W<br>F    G Y A Y      L<br>     Y    G<br>     W    V |

Note:
Except for CDR-H1, the CDR and residue position are defined by Kabat et al (1991) Sequences of Proteins of Immunological Interest, Fifth Edition. NIH Publication No. 91-3242. For CDR-H1 residues 26 to 30 are included.

2. Anti PRLR Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454, each of which are incorporated herein by reference in their entireties) by splicing genes from a mouse antibody molecule of appropriate antigen specificity together with genes from a human antibody molecule of appropriate biological activity can be used.

In a specific embodiment, the chimeric antibody of the invention comprises a heavy chain variable region ($V_H$) comprising the amino acid sequence of SEQ ID NO: 112; SEQ ID NO: 113; SEQ ID NO: 114; SEQ ID NO: 115; SEQ ID NO: 116; SEQ ID NO: 117; SEQ ID NO: 118; SEQ ID NO:119 or SEQ ID NO:120 and a light chain variable region ($V_L$) comprising the amino acid sequence of SEQ ID NO: 103; SEQ ID NO: 104; SEQ ID NO: 105, SEQ ID NO: 106, SEQ ID NO: 107; SEQ ID NO: 108; SEQ ID NO: 109; SEQ ID NO: 110 or SEQ ID NO: 111 set forth in Table 8 below.

TABLE 8

Murine Anti-PRLR Antibody Variable Chain Sequences

| Protein Region | Sequence Identifier | Variable Sequence |
|---|---|---|
| Ab5 Variable Light Chain | SEQ ID NO.: 103 | DVVMTQTPLSLPVSLGDQASTSCRSSQ RLVHSNGNTYLHWYLQKPGQSPKLLIY KVSNRFSGVPDRFSGSGSGTDFTLKIS RVEAEDLGVYFCSQSTHVPWTFGGGTK LEIK |
| Ab6 Variable Light Chain | SEQ ID NO.: 104 | DIVMTQSQKFMSTTVGDRVSITCKASQ YVGTAVAWYQQKPGQSPKLLIYSASNR YTGVPDRFTDSGSGTDFTLTISNLQSE DLADYFCQQYSSYPWTFGGGTKLEIK |
| Ab7 Variable Light Chain | SEQ ID NO.: 105 | DVVMTQTPLSLPVSLGDQASTSCRSSQ SLVHSNGNTYLHWYLQKPGQSPKLLIY KVSNRFSGVPDRFSGSGSGTDFTLKIN RVEAEDLGVYFCSQSTHVPFTFGSGTK LEIK |
| Ab8 Variable Light Chain | SEQ ID NO.: 106 | DIQMTQSPASLSASVGETVTITCRASE NIYSYLAWYQQKQGKPPQLLVYNAKTL AEGVPSRFSGGGSGTQFSLKINSLQPE DFGSYYCQHHYATPFTFGSGTKLEIK |
| Ab9 Variable Light Chain | SEQ ID NO.: 107 | DIQMTQSPASLSASVGETVTITCRASE NIYSYLAWYQQKQGKSPQLLVYNAKTL AEGVPSRFSGSGSGTQFSLKINSLQPE DFGSYYCQHHSGTPFTFGSGTKLEIK |
| Ab10 Variable Light Chain | SEQ ID NO.: 108 | DIQMTQSPASLSASVGETVTITCRASE NIYSYLTWYQQKQGKSPQLLVYNAKTL AEGVPSRFSGSGSGTQFSLKINSLQPE DFGSYHCQHHSVTPLTFGAGTKLELK |
| Ab11 Variable Light Chain | SEQ ID NO.: 109 | DVLMTQTPLSLPVSLGDQASTSCRSSQ SIVHSNGNTYLEWYLQKPGQSPKLLIY KVSNRFSGVPDRFSGSGSGTDFTLKIS RVEAEDLGVYYCFQGSHVPFTFGSGTK LEIK |
| Ab12 Variable Light Chain | SEQ ID NO.: 110 | QIVLTQSPGIMSASPGEKVTMTCSASS SVTYMYWYQQKPRSSPKPWIYLTSNLA SGVPARFSGSGSGTSYSLTISSMEAED GATYYCQQWSSTPPLTFGGGTKLELN |
| Ab13 Variable Light Chain | SEQ ID NO.: 111 | DVVMTQTPFSLPVSLGDQASTSCRSSQ SLVHSNGNTYLHWYLQKPGQSPKLLIY KVSNRFSGVPDRFSGSGSGTDFTLKIS RVEAEDLELYFCSQSTHVPWTFGGGTK LEIK |
| Ab5 Variable Heavy Chain | SEQ ID NO.: 112 | QVQLQQPGAELVRPGTSVKLSCKASGY TFTSFWMHWVKQRPGQGLEWIGVIDPS DTYTNYNQKFKGKATLTVDTSSSTAYM QLSSLTSEDSAVYYCARGDYSNWFTYW GQGTLVTVSA |
| Ab6 Variable Heavy Chain | SEQ ID NO.: 113 | QVQLQQPGAELVMPGSSVKLSCKASGY TFTTYWMHWVKQRPGQGLEWIGEIDPS DSYSNYNQKFKDKATLTVDKSSSTAYM QLSSLTSEDSAVYYCARNGGLGPAWFS YWGQGTLVTVSA |

TABLE 8 -continued

Murine Anti-PRLR Antibody Variable Chain Sequences

| Protein Region | Sequence Identifier | Variable Sequence |
|---|---|---|
| Ab7 Variable Heavy Chain | SEQ ID NO.: 114 | QVQLQQPGAELVMPGTSVKLSCKASGY TFTSYWIHWVKQRPGQGLEWIGEIDPS DSYTNYNQKFKGKATLTVDRSSSTAYM QLSSLTSEDSAVYYCGRSFFTNWFAYW GQGTLVTVSA |
| Ab8 Variable Heavy Chain | SEQ ID NO.: 115 | EVQLQQSGPELVKPGASVKISCKASGY TFTDYNIHWVKQSHGKSLEWIGYIYPN NDGTGYNQKFKSKATLTVDNSSSTAYM EVRSLTSEDSAVYYCARGDGNYVGDMD YWGQGTSVTVSS |
| Ab9 Variable Heavy Chain | SEQ ID NO.: 116 | EVQLQQSGPELVRPGASVKISCKASGY SFTDYNMHWVKQSHGKSLEWIGYIYPY NGGAGYNQKFKSKATMNVGISSSTAYM ELRSLTSEDSAVYYCARGDGNYVGDMD YWGQGTSVTVSS |
| Ab10 Variable Heavy Chain | SEQ ID NO.: 117 | EVQLHQSGPELVKPGASVKISCKASGY TFTDYNMHWMKQSHGKSLEWIGYFYPY NGGTGYNQEFKNKATLTVDISSSTAYM ELRRLTSEDSAVYYCARGGWGIYYAMD YWGQGTSVTVSS |
| Ab11 Variable Heavy Chain | SEQ ID NO.: 118 | EVKLVESGGGLVQPGGSLKLSCAASGF TFSDYYMFWVRQTPEKSLEWVAYISNG GGSTYYPDTVKGRFTISRDNAKNTLYL QMSRLKSEDTAMYYCSRQLFYYGSRGA MGYWGQGTSVTVSS |
| Ab12 Variable Heavy Chain | SEQ ID NO.: 119 | DVQLQESGPGLVKPSQSLSLTCTVTGY SITSDYAWNWIRQFPGNKLEWMGYTGY SGRTSFNPSLKSRISITRDTSKNQFFL QLNSVTTEDTATYYCARGGFAMDYWGQ GTSVTVSS |
| Ab13 Variable Heavy Chain | SEQ ID NO.: 120 | QVQLQQPGAELVRPGTSVKLSCKASGY TFTSFWMHWVKQRPGQGLEWIGVIDPS DSHTNYNQKFKGKATLTVNTSSSTAYM HLSSLTSEDSAVYYCARGDYSNWFTYW GQGTLVTVSA |

An alignment of the variable heavy chain amino acid sequences for murine antibodies Ab5, Ab6, Ab7, Ab8, Ab9, Ab10, Ab11, Ab12, and Ab13 is shown in FIGS. 1 and 3. An alignment of the variable light chain amino acid sequences for murine antibodies Ab5, Ab6, Ab7, Ab8, Ab9, Ab10, Ab11, Ab12, and Ab13 is shown in FIGS. 2 and 4.

As used herein, the term "Ab5" refers to an antibody comprising the variable heavy chain amino acid sequence set forth in SEQ ID NO:112 and the variable light chain amino acid sequence set forth in SEQ ID NO:103. As used herein, the term "chAb5" refers to a chimeric antibody comprising the variable heavy chain amino acid sequence set forth in SEQ ID NO:112, the constant heavy chain amino acid sequence set forth in SEQ ID NO: 10, the variable light chain amino acid sequence set forth in SEQ ID NO:103 and the constant light chain amino acid sequence set forth in SEQ ID NO: 12.

As used herein, the term "Ab6" refers to an antibody comprising the variable heavy chain amino acid sequence set forth in SEQ ID NO:113 and the variable light chain amino acid sequence set forth in SEQ ID NO:104. As used herein, the term "chAb6" refers to a chimeric antibody comprising the variable heavy chain amino acid sequence set forth in SEQ ID NO:113, the constant heavy chain amino acid sequence set forth in SEQ ID NO: 10, the variable light chain amino acid sequence set forth in SEQ ID NO:104 and the constant light chain amino acid sequence set forth in SEQ ID NO: 12.

As used herein, the term "Ab7" refers to an antibody comprising the variable heavy chain amino acid sequence set forth in SEQ ID NO:114 and the variable light chain amino acid sequence set forth in SEQ ID NO:105. As used herein, the term "chAb7" refers to a chimeric antibody comprising the variable heavy chain amino acid sequence set forth in SEQ ID NO:114, the constant heavy chain amino acid sequence set forth in SEQ ID NO: 10, the variable light chain amino acid sequence set forth in SEQ ID NO:105 and the constant light chain amino acid sequence set forth in SEQ ID NO: 12.

As used herein, the term "Ab8" refers to an antibody comprising the variable heavy chain amino acid sequence set forth in SEQ ID NO:115 and the variable light chain amino acid sequence set forth in SEQ ID NO:106. As used herein, the term "chAb8" refers to a chimeric antibody comprising the variable heavy chain amino acid sequence set forth in SEQ ID NO:115, the constant heavy chain amino acid sequence set forth in SEQ ID NO: 10, the variable light chain amino acid sequence set forth in SEQ ID NO:106 and the constant light chain amino acid sequence set forth in SEQ ID NO: 12.

As used herein, the term "Ab9" refers to an antibody comprising the variable heavy chain amino acid sequence set forth in SEQ ID NO:116 and the variable light chain amino acid sequence set forth in SEQ ID NO:107. As used herein, the term "chAb9" refers to a chimeric antibody comprising the variable heavy chain amino acid sequence set forth in SEQ ID NO:116, the constant heavy chain amino acid sequence set forth in SEQ ID NO: 10, the variable light chain amino acid sequence set forth in SEQ ID NO:107 and the constant light chain amino acid sequence set forth in SEQ ID NO: 12.

As used herein, the term "Ab10" refers to an antibody comprising the variable heavy chain amino acid sequence set forth in SEQ ID NO:117 and the variable light chain amino acid sequence set forth in SEQ ID NO:108. As used herein, the term "chAb10" refers to a chimeric antibody comprising the variable heavy chain amino acid sequence set forth in SEQ ID NO:117, the constant heavy chain amino acid sequence set forth in SEQ ID NO: 10, the variable light chain amino acid sequence set forth in SEQ ID NO:108 and the constant light chain amino acid sequence set forth in SEQ ID NO: 12.

As used herein, the term "Ab11" refers to an antibody comprising the variable heavy chain amino acid sequence set forth in SEQ ID NO:118 and the variable light chain amino acid sequence set forth in SEQ ID NO:109. As used herein, the term "chAb11" refers to a chimeric antibody comprising the variable heavy chain amino acid sequence set forth in SEQ ID NO:118, the constant heavy chain amino acid sequence set forth in SEQ ID NO: 10, the variable light chain amino acid sequence set forth in SEQ ID NO:109 and the constant light chain amino acid sequence set forth in SEQ ID NO: 12.

As used herein, the term "Ab12" refers to an antibody comprising the variable heavy chain amino acid sequence set forth in SEQ ID NO:119 and the variable light chain amino acid sequence set forth in SEQ ID NO:110. As used herein, the term "chAb12" refers to a chimeric antibody comprising the variable heavy chain amino acid sequence set forth in SEQ ID NO:119, the constant heavy chain amino acid sequence set forth in SEQ ID NO: 10, the variable light chain amino acid sequence set forth in SEQ ID NO:110 and the constant light chain amino acid sequence set forth in SEQ ID NO: 12.

As used herein, the term "Ab13" refers to an antibody comprising the variable heavy chain amino acid sequence set forth in SEQ ID NO:120 and the variable light chain amino acid sequence set forth in SEQ ID NO:111. As used herein, the term "chAb13" refers to a chimeric antibody comprising the variable heavy chain amino acid sequence set forth in SEQ ID NO:120, the constant heavy chain amino acid sequence set forth in SEQ ID NO: 10, the variable light chain amino acid sequence set forth in SEQ ID NO:111 and the constant light chain amino acid sequence set forth in SEQ ID NO: 12.

3. Generation of Anti-PRLR Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource.com/onlinecomp.html; www.public.iastate.edu/.about.pedro/research_tools.html; www.mgen.uni-heidelberg.de/SD/IT/IT.html; www.whfreeman.com/immunology/CH-05/kuby05.htm; www.library.thinkquest.org/12429/Immune/Antibody.html; www hhmi.org/grants/lectures/1996/vlab/; www.path.cam.ac.uk/.about.mrc7/m-ikeimages.html; www.antibodyresource.com/; mcb.harvard.edu/BioLinks/Immunology.html.www.immunologylink.com/; pathbox.wustl.edu/.about.hcenter/index.-html; www.biotech.ufl.edu/.about.hcl/; www.pebio.com/pa/340913/340913.html-; www.nal.usda.gov/awic/pubs/antibody/; www.m.ehime-u.acjp/.about.yasuhito-/Elisa.html; www.biodesign.com/table.asp; www.icnet.uk/axp/facs/davies/lin-ks.html; www.biotech.ufl.edu/.about.fccl/protocol.html; www.isac-net.org/sites_geo.html; aximtl imt.uni-marburg.de/.about.rek/AEP-Start.html; baserv.uci.kun.nl/.about.jraats/linksl.html; www.recab.uni-hd.de/immuno.bme.nwu.edu/; www.mrc-cpe.cam.ac.uk/imt-doc/pu-blic/INTRO.html; www.ibt.unam.mx/vir/V_mice.html; imgt.cnusc.fr:8104/; www.biochem.ucl.ac.uk/.about.martin/abs/index.html; antibody.bath.ac.uk/; abgen.cvm.tamu.edu/lab/wwwabgen.html; www.unizh ch/.about.honegger/AHOsem-inar/ Slide01.html; www.cryst.bbk.ac.uld.aboutubcg07s/; www.nimr mrc.ac.uk/CC/ccaewg/ccaewg.htm; www.path.cam.ac.uk/.about.mrc7/h-umanisation/TAHHP.html; www.ibt.unam.mx/vir/structure/stat_aim.html; www.biosci missouri.edu/smithgp/index.html; www.cryst.bioc.cam.ac.uk/.abo-ut.fmolina/Web-pages/Pept/spottech.html; www.jerini.de/fr roducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

Examples of anti-PRLR humanized antibodies are provided in Section 1 above.

4. Additional Competing Antibodies

The term "competing antibodies" herein refers to any number of antibodies targeting the same molecular or stably but non-covalently linked supermolecular entity, preferably the same molecule, i.e., PRLR, wherein at least one is capable of specifically reducing the measurable binding of another, preferably by sterically hampering the other's access to its target epitope or by inducing and/or stabilizing a conformation in the target entity that reduces the target's affinity for the other antibody, more preferably by directly blocking access to the other's target epitope by binding to an epitope in sufficiently close vicinity of the former, overlapping with the former or identical to the former, most preferably overlapping or identical, in particular identical. Two epitopes are herein said to be "overlapping" if they share part of their chemical structures, preferably their amino acid sequences, and to be "identical", if their chemical structures, preferably their amino acid sequences, are identical.

In particular embodiments, the competing antibody, or antigen binding portion thereof, is an antibody, or antigen binding portion thereof, that competes with Ab1, Ab2, Ab3, Ab4, Ab5, chAb5, Ab6, chAb6, Ab7, chAb7, Ab8, chAb8, Ab9, chAb9, Ab10, chAb10, Ab11, chAb11, Ab12, chAb12, Ab13, chAb13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 or Ab55. In various embodiments, the binding may be assayed according to the protocol set forth in Example 4.

In one embodiment, the invention is directed to an antibody that competes with Ab1, i.e., comprising (i) one variable heavy chain having an amino acid sequence selected from the group consisting of SEQ ID NO: 39; SEQ ID NO: 43; SEQ ID NO: 44 and SEQ ID NO: 45; and (ii) one variable light chain having an amino acid sequence selected from the group consisting of SEQ ID NO:48, SEQ ID NO:52, SEQ ID NO: 53 and SEQ ID NO:54.

In another embodiment, the invention is directed to an antibody that competes with Ab2, i.e., comprising (i) one variable heavy chain having an amino acid sequence selected from the group consisting of SEQ ID NO: 55; SEQ ID NO: 59; SEQ ID NO: 60 and SEQ ID NO: 61; and (ii) one variable light chain having an amino acid sequence selected from the group consisting of SEQ ID NO:64, SEQ ID NO:68 and SEQ ID NO: 69.

In another embodiment, the invention is directed to an antibody that competes with Ab3, i.e., comprising (i) one variable heavy chain having an amino acid sequence selected from the group consisting of SEQ ID NO: 70; SEQ ID NO: 74; SEQ ID NO: 75 and SEQ ID NO: 76; and (ii) one variable light chain having an amino acid sequence selected from the group consisting of SEQ ID NO:78, SEQ ID NO:82 and SEQ ID NO: 83.

In another embodiment, the invention is directed to an antibody that competes with Ab4, i.e., comprising (i) one variable heavy chain having an amino acid sequence selected from the group consisting of SEQ ID NO: 84; SEQ ID NO: 88; SEQ ID NO: 89, SEQ ID NO: 90, SEQ ID NO:121, SEQ ID NO:122 and SEQ ID NO:123; and (ii) one variable light chain having an amino acid sequence selected from the group consisting of SEQ ID NO:91, SEQ ID NO:95 and SEQ ID NO:96.

In another embodiment, the invention is directed to an antibody that competes with Ab5, i.e., comprising the variable heavy chain amino acid sequence set forth in SEQ ID NO:112 and the variable light chain amino acid sequence set forth in SEQ ID NO:103.

In another embodiment, the invention is directed to an antibody that competes with Ab6, i.e., the variable heavy chain amino acid sequence set forth in SEQ ID NO:113 and the variable light chain amino acid sequence set forth in SEQ ID NO:104.

In another embodiment, the invention is directed to an antibody that competes with Ab7, i.e., comprising the variable heavy chain amino acid sequence set forth in SEQ ID NO:114 and the variable light chain amino acid sequence set forth in SEQ ID NO:105.

In another embodiment, the invention is directed to an antibody that competes with Ab8, i.e., comprising the variable heavy chain amino acid sequence set forth in SEQ ID NO:115 and the variable light chain amino acid sequence set forth in SEQ ID NO:106.

In another embodiment, the invention is directed to an antibody that competes with Ab9, i.e., comprising the variable heavy chain amino acid sequence set forth in SEQ ID NO:116 and the variable light chain amino acid sequence set forth in SEQ ID NO:107.

In another embodiment, the invention is directed to an antibody that competes with Ab10, i.e., comprising the variable heavy chain amino acid sequence set forth in SEQ ID NO:117 and the variable light chain amino acid sequence set forth in SEQ ID NO:108.

In another embodiment, the invention is directed to an antibody that competes with Ab11, i.e., comprising the variable heavy chain amino acid sequence set forth in SEQ ID NO:118 and the variable light chain amino acid sequence set forth in SEQ ID NO:109.

In another embodiment, the invention is directed to an antibody that competes with Ab12, i.e., comprising the variable heavy chain amino acid sequence set forth in SEQ ID NO:119 and the variable light chain amino acid sequence set forth in SEQ ID NO:110.

In another embodiment, the invention is directed to an antibody that competes with Ab13, i.e., comprising the variable heavy chain amino acid sequence set forth in SEQ ID NO:120 and the variable light chain amino acid sequence set forth in SEQ ID NO:111.

In another embodiment, the invention is directed to an antibody that competes with Ab14, i.e., comprising a heavy chain having the amino acid sequence of SEQ ID NO: 124; and a light chain having the amino acid sequence of SEQ ID NO: 125.

In another embodiment, the invention is directed to an antibody that competes with Ab15, i.e., comprising a heavy chain having the amino acid sequence of SEQ ID NO: 124; and a light chain having the amino acid sequence of SEQ ID NO: 126.

In another embodiment, the invention is directed to an antibody that competes with Ab16, i.e., comprising a heavy chain having the amino acid sequence of SEQ ID NO: 124; and a light chain having the amino acid sequence of SEQ ID NO: 127.

In another embodiment, the invention is directed to an antibody that competes with Ab17, i.e., comprising a heavy chain having the amino acid sequence of SEQ ID NO: 124; and a light chain having the amino acid sequence of SEQ ID NO: 128.

In another embodiment, the invention is directed to an antibody that competes with Ab18, i.e., comprising a heavy chain having the amino acid sequence of SEQ ID NO: 129; and a light chain having the amino acid sequence of SEQ ID NO: 125.

In another embodiment, the invention is directed to an antibody that competes with Ab19, i.e., comprising a heavy chain having the amino acid sequence of SEQ ID NO: 129; and a light chain having the amino acid sequence of SEQ ID NO: 126.

In another embodiment, the invention is directed to an antibody that competes with Ab20, i.e., comprising a heavy chain having the amino acid sequence of SEQ ID NO: 129; and a light chain having the amino acid sequence of SEQ ID NO: 127.

In another embodiment, the invention is directed to an antibody that competes with Ab21, i.e., comprising a heavy chain having the amino acid sequence of SEQ ID NO: 129; and a light chain having the amino acid sequence of SEQ ID NO: 128.

In another embodiment, the invention is directed to an antibody that competes with Ab22, i.e., comprising a heavy chain having the amino acid sequence of SEQ ID NO: 130; and a light chain having the amino acid sequence of SEQ ID NO: 125.

In another embodiment, the invention is directed to an antibody that competes with Ab23, i.e., comprising a heavy chain having the amino acid sequence of SEQ ID NO: 130; and a light chain having the amino acid sequence of SEQ ID NO: 126.

In another embodiment, the invention is directed to an antibody that competes with Ab24, i.e., comprising a heavy chain having the amino acid sequence of SEQ ID NO: 130; and a light chain having the amino acid sequence of SEQ ID NO: 127.

In another embodiment, the invention is directed to an antibody that competes with Ab25, i.e., comprising a heavy chain having the amino acid sequence of SEQ ID NO: 130; and a light chain having the amino acid sequence of SEQ ID NO: 128.

In another embodiment, the invention is directed to an antibody that competes with Ab26, i.e., comprising a heavy chain having the amino acid sequence of SEQ ID NO: 131; and a light chain having the amino acid sequence of SEQ ID NO: 132.

In another embodiment, the invention is directed to an antibody that competes with Ab27, i.e., comprising a heavy chain having the amino acid sequence of SEQ ID NO: 131; and a light chain having the amino acid sequence of SEQ ID NO: 133.

In another embodiment, the invention is directed to an antibody that competes with Ab28, i.e., comprising a heavy chain having the amino acid sequence of SEQ ID NO: 131; and a light chain having the amino acid sequence of SEQ ID NO: 134.

In another embodiment, the invention is directed to an antibody that competes with Ab29, i.e., comprising a heavy chain having the amino acid sequence of SEQ ID NO: 135; and a light chain having the amino acid sequence of SEQ ID NO: 132.

In another embodiment, the invention is directed to an antibody that competes with Ab30, i.e., comprising a heavy chain having the amino acid sequence of SEQ ID NO: 135; and a light chain having the amino acid sequence of SEQ ID NO: 133.

In another embodiment, the invention is directed to an antibody that competes with Ab31, i.e., comprising a heavy chain having the amino acid sequence of SEQ ID NO: 135; and a light chain having the amino acid sequence of SEQ ID NO: 134.

In another embodiment, the invention is directed to an antibody that competes with Ab32, i.e., comprising a heavy chain having the amino acid sequence of SEQ ID NO: 136; and a light chain having the amino acid sequence of SEQ ID NO: 132.

In another embodiment, the invention is directed to an antibody that competes with Ab33, i.e., comprising a heavy chain having the amino acid sequence of SEQ ID NO: 136; and a light chain having the amino acid sequence of SEQ ID NO: 133.

In another embodiment, the invention is directed to an antibody that competes with Ab34, i.e., comprising a heavy chain having the amino acid sequence of SEQ ID NO: 136; and a light chain having the amino acid sequence of SEQ ID NO: 134.

In another embodiment, the invention is directed to an antibody that competes with Ab35, i.e., comprising a heavy chain having the amino acid sequence of SEQ ID NO: 137; and a light chain having the amino acid sequence of SEQ ID NO: 138.

In another embodiment, the invention is directed to an antibody that competes with Ab36, i.e., comprising a heavy chain having the amino acid sequence of SEQ ID NO: 137; and a light chain having the amino acid sequence of SEQ ID NO: 139.

In another embodiment, the invention is directed to an antibody that competes with Ab37, i.e., comprising a heavy chain having the amino acid sequence of SEQ ID NO: 137; and a light chain having the amino acid sequence of SEQ ID NO: 140.

In another embodiment, the invention is directed to an antibody that competes with Ab38, i.e., comprising a heavy chain having the amino acid sequence of SEQ ID NO: 141; and a light chain having the amino acid sequence of SEQ ID NO: 138.

In another embodiment, the invention is directed to an antibody that competes with Ab39, i.e., comprising a heavy chain having the amino acid sequence of SEQ ID NO: 141; and a light chain having the amino acid sequence of SEQ ID NO: 139.

In another embodiment, the invention is directed to an antibody that competes with Ab40, i.e., comprising a heavy chain having the amino acid sequence of SEQ ID NO: 141; and a light chain having the amino acid sequence of SEQ ID NO: 140.

In another embodiment, the invention is directed to an antibody that competes with Ab41, i.e., comprising a heavy chain having the amino acid sequence of SEQ ID NO: 142; and a light chain having the amino acid sequence of SEQ ID NO: 138.

In another embodiment, the invention is directed to an antibody that competes with Ab42, i.e., comprising a heavy chain having the amino acid sequence of SEQ ID NO: 142; and a light chain having the amino acid sequence of SEQ ID NO: 139.

In another embodiment, the invention is directed to an antibody that competes with Ab43, i.e., comprising a heavy chain having the amino acid sequence of SEQ ID NO: 142; and a light chain having the amino acid sequence of SEQ ID NO: 140.

In another embodiment, the invention is directed to an antibody that competes with Ab44, i.e., comprising a heavy chain having the amino acid sequence of SEQ ID NO: 143; and a light chain having the amino acid sequence of SEQ ID NO: 144.

In another embodiment, the invention is directed to an antibody that competes with Ab45, i.e., comprising a heavy chain having the amino acid sequence of SEQ ID NO: 143; and a light chain having the amino acid sequence of SEQ ID NO: 145.

In another embodiment, the invention is directed to an antibody that competes with Ab46, i.e., comprising a heavy chain having the amino acid sequence of SEQ ID NO: 143; and a light chain having the amino acid sequence of SEQ ID NO: 146.

In another embodiment, the invention is directed to an antibody that competes with Ab47, i.e., comprising a heavy chain having the amino acid sequence of SEQ ID NO: 147; and a light chain having the amino acid sequence of SEQ ID NO: 144.

In another embodiment, the invention is directed to an antibody that competes with Ab48, i.e., comprising a heavy chain having the amino acid sequence of SEQ ID NO: 147; and a light chain having the amino acid sequence of SEQ ID NO: 145.

In another embodiment, the invention is directed to an antibody that competes with Ab49, i.e., comprising a heavy chain having the amino acid sequence of SEQ ID NO: 147; and a light chain having the amino acid sequence of SEQ ID NO: 146.

In another embodiment, the invention is directed to an antibody that competes with Ab50, i.e., comprising a heavy chain having the amino acid sequence of SEQ ID NO: 148; and a light chain having the amino acid sequence of SEQ ID NO: 144.

In another embodiment, the invention is directed to an antibody that competes with Ab51, i.e., comprising a heavy chain having the amino acid sequence of SEQ ID NO: 148; and a light chain having the amino acid sequence of SEQ ID NO: 145.

In another embodiment, the invention is directed to an antibody that competes with Ab52, i.e., comprising a heavy chain having the amino acid sequence of SEQ ID NO: 148; and a light chain having the amino acid sequence of SEQ ID NO: 146.

In another embodiment, the invention is directed to an antibody that competes with Ab53, i.e., comprising a heavy chain having the amino acid sequence of SEQ ID NO: 153; and a light chain having the amino acid sequence of SEQ ID NO: 139.

In another embodiment, the invention is directed to an antibody that competes with Ab54, i.e., comprising a heavy chain having the amino acid sequence of SEQ ID NO: 154; and a light chain having the amino acid sequence of SEQ ID NO: 139.

In another embodiment, the invention is directed to an antibody that competes with Ab55, i.e., comprising a heavy chain having the amino acid sequence of SEQ ID NO: 155; and a light chain having the amino acid sequence of SEQ ID NO: 139.

In a particular embodiment, the present invention is directed to a binding protein, e.g., antibody, that competes with an antibody comprising a heavy chain variable domain and a light chain variable domain selected from the group consisting of:

(1) a variable heavy chain having an amino acid sequence selected from the group consisting of SEQ ID NO: 39; SEQ ID NO: 43; SEQ ID NO: 44 and SEQ ID NO: 45; and a variable light chain having an amino acid sequence selected from the group consisting of SEQ ID NO:48, SEQ ID NO:52, SEQ ID NO: 53 and SEQ ID NO:54;

(2) a variable heavy chain having an amino acid sequence selected from the group consisting of SEQ ID NO: 55; SEQ ID NO: 59; SEQ ID NO: 60 and SEQ ID NO: 61; and a variable light chain having an amino acid sequence selected from the group consisting of SEQ ID NO:64, SEQ ID NO:68 and SEQ ID NO: 69;

(3) a variable heavy chain having an amino acid sequence selected from the group consisting of SEQ ID NO: 84; SEQ ID NO: 88; SEQ ID NO: 89; SEQ ID NO: 90; SEQ ID NO: 121; SEQ ID NO: 122; and SEQ ID NO: 123; and a variable light chain having an amino acid sequence selected from the group consisting of SEQ ID NO:91, SEQ ID NO:95 and SEQ ID NO:96;

(4) the variable heavy chain amino acid sequence set forth in SEQ ID NO:112 and the variable light chain amino acid sequence set forth in SEQ ID NO:103;

(5) the variable heavy chain amino acid sequence set forth in SEQ ID NO:113 and the variable light chain amino acid sequence set forth in SEQ ID NO:104;

(6) the variable heavy chain amino acid sequence set forth in SEQ ID NO:114 and the variable light chain amino acid sequence set forth in SEQ ID NO:105; and (7) the variable heavy chain amino acid sequence set forth in SEQ ID NO:120 and the variable light chain amino acid sequence set forth in SEQ ID NO:111.

In another particular embodiment, the present invention is directed to a binding protein, e.g., antibody, that competes with an antibody comprising the variable heavy chain amino acid sequence set forth in SEQ ID NO:119 and the variable light chain amino acid sequence set forth in SEQ ID NO:110.

5. PRLR Epitopes

In another aspect, the invention pertains to a binding protein, e.g., antibody, or antigen binding fragment thereof, capable of binding PRLR that binds to an epitope in PRLR comprising three, four, five, six, seven, eight, nine or all of the amino acid residues E8, F10, C12, R25, E43, G44, I76, D91, E92, L93, Y94, V95, D96, Y99, I100, E145, F160, K185, D187, H188, Y190 and W191 of SEQ ID NO:2. In one embodiment, the binding protein, e.g., antibody, or antigen binding fragment thereof, capable of binding PRLR, binds to an epitope, wherein the epitope comprises at least five of the amino acid residues. In another embodiment, the binding protein, e.g., antibody, or antigen binding fragment thereof, capable of binding PRLR, binds to an epitope, wherein the epitope comprises all of amino acid residues E8, F10, C12, R25, E43, G44, I76, D91, E92, L93, Y94, V95, D96, Y99, I100, E145, F160, K185, D187, H188, Y190 and W191 of SEQ ID NO:2.

In a particular embodiment, the binding protein that binds to said epitope is an antibody, or antigen binding portion thereof, selected from the group consisting of Ab1, Ab6, chAb6, Ab14, Ab15, Ab16, Ab17, Ab18, Ab19, Ab20, Ab21, Ab22, Ab23, Ab24, and Ab25.

In another aspect, the invention pertains to a binding protein, e.g., antibody, or antigen binding fragment thereof, capable of binding PRLR that binds to an epitope in PRLR comprising three, four, five, six, seven, eight, nine or all of the amino acid residues E8, I9, F10, K11, C12, R25, E43, G44, W72, T74, I76, D91, E92, L93, Y94, V95, D96, T98, Y99, I100, W139, L143, E145, F160, K185, D187, H188, Y190 and W191 of SEQ ID NO:2. In one embodiment, the binding protein, e.g., antibody, or antigen binding fragment thereof, capable of binding PRLR, binds to an epitope, wherein the epitope comprises at least five of the amino acid residues. In another embodiment, the binding protein, e.g., antibody, or antigen binding fragment thereof, capable of binding PRLR, binds to an epitope, wherein the epitope comprises all of amino acid residues E8, I9, F10, K11, C12, R25, E43, G44, W72, T74, I76, D91, E92, L93, Y94, V95, D96, T98, Y99, I100, W139, L143, E145, F160, K185, D187, H188, Y190 and W191 of SEQ ID NO:2.

In a particular embodiment, the binding protein that binds to said epitope is an antibody, or antigen binding portion thereof, selected from the group consisting of Ab4, Ab7, chAb7, Ab35, Ab36, Ab37, Ab38, Ab39, Ab40, Ab41, Ab42, Ab43, Ab53, Ab54 and Ab55. In another embodiment, the binding protein that binds to said epitope is an antibody or antigen binding portion thereof, selected from the group consisting of Ab2, Ab5, chAb5, Ab26, Ab27, Ab28, Ab29, Ab30, Ab31, Ab32, Ab33 and Ab34.

In another aspect, the invention pertains to a binding protein, e.g., antibody, or antigen binding fragment thereof, capable of binding PRLR that binds to an epitope in PRLR comprising 13, 14, 15, 16, 17, 18, 19, 20, 21 or all of the amino acid residues R25, T141, L143, E145, R147, E155, W156, E157, I158, H159, F160, A161, G162, Q163, Q164, F167, S171, R183, K185, D187, H188, W191, and W194 of SEQ ID NO:2. In one embodiment, the binding protein, e.g., antibody, or antigen binding fragment thereof, capable of binding PRLR, binds to an epitope, wherein the epitope comprises at least 15 of the amino acid residues. In some embodiments, the binding protein, e.g., antibody, or antigen binding fragment thereof, capable of binding PRLR, binds to an epitope, wherein the epitope comprises all of amino acid residues R25, T141, L143, E145, R147, E155, W156, E157, I158, H159, F160, A161, G162, Q163, Q164, F167, S171, R183, K185, D187, H188, W191, and W194 of SEQ ID NO:2.

In a particular embodiment, the binding protein that binds to said epitope is an antibody, or antigen binding portion thereof, selected from the group consisting of Ab3, Ab8, Ab44, Ab45, Ab46, Ab47, Ab48, Ab49, Ab50, Ab51 and Ab52.

In another aspect, the invention pertains to a binding protein, e.g., antibody, or antigen binding fragment thereof, capable of binding PRLR that binds to an epitope in PRLR comprising at least one, two, three, four or all of the amino acid residues R25, K185, D187, H188 or W191 of SEQ ID NO:2. In some embodiments, the binding protein, e.g., antibody, or antigen binding fragment thereof, capable of binding PRLR, binds to an epitope, wherein the epitope comprises all of amino acid residues R25, K185, D187, H188 or W191 of SEQ ID NO:2.

In a particular embodiment, the binding protein that binds to said epitope is an antibody, or antigen binding portion thereof, selected from the group consisting of Ab1, Ab2, Ab3, Ab4, Ab5, chAb5, Ab6, chAb6, Ab7, chAb7, Ab8, chAb8, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 and Ab55.

In another aspect, the invention pertains to a binding protein, e.g., antibody, or antigen binding fragment thereof, capable of binding PRLR that binds to an epitope in PRLR comprising amino acids 91-96 of SEQ ID NO:2.

In a particular embodiment, the binding protein that binds to said epitope is an antibody, or antigen binding portion thereof, selected from the group consisting of Ab1, Ab4, Ab6, Ab7, chAb6, chAb7, Ab14, Ab15, Ab16, Ab17, Ab18, Ab19, Ab20, Ab21, Ab22, Ab23, Ab24, Ab25, Ab35, Ab36, Ab37, Ab38, Ab39, Ab40, Ab41, Ab42, Ab43, Ab53, Ab54 and Ab55. In another embodiment, the binding protein that binds to said epitope is an antibody or antigen binding portion thereof, selected from the group consisting of Ab2, Ab5, chAb5, Ab26, Ab27, Ab28, Ab29, Ab30, Ab31, Ab32, Ab33 and Ab34.

In another aspect, the invention pertains to a binding protein, e.g., antibody, or antigen binding fragment thereof, capable of binding PRLR that binds to an epitope having residues within at least amino acids 8-100, 185-191, 8-143, or 183-194 of SEQ ID NO:2. In a particular embodiment, the binding protein that binds to said epitope is an antibody, or antigen binding portion thereof, selected from the group consisting of Ab1, Ab2, Ab3, Ab4, Ab5, chAb5, Ab6, chAb6, Ab7, chAb7, Ab8, chAb8, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 and Ab55.

In another aspect, the invention pertains to a binding protein, e.g., antibody, or antigen binding fragment thereof, capable of binding PRLR and having the same epitopic specificity as an antibody, or antigen-binding portion thereof, selected from the group consisting of Ab1, Ab2, Ab3, Ab4, Ab5, chAb5, Ab6, chAb6, Ab7, chAb7, Ab8, chAb8, Ab9, chAb9, Ab10, chAb10, Ab11, chAb11, Ab12, chAb12, Ab13, chAb13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 and Ab55.

In various embodiments of the foregoing aspects, the binding protein, e.g., antibody, or antigen binding fragment thereof, is capable of modulating a biological function of PRLR. In other embodiments of the foregoing aspects, the binding protein, e.g., antibody, or antigen binding fragment thereof, is capable of neutralizing PRLR. In other embodiments of the foregoing aspects, the binding protein, e.g., antibody, or antigen binding fragment thereof, binds an epitope of PRLR which does not inhibit dimerization of PRLR. In further embodiments of the foregoing aspects, the binding protein, e.g., antibody, or antigen binding fragment thereof, does not bind the D2 domain of PRLR. In further embodiments of the foregoing aspects, the binding protein, e.g., antibody, or antigen binding fragment thereof, binds the ligand binding region of the D1 domain of PRLR. In additional embodiments of the foregoing aspects, the binding protein, e.g., antibody, or antigen binding fragment thereof, does not compete with antibody LFA102 for binding of PRLR. In additional embodiments of the foregoing aspects, the binding protein, e.g., antibody, or antigen binding fragment thereof, blocks binding of prolactin to PRLR.

C. Production of Antibodies and Antibody-Producing Cell Lines

Preferably, anti-PRLR antibodies of the present invention, exhibit a high capacity to reduce or to neutralize PRLR activity, e.g., as assessed by any one of several in vitro and in vivo assays known in the art. For example, inhibition of phosphorylation of PRLR, pSTAT5 or ERK1/2 in a PRLR expressing cell line, e.g., the human breast carcinoma cell line T47D, can be measured. Alternatively, inhibition of proliferation of PRLR expressing cell lines, e.g., Baf3 pro-B lymphoid cells transfected with human PRLR, or Nb2-11 rat lymphoma cells, can be measured. In preferred embodiments, the isolated antibody, or antigen-binding portion thereof, binds human PRLR, wherein the antibody, or antigen-binding portion thereof, dissociates from human PRLR with a $k_{off}$ rate constant of about $0.1\ s^{-1}$ or less, as determined by surface plasmon resonance, or which inhibits human PRLR activity with an $IC_{50}$ of about $1\times10^{-6}$M or less. Alternatively, the antibody, or an antigen-binding portion thereof, may dissociate from human PRLR with a $k_{off}$ rate constant of about $1\times10^{-2}\ s^{-1}$ or less, as determined by surface plasmon resonance, or may inhibit human PRLR activity with an $IC_{50}$ of about $1\times10^{-7}$M or less. Alternatively, the antibody, or an antigen-binding portion thereof, may dissociate from human PRLR with a $k_{off}$ rate constant of about $1\times10^{-3}\ s^{-1}$ or less, as determined by surface plasmon resonance, or may inhibit human PRLR with an $IC_{50}$ of about $1\times10^{-8}$M or less. Alternatively, the antibody, or an antigen-binding portion thereof, may dissociate from human PRLR with a $k_{off}$ rate constant of about $1\times10^{-4}\ s^{4}$ or less, as determined by surface plasmon resonance, or may inhibit PRLR activity with an $IC_{50}$ of about $1\times10^{-9}$M or less. Alternatively, the antibody, or an antigen-binding portion thereof, may dissociate from human PRLR with a $k_{off}$ rate constant of about $1\times10^{-5}\ s^{-1}$ or less, as determined by surface plasmon resonance, or may inhibit PRLR with an $IC_{50}$ of about $1\times10^{-10}$M or less. Alternatively, the antibody, or an antigen-binding portion thereof, may dissociate from human PRLR with a $k_{off}$ rate constant of about $1\times10^{-5}\ s^{-1}$ or less, as determined by surface plasmon resonance, or may inhibit PRLR activity with an $IC_{50}$ of about $1\times10^{-11}$M or less.

Prolactin binds to PRLR and induces homodimerization. PRLR has no intrinsic kinase activity but is associated with protein kinases such as FYN and JAK2 (Kline, J. B., et al. (1999) *J. Biol. Chem.* 274:35461-35468). Prolactin binding activates signal transducer and activator of transcription-5 (STAT5) through JAK2 and extracellular signal-related kinase-1 and -2 (ERK1 and ERK2) (Huang, Y., et al., (2006) *Oncogene* 25:7565-7576). JAK2 phosphorylated STAT5A and STAT5B form homo- and heterodimers and modulate gene expression affecting cell growth and differentiation (Hennighausen, L., and Robinson, G. W. (2001) *Develop. Cell* 1:467-475). Activation of PRLR by prolactin alone stimulates cell proliferation, and in combination with dexamethasone, stimulates mammary specific gene expression in cell lines, e.g., γ-casein (Sasaki, M., et al. (1996) *Endocrine J.* 43:45-52). Moreover, PRLR has been found to be over-expressed in human breast cancer and prostate cancer tissues (Li et al., *Cancer Res.,* 64:4774-4782, 2004; Gill et al., *J Clin Pathol.,* 54:956-960, 2001; Touraine et al., *J Clin Endocrinol Metab.,* 83:667-674, 1998). Phosphorylation and proliferation assays demonstrated that the antibodies described herein inhibited prolactin mediated phosphorylation and proliferation. For example, as set forth in Example 2 and in Tables 13 and 14, the PRLR antibodies were shown to inhibit phosphorylation of PRLR. In addition, as set forth in Example 2 and in Tables 13 and 14, the PRLR antibodies were shown to inhibit proliferation of PRLR expressing cell lines, e.g., Baf3 pro-B lymphoid cells transfected with human PRLR and Nb2-11 rat lymphoma cells. Moreover, as set forth in Example 3, the PRLR antibodies, in particular, AB5, were shown to reduce tumor growth in in vivo studies. One particular antibody disclosed herein, i.e., Ab12, was shown to exhibit PRLR agonist activity.

The antibodies were humanized as described in Example 1. Framework back-mutations were introduced into the CDR-grafted antibody sequences by de novo synthesis of the variable domain or by mutagenic oligonucleotide primers and polymerase chain reaction, or by both allowing different combinations of back mutations and other mutations for each of the CDR-grafts. The humanized variable regions of the murine monoclonal PRLR antibodies were cloned into IgG expression vectors for functional characterization.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260; 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to one or more functional molecule(s) (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably the invention relates to crystals of whole anti-PRLR antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain.

Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

II. Anti-PRLR Antibody Drug Conjugates (ADCs)

The anti-PRLR antibodies described herein may be conjugated to an agent to form an anti-PRLR Antibody Drug Conjugate (ADC). Antibody-drug conjugates (ADCs) may increase the therapeutic efficacy of antibodies in treating disease, e.g., cancer, due to the ability of the ADC to selectively deliver one or more agent(s) to target tissues, such as a tumor-associated antigen, e.g., PRLR expressing tumors. Thus, the invention provides anti-PRLR ADCs for therapeutic use, e.g., treatment of cancer.

The anti-PRLR ADC of the instant invention comprises an anti-PRLR antibody, i.e., an antibody that specifically binds to PRLR, linked to one or more drug moieties. The specificity of the ADC of the invention is defined by the specificity of the antibody, i.e., anti-PRLR. In one embodiment, an anti-PRLR antibody of the invention is linked to one or more cytotoxin(s) which is delivered internally to a transformed cancer cell expressing PRLR. Examples of drugs that may be used in the anti-PRLR ADC of the invention are provided below, as are linkers that may be used to conjugate the antibody and the one or more drug(s). The terms "drug" and "agent" are used interchangeably herein. The terms "linked" and "conjugated" are also used interchangeably herein.

A. Drugs for Conjugation

Anti-PRLR antibodies of the invention may be used in an ADC to target one or more drug(s) to a cell of interest, e.g., a transformed cancer cell expressing PRLR. The anti-PRLR ADC of the invention provides a targeted therapy that may, for example, reduce the side effects often seen with anti-cancer therapies, as the one or more drug(s) is delivered to a specific cell. Examples of drugs that may be used in ADCs of the invention, i.e., drugs that may be conjugated to the anti-PRLR antibodies of the invention, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

Anti-PRLR antibodies of the invention may be conjugated to one or more mitotic inhibitor(s) for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by affecting microtubule polymerization or microtubule depolymerization. Thus, in one embodiment, an anti-PRLR antibody of the invention is conjugated to one or more mitotic inhibitor(s) that disrupts microtubule formation by inhibiting tubulin polymerization. In one embodiment, the mitotic inhibitor used in the ADCs of the invention is Ixempra (ixabepilone). Examples of mitotic inhibitors that may be used in the anti-PRLR ADCs of the invention are provided below.

a. Dolastatins

The anti-PRLR antibody of the invention may be conjugated to at least one dolastatin. Dolastatins are short peptidic compounds isolated from the Indian Ocean sea hare *Dolabella auricularia* (see Pettit et al., *J. Am. Chem. Soc.,* 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-PRLR ADC of the invention comprises an anti-PRLR antibody, as described herein, and at least one dolastatin. Auristatins, described below, are synthetic derivatives of dolastatin 10.

b. Auristatins

The anti-PRLR antibody of the invention may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635, 483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70:1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, the anti-PRLR antibody of the invention is conjugated to at least one MMAF (monomethylauristatin F). Monomethyl auristatin F (MMAF) inhibits cell division by blocking the polymerization of tubulin. It has a charged C-terminal phenylalanine residue that attenuates its cytotoxic activity compared to its uncharged counterpart MMAE. Because of its super toxicity, it cannot be used as a drug itself, but can be linked to a monoclonal antibody (mAb) that directs it to the cancer cells. In one embodiment, the linker to the anti-PRLR antibody is stable in extracellular fluid, but is cleaved by cathepsin once the conjugate has entered a tumor cell, thus activating the anti-mitotic mechanism.

In one embodiment, the anti-PRLR antibody of the invention is conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-PRLR antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism. The structures of MMAF and MMAE are provided below.

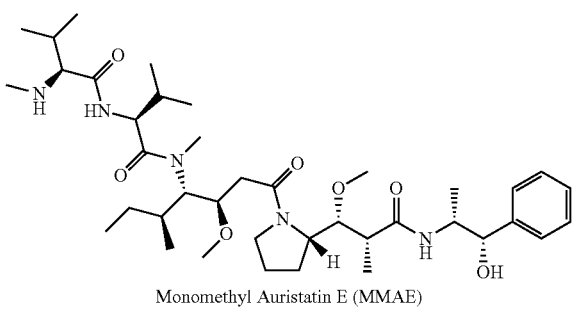

Monomethyl Auristatin E (MMAE)

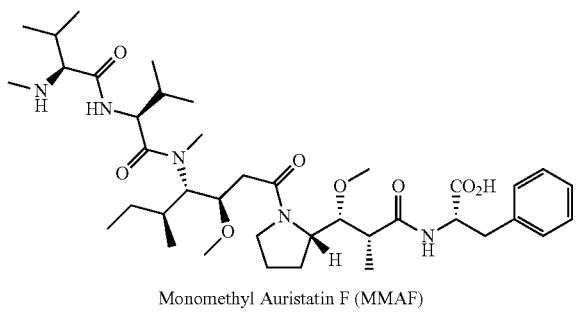

Monomethyl Auristatin F (MMAF)

c. Maytansinoids

The anti-PRLR antibody of the invention may be conjugated to at least one maytansinoid. Maytansinoids are potent antitumor agents that were originally isolated from members of the higher plant families Celastraceae, Rhamnaceae and Euphorbiaceae, as well as some species of mosses (Kupchan et al, J. Am. Chem. Soc. 94:1354-1356 [1972]; Wani et al, J. Chem. Soc. Chem. Commun 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids are known in the art to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., J. Med. Chem., 21, 31-37 (1978).

Suitable maytansinoids for use in ADCs of the invention can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule. In this regard, maytansinoids lack suitable functional groups to which antibodies can be linked A linking moiety desirably is utilized to link the maytansinoid to the antibody to form the conjugate, and is described in more detail in section IIB. The structure of an exemplary maytansinoid, mertansine (DM1), is provided below.

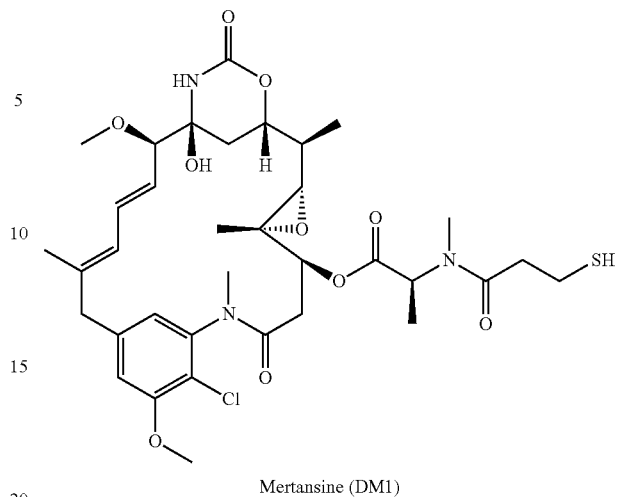

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine) and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment, the anti-PRLR antibody of the invention is conjugated to at least one DM1. In one embodiment, the anti-PRLR antibody of the invention is conjugated to at least one DM2. In one embodiment, the anti-PRLR antibody of the invention is conjugated to at least one DM3. In one embodiment, the anti-PRLR antibody of the invention is conjugated to at least one DM4.

d. Plant Alkaloids

The anti-PRLR antibody of the invention may be conjugated to at least one plant alkaloid, e.g., a taxane or vinca alkaloid. Plant alkaloids are chemotherapy treatments derived made from certain types of plants. The vinca alkaloids are made from the periwinkle plant (catharanthus rosea), whereas the taxanes are made from the bark of the Pacific Yew tree (taxus). Both the vinca alkaloids and taxanes are also known as antimicrotubule agents, and are described in more detail below.

Taxanes

The anti-PRLR antibody of the invention may be conjugated to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (Taxotere; Sanofi Aventis), paclitaxel (Abraxane or Taxol; Abraxis Oncology), and nanoparticle paclitaxel (ABI-007/Abraxene; Abraxis Bioscience).

In one embodiment, the anti-PRLR antibody of the invention is conjugated to at least one doxetaxel. In one embodiment, the anti-PRLR antibody of the invention is conjugated to at least one paclitaxel.

Vinca Alkaloids

In one embodiment, the anti-PRLR antibody of the invention is conjugated to at least one vinca alkaloid. Vinca alkaloids are a class of cell-cycle-specific drugs that work by inhibiting the ability of cancer cells to divide by acting upon tubulin and preventing the formation of microtubules. Examples of vinca alkaloids that may be used in the ADCs of the invention include, but are not limited to, vindesine sulfate, vincristine, vinblastine and vinorelbine.

2. Antitumor Antibiotics

Anti-PRLR antibodies of the invention may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-PRLR ADCs of the invention include, but are not limited to, actinomycines (e.g., pyrrolo[2,1-c][1,4]benzodiazepines), anthracyclines, calicheamicins, and duocarmycins, described in more detail below.

a. Actinomycines

The anti-PRLR antibody of the invention may be conjugated to at least one actinomycine. Actinomycines are a subclass of antitumor antibiotics isolated from bacteria of the genus *Streptomyces*. Representative examples actinomycines include, but are not limited to, actinomycin D (Cosmegen [also known as actinomycin, dactinomycin, actinomycin IV, actinomycin C1], Lundbeck, Inc.), anthramycin, chicamycin A, DC-18, mazethramycin, neothramycin A, neothramycin B, porothramycin, prothracarcin B, SG2285, sibanomicin, sibiromycin and tomaymycin. In one embodiment, the anti-PRLR antibody of the invention is conjugated to at least one pyrrolo[2,1-c][1,4]benzodiazepine (PBD). Examples of PDBs include, but are not limited to, anthramycin, chicamycin A, DC-81, mazethramycin, neothramycin A, neothramycin B, porothramycin, prothracarcin B, SG2285, sibanomicin, sibiromycin and tomaymycin. Thus, in one embodiment, the anti-PRLR antibody of the invention is conjugated to at least one actinomycine, e.g., actinomycin D or at least one PBD, e.g., a pyrrolobenzodiazepine (PBD) dimer.

b. Anthracyclines

The anti-PRLR antibody of the invention may be conjugated to at least one anthracycline. Anthracyclines are a subclass of antitumor antibiotics isolated from bacteria of the genus *Streptomyces*. Representative examples include, but are not limited to daunorubicin (Cerubidine, Bedford Laboratories), doxorubicin (Adriamycin, Bedford Laboratories; also referred to as doxorubicin hydrochloride, hydroxydaunorubicin, and Rubex), epirubicin (Ellence, Pfizer), and idarubicin (Idamycin; Pfizer Inc.). Thus, in one embodiment, the anti-PRLR antibody of the invention is conjugated to at least one anthracycline, e.g., doxorubicin.

c. Calicheamicins

The anti-PRLR antibody of the invention may be conjugated to at least one calicheamicin. Calicheamicins are a family of enediyne antibiotics derived from the soil organism *Micromonospora echinospora*. Calicheamicins bind the minor groove of DNA and induce double-stranded DNA breaks, resulting in cell death with a 100 fold increase over other chemotherapeutics (Damle et al. (2003) *Curr Opin Pharmacol* 3:386). Preparation of calicheamicins that may be used as drug conjugates in the invention are known in the art, see U.S. Pat. Nos. 5,712,374, 5,714,586, 5,739,116, 5,767,285, 5,770,701, 5,770,710, 5,773,001 and 5,877,296. Structural analogues of calicheamicin which may be used include, but are not limited to, $\gamma_1^I$, $\alpha_2^I$, $\alpha_3^I$, N-acetyl-$\Gamma_1^I$, PSAG and $\theta^I_1$ (Hinman et al., Cancer Research 53:3336-3342 (1993), Lode et al., Cancer Research 58:2925-2928 (1998) and the aforementioned U.S. Pat. Nos. 5,712,374, 5,714,586, 5,739,116, 5,767,285, 5,770,701, 5,770,710, 5,773,001 and 5,877,296). Thus, in one embodiment, the anti-PRLR antibody of the invention is conjugated to at least one calicheamicin.

d. Duocarmycins

The anti-PRLR antibody of the invention may be conjugated to at least one duocarmycin. Duocarmycins are a subclass of antitumor antibiotics isolated from bacteria of the genus *Streptomyces*. (see Nagamura and Saito (1998) *Chemistry of Heterocyclic Compounds*, Vol. 34, No. 12). Duocarmycins bind to the minor groove of DNA and alkylate the nucleobase adenine at the N3 position (Boger (1993) *Pure and Appl Chem* 65(6):1123; and Boger and Johnson (1995) *PNAS USA* 92:3642). Synthetic analogs of duocarmycins include, but are not limited to, adozelesin, bizelesin, and carzelesin. Thus, in one embodiment, the anti-PRLR antibody of the invention is conjugated to at least one duocarmycin.

e. Other Antitumor Antibiotics

In addition to the foregoing, additional antitumor antibiotics that may be used in the anti-PRLR ADCs of the invention include bleomycin (Blenoxane, Bristol-Myers Squibb), mitomycin, and plicamycin (also known as mithramycin).

3. Immunomodulating Agents

The anti-PRLR antibody of the invention may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, meagakaryocytes and granulocytes) or lymphoid cells (T cells, B cells and natural killer (NK) cells) and any further differentiated cell thereof. Representative examples include, but are not limited to, *bacillus* calmette-guerin (BCG) and levamisole (Ergamisol). Other examples of immunomodulating agents that may be used in the ADCs of the invention include, but are not limited to, cancer vaccines, cytokines, and immunomodulating gene therapy.

a. Cancer Vaccines

The anti-PRLR antibody of the invention may be conjugated to a cancer vaccine. As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant invention, administering an ADC comprising an anti-PRLR antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-PRLR ADCs of the invention include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-PRLR antibody of the invention is conjugated to at least one cancer vaccine that is either an immunostimulator or is an immunosuppressant.

b. Cytokines

The anti-PRLR antibody of the invention may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) Cancers 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs of the invention include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the invention provides an ADC comprising an anti-PRLR antibody described herein and a cytokine.

c. Colony-Stimulating Factors (CSFs)

The anti-PRLR antibody of the invention may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-PRLR ADCs of the invention include, but are not limited to erythropoietin (epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, the invention provides an ADC comprising an anti-PRLR antibody described herein and a CSF.

4. Gene Therapy

The anti-PRLR antibody of the invention may be conjugated to at least one nucleic acid (directly or indirectly via a carrier) for gene therapy. Gene therapy generally refers to the introduction of genetic material into a cell whereby the genetic material is designed to treat a disease. As it pertains to immunomoduatory agents, gene therapy is used to stimulate a subject's natural ability to inhibit cancer cell proliferation or kill cancer cells. In one embodiment, the anti-PRLR ADC of the invention comprises a nucleic acid encoding a functional, therapeutic gene that is used to replace a mutated or otherwise dysfunctional (e.g. truncated) gene associated with cancer. In other embodiments, the anti-PRLR ADC of the invention comprises a nucleic acid that encodes for or otherwise provides for the production of a therapeutic protein to treat cancer. The nucleic acid that encodes the therapeutic gene may be directly conjugated to the anti-PRLR antibody, or alternatively, may be conjugated to the anti-PRLR antibody through a carrier. Examples of carriers that may be used to deliver a nucleic acid for gene therapy include, but are not limited to, viral vectors or liposomes.

5. Alkylating Agents

The anti-PRLR antibody of the invention may be conjugated to one or more alkylating agent(s). Alkylating agents are a class of antineoplastic compounds that attaches an alkyl group to DNA. Examples of alkylating agents that may be used in the ADCs of the invention include, but are not limited to, alkyl sulfonates, ethylenimimes, methylamine derivatives, epoxides, nitrogen mustards, nitrosoureas, triazines and hydrazines.

a. Alkyl Sulfonates

The anti-PRLR antibody of the invention may be conjugated to at least one alkyl sulfonate. Alkyl sulfonates are a subclass of alkylating agents with a general formula: $R—SO_2—O—R^1$, wherein R and $R^1$ are typically alkyl or aryl groups. A representative example of an alkyl sulfonate includes, but is not limited to, busulfan (Myleran, GlaxoSmithKline; Busulfex IV, PDL BioPharma, Inc.).

b. Nitrogen Mustards

The anti-PRLR antibody of the invention may be conjugated to at least one nitrogen mustard. Representative examples of this subclass of anti-cancer compounds include, but are not limited to chlorambucil (Leukeran, GlaxoSmith- Kline), cyclophosphamide (Cytoxan, Bristol-Myers Squibb; Neosar, Pfizer, Inc.), estramustine (estramustine phosphate sodium or Estracyt), Pfizer, Inc.), ifosfamide (Ifex, Bristol-Myers Squibb), mechlorethamine (Mustargen, Lundbeck Inc.), and melphalan (Alkeran or L-Pam or phenylalanine mustard; GlaxoSmithKline).

c. Nitrosoureas

The anti-PRLR antibody of the invention may be conjugated to at least one nitrosourea. Nitrosoureas are a subclass of alkylating agents that are lipid soluble. Representative examples include, but are not limited to, carmustine (BCNU [also known as BiCNU, N,N-Bis(2-chloroethyl)-N-nitrosourea, or 1,3-bis(2-chloroethyl)-1-nitrosourea], Bristol-Myers Squibb), fotemustine (also known as Muphoran), lomustine (CCNU or 1-(2-chloro-ethyl)-3-cyclohexyl-1-nitrosourea, Bristol-Myers Squibb), nimustine (also known as ACNU), and streptozocin (Zanosar, Teva Pharmaceuticals).

d. Triazines and Hydrazines

The anti-PRLR antibody of the invention may be conjugated to at least one triazine or hydrazine. Triazines and hydrazines are a subclass of nitrogen-containing alkylating agents. In some embodiments, these compounds spontaneously decompose or can be metabolized to produce alkyl diazonium intermediates that facilitate the transfer of an alkyl group to nucleic acids, peptides, and/or polypeptides, thereby causing mutagenic, carcinogenic, or cytotoxic effects. Representative examples include, but are not limited to dacarbazine (DTIC-Dome, Bayer Healthcare Pharmaceuticals Inc.), procarbazine (Mutalane, Sigma-Tau Pharmaceuticals, Inc.), and temozolomide (Temodar, Schering Plough).

e. Other Alkylating Agents

The anti-PRLR antibody of the invention may be conjugated to at least one ethylenimine, methylamine derivative, or epoxide. Ethylenimines are a subclass of alkylating agents that typically containing at least one aziridine ring. Epoxides represent a subclass of alkylating agents that are characterized as cyclic ethers with only three ring atoms.

Representatives examples of ethylenimines include, but are not limited to thiopeta (Thioplex, Amgen), diaziquone (also known as aziridinyl benzoquinone (AZQ)), and mitomycin C. Mitomycin C is a natural product that contains an aziridine ring and appears to induce cytoxicity through cross-linking DNA (Don R T, et al. *Cancer Res.* 1985; 45:3510; Kennedy K A, et al *Cancer Res.* 1985; 45:3541). Representative examples of methylamine derivatives and their analogs include, but are not limited to, altretamine (Hexylen, MGI Pharma, Inc.), which is also known as hexamethylamine and hexastat. Representative examples of epoxides of this class of anti-cancer compound include, but are not limited to dianhydrogalactitol. Dianhydrogalactitol (1,2:5,6-dianhydrodulcitol) is chemically related to the aziridines and generally facilitate the transfer of an alkyl group through a similar mechanism as described above. Dibromodulcitol is hydrolyzed to dianhydrogalactitol and thus is a pro-drug to an epoxide (Sellei C, et al. *Cancer Chemother Rep.* 1969; 53:377).

6. Antiangiogenic Agents

The anti-PRLR antibody of the invention may be conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs of the invention include, but are not limited to, angiostatin, ABX EFG, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

7. Antimetabolites

The anti-PRLR antibody of the invention may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs of the invention include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

a. Antifolates

The anti-PRLR antibody of the invention may be conjugated to at least one antifolate. Antifolates are a subclass of antimetabolites that are structurally similar to folate. Representative examples include, but are not limited to, methotrexate, 4-amino-folic acid (also known as aminopterin and 4-aminopteroic acid), lometrexol (LMTX), pemetrexed (Alimpta, Eli Lilly and Company), and trimetrexate (Neutrexin, Ben Venue Laboratories, Inc.)

b. Purine Antagonists

The anti-PRLR antibody of the invention may be conjugated to at least one purine antagonist. Purine analogs are a subclass of antimetabolites that are structurally similar to the group of compounds known as purines. Representative examples of purine antagonists include, but are not limited to, azathioprine (Azasan, Salix; Imuran, GlaxoSmithKline), cladribine (Leustatin [also known as 2-CdA], Janssen Biotech, Inc.), mercaptopurine (Purinethol [also known as 6-mercaptoethanol], GlaxoSmithKline), fludarabine (Fludara, Genzyme Corporation), pentostatin (Nipent, also known as 2'-deoxycoformycin (DCF)), 6-thioguanine (Lanvis [also known as thioguanine], GlaxoSmithKline).

c. Pyrimidine Antagonists

The anti-PRLR antibody of the invention may be conjugated to at least one pyrimidine antagonist. Pyrimidine antagonists are a subclass of antimetabolites that are structurally similar to the group of compounds known as purines. Representative examples of pyrimidine antagonists include, but are not limited to azacitidine (Vidaza, Celgene Corporation), capecitabine (Xeloda, Roche Laboratories), Cytarabine (also known as cytosine arabinoside and arabinosylcytosine, Bedford Laboratories), decitabine (Dacogen, Eisai Pharmaceuticals), 5-fluorouracil (Adrucil, Teva Pharmaceuticals; Efudex, Valeant Pharmaceuticals, Inc), 5-fluoro-2'-deoxyuridine 5'-phosphate (FdUMP), 5-fluorouridine triphosphate, and gemcitabine (Gemzar, Eli Lilly and Company).

8. Boron-Containing Agents

The anti-PRLR antibody of the invention may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

9. Chemoprotective Agents

The anti-PRLR antibody of the invention may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

10. Hormone Agents

The anti-PRLR antibody of the invention may be conjugated to at least one hormone agent. A hormone agent (including synthetic hormones) is a compound that interferes with the production or activity of endogenously produced hormones of the endocrine system. In some embodiments, these compounds interfere with cell growth or produce a cytotoxic effect. Non-limiting examples include androgens, estrogens, medroxyprogesterone acetate (Provera, Pfizer, Inc.), and progestins.

11. Antihormone Agents

The anti-PRLR antibody of the invention may be conjugated to at least one antihormone agent. An "antihormone" agent is an agent that suppresses the production of and/or prevents the function of certain endogenous hormones. In one embodiment, the antihormone agent interferes with the activity of a hormone selected from the group comprising androgens, estrogens, progesterone, and goanadotropin-releasing hormone, thereby interfering with the growth of various cancer cells. Representative examples of antihormone agents include, but are not limited to, aminoglutethimide, anastrozole (Arimidex, AstraZeneca Pharmaceuticals), bicalutamide (Casodex, AstraZeneca Pharmaceuticals), cyproterone acetate (Cyprostat, Bayer PLC), degarelix (Firmagon, Ferring Pharmaceuticals), exemestane (Aromasin, Pfizer Inc.), flutamide (Drogenil, Schering-Plough Ltd), fulvestrant (Faslodex, AstraZeneca Pharmaceuticals), goserelin (Zolodex, AstraZeneca Pharmaceuticals), letrozole (Femara, Novartis Pharmaceuticals Corporation), leuprolide (Prostap), lupron, medroxyprogesterone acetate (Provera, Pfizer Inc.), Megestrol acetate (Megace, Bristol-Myers Squibb Company), tamoxifen (Nolvadex, AstraZeneca Pharmaceuticals), and triptorelin (Decapetyl, Ferring).

12. Corticosteroids

The anti-PRLR antibody of the invention may be conjugated to at least one corticosteroid. Corticosteroids may be used in the ADCs of the invention to decrease inflammation. An example of a corticosteroid includes, but is not limited to, a glucocorticoid, for example, prednisone (Deltasone, Pharmacia & Upjohn Company, a division of Pfizer, Inc.).

13. Photoactive Therapeutic Agents

The anti-PRLR antibody of the invention may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

14. Oligonucleotides

The anti-PRLR antibody of the invention may be conjugated to at least one oligonucleotide. Oligonucleotides are made of short nucleic acid chains that work by interfering with the processing of genetic information. In some embodiments, the oligonucleotides for use in ADCs are unmodified single-stranded and/or double-stranded DNA or RNA molecules, while in other embodiments, these therapeutic oligonucleotides are chemically-modified single-stranded and/or double-stranded DNA or RNA molecules. In one embodiment, the oligonulceotides used in the ADCs are relatively short (19-25 nucleotides) and hybridize to a unique nucleic acid sequence in the total pool of nucleic acid targets present in cells. Some of the important oligonucleotide technologies include the antisense oligonucleotides (including RNA interference (RNAi)), aptamers, CpG oligonucleotides, and ribozymes.

a. Antisense Oligonucleotides

The anti-PRLR antibody of the invention may be conjugated to at least one antisense oligonucleotide. Antisense oligonucleotides are designed to bind to RNA through Watson-Crick hybridization. In some embodiments the antisense oligonucleotide is complementary to a nucleotide encoding a region, domain, portion, or segment of PRLR. In some embodiments, the antisense oligonucleotide comprises from about 5 to about 100 nucleotides, from about 10 to about 50 nucleotides, from about 12 to about 35, and from about 18 to about 25 nucleotides. In some embodiments, the oligonucleotide is at least 50%, at least 60%, at least 70%, at least 80%, at least 90%, at least 95%, at least 96%, at least 97%, at least 98%, at least 99%, or at least 100% homologous to a region, portion, domain, or segment of the PRLR gene. In some embodiments there is substantial sequence homology over at least 15, 20, 25, 30, 35, 40, 50, or 100 consecutive nucleotides of the PRLR gene. In preferred embodiments, the size of these antisense oligonucleotides ranges from 12 to 25 nucleotides in length, with the majority of antisense oligonucleotides being 18 to 21 nucleotides in length. There are multiple mechanisms that can be exploited to inhibit the function of the RNA once the oligonucleotide binds to the target RNA (Crooke S T. (1999). *Biochim. Biophys. Acta,* 1489, 30-42). The best-characterized antisense mechanism results in cleavage of the targeted RNA by endogenous cellular nucleases, such as RNase H or the nuclease associated with the RNA interference mechanism. However, oligonucleotides that inhibit expression of the target gene by non-catalytic mechanisms, such as modulation of splicing or translation arrest, can also be potent and selective modulators of gene function.

Another RNase-dependent antisense mechanism that has recently received much attention is RNAi (Fire et al. (1998). *Nature,* 391, 806-811; Zamore P D. (2002). *Science,* 296, 1265-1269.). RNA interference (RNAi) is a post-transcriptional process where a double stranded RNA inhibits gene expression in a sequence specific fashion. In some embodiments, the RNAi effect is achieved through the introduction of relatively longer double-stranded RNA (dsRNA), while in preferred embodiments, this RNAi effect is achieved by the introduction of shorter double-stranded RNAs, e.g. small interfering RNA (siRNA) and/or microRNA (miRNA). In yet another embodiment, RNAi can also be achieved by introducing of plasmid that generate dsRNA complementary to target gene. In each of the foregoing embodiments, the double-stranded RNA is designed to interfere with the gene expression of a particular the target sequence within cells. Generally, the mechanism involves conversion of dsRNA into short RNAs that direct ribonucleases to homologous mRNA targets (summarized, Ruvkun, *Science* 2294:797 (2001)), which then degrades the corresponding endogenous mRNA, thereby resulting in the modulation of gene expression. Notably, dsRNA has been reported to have antiproliferative properties, which makes it possible also to envisage therapeutic applications (Aubel et al., *Proc. Natl. Acad. Sci., USA* 88:906 (1991)). For example, synthetic dsRNA has been shown to inhibit tumor growth in mice (Levy et al. *Proc. Nat. Acad. Sci. USA,* 62:357-361 (1969)), is active in the treatment of leukemic mice (Zeleznick et al., *Proc. Soc. Exp. Biol. Med.* 130:126-128 (1969)), and inhibits chemically induced tumorigenesis in mouse skin (Gelboin et al., *Science* 167:205-207 (1970)). Thus, in a preferred embodiment, the invention provides for the use of antisense oligonucleotides in ADCs for the treatment of breast cancer. In other embodiments, the invention provides compositions and methods for initiating antisense oligonucleotide treatment, wherein dsRNA interferes with target cell expression of PRLR at the mRNA level. dsRNA, as used above, refers to naturally-occurring RNA, partially purified RNA, recombinantly produced RNA, synthetic RNA, as well as altered RNA that differs from naturally-occurring RNA by the inclusion of non-standard nucleotides, non-nucleotide material, nucleotide analogs (e.g. locked nucleic acid (LNA)), deoxyribonucleotides, and any combination thereof. RNA of the present invention need only be sufficiently similar to natural RNA that it has the ability to mediate the antisense oligonucleotide-based modulation described herein.

b. Aptamers

The anti-PRLR antibody of the invention may be conjugated to at least one aptamer. An aptamer is a nucleic acid molecule that has been selected from random pools based on its ability to bind other molecules. Like antibodies, aptamers can bind target molecules with extraordinary affinity and specificity. In many embodiments, aptamers assume complex, sequence-dependent, three-dimensional shapes that allow them to interact with a target protein, resulting in a tightly bound complex analogous to an antibody-antigen interaction, thereby interfering with the function of said protein. The particular capacity of aptamers to bind tightly and specifically to their target protein underlines their potential as targeted molecular therapies.

c. CpG Oligonucleotides

The anti-PRLR antibody of the invention may be conjugated to at least one CpG oligonucleotide. Bacterial and viral DNA are known to be a strong activators of both the innate and specific immunity in humans. These immunologic characteristics have been associated with unmethylated CpG dinucleotide motifs found in bacterial DNA. Owing to the fact that these motifs are rare in humans, the human immune system has evolved the ability to recognize these motifs as an early indication of infection and subsequently initiate immune responses. Therefore, oligonucleotides containing this CpG motif can be exploited to initiate an antitumor immune response.

d. Ribozymes

The anti-PRLR antibody of the invention may be conjugated to at least one ribozyme. Ribozymes are catalytic RNA molecules ranging from about 40 to 155 nucleotides in length. The ability of ribozymes to recognize and cut specific RNA molecules makes them potential candidates for therapeutics. A representative example includes angiozyme.

15. Radionuclide Agents (Radioactive Isotopes)

The anti-PRLR antibody of the invention may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111 1, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, 105Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

16. Radiosensitizers

The anti-PRLR antibody of the invention may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

17. Topoisomerase Inhibitors

The anti-PRLR antibody of the invention may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

18. Tyrosine Kinase Inhibitors

The anti-PRLR antibody of the invention may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs of the invention include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

19. Other Agents

Examples of other agents that may be used in the ADCs of the invention include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *momordica charantia* inhibitor, neomycin, onconase, phenomycin, *Phytolaca americana* proteins (PAPI, PAM, and PAP-S), pokeweed antiviral protein, *Pseudomonas endotoxin, Pseudomonas* exotoxin (e.g. exotoxin A chain (from *Pseudomonas aeruginosa*)), restrictocin, ricin A chain, ribonuclease (Rnase), sapaonaria officinalis inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-PRLR ADCs of the invention are not exclusive, in that certain examples of drugs may be found in more than one category, e.g., ansamitocins are both mitotic inhibitors and antitumor antibiotics.

All stereoisomers of the above drug moieties are contemplated for the compounds of the invention, i.e. any combination of R and S configurations at the chiral carbons of D.

The above agents (i.e., naked agents not conjugated to an antibody) may also be used in combination therapies with the anti-PRLR antibodies described herein. In one embodiment, the anti-PRLR antibodies of the invention are used with any of the foregoing agents in a combination therapy to treat cancer, where the agent is administered prior to, at the same time as, or following administration of the anti-PRLR antibody to the subject.

B. Linkers

The present invention provides anti-PRLR ADCs for targeted delivery of drugs. The anti-PRLR ADC of the invention comprises an anti-PRLR antibody and a drug, whereby the antibody and drug may be attached through a linker. Thus, in one embodiment, the antibody drug conjugate (ADC) comprises a linker, a cytotoxic drug, and an anti-PRLR antibody. The term "linker" as used herein, refers to a chemical moiety comprising a covalent bond or a chain of atoms that covalently attaches an antibody to a drug moiety. An ADC is prepared using a linker having reactive functionality for binding to the antibody and the drug. For example, a cysteine thiol, or an amine. e.g., N-terminus or amino acid side chain such as lysine, of the antibody may form a bond with a functional group of the linker.

The linkers are preferably stable extracellularly. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow delivery, e.g., intracellular delivery, of the conjugate or drug moiety; and (iii) maintain a cytotoxic, cell-killing effect, a cytostatic effect, or otherwise a therapeutic effect of a drug moiety. Stability of the ADC may be measured by standard analytical techniques such as mass spectroscopy, HPLC, and the separation/analysis technique LC/MS.

Generally, ADCs comprise an antibody covalently linked to at least one drug unit. The drug unit(s) can be covalently linked directly or via a linker Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

In some embodiments, the ADC has the following formula (formula I):

$$L\text{-}(LU\text{-}D)_p \qquad (I)$$

or a pharmaceutically acceptable salt or solvate thereof;
wherein:
L is the antibody, e.g., anti-PRLR antibody of the present invention, and
(LU-D) is a Linker-Drug moiety, wherein:
LU- is a Linker unit (also referred to as a linker), and
-D is a drug moiety having, for example, cytostatic, cytotoxic, or otherwise therapeutic activity against a target cell, e.g., a cell expressing PRLR; and
p is an integer from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, p is 2, 4, 6 or 8.

In some embodiments, the -D moieties are the same. In yet another embodiment, the -D moieties are different.

In some embodiments, the ADC has the following formula (II):

$$L\text{-}(A_a\text{-}W_w\text{—}Y_y\text{-}D)_p \qquad (II)$$

or a pharmaceutically acceptable salt or solvate thereof, wherein:
L is the antibody, e.g., anti-PRLR antibody, and
-$A_a$-$W_w$—$Y_y$— is a Linker unit (LU), wherein:
-A- is an optional Stretcher unit,
a is 0 or 1,
each —W— is independently an Amino Acid unit (or in some embodiments, a Glucuronide unit, See also US Publication No. 2012/0107332 A1),
w is an integer ranging from 0 to 12,
—Y— is a self-immolative spacer unit,
y is 0, 1 or 2;
-D is a drug unit having, for example, cytostatic, cytotoxic, or otherwise therapeutic activity against the target cell, e.g., cell expressing PRLR; and
p is an integer from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2.

In some embodiments, p ranges from 2 to 8, 2 to 7, 2 to 6, 2 to 5, 2 to 4 or 2 to 3. In other embodiments, p is 1, 2, 3, 4, 5 or 6. In some embodiments, p is 2 or 4. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

For compositions comprising a plurality of antibodies, the drug loading is represented by p, the average number of drug molecules per antibody. Drug loading may range from 1 to 20 drugs (D) per antibody. The average number of drugs per antibody in preparation of conjugation reactions may be characterized by conventional means such as mass spectroscopy, ELISA assay, and HPLC. The quantitative distribution of ADCs in terms of p may also be determined. In some instances, separation, purification, and characterization of homogeneous ADCs where p is a certain value from ADCs with other drug loadings may be achieved by means such as reverse phase HPLC or electrophoresis. In exemplary embodiments, p is from 2 to 8.

The generation of ADCs can be accomplished by any technique known to the skilled artisan. ADCs of the invention comprise anti-PRLR antibodies described herein, a drug, and optionally a linker that joins the drug and the antibody. In one embodiment, the antibody is an anti-PRLR antibody comprising at least one variable region set forth in SEQ ID NO: 39; SEQ ID NO: 43; SEQ ID NO: 44; SEQ ID NO: 45; SEQ ID NO:48; SEQ ID NO: 52; SEQ ID NO: 53; SEQ ID NO: 54; SEQ ID NO: 55; SEQ ID NO: 59; SEQ ID NO: 60; SEQ ID NO: 61; SEQ ID NO: 64; SEQ ID NO: 68; SEQ ID NO: 69; SEQ ID NO: 70; SEQ ID NO: 74; SEQ ID NO: 75; SEQ ID NO: 76; SEQ ID NO: 78; SEQ ID NO: 82; SEQ ID NO: 83; SEQ ID NO: 84; SEQ ID NO: 88; SEQ ID NO: 89; SEQ ID NO: 90; SEQ ID NO: 91; SEQ ID NO: 95; SEQ ID NO: 96; SEQ ID NO: 103; SEQ ID NO: 104; SEQ ID NO: 105; SEQ ID NO: 106; SEQ ID NO: 107; SEQ ID NO: 108; SEQ ID NO: 109; SEQ ID NO: 110; SEQ ID NO: 111; SEQ ID NO: 112; SEQ ID NO: 113; SEQ ID NO: 114; SEQ ID NO: 115; SEQ ID NO: 116; SEQ ID NO: 117; SEQ ID NO: 118; SEQ ID NO: 119; SEQ ID NO: 120, SEQ ID NO: 121; SEQ ID NO: 122 and SEQ ID NO: 123. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the present invention.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-PRLR antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference in its entirety. Examples of linkers are provided below.

In a preferred embodiment, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the ADC presents in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

In some embodiments, the linker is cleavable under intracellular conditions, such that cleavage of the linker releases the drug unit from the antibody in the intracellular environment. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker) A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in PRLR-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker of the ADC of the invention is a malonate linker (Johnson et al., 1995, Anti-cancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker unit is substantially hydrophilic linker (e.g., PEG4Mal and sulfo-SPDB). A hydrophilic linker may be used to prevent the drug from being pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker unit-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the ADC of the invention is a non-cleavable linker that promotes cellular internalization.

As described in Formula II above, in some embodiments the anti-PRLR ADC of the invention includes a stretcher unit. The stretcher unit (A), when present, is capable of linking an antibody to an amino acid unit (—W—), if present, to a spacer unit (—Y—), if present; or to a drug (-D) (see Formula II). Useful functional groups that can be present on the anti-PRLR antibodies described herein, either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an anti-PRLR antibody. In another embodiment, sulfhydryl groups can be generated by reaction of an amino group of a lysine moiety of an anti-PRLR antibody with 2-iminothiolane (Traut's reagent) or other sulfhydryl generating reagents. In certain embodiments, the anti-PRLR antibody is a recombinant antibody and is engineered to carry one or more lysine moieties. In certain other embodiments, the recombinant anti-PRLR antibody is engineered to carry additional sulfhydryl groups, e.g., additional cysteines.

In one embodiment, the stretcher unit forms a bond with a sulfur atom of the antibody. The sulfur atom can be derived from a sulfhydryl group of an antibody. Representative stretcher units of this embodiment are depicted within the square brackets of Formulas IIIa and IIIb as shown below,

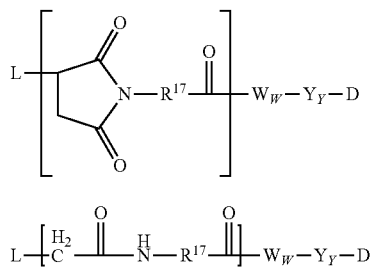

IIIa

IIIb wherein L-, —W—, —Y—, -D, w and y are as defined above, and IC is selected from —$C_1$-$C_{10}$ alkylene-, —$C_1$-$C_{10}$ alkenylene-, —$C_1$-$C_{10}$ alkynylene-, carbocyclo-, —O—($C_1$-$C_8$ alkylene)-, O—($C_1$-$C_8$ alkenylene)-, —O—($C_1$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, arylene-$C_1$-$C_{10}$ alkylene-, -arylene-$C_2$-$C_{10}$ alkenylene-, -arylene-$C_2$-$C_{10}$ alkynylene-, —$C_1$-$C_{10}$ alkylene-(carbocyclo)-, —$C_2$-$C_{10}$ alkenylene-(carbocyclo)-, $C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, -heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_1$-$C_{10}$ alkynylene-, —($CH_2CH_2O)_r$—, or —($CH_2CH_2O)_r$—$CH_2$—, and r is an integer ranging from 1-10, wherein said alkyl, alkenyl, alkynyl, alkylene, alkenylene, alkynylene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynyklene, aryl, carbocyle, carbocyclo, heterocyclo, and arylene radicals, whether alone or as part of another group, are unsubstituted. In some embodiments, $R^{17}$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, —$C_1$-$C_{10}$ alkylene-(heterocyclo)-, -(heterocyclo)-$C_1$-$C_{10}$ alkylene-, —($CH_2CH_2O)_r$—, and —($CH_2CH_2O)_r$—$CH_2$—; and r is an integer ranging from 1-10, wherein said alkylene groups are unsubstituted and the remainder of the groups are optionally substituted.

An illustrative stretcher unit is that of Formula IIIa wherein $R^{17}$ is —($CH_2)_5$— as depicted below (see also U.S. Pat. No. 8,309,093).

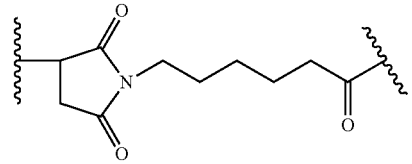 [SMILES: *C(=O)CCCCCN1C(=O)CC(*)C1=O]

Another illustrative stretcher unit is that of Formula IIIa wherein IC is —($CH_2CH_2O)_r$—$CH_2$—; and r is 2, as depicted below (see also U.S. Pat. No. 8,309,093).

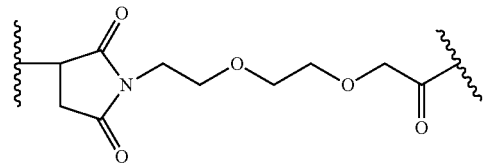 [SMILES: *C(=O)COCCOCCN1C(=O)CC(*)C1=O]

Another illustrative stretcher unit is that of Formula IIIa wherein $R^{17}$ is arylene- or arylene-$C_1$-$C_{10}$ alkylene-. In some embodiments, the aryl group is an unsubstituted phenyl group. Still, another illustrative stretcher unit is that of Formula IIIb wherein $R^{17}$ is —($CH_2)_5$—, as depicted below (see also U.S. Pat. No. 8,309,093).

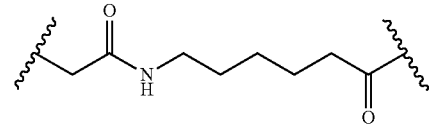 [SMILES: *CC(=O)NCCCCCC(*)=O]

In certain embodiments, the stretcher unit is linked to the anti-PRLR antibody via a disulfide bond between a sulfur atom of the anti-PRLR antibody unit and a sulfur atom of the stretcher unit. A representative stretcher unit of this embodiment is depicted within the square brackets of Formula IV (See below, and see also U.S. Pat. No. 8,309,093), wherein $R^{17}$, L-, —W—, —Y—, -D, w, and y are as defined above.

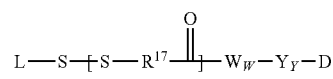

IV

It should be noted that the S moiety in the formula shown below (see also U.S. Pat. No. 8,309,093) refers to a sulfur atom of the antibody, unless otherwise indicated by the context.

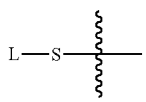

In yet other embodiments, the stretcher contains a reactive site that can form a bond with a primary or secondary amino group of an antibody. Examples of these reactive sites include but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative stretcher units of this embodiment are depicted within the square brackets of Formulas Va and Vb (See below (see also U.S. Pat. No. 8,309,093)), wherein $R^{17}$, L-, —W—, —Y—, -D, w, and y are as defined above.

Va

Vb

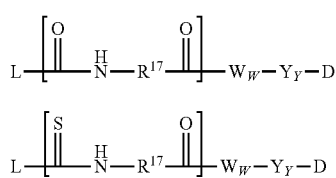

In some embodiments, the stretcher contains a reactive site that is reactive to a modified carbohydrate's (—CHO) group that can be present on an antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc (See below (see also U.S. Pat. No. 8,309,093), wherein —$R^{17}$—, L-, —W—, —Y—, -D, w and y are as defined as above.

VIa

VIb

VIc

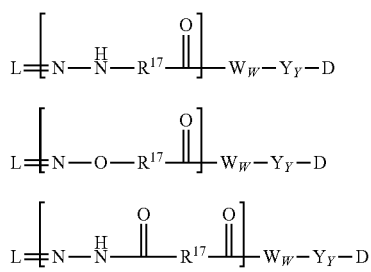

The amino acid unit (—W—), when present, links the stretcher unit to the spacer unit if the spacer unit is present, links the stretcher unit to the drug moiety if the spacer unit is absent, and links the antibody unit to the drug unit if the stretcher unit and spacer unit are absent. $W_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below (see also U.S. Pat. No. 8,309,093) in the square brackets, and w is an integer ranging from 0 to 12,

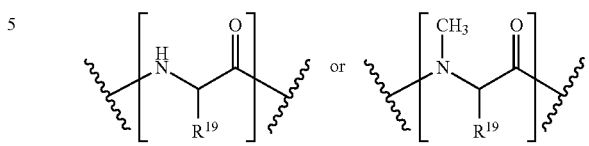

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3HCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl, and other non-limiting representative $R^{19}$ groups, as depicted below.

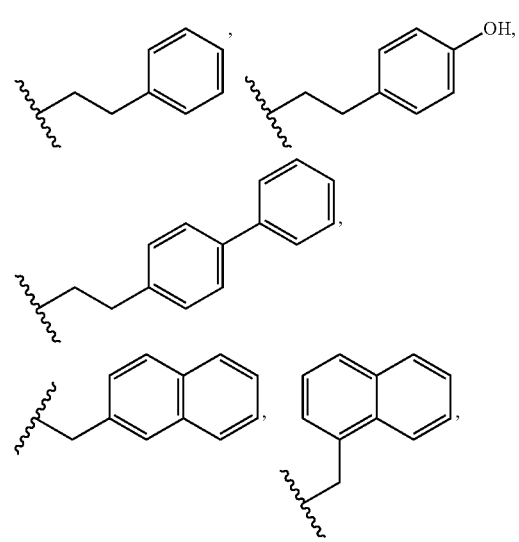

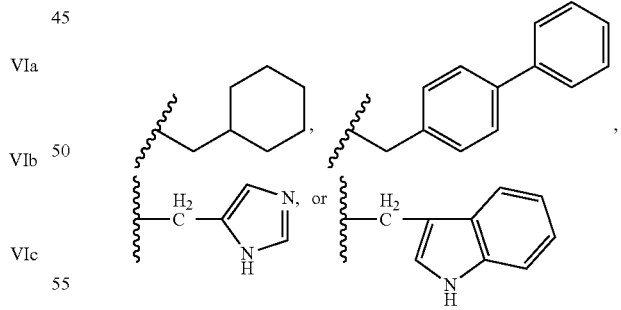

In some embodiments, the amino acid unit can be enzymatically cleaved by one or more enzymes, including a cancer or tumor-associated protease, to liberate the drug (-D), which in one embodiment is protonated in vivo upon release to provide a drug.

In certain embodiments, the amino acid unit can comprise natural amino acids. In other embodiments, the amino acid unit can comprise non-natural amino acids. Illustrative $W_w$ units are represented by formula (VII) (as depicted below (see also U.S. Pat. No. 8,309,093),

VII

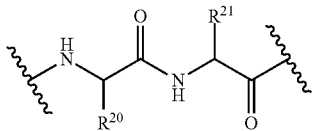

wherein $R^{20}$ and $R^{21}$ are as depicted below;

| $R^{20}$ | $R^{21}$ |
|---|---|
| Benzyl | $(CH_2)_4NH_2$; |
| Methyl | $(CH_2)_4NH_2$; |
| Isopropyl | $(CH_2)_4NH_2$; |
| Isopropyl | $(CH_2)_3NHCONH_2$; |
| Benzyl | $(CH_2)_3NHCONH_2$; |
| Isobutyl | $(CH_2)_3NHCONH_2$; |
| Sec-butyl | $(CH_2)_3NHCONH_2$; |
| 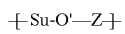 | $(CH_2)_3NHCONH_2$; |
| Benzyl | Methyl; |
| Benzyl | $(CH_2)_3NHC(=NH)NH_2$; | formula (VIII) (as depicted below (see also U.S. Pat. No. 8,309,093),

VIII

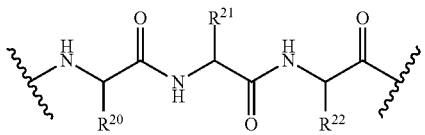

wherein $R^{20}$, $R^{21}$, and $R^{22}$ are as depicted below;

| $R^{20}$ | $R^{21}$ | $R^{22}$ |
|---|---|---|
| Benzyl | Benzyl | $(CH_2)_4NH_2$; |
| Isopropyl | Benzyl | $(CH_2)_4NH_2$; |
| H | Benzyl | $(CH_2)_4NH_2$; | and formula (IX) (as depicted below (see also U.S. Pat. No. 8,309,093),

IX

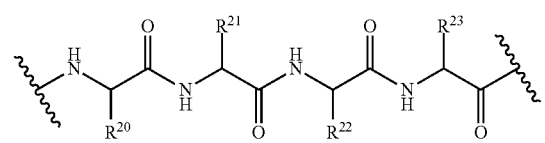

wherein $R^{20}$, $R^{21}$, $R^{22}$, and $R^{23}$ are as depicted below:

| $R^{20}$ | $R^{21}$ | $R^{22}$ | $R^{23}$ |
|---|---|---|---|
| H | Benzyl | Isobutyl | H |
| Methyl | Isobutyl | Methyl | Isobutyl |

Exemplary amino acid units include, but are not limited to, units of formula VII where: $R^{20}$ is benzyl and $R^{21}$ is —$(CH_2)_4NH_2$; $R^{20}$ is isopropyl and $R^{21}$ is —$(CH_2)_4NH_2$; or $R^{20}$ is isopropyl and $R^{21}$ is —$(CH_2)_3NHCONH_2$. Another exemplary amino acid unit is a unit of formula VIII wherein $R^{20}$ is benzyl, $R^{21}$ is benzyl, and $R^{22}$ is —$(CH_2)_4NH_2$.

Useful —$W_w$— units can be designed and optimized in their selectivity for enzymatic cleavage by a particular enzyme, for example, a tumor-associated protease. In one embodiment, a —$W_w$— unit is that whose cleavage is catalyzed by cathepsin B, C and D, or a plasmin protease. In one embodiment, —$W_w$— is a dipeptide, tripeptide, tetrapeptide or pentapeptide. When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral. Each carbon atom to which $R^{19}$, $R^{20}$, $R^{21}$, $R^{22}$ or $R^{23}$ is attached is independently in the (S) or (R) configuration.

In one embodiment of the amino acid unit, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Alternatively, in some embodiments, —W— is a glucuronide unit that links a stretcher unit to a spacer unit if the stretcher and spacer units are present, links a stretcher unit to the drug moiety if the spacer unit is absent, and links the linker unit to the drug if the stretcher and spacer units are absent. The glucuronide unit includes a site that can be cleaved by a β-glucuronidase enzyme (See also US 2012/0107332 A1). In some embodiments, the glucuronide unit comprises a sugar moiety (Su) linked via a glycoside bond (—O'—) to a self-immolative group (Z) of the formula as depicted below (See also US 2012/0107332, incorporated by reference herein).

$$\pm Su\text{-}O'\text{---}Z\pm$$

The glycosidic bond (—O'—) is typically a β-glucuronidase-cleavage site, such as a bond cleavable by human, lysosomal β-glucuronidase. In the context of a glucuronide unit, the term "self-immolative group" refers to a di- or tri-functional chemical moiety that is capable of covalently linking together two or three spaced chemical moieties (i.e., the sugar moiety (via a glycosidic bond), a drug unit (directly or indirectly via a spacer unit), and, in some embodiments, a linker (directly or indirectly via a stretcher unit) into a stable molecule. The self-immolative group will spontaneously separate from the first chemical moiety (e.g., the spacer or drug unit) if its bond to the sugar moiety is cleaved.

In some embodiments, the sugar moiety (Su) is cyclic hexose, such as a pyranose, or a cyclic pentose, such as a furanose. In some embodiments, the pyranose is a glucuronide or hexose. The sugar moiety is usually in the β-D conformation. In a specific embodiment, the pyranose is a β-D-glucuronide moiety (i.e., β-D-glucuronic acid linked to the self-immolative group —Z— via a glycosidic bond that is cleavable by β-glucuronidase). In some embodiments, the sugar moiety is unsubstituted (e.g., a naturally occurring cyclic hexose or cyclic pentose). In other embodiments, the sugar moiety can be a substituted β-D-glucuronide (i.e., glucuronic acid substituted with one or more group, such hydrogen, hydroxyl, halogen, sulfur, nitrogen or lower alkyl.

In some embodiments, the self-immolative group Z is a p-aminobenzyl alcohol (PAB) unit, as further described herein. Other suitable self immolative groups are known in the art.

In some embodiments, the glucuronide unit has one of the formulas as depicted below (See also US 2012/0107332 A1),

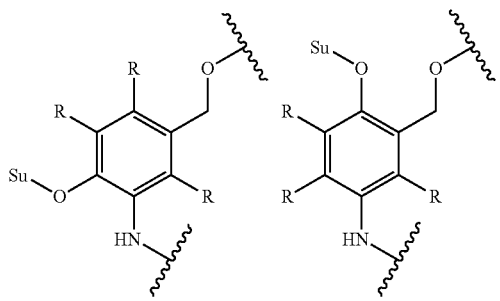

wherein Su is the sugar moiety, the glycosidic bond comprises the oxygen bond between Su and the self immolative group Z, and each R is independently hydrogen, halo (e.g., chloro, bromo, fluoro, etc), —CN, —NO$_2$, or other electron withdrawing or donating group, provided that the Glucuronide unit (and Z in particular) undergoes self-immolation upon cleavage of the glycosidic bond. In some embodiments, each R is independently hydrogen, halo (e.g., chloro, bromo, fluoro, etc), —CN or —NO$_2$.

In some embodiments, the glucuronide unit has one of the formulas as depicted below (See also US 2012/0107332 A1),

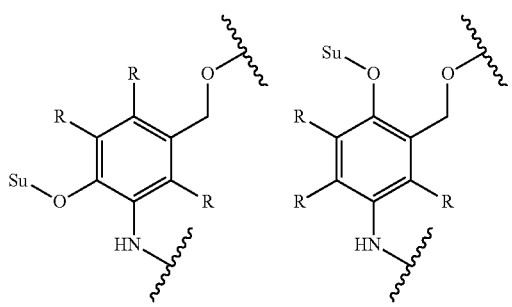

wherein Su is the Sugar moiety, the glycosidic bond (—O'—) comprises the oxygen bond between Su and the self immolative group Z, and each R is independently hydrogen.

In some embodiments, the self-immolative group (Z) is covalently linked to the sugar moiety, to the drug (directly or indirectly via the spacer unit(s)), and to the linker (directly or indirectly via the stretcher unit(s)). In some embodiments, a Drug Linker conjugate has the formula as depicted below (See also US 2012/0107332 A1),

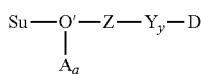

wherein Su, O', Z, Y, y, D, A and a are defined herein. Typically from 1 to 20 of such drug-linker conjugates can be linked to a linker.

In some embodiments, an ADC comprising the glucuronide unit has one of the formulas as depicted below (See also US 2012/0107332 A1), wherein Su, Y, y, D, A, a, and L are defined as described herein.

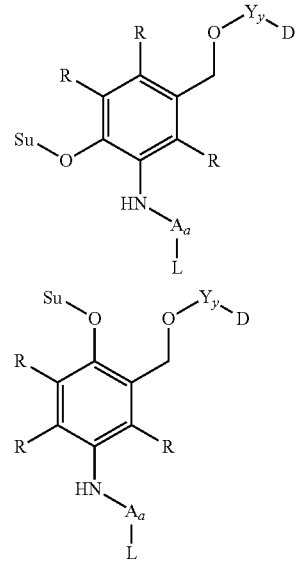

In some embodiments, an ADC comprising the glucuronide unit has the formula as depicted below (See also US 2012/0107332 A1), wherein Y, y, D, A, a, and L are defined herein.

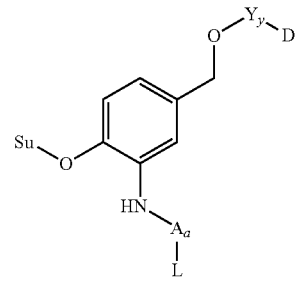

In some embodiments, an ADC comprising the Glucuronide unit has the formula as depicted below (See also US 2012/0107332 A1), wherein Y, y, D and L are defined as described herein.

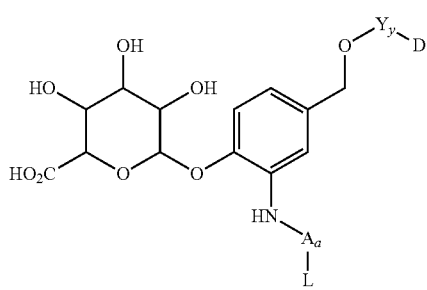

In some embodiments, an ADC comprising the Glucuronide unit has the formula as depicted below (See also US 2012/0107332 A1), wherein Y, y, D and L are defined as described herein.

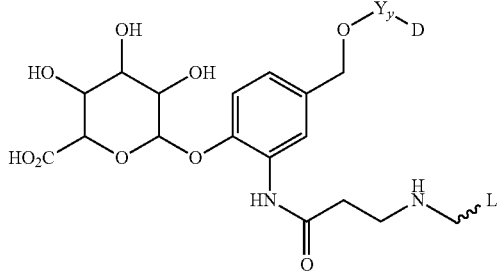

In some embodiments, an ADC comprising the Glucuronide unit has the formula as depicted below (See also US 2012/0107332 A1), wherein D is as described herein and mAb is a monoclonal antibody.

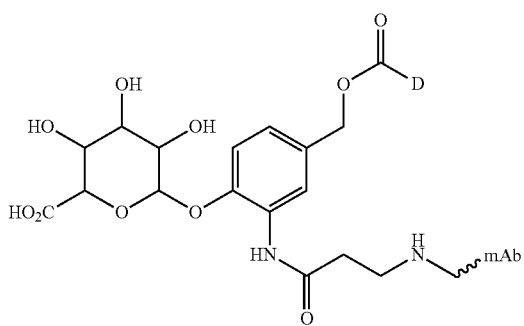

In another group of embodiments, the linker is linked (directly or indirectly) to the sugar moiety (Su), which is linked to the self-immolative group (Z) which is linked (directly or indirectly) to the drug, according to the formula as depicted below (See also US 2012/0107332 A1), wherein A, a, Su, O', Z, w, Y, y, D and L are defined as described herein.

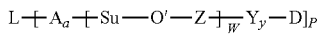

For example, the sugar moiety (Su) can be linked directly to the antibody or indirectly via a stretcher unit. The self-immolative group (Z) can be linked directly to the drug or indirectly via a spacer unit.

In related embodiments, a drug-linker compound has the following formula as depicted below (See also US 2012/0107332 A1), wherein A, a, Su, O', Z, w, Y, y and D are defined herein.

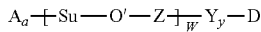

Typically from 1 to 20 of such drug-linker compounds can be linked to an antibody.

The spacer unit (—Y—), when present, links an Amino Acid unit (or Glucuronide unit, See also US 2012/0107332 A1 to the Drug unit when an Amino Acid unit is present. Alternately, the Spacer unit links the Stretcher unit to the Drug unit when the Amino Acid unit is absent. The Spacer unit also links the Drug unit to the Antibody unit when both the Amino Acid unit and Stretcher unit are absent.

Spacer units are of two general types: non self-immolative or self-immolative. A non self-immolative Spacer unit is one in which part or all of the spacer unit remains bound to the drug moiety after cleavage, particularly enzymatic, of an amino acid unit (or glucuronide unit) from the antibody-drug conjugate. Examples of a non self-immolative spacer unit include, but are not limited to a (glycine-glycine) Spacer unit and a glycine spacer unit (both depicted in Scheme 1 below (see also U.S. Pat. No. 8,309,093)).

Scheme 1

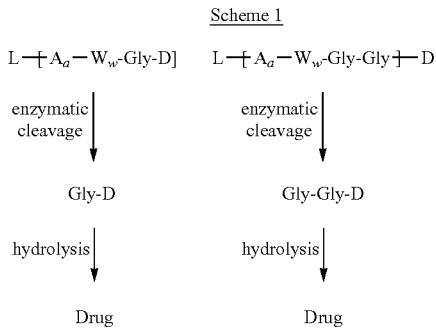

When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-drug moiety or a glycine-drug moiety is cleaved from L-$A_a$-$W_w$—. In one embodiment, an independent hydrolysis reaction takes place within the target cell, cleaving the glycine-drug moiety bond and liberating the drug.

In some embodiments, a non self-immolative spacer unit (—Y—) is -Gly-. In some embodiments, a non self-immolative spacer unit (—Y—) is -Gly-Gly-.

In one embodiment, a drug-linker conjugate is provided in which the spacer unit is absent (y=0), or a pharmaceutically acceptable salt or solvate thereof.

Alternatively, a conjugate containing a self-immolative spacer unit can release -D. As used herein, the term "self-immolative spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit whose phenylene portion is substituted with $Q_m$ wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 below (see also U.S. Pat. No. 8,309,093) depicts a possible mechanism of drug release of a PAB group which is attached directly to -D via a carbamate or carbonate group as described by Told et al., 2002, J. Org. Chem. 67:1866-1872.

Scheme 2

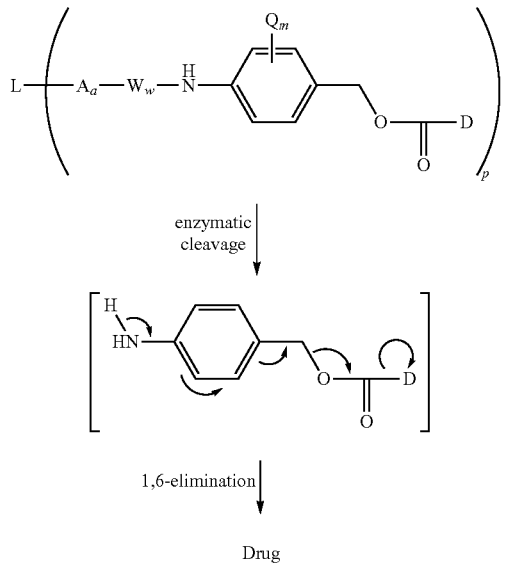

In Scheme 2, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Without being bound by any particular theory or mechanism, Scheme 3 below (see also U.S. Pat. No. 8,309,093) depicts a possible mechanism of Drug release of a PAB group which is attached directly to -D via an ether or amine linkage, wherein D includes the oxygen or nitrogen group that is part of the drug.

Scheme 3

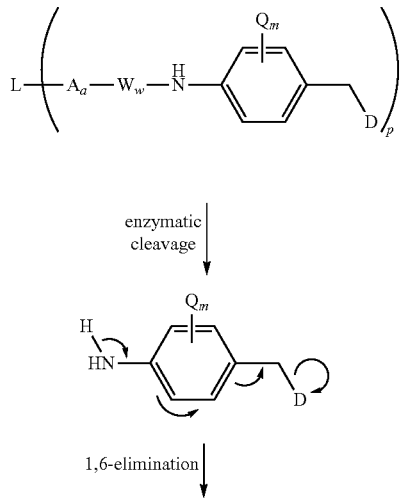

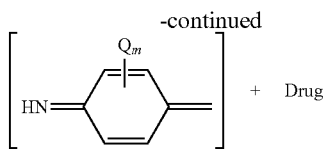

In Scheme 3, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury et al., 1984, J. Med. Chem. 27:1447) are also examples of self-immolative spacers.

In one embodiment, the spacer unit is a branched bis (hydroxymethyl)-styrene (BHMS) unit as depicted in Scheme 4 below (see also U.S. Pat. No. 8,309,093), which can be used to incorporate and release multiple drugs.

Scheme 4

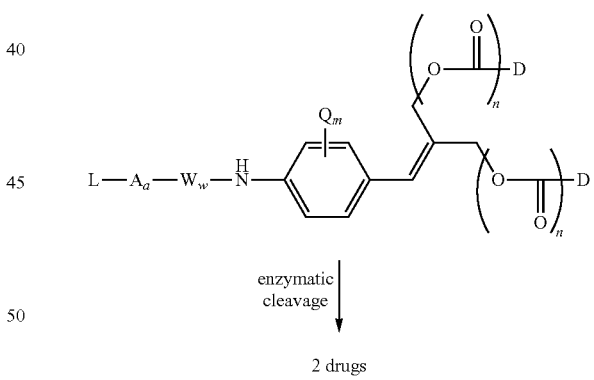

In Scheme 4 above, Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; m is an integer ranging from 0-4; n is 0 or 1; and p ranges from 1 to about 20. The alkyl, alkenyl and alkynyl groups, whether alone or as part of another group, can be optionally substituted.

In one aspect, spacer units (—$Y_y$—) are represented by Formulas (X)-(XII) (See below (see also U.S. Pat. No. 8,309,093) wherein Q is —$C_1$-$C_8$ alkyl, —$C_1$-$C_8$ alkenyl, —$C_1$-$C_8$ alkynyl, —O—($C_1$-$C_8$ alkyl), —O—($C_1$-$C_8$ alkenyl), —O—($C_1$-$C_8$ alkynyl), -halogen, -nitro or -cyano; and m is an integer ranging from 0-4.

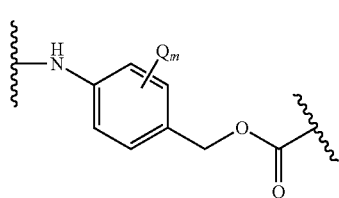

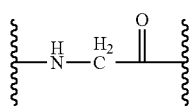

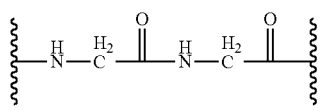

The alkyl, alkenyl and alkynyl groups, whether alone or as part of another group, can be optionally substituted.

Embodiments of the Formula I and II comprising ADCs can also include, the compound with the structure as depicted below (see also U.S. Pat. No. 8,309,093),

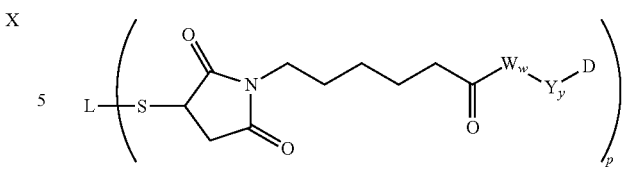

XI wherein w and y are each 0, 1 or 2, and, the compound with the structure as depicted below (see also U.S. Pat. No. 8,309,093),

XII

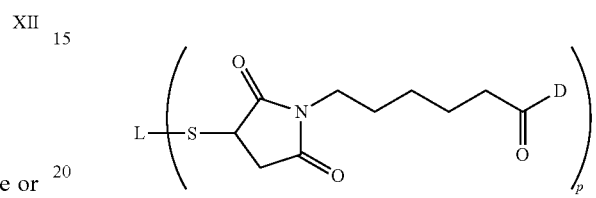

wherein w and y are each 0, and the compounds as depicted below (see also U.S. Pat. No. 8,309,093).

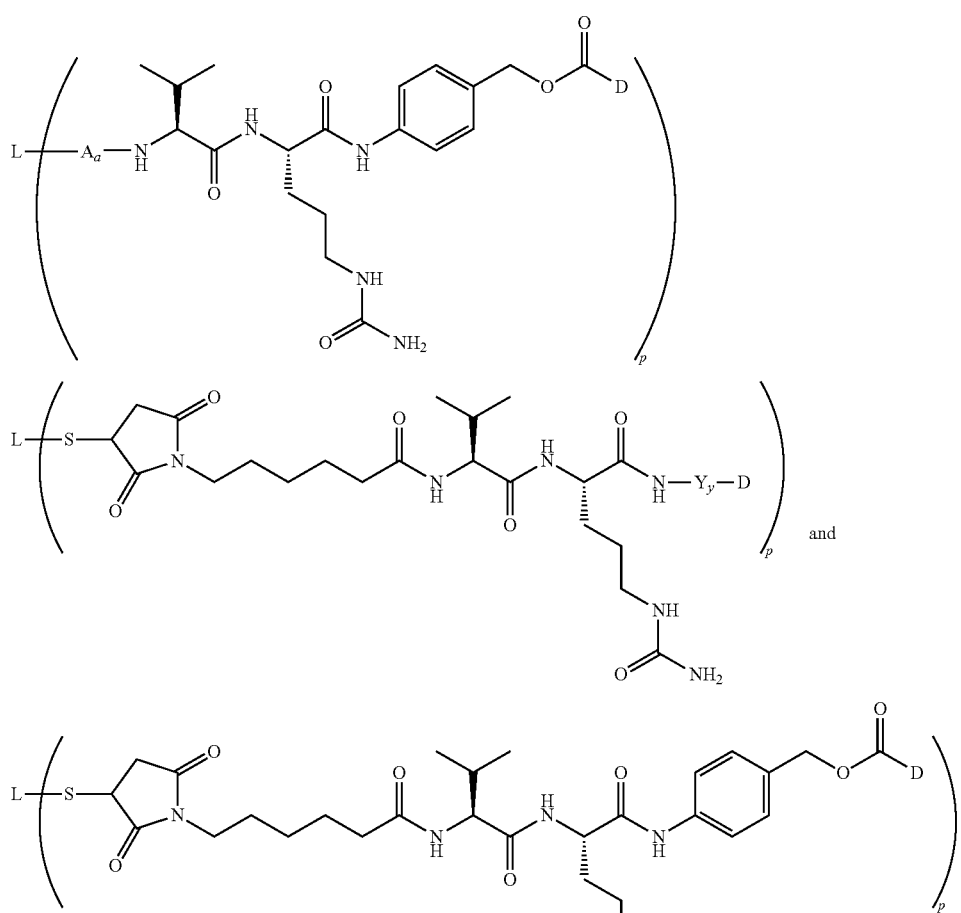

and

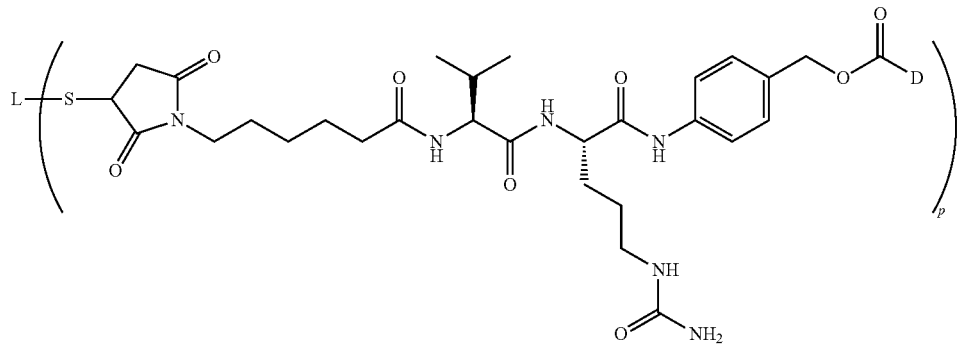

In yet other embodiments, the spacer unit (—Y—), when present, links a glucuronide unit, when present, to the drug moiety. In some embodiments, the spacer unit(s) of these embodiments are self-immolative spacers. In this context, the term "self-immolative spacer" refers to a bifunctional chemical moiety that is capable of covalently linking together two spaced chemical moieties into a normally stable tripartite molecule. It will spontaneously separate from the second chemical moiety if its bond to the first moiety is cleaved.

In some embodiments, —Y— is linked to —$W_w$— via the methylene carbon atom of the self-immolative group, and linked connected directly to -D via a carbonate, carbamate or ether group.

In some embodiments, —Yy- is a p-aminobenzyl alcohol (PAB) unit whose phenylene portion is substituted with $Q_m$ wherein Q is as defined herein, and m is an integer ranging from 0-4. In another embodiment, —$Y_y$— can be a carbonate group.

Other examples of self-immolative spacers include, but are not limited to, aromatic compounds that are electronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) and 2-aminophenylpropionic acid amides (see, e.g., Amsberry et al., 1990, *J. Org. Chem.* 55:5867). Elimination of amine-containing drugs that are substituted at the a-position of glycine (see, e.g., Kingsbury et al., 1984, *J. Med. Chem.* 27:1447) are also examples of self-immolative spacers.

Other suitable spacer units are disclosed in Published U.S. Patent Application No. 2005-0238649, the disclosure of which is incorporated by reference herein.

Another approach for the generation of ADCs involves the use of heterobifunctional cross-linkers which link the anti-PRLR antibody to the drug of interest. Preferably, the cross-linkers are N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio)butyrate (SPDB), N-succinimidyl-4-(5-nitro-2-pyridyldithio)butyrate (SNPB), and N-sulfosuccinimidyl-4-(5-nitro-2-pyridyldithio)butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio)butyrate (SCPB) or N-sulfosuccinimidyl-4-(5-N,N-dimethylcarboxamido-2-pyridyldithio)butyrate (SSCPB)). The antibodies of the present invention modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC. Preferably, the cross-linkers are compounds of the formula as depicted below (See also U.S. Pat. No. 6,913,748),

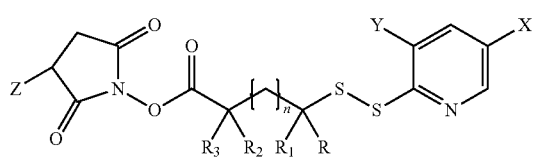

-continued

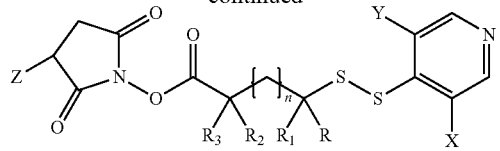

wherein R, $R_1$, $R_2$ and $R_3$ are the same or different and are H, methyl, ethyl, or linear, branched, or cyclic alkyl having 3 to 6 carbon atoms, n is 0 or an integer from 1 to 4, X and Y are the same or different and are H, $CONR_4R_5$ or $NO_2$, provided that X and Y are not both H at the same time, $R_4$ and $R_5$ are the same or different and are each H, methyl, ethyl, n-propyl, isopropyl, n-butyl, sec-butyl, iso-butyl or tert-butyl, and Z is $SO_3^-M^+$ or H, wherein $M^+$ represents a metal ion or a tetra alkyl ammonium ion, provided that when X and/or Y is $NO_2$, Z is not H. Additional heterobifunctional crosslinkers and methods of making ADCs using the same are described in U.S. Pat. No. 6,913,748, which is expressly incorporated by reference herein.

In one embodiment, charged linkers (also referred to as pro-charged linkers) are used to conjugate anti-PRLR antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319 and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

In a further embodiment, the ADC of the invention comprises a linker having the formula as depicted below (see also U.S. Pat. No. 8,236,319),

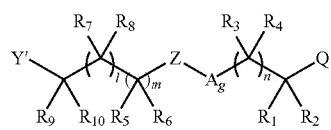

wherein Y' represents a functional group that enables reaction with an antibody; Q represents a functional group that enables linkage of a drug via a disulfide, thioether, thioester, peptide, hydrazone, ester, ether, carbamate or amide bond; $R_1$, $R_2$, $R_3$, $R_4$, $R_5$, $R_6$, $R_7$, $R_8$, $R_9$, and $R_{10}$ are the same or different and are H, linear alkyl having from 1 to 6 carbon atoms, branched or cyclic alkyl having from 3 to 6 carbon atoms, linear, branched or cyclic alkenyl or alkynyl having from 2 to 6 carbon atoms, anions, such as but not limited to, $SO_3^-$, $OPO_3^{2-}$, X—$OPO_3^{2-}$, $PO_3^{2-}$, X—$PO_3^2$, $CO_2$—, cations, such as but not limited to, a nitrogen containing heterocycle, $N^+R_{11}R_{12}R_{13}$, or X—$N^+R_{11}R_{12}R_{13}$ or a phenyl, wherein: $R_{11}$, $R_{12}$, and $R_{13}$ are the same or different and are H, linear alkyl having from 1 to 6 carbon atoms, or branched or cyclic alkyl having from 3 to 6 carbon atoms and X represents phenyl or a linear alkyl having from 1 to 6 carbon atoms, or a branched or cyclic alkyl having from 3 to 6 carbon atoms; l, m, and n are 0 or an integer from 1 to 4; A is a phenyl or substituted phenyl, wherein the substituent is a linear alkyl having from 1 to 6 carbon atoms, or a branched or cyclic alkyl having from 3 to 6 carbon atoms, or a charged substituent selected from anions, such as but not limited to, $SO_3^-$, X—$SO_3^-$, $OPO_3^{2-}$, X—$OPO_3^{2-}$, $PO_3^2$, X—$PO_3^2$, $CO_2$—, and cations, such as but not limited to, a nitrogen containing heterocycle, $N^+R_{11}R_{12}R_{13}$ or X—$N^+R_{11}R_{12}R_{13}$, wherein X has the same definition as above, and wherein g is 0 or 1; Z is an optional polyethyleneoxy unit of formula $(OCH_2CH_2)_p$ wherein p is 0 or an integer from 2 to about 1000, or F1-E1-P-E2-F2 unit in which E1 and E2 are the same or different and are C=O, O, or NR14, wherein $R_{14}$ is H, a linear alkyl having from 1 to 6 carbon atoms, a branched or cyclic alkyl having from 3 to 6 carbon atoms, a linear, branched or cyclic alkenyl or alkynyl having from 2 to 6 carbon atoms; P is a peptide unit between 2 and 20 amino acids in length, wherein E1 or E2 can be linked to the peptide through the terminal nitrogen, terminal carbon or through a side chain of one of the amino acids of the peptide; and F1 and F2 are the same or different and are an optional polyethyleneoxy unit of formula $(OCH_2CH_2)_p$, wherein p is 0 or an integer from 2 to about 1000, provided that when Z is not F1-E1-P-E2-F2, at least one of $R_1$, $R_2$, $R_3$, $R_4$, $R_5$, $R_6$, $R_7$, $R_8$, $R_9$, and $R_{10}$ is a charged substituent or when g is 1, at least one of A, $R_1$, $R_2$, $R_3$, $R_4$, $R_5$, $R_6$, $R_7$, $R_8$, $R_9$, and $R_{10}$ is a charged substituent.

Examples of the functional group, Y', that enables reaction with an antibody include amine reacting agents such as but not limited to N-hydroxysuccinmide esters, p-nitrophenyl esters, dinitrophenyl esters, pentafluorophenyl esters; thiol reactive agents such as but not limited to pyridyldisulfides, nitropyridyldisulfides, maleimides, haloacetates and carboxylic acid chlorides.

Examples of the functional group, Q, which enables linkage of a drug, include groups that enable linkage via a disulfide, thioether, thioester, peptide, hydrazone, ester, carbamate, or amide bond. Such functional groups include, but are not limited to, thiol, disulfide, amino, carboxy, aldehydes, maleimido, haloacetyl, hydrazines, and hydroxy.

Examples of linear alkyls include methyl, ethyl, propyl, butyl, pentyl and hexyl. Examples of branched or cyclic alkyls having 3 to 6 carbon atoms include isopropyl, sec-butyl, isobutyl, tert-butyl, pentyl, hexyl, cyclopropyl, cyclobutyl, cyclopentyl, and cyclohexyl.

Examples of linear alkenyls having 2 to 6 carbon atoms include ethenyl, propenyl, butenyl, pentenyl, hexenyl. Examples of branched or cyclic alkenyls having 2 to 6 carbon atoms include isobutenyl, isopentenyl, 2-methyl-1-pentenyl, 2-methyl-2-pentenyl.

Examples of linear alkynyls having 2 to 6 carbon atoms include ethynyl, propynyl, butynyl, pentynyl, hexynyl. Examples of branched or cyclic alkynyls having up to 6 carbon atoms include 3-methyl-1-butynyl, 3-methyl-1-penynyl, 4-methyl-2-hexynyl.

In one embodiment, one of $R_1$, $R_2$, $R_3$, $R_4$, $R_9$, or $R_{10}$ is a charged substituent selected from sulfonate, phosphate or trialkylammonium, and the rest are H, l, g and m are each 0, n=1, Q and Y' are each independently, a disulfide substituent, a maleimido, a haloacetyl group, or a N-hydroxy succinimide ester. In another more preferred embodiment, one of $R_1$, $R_2$, $R_3$, $R_4$, $R_9$, or $R_{10}$ is a sulfonate, and the rest are H, l, g and m are each 0, n=1, Q is a disulfide, maleimido or haloacetyl moiety, and Y' is a maleimido moiety or a N-hydroxy succinimide ester. In a further more preferred embodiment, one of $R_1$, $R_2$, $R_3$, $R_4$, $R_9$, or $R_{10}$ is a sulfonate, and the rest are H, l, g and m are each 0, n=1, Q is a pyridyldithio or nitropyridyldithio group, maleimido or haloacetyl moiety, and Y' is a N-hydroxy succinimide ester.

Additional examples of linkers that can be used with the present compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use in the present invention includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers for use in the present invention may contain a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers for use in the present invention may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317 (each of which is incorporated by reference herein in its entirety and for all purposes).

For an ADC of the invention comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

III. Uses of Anti-PRLR Antibodies

Given their ability to bind to human PRLR, the anti-human PRLR antibodies, or portions thereof, of the invention can be used to detect human PRLR (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting human PRLR in a biological sample comprising contacting a biological sample with an antibody, or antibody portion, of the invention and detecting either the antibody (or antibody portion) bound to human PRLR or unbound antibody (or antibody portion), to thereby detect human PRLR in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, $^{153}$Sm.

Alternative to labeling the antibody, human PRLR can be assayed in biological fluids by a competition immunoassay utilizing rhPRLR standards labeled with a detectable substance and an unlabeled anti-human PRLR antibody. In this assay, the biological sample, the labeled rhPRLR standards and the anti-human PRLR antibody are combined and the amount of labeled rhPRLR standard bound to the unlabeled antibody is determined. The amount of human PRLR in the biological sample is inversely proportional to the amount of labeled rhPRLR standard bound to the anti-PRLR antibody. Similarly, human PRLR can also be assayed in biological fluids by a competition immunoassay utilizing rhPRLR standards labeled with a detectable substance and an unlabeled anti-human PRLR antibody.

The antibodies and antibody portions of the invention preferably are capable of neutralizing human PRLR activity both in vitro and in vivo. Accordingly, such antibodies and antibody portions of the invention can be used to inhibit hPRLR activity, e.g., in a cell culture containing hPRLR, in human subjects or in other mammalian subjects having PRLR with which an antibody of the invention cross-reacts. In one embodiment, the invention provides a method for inhibiting hPRLR activity comprising contacting hPRLR with an antibody or antibody portion of the invention such that hPRLR activity is inhibited. For example, in a cell culture containing, or suspected of containing hPRLR, an antibody or antibody portion of the invention can be added to the culture medium to inhibit hPRLR activity in the culture.

In another embodiment, the invention provides a method for reducing hPRLR activity in a subject, advantageously from a subject suffering from a disease or disorder in which PRLR activity is detrimental. The invention provides methods for reducing PRLR activity in a subject suffering from such a disease or disorder, which method comprises administering to the subject an antibody or antibody portion of the invention such that PRLR activity in the subject is reduced. Preferably, the PRLR is human PRLR, and the subject is a human subject. Alternatively, the subject can be a mammal expressing a PRLR to which an antibody of the invention is capable of binding. Still further the subject can be a mammal into which PRLR has been introduced (e.g., by administration of PRLR or by expression of a PRLR transgene). An antibody of the invention can be administered to a human subject for therapeutic purposes. Moreover, an antibody of the invention can be administered to a non-human mammal expressing a PRLR with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which PRLR activity is detrimental" is intended to include diseases and other disorders in which the presence of PRLR in a subject suffering from the disorder has been shown to be or is suspected of being either responsible for the pathophysiology of the disorder or a factor that contributes to a worsening of the disorder. Accordingly, a disorder in which PRLR activity is detrimental is a disorder in which reduction of PRLR activity is expected to alleviate the symptoms and/or progression of the disorder. Such disorders may be evidenced, for example, by an increase in the concentration of PRLR in a biological fluid of a subject suffering from the disorder (e.g., an increase in the concentration of PRLR in serum, plasma, synovial fluid, etc. of the subject), which can be detected, for example, using an anti-PRLR antibody as described above. Non-limiting examples of disorders that can be treated with the antibodies of the invention, for example, Ab1, Ab2, Ab3, Ab4, Ab5, chAb5, Ab6, chAb6, Ab7, chAb7, Ab8, chAb8, Ab9, chAb9, Ab10, chAb10, Ab11, chAb11, Ab13, chAb13, Ab14, Ab15, Ab16, Ab17, Ab18, Ab19, Ab20, Ab21, Ab22, Ab23, Ab24, Ab25, Ab26, Ab27, Ab28, Ab29, Ab30, Ab31, Ab32, Ab33, Ab34, Ab35, Ab36, Ab37, Ab38, Ab39, Ab40, Ab41, Ab42, Ab43, Ab44, Ab45, Ab46, Ab47, Ab48, Ab49, Ab50, Ab51, Ab52, Ab53, Ab54 or Ab55, variants thereof, or antigen binding fragments thereof, include those disorders discussed in the section below pertaining to pharmaceutical compositions of the antibodies of the invention. For example, suitable disorders include, but are not limited to, a variety of cancers including, but not limited to, melanoma, lymphoma, breast cancer, ovarian cancer, renal carcinoma, gastrointestinal cancer, colon cancer, lung cancer, pancreatic cancer, endometrial cancer and prostate cancer. In particular embodiments, the cancer is breast cancer, renal cancer, prostate cancer, ovarian cancer, endometrial cancer or lung cancer. In a particular embodiment, the cancer is breast cancer. In a particular embodiment, the cancer is prostate cancer.

In another embodiment, the present invention is directed to treatment of "a disorder associated with underexpression or reduced activity of PRLR." As used herein the term "a disorder associated with underexpression or reduced activity of PRLR" is intended to include diseases and other disorders in which the underexpression or reduced activity of PRLR has been shown to be or is suspected of being either responsible for the pathophysiology of the disorder or a factor that contributes to a worsening of the disorder. Accordingly, increasing the activity of PRLR activity is expected to alleviate the symptoms and/or progression of these disorders. Such disorders may be evidenced, for example, by a decrease in the concentration of PRLR in a biological fluid of a subject suffering from the disorder (e.g., a decrease in the concentration of PRLR in serum, plasma, synovial fluid, etc. of the subject), which can be detected, for example, using an anti-PRLR antibody as described above. Non-limiting examples of disorders that can be treated with the antibodies of the invention, for example, Ab12, chAb12 variants thereof, or antigen binding fragments thereof, include enhancing mammary development or increasing lactation.

IV. Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which PRLR activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397, Cleek et al., 1997, "Biodegradable Polymeric Carriers for a bFGF Antibody for Cardiovascular Application," *Pro. Int'l. Symp. Control. Rel. Bioact. Mater.* 24:853-854, and Lam et al., 1997, "Microencapsulation of Recombinant Humanized Monoclonal Antibody for Local Delivery," *Proc. Intl. Symp. Control Rel. Bioact. Mater.* 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5, 985,309, 5,934, 272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion).

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In other embodiments, an antibody or antibody portion of the invention may be conjugated to a polymer-based species such that said polymer-based species may confer a sufficient size upon said antibody or antibody portion of the invention such that said antibody or antibody portion of the invention benefits from the enhanced permeability and retension effect (EPR effect) (See also PCT Publication No. WO2006/042146A2 and U.S. Publication Nos. 2004/0028687A1, 2009/0285757A1, and 2011/0217363A1, and U.S. Pat. No. 7,695,719 (each of which is incorporated by reference herein in its entirety and for all purposes).

Supplementary active compounds can also be incorporated into the compositions. In certain embodiments, an antibody or antibody portion of the invention is formulated with and/or co-administered with one or more additional therapeutic agents that are useful for treating disorders in which PRLR activity is detrimental. For example, an anti-hPRLR antibody or antibody portion of the invention may be formulated and/or co-administered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to PRLR or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley &Sons, NY (1993); and Kriegler, Gene Transfer and Expression, A Laboratory Manual, Stockton Press, NY (1990). Detailed description of various methods of gene therapy is provided in US20050042664 A1 which is incorporated herein by reference.

In another aspect, this application features a method of treating (e.g., curing, suppressing, ameliorating, delaying or preventing the onset of, or preventing recurrence or relapse of) or preventing a PRLR-associated disorder, in a subject. The method includes: administering to the subject a PRLR binding agent (particularly an antagonist), e.g., an anti-PRLR antibody or fragment thereof as described herein, in an amount sufficient to treat or prevent the PRLR-associated disorder. The PRLR antagonist, e.g., the anti-PRLR antibody or fragment thereof, can be administered to the subject, alone or in combination with other therapeutic modalities as described herein.

In another aspect, this application provides a method for detecting the presence of PRLR in a sample in vitro (e.g., a biological sample, such as serum, plasma, tissue, biopsy). The subject method can be used to diagnose a disorder, e.g., a cancer. The method includes: (i) contacting the sample or a control sample with the anti-PRLR antibody or fragment thereof as described herein; and (ii) detecting formation of a complex between the anti-PRLR antibody or fragment thereof, and the sample or the control sample, wherein a statistically significant change in the formation of the complex in the sample relative to the control sample is indicative of the presence of PRLR in the sample.

In yet another aspect, this application provides a method for detecting the presence of PRLR in vivo (e.g., in vivo imaging in a subject). The subject method can be used to diagnose a disorder, e.g., a PRLR-associated disorder. The method includes: (i) administering the anti-PRLR antibody or fragment thereof as described herein to a subject or a control subject under conditions that allow binding of the antibody or fragment to PRLR; and (ii) detecting formation of a complex between the antibody or fragment and PRLR, wherein a statistically significant change in the formation of the complex in the subject relative to the control subject is indicative of the presence of PRLR.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition, e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more PRLR antagonists, e.g., anti-PRLR antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-PRLR binding proteins described herein, for example, anti-PRLR antibodies, are used in combination with an anti-cancer agent or an antineoplastic agent. The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone. Anti-cancer agents that may be used in conjunction with the anti-PRLR antibodies of the present invention include, among others, the following agents:

| Anti-Cancer Agent | Comments | Examples |
|---|---|---|
| Antibodies (a) antibodies other than anti-PRLR antibodies; and (b) anti-PRLR antibodies which bind different epitopes | Antibodies which bind IGF-1R (insulin-like growth factor type 1 receptor), which is expressed on the cell surface of most human cancers | A12 (fully humanized mAb) 19D12 (fully humanized mAb) Cp751-871 (fully humanized mAb) H7C10 (humanized mAb) alphaIR3 (mouse) ScFV/FC (mouse/human chimera) EM/164 (mouse) |
| | Antibodies which bind EGFR (epiderman growth factor receptor); Mutations affecting EGFR expression or activity could result in cancer | Matuzumab (EMD72000) Erbitux ®/Cetuximab (Imclone) Vectibix ®/Panitumumab (Amgen) mAb 806 Nimotuxumab (TheraCIM) |
| | Antibodies which bind cMET (Mesechymal epithelial transition factor); a member of the MET family of receptor tyrosine kinases) | AVEO (AV299) (AVEO) AMG102 (Amgen) 5D5 (OA-5d5) (Genentech) H244G11 (Pierre Fabre) |
| | Anti-ErbB3 antibodies which bind different epitopes | Ab #14 (MM 121-14) Herceptin ® (Trastuzumab; Genentech) 1B4C3; 2D1D12 (U3 Pharma AG) |
| Small Molecules Targeting IGF1R | Insulin-like growth factor type 1 receptor which is expressed on the cell surface of many human cancers | NVP-AEW541-A BMS-536,924 (1H-benzoimi-dazol-2-yl)-1H-pyridin-2-one) BMS-554,417 Cycloligan TAE226 PQ401 |
| Small Molecules Targeting EGFR | EGFR (epiderman growth factor receptor); Overexpression or mutations affecting EGFR expression or activity could result in cancer | Iressa ®/Gefitinib (AstraZeneca) CI-1033 (PD 183805) (Pfizer) Lapatinib (GW-572016) (GlaxoSmithKline) Tykerb ®/Lapatinib Ditosylate (Smith Kline Beecham) Tarceva ®/Erlotinib HCL (OSI-774) (OSI Pharma) PKI-166 (Novartis) PD-158780 EKB-569 Tyrphostin AG 1478 (4-(3-Chloroanillino)-6,7-dimethoxyquinazoline) |
| Small Molecules Targeting cMET | cMET (Mesenchymal epithelial transition factor); a member of the MET family of receptor tyrosine kinases) | PHA665752 ARQ 197 |
| Antimetabolites | | Flourouracil (5-FU) Capecitabine/XELODA ® (HLR Roche) 5-Trifluoromethyl-2'-deoxyuridine Methotrexate sodium (Trexall) (Barr) Raltitrexed/Tomudex ® (AstraZeneca) Pemetrexed/Alimta ® (Lilly) Tegafur Cytosine Arabinoside (Cytarabine, Ara-C)/Thioguanine ® (GlaxoSmithKline) |

-continued

| Anti-Cancer Agent | Comments | Examples |
|---|---|---|
| | | 5-azacytidine |
| | | 6-mercaptopurine (Mercaptopurine, 6-MP) |
| | | Azathioprine/Azasan ® (AAIPHARMA LLC) |
| | | 6-thioguanine (6-TG)/Purinethol ® (TEVA) |
| | | Pentostatin/Nipent ® (Hospira Inc.) |
| | | Fludarabine phosphate/Fludara ® (Bayer Health Care) |
| | | Cladribine (2-CdA, 2-chloro-deoxyadenosine)/Leustatin ® (Ortho Biotech) |
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | Ribonucleotide Reductase Inhibitor (RNR) Cyclophosphamide/Cytoxan (BMS) Neosar (TEVA) Ifosfamide/Mitoxana ® (ASTA Medica) Thiotepa (Bedford, Abraxis, Teva) BCNU→ 1,3-bis(2-chloroethyl)-1-nitrosourea CCNU→ 1,-(2-chloroethyl)-3-cyclohexyl-1-nitrosourea (methyl CCNU) Hexamethylmelamine (Altretamine, HMM)/Hexalen ® (MGI Pharma Inc.) Busulfan/Myleran (GlaxoSmithKline) Procarbazine HCL/Matulane (Sigma Tau Pharmaceuticals, Inc.) Dacarbazine (DTIC) Chlorambucil/Leukara ® (SmithKline Beecham) Melphalan/Alkeran ® (GlaxoSmithKline) Cisplatin (Cisplatinum, CDDP)/ Platinol (Bristol Myers) Carboplatin/Paraplatin (BMS) Oxaliplatin/Eloxitan ® (Sanofi-Aventis US) |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | Doxorubicin HCL/Doxil ® (Alza) Daunorubicin citrate/Daunoxome ® (Gilead) Mitoxantrone HCL/Novantrone (EMD Serono) Actinomycin D Etoposide/Vepesid ® (BMS)/Etopophos ® (Hospira, Bedford, Teva Parenteral, Etc.) Topotecan HCL/Hycamtin ® (GlaxoSmithKline) Teniposide (VM-26)/Vumon ® (BMS) Irinotecan HCL(CPT-ll)/Camptosar ® (Pharmacia & Upjohn) |
| Microtubule targeting agents | Microtubules are one of the components of the cytoskeleton. They have diameter of ~24 nm and length varying from several micrometers to possibly millimeters in axons of nerve cells. Microtubules serve as structural components within cells and are involved in many cellular processes including mitosis, cytokinesis, and vesicular transport. | Vincristine/Oncovin ® (Lilly) Vinblastine sulfate/Velban ® (discontinued) (Lilly) Vinorelbine tartrate/Navelbine ® (PierreFabre) Vindesine sulphate/Eldisine ® (Lilly) Paclitaxel/Taxol ® (BMS) Docetaxel/Taxotere ® (Sanofi Aventis US) Nanoparticle paclitaxel (ABI-007)/Abraxane ® (Abraxis BioScience, Inc.) Ixabepilone/IXEMPRA ™ (BMS) |
| Kinase inhibitors | Tyrosine kinases are enzymes within the cell that function to attach phosphate groups to the amino acid tyrosine. By blocking the ability of protein tyrosine kinases to function, these compounds provide a tool for controlling cancerous cell growth. | Imatinib mesylate/Gleevec (Novartis) Sunitinib malate/Sutent ® (Pfizer) Sorafenib toslate/Nexavar ® (Bayer) Nilotinib hydrochloride monohydrate/Tasigna ® (Novartis) |
| Protein synthesis inhibitors | Induces cell apoptosis | L-asparaginase/Elspar ® (Merck & Co.) |
| Immuno-therapeutic agents | Induces cancer patients to exhibit immune responsiveness | Alpha interferon Angiogenesis Inhibitor/Avastin ® (Genentech) IL-2→ Interleukin 2 (Aldesleukin)/Proleukin ® (Chiron) IL-12→ Interleukin 12 |
| Hormones | Hormone therapies associated with menopause and aging seek to increase the amount of certain hormones in your body to compensate for age- or disease-related hormonal declines. Hormone therapy as a cancer treatment either reduces the level of specific hormones or alters the cancer's ability to use these hormones to grow and spread. | Toremifene citrate/Fareston ® (GTX, Inc.) Fulvestrant/Faslodex ® (AstraZeneca) Raloxifene HCL/Evista ® (Lilly) Anastrazole/Arimidex ® (AstraZeneca) Letrozole/Femara ® (Novartis) Fadrozole (CGS 16949A) Exemestane/Aromasin ® (Pharmacia & Upjohn) Leuprolide acetate/Eligard ® (QTL USA) Lupron ® (TAP Pharm) Goserelin acetate/Zoladex ® (AstraZeneca) Triptorelin pamoate/Trelstar ® (Watson Labs) Buserelin/Suprefact ® (Sanofi Aventis) Nafarelin Cetrorelix/Cetrotide ® (EMD Serono) Bicalutamide/Casodex ® (AstraZeneca) Nilutamide/Nilandron ® (Aventis Pharm.) Megestrol acetate/Megace ® (BMS) Somatostatin Analogs (Octreotide acetate/Sandostatin ® (Novartis) |
| Glucocorticoids | Anti-inflammatory drugs used to reduce swelling that causes cancer pain. | Predinsolone Dexamethasone/Decadron ® (Wyeth) |
| Aromatose inhibitors | Includes imidazoles | Ketoconazole |
| mTOR inhibitors | the mTOR signaling pathway was originally discovered during studies of the immunosuppressive agent | Sirolimus (Rapamycin)/Rapamune ® (Wyeth) Temsirolimus (CCI-779)/Torisel ® (Wyeth) Deforolimus (AP23573)/(Ariad |

| Anti-Cancer Agent | Comments | Examples |
|---|---|---|
| | rapamycin. This highly conserved pathway regulates cell proliferation and metabolism in response to environmental factors, linking cell growth factor receptor signaling via phosphoinositide-3-kinase(PI-3K) to cell growth, proliferation, and angiogenesis. | Pharm.) Everolimus (RAD00I)/ Certican ® (Novartis) |

In addition to the above anti-cancer agents, the anti-PRLR antibodies described herein may be administered in combination with the agents described in section II. Further, the aforementioned anti-cancer agents may also be used in the ADCs of the invention.

In particular embodiments, the anti-PRLR antibodies can be administered alone or with another anti-cancer agent which acts in conjunction with or synergistically with the antibody to treat the disease associated with PRLR activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof of the present invention.

Further examples of preferred additional therapeutic agents that can be co-administered and/or formulated with one or more PRLR antagonists, e.g., anti-PRLR antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be co-administered and/or formulated with one or more anti-PRLR antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade; preferred examples include TNF antagonists like chimeric, humanized or human TNF antibodies, adalimumab, (HUMIRA; D2E7; PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1

Generation and Isolation of Anti Human PRLR Monoclonal Antibodies

1. Humanization of PRLR Antibodies
1.1 Human Germline Sequence Selections for Constructing CDR-Grafted, Humanized PRLR Antibodies By applying the humanization methodology, the CDR sequences of VH and VL chains of monoclonal antibodies Ab5, Ab6, Ab7 and Ab8 were grafted onto different human heavy and light chain acceptor sequences as follows:
1.1.1 Ab6

Ab1 refers to humanized antibodies derived from murine Ab6. Based on the alignments with the VH and VL sequences of monoclonal antibody Ab6 of the present invention, the following known human sequences were selected:
 1. IGHV1-69*02 and IGHJ6*01 for constructing heavy chain acceptor sequences
 2. IGKV1-12*01 or IGKV3-15*01 and IGKJ4*01 for constructing light chain acceptor sequences By grafting the corresponding VH and VL CDRs of Ab6 into said acceptor sequences, the CDR-grafted, humanized, and modified VH and VL sequences were prepared.
1.1.2 Ab5

Ab2 refers to humanized antibodies derived from murine Ab5. Based on the alignments with the VH and VL sequences of monoclonal antibody Ab5 of the present invention, the following known human sequences were selected:
 1. IGHV1-69*01 and IGHJ4*01 for constructing heavy chain acceptor sequences
 2. IGKV2-29*02 and IGKJ4*01 for constructing light chain acceptor sequences By grafting the corresponding VH and VL CDRs of Ab5 into said acceptor sequences, the CDR-grafted, humanized, and modified VH and VL sequences were prepared.
1.1.3 Ab8

Ab3 refers to humanized antibodies derived from murine Ab8. Based on the alignments with the VH and VL sequences of monoclonal antibody Ab8 of the present invention the following known human sequences were selected:
 1. IGHV1-18*01 and IGHJ6*01 for constructing heavy chain acceptor sequences
 2. IGKV1D-39*01 and IGKJ2*01 for constructing light chain acceptor sequences By grafting the corresponding VH and VL CDRs of Ab8 into said acceptor sequences, the CDR-grafted, humanized, and modified VH and VL sequences were prepared.
1.1.4 Ab7

Ab4 refers to humanized antibodies derived from murine Ab7. Based on the alignments with the VH and VL sequences of monoclonal antibody Ab7 of the present invention the following known human sequences were selected:
 1. IGHV1-69*06 and IGHJ4*01 for constructing heavy chain acceptor sequences
 2. IGKV2-29*02 and IGKJ4*01 for constructing light chain acceptor sequences By grafting the corresponding VH and VL CDRs of Ab7 into said acceptor sequences, the CDR-grafted, humanized, and modified VH and VL sequences were prepared.
1.2 Introducing Potential Framework Back-Mutations in CDR-Grafted Antibodies To generate humanized antibody with potential framework back-mutations, the mutations were identified and introduced into the CDR-grafted antibody sequences by de novo synthesis of the variable domain, or mutagenic oligonucleotide primers and polymerase chain reactions, or both by methods well known in the art. Different combinations of back mutations and other mutations were constructed for each of the CDR-grafts as follows. Residue numbers for these mutations were based on the Kabat numbering system.
1.2.1 Ab1

For heavy chains Ab1VH.1z, one or more of the following residues were back mutated as follows: M48→I, V67→A, I69→L, and A71→V. Additional mutations included the following: Q1→E, Y27→G, N60→A, K64=Q, and D65→G.

For light chain Ab1VL.1, one or more of the following residues were back mutated as follows: A43→S, G64→D, and Y87→F.
1.2.2 Ab2

For heavy chains Ab2VH.1z, one or more of the following residues were back mutated as follows: M48→I, V67→A, I69→L, A71→V, and T75→S. Additional mutations included the following: Q1→E, Y27→G, N60→A, and K64→Q.

For light chain Ab2VL.1, one or more of the following residues were back mutated as follows: I2→V and Y87→F.
1.2.3 Ab3

For heavy chains Ab3VH.1z, one or more of the following residues were back mutated as follows: M48→I, V67→A, M69→L, T71→V, and T73→N. Additional mutations included the following: Q1→E, N60→A, F63→L, K64→Q, and S65→G.

For light chain Ab3VL.1, one or more of the following residues were back mutated as follows: A43→P and I48→V.
1.2.4 Ab4

For heavy chains Ab4 VH.1z, one or more of the following residues were back mutated as follows: M48→I, V67→A, I69→L, A71→V, K73→R, T75→S, and A93→G. Additional mutations included the following: Q1→E.

For light chain Ab4 VL.1, one or more of the following residues were back mutated as follows: I2→V and Y87→F.
1.3 Generation of Humanized Antibodies to PRLR Containing Framework Back-Mutations in CDR-Grafted Antibodies The following humanized variable regions of the murine monoclonal PRLR antibodies were cloned into IgG expression vectors for functional characterization.

1.3.1 Ab1

TABLE 9

Sequences of humanized variable regions for Ab1 antibody

| SEQ ID NO: | Protein region | Sequence 1234567890123456789012345678901234567890 |
|---|---|---|
| 39 | Ab1 VH.1z | QVQLVQSGAEVKKPGSSVKVSCKASGYTFTTYWM HWVRQAPGQGLEWMGEIDPSDSYSNYNQKFKDRV TITADKSTSTAYMELSSLRSEDTAVYYCARNGGL GPAWFSYWGQGTLVTVSS |
| 43 | Ab1 VH1.1 | EVQLVQSGAEVKKPGSSVKVSCKASGYTFTTYWM HWVRQAPGQGLEWMGEIDPSDSYSNYNQKFKDRV TITADKSTSTAYMELSSLRSEDTAVYYCARNGGL GPAWFSYWGQGTLVTVSS |
| 44 | Ab1 VH.1a | EVQLVQSGAEVKKPGSSVKVSCKASGYTFTTYWM HWVRQAPGQGLEWIGEIDPSDSYSNYNQKFKDRA TLTVDKSTSTAYMELSSLRSEDTAVYYCARNGGL GPAWFSYWGQGTLVTVSS |
| 45 | Ab1 VH.1b | EVQLVQSGAEVKKPGSSVKVSCKASGGTFTTYWM HWVRQAPGQGLEWIGEIDPSDSYSNYAQKFQGRV TITVDKSTSTAYMELSSLRSEDTAVYYCARNGGL GPAWFSYWGQGTLVTVSS |
| 48 | Ab1 VL.1 | DIQMTQSPASLSASVGDTVTITCKASQYVGT AVAWYQQKPGKPPQLLIYSASNRYTGVPSRF SGGGSGTDFFTLISSLQPEDFATYYCQQYSS YPWTFGGGTKVEIK |
| 52 | Ab1 VL.1a | DIQMTQSPASLSASVGDTVTITCKASQYVGT AVAWYQQKPGK<u>S</u>PKLLIYSASNRYTGVPSRF SDSGSGTDFTLTISSLQPEDFATY<u>F</u>CQQYSS YPWTFGGGTKVEIK |
| 53 | Ab1 VL.2 | EIVMTQSPATLSVSPGERATLSCKASQYVGT AVAWYQQKPGQAPRLLIYSASNRYTGIPARF SGGGSGTEFTLTISSLQSEDFAVYYCQQYSS YPWTFGGGTKVEIK |
| 54 | Ab1 VL.2a | EIVMTQSPATLSVSPGERATLSCKASQYVGT AVAWYQQKPGQ<u>S</u>PRLLIYSASNRYTGVPARF SDSGSGTEFTLTISSLQSEDFAVY<u>F</u>CQQYSS YPWTFGGGTKVEIK |

Ab1 VH.1z is a CDR-grafted, humanized Ab6 VH containing IGHV1-69*02 and IGHJ6*01 framework sequences.

Ab1 VH.1 is based on .1z with a Q1E change.

Ab1 VH.1a is a humanized design based on .1 and contains four proposed framework back-mutations M48I, V67A, I69L, and A71V.

Ab1 VH.1b is an intermediate design between .1 and .1a and only has two back-mutations M48I and A71V. It also has four CDR human germlining changes Y27G, N60A, K64Q, and D65G.

Ab1 VL.1 is a CDR-grafted humanized Ab6 VL containing IGKV1-12*01 and IGKJ4*01 framework sequences.

Ab1 VL.1a is a humanized design based on .1 with 3 proposed framework back-mutations (A43S, G64D, and Y87F).

Ab1 VL.2 is a CDR-grafted humanized Ab6 VL containing IGKV3-15*01 and IGKJ4*01 framework sequences.

Ab1 VL.2a is a humanized design based on .1 with 4 proposed framework back-mutations (A43S, I8V, G64D, and Y87F).

1.3.2 Ab2

TABLE 10

Sequences of humanized variable regions for Ab2 Antibody

| SEQ ID NO: | Protein region | Sequence 1234567890123456789012345678901234567890 |
|---|---|---|
| 55 | Ab2 VH.1z | QVQLVQSGAEVKKPGSSVKVSCKASGYTFTSFWM HWVRQAPGQGLEWMGVIDPSDTYTNYNQKFKGRV TITADESTSTAYMELSSLRSEDTAVYYCARGDYS NWFTYWGQGTLVTVSS |
| 59 | Ab2 VH.1 | EVQLVQSGAEVKKPGSSVKVSCKASGYTFTSFWM HWVRQAPGQGLEWMGVIDPSDTYTNYNQKFKGRV TITADESTSTAYMELSSLRSEDTAVYYCARGDYS NWFTYWGQGTLVTVSS |
| 60 | Ab2 VH.1a | EVQLVQSGAEVKKPGSSVKVSCKASGYTFTSFWM HWVRQAPGQGLEWIGVIDPSDTYTNYNQKFKGRA TLTADESSSTAYMELSSLRSEDTAVYYCARGDYS NWFTYWGQGTLVTVSS |
| 61 | Ab2 VH.1b | EVQLVQSGAEVKKPGSSVKVSCKASGGTFTSFWM HWVRQAPGQGLEWIGVIDPSDTYTNYAQKFKGRV TITADESTSTAYMELSSLRSEDTAVYYCARGDYS NWFTYWGQGTLVTVSS |
| 64 | Ab2 VL.1 | DIVMTQTPLSLSVTPGQPASTSCRSSQRLVH SNGNTYLHWYLQKPGQSPQLLIYKVSNRFSG VPDRFSGSGSGTDFTLKISRVEAEDVGVYYC SQSTHVPWTFGGGTKVEIK |
| 68 | Ab2 VL.1a | DVVMTQTPLSLSVTPGQPASTSCRSSQRLVH SNGNTYLHWYLQKPGQSPQLLIYKVSNRFSG VPDRFSGSGSGTDFTLKISRVEAEDVGVYFC SQSTHVPWTFGGGTKVEIK |
| 69 | Ab2 VL.1b | DVVMTQTPLSLSVTPGQPASTSCRSSQRLVH SNGNTYLHWYLQKPGQSPQLLIYKVSNRFSG VPDRFSGSGSGTDFTLKISRVEAEDVGVYYC SQSTHVPWTFGGGTKVEIK |

Ab2 VH.1z is a CDR-grafted, humanized Ab5 VH containing IGHV1-69*01 and IGHJ4*01 framework sequences.

Ab2 VH.1 is based on .1z with a Q1E change.

Ab2 VH.1a is a humanized design based on .1 and contains five proposed framework back-mutations M48I, V67A, I69L, A71V, and T75S.

Ab2 VH.1b is an intermediate design between .1 and .1a and only has two back-mutations M48I and A71V. It also has three CDR human germlining changes Y27G, N60A, and K64Q.

Ab2VL.1 is a CDR-grafted humanized Ab5 VL containing IGKV2-29*02 and IGKJ4*01 framework sequences.

Ab2 VL.1a is a humanized design based on .1 with 2 proposed framework back-mutations (I2V and Y87F).

Ab2 VL.1b is an intermediate design between .1 and .1a with 1 proposed framework back-mutation I2V.

1.3.3 Ab3

TABLE 11

Sequences of humanized variable regions for Ab3 Antibody

| SEQ ID NO: | Protein region | Sequence 1234567890123456789012345678901234567890 |
|---|---|---|
| 70 | Ab3 VH.1z | QVQLVQSGAEVKKPGASVKVSCKASGYTFTDYNI HWVRQAPGQGLEWMGYIYPNNDGTGYNQKFKSRV |

TABLE 11 -continued

Sequences of humanized variable regions for Ab3 Antibody

| SEQ ID NO: | Protein region | Sequence 12345678901234567890123456789 0 |
|---|---|---|
| | | TMTTDTSTSTAYMELRSLRSDDTAVYYCARGDGN YVGDMDYWGQGTTVTSS |
| 74 | Ab3 VH.1 | EVQLVQSGAEVKKPGASVKVSCKASGYTFTDYNI HWVRQAPGQGLEWMGYIYPNNDGTGYNQKFKSRV TMTTDTSTSTAYMELRSLRSDDTAVYYCARGDGN YVGDMDYWGQGTTVTSS |
| 75 | Ab3 VH.1a | EVQLVQSGAEVKKPGASVKVSCKASGYTFTDYNI HWVRQAPGQGLEWIGYIYPNNDGTGYNQKFKSRA TLTVDNSTSTAYMELRSLRSDDTAVYYCARGDGN YVGDMDYWGQGTTVTSS |
| 76 | Ab3 VH.1b | EVQLVQSGAEVKKPGASVKVSCKASGYTFTDYNI HWVRQAPGQGLEWIGYIYPNNDGTGYAQKLQGRV TMTVDTSTSTAYMELRSLRSDDTAVYYCARGDGN YVGDMDYWGQGTTVTSS |
| 78 | Ab3 VL.1 | DIQMTQTPSSLSASVGDRVTITCRASENIYS YLAWYQQKPGKAPKLLIYNAKTLAEGVPSRF SGSGSGTDFTLTISSLQPEDFATYYCQHHYA TPFTFGQGTKLEIK |
| 82 | Ab3 VL.1a | DIQMTQTPSSLSASVGDRVTITCRASENIYS YLAWYQQKPGKPPKLLVYNAKTLAEGVPSRF SGSGSGTDFTLTISSLQPEDFATYYCQHHYA TPFTFGQGTKLEIK |
| 83 | Ab3 VL.1b | DIQMTQTPSSLSASVGDRVTITCRASENIYS YLAWYQQKPGKAPKLLVYNAKTLAEGVPSRF SGSGSGTDFTLTISSLQPEDFATYYCQHHYA TPFTFGQGTKLEIK |

Ab3 VH.1z is a CDR-grafted, humanized Ab8 VH containing IGHV1-18*01 and IGHJ6*01 framework sequences.

Ab3 VH.1 is based on .1z with a Q1E change.

Ab3 VH.1a is a humanized design based on .1 and contains five proposed framework back-mutations M48I, V67A, M69L, T71V, and T73N.

Ab3 VH.1b is an intermediate design between .1 and .1a and only has two back-mutations M48I and T71V. It also has four HCDR2 human germlining changes N60A, F63L, K64Q, and S65G.

Ab3 VL.1 is a CDR-grafted humanized Ab8 VL containing IGKV1D-39*01 and IGKJ2*01 framework sequences.

Ab3 VL.1a is a humanized design based on .1 with 2 proposed framework back-mutations (A43P and I48V).

Ab3 VL.1b is an intermediate design between .1 and .1a with 1 proposed framework back-mutation I48V.

1.3.4 Ab4

TABLE 12

Sequences of humanized variable regions for Ab4 antibody

| SEQ ID NO: | Protein region | Sequence 12345678901234567890123456789 0 |
|---|---|---|
| 84 | Ab4 VH.1z | QVQLVQSGAEVKKPGSSVKVSCKASGYTFTSYWI HWVRQAPGQGLEWMGEIDPSDSYTNYNQKFKGRV TITADKSTSTAYMELSSLRSEDTAVYYCARSFFT NWFAYWGQGTLVTSS |
| 88 | Ab4 VH.1 | EVQLVQSGAEVKKPGSSVKVSCKASGYTFTSYWI HWVRQAPGQGLEWMGEIDPSDSYTNYNQKFKGRV TITADKSTSTAYMELSSLRSEDTAVYYCARSFFT NWFAYWGQGTLVTSS |
| 89 | Ab4 VH.1a | EVQLVQSGAEVKKPGSSVKVSCKASGYTFTSYWI HWVRQAPGQGLEWIGEIDPSDSYTNYNQKFKGRA TLTVDKSSSTAYMELSSLRSEDTAVYYCARSFFT NWFAYWGQGTLVTSS |
| 121 | Ab4 VH.1a.2 | EVQLVQSGAEVKKPGSSVKVSCKASGYTFTSYWI HWVRQAPGQGLEWIGEIDPSDSYTNYNQKFKGRA TLTVDRSSSTAYMELSSLRSEDTAVYYCGRSFFT NWFAYWGQGTLVTSS |
| 122 | Ab4 VH.1a.3 | EVQLVQSGAEVKKPGSSVKVSCKASGYTFTSYWI HWVRQAPGQGLEWIGEIDPSDSYTNYNQKFKGRA TLTVDRSSSTAYMELSSLRSEDTAVYYCGRSFFT NWFAYWGQGTLVTSS |
| 123 | Ab4 VH.1b | EVQLVQSGAEVKKPGSSVKVSCKASGGTFTSYWI HWVRQAPGQGLEWIGEIDPSDSYTNYAQKFKGRV TITVDKSTSTAYMELSSLRSEDTAVYYCGRSFFT NWFAYWGQGTLVTSS |
| 90 | Ab4 VH.1b.2 | EVQLVQSGAEVKKPGSSVKVSCKASGYTFTSYWI HWVRQAPGQGLEWIGEIDPSDSYTNYNQKFKGRV TITVDKSTSTAYMELSSLRSEDTAVYYCGRSFFT NWFAYWGQGTLVTSS |
| 91 | Ab4 VL.1 | DIVMTQTPLSLSVTPGQPASTCRSSQRLVH SNGNTYLHWYLQKPGQSPQLLIYKVSNRFSG VPDRFSGSGSGTDFTLKISRVEAEDVGVYYC SQSTHVPFTFGGGTKVEIK |
| 95 | Ab4 VL.1a | DVVMTQTPLSLSVTPGQPASTCRSSQRLVH SNGNTYLHWYLQKPGQSPQLLIYKVSNRFSG VPDRFSGSGSGTDFTLKISRVEAEDVGVYFC SQSTHVPFTFGGGTKVEIK |
| 96 | Ab4 VL.1b | DVVMTQTPLSLSVTPGQPASTCRSSQRLVH SNGNTYLHWYLQKPGQSPQLLIYKVSNRFSG VPDRFSGSGSGTDFTLKISRVEAEDVGVYYC SQSTHVPFTFGGGTKVEIK |

Ab4 VH.1z is a CDR-grafted, humanized Ab7 VH containing IGHV1-69*6 and JH4 framework sequences.

Ab4 VH.1 is based on .1z with a Q1E change.

Ab4 VH.1a is a humanized design based on .1 and contains seven proposed framework back-mutations M48I, V67A, I69L, A71V, K73R, T75S, and A93G.

Ab4 VH.1b is an intermediate design between .1 and .1a and only has two back-mutations M48I and A71V.

Ab4 VL.1 is a CDR-grafted humanized Ab7 VL containing IGKV2-29 and Jk4 framework sequences.

Ab4 VL.1a is a humanized design based on .1 with 2 proposed framework back-mutations (I2V and Y87F).

Ab4 VL.1b is an intermediate design between .1 and .1a with 1 proposed framework back-mutation I2V.

Example 2

Assaying Binding and Activity of PRLR Antibodies

The binding and activity of the PRLR antibodies of the invention were assayed as follows.

2.1 T47D pPRLR ELISA

T47D cells were plated at 60,000/well in 96-well plate in RPMI1640 medium containing 10% FBS, and were incubated overnight. The next day, the cell culture medium was switched to RPMI1640 medium without FBS. Cells were then treated with testing PRLR antibodies diluted in PBS buffer containing 0.1% BSA at concentrations ranging from 0.001 to 10 ug/mL for 60 min at 37 C. At the end of treatment, cells were stimulated with 100 ng/mL hPRL (R&D Systems) for 15 min at 37 C. Cells were then lysed with cell lysis buffer (Cell Signaling) for 20 min at 4 C. The cell lysates were analyzed for phospho-PRLR levels using the human phosphor-PRLR ELISA DuoSet IC kit from R&D System (#DYC4058). Results are depicted in Table 13.

This assay was used as an initial screen because phosphorylation of PRLR is a direct response to stimulation of the receptor, and blocking of this activity is correlated to inhibition of PRLR signaling. All antibodies exhibited inhibition of phosphorylation of PRLR.

2.2 Cell Proliferation Assays

2.2.1 Baf3-xPRLR Cell Proliferation Assay

Engineered Baf3-xPRLR cell lines were maintained in RPMI1640 medium with 10% FBS and 10 ng/mL hPRL (R&D Systems). Cells were seeded in 96-well plate at 10,000/well in regular culture medium containing 10 ng/mL hPRL. Cells were then treated with testing PRLR antibodies diluted in PBS buffer with 0.1% BSA at concentrations 0.001-10 ug/mL for 3 days at 37 C. After incubation, cell proliferation was measured using standard CellTiter-Glo Luminescent Viability Assay kit (Promega). Results are depicted in Table 13.

2.2.2 Nb2-11 Cell Proliferation Assay

Nb2-11 cells (Sigma) were maintained in Complete medium (RPMI1640, 10% FBS, 10% horse serum, 0.05 mM 2-mercaptoethanol, 0.075% sodium bicarbonate). Cells were switched to Stationary medium (RPMI1640, 10% horse serum, 0.05 mM 2-mercaptoethanol, 0.075% sodium bicarbonate) plus 1% FBS on the day before the assay. For PRL-dependent proliferation assay, Nb2-11 cells were washed and resuspended in Stationary medium plus 1 ng/mL hPRL (R&D Systems) at 250 k cells/mL. Cells were plated in 96-well plate at 90 uL/well, and were treated with 10 uL of testing PRLR antibodies diluted in PBS buffer with 0.1% BSA at final concentrations 0.001-10 ug/mL for 3 days at 37 C. After incubation, cell proliferation was measured using standard CellTiter-Glo Luminescent Viability Assay kit (Promega). Results are depicted in Table 13.

2.2.3 Conclusions

Rat Nb-211 and Ba/F3 cells expressing mouse, cyno, and human PRLR expression are all dependent on PRLR signaling for proliferation, so this sensitive assay was used to assess blockage of PRLR signaling on cells for these different species in vitro. The human results paralleled those seen with the pPRLR assay. Activity was generally maintained in the humanized versions, e.g., Ab1, Ab2, Ab3 and Ab4. Ab1, Ab2, Ab3, Ab4, Ab5, Ab6, Ab7, Ab8, Ab9, Ab11 and Ab13 demonstrated PRLR inhibition for cynoPRLR and human PRLR, with Ab1, Ab2, Ab4, Ab5, Ab6, Ab7, Ab9 and Ab13 being particularly efficacious. Ab2, Ab4 and Ab7 demonstrated particularly efficacious PRLR inhibitory activity for mouse and rat PRLR.

2.3 ELISA Binding Assay for Extra Cellular Domains (ECD)

Plates were coated overnight with goat anti-human Fc region antibody (1 ug/ml) for human, mouse and rat PRLR ECD-Fc fusion proteins, and mouse anti-his for cyno PRLR ECD-his6 protein ("his6" disclosed as SEQ ID NO: 159) in 1×PBS (pH 7.4). For cyno PRLR ECD binding experiments to mouse antibodies, cyno PRLR ECD-his6 protein ("his6" disclosed as SEQ ID NO: 159) was directly bound to the ELISA plate. Plates were blocked for 1 hour with Superblock (Pierce) and washed (3×) with wash buffer (1×PBS (pH 7.4), 0.05% Tween 20). ECD proteins were bound to the appropriate antibody (1 hour) in binding buffer (wash buffer plus 10% Superblock), washed (3×, wash buffer), and then incubated with serial dilutions of antibodies (1 hour) in binding buffer. After washing (3×, wash buffer), secondary antibodies conjugated to HRP were bound (1 hour) in binding buffer, washed (3×, wash buffer), and incubated with TMB substrate (Pierce) to develop signal for 3-5 minutes, stopped with 2N $H_2SO_4$ and scanned at 450 nM. Curves were fit with GraphPad 5 (Prizm) and EC50's were determined with curve fitting function of GraphPad 5. Results are depicted in Table 13.

The binding ELISA data correlated to the proliferation inhibition data.

2.4 FACS Binding Assay:

Nb2-11 and Baf3-xPRLR cells were resuspended in FACS buffer (PBS+1% FBS) at 2 millions cells/mL. Cells were added to round bottom 96-well plate (100 uL/well) and treated with testing PRLR antibodies for 1 hr at 4 C. Cells were then washed with FACS buffer twice and incubated with $2^{nd}$ antibody conjugated to ALEXA488 (Invitrogen) for 1 hr at 4 C. After two washes in FACS buffer, cells were resuspended in 1% formaldehyde in PBS. Cells were analyzed using LSRII flowcytometer. Results are depicted in Table 13.

The FACS data also correlated with the proliferation data. Humanized antibodies were not subjected to the FACS binding assay.

2.5 Biacore Binding

Running buffer was HBS-EP+ (10 mM Hepes, pH7.5, 150 mM NaCl, 3 mM EDTA, 0.05% Tween 20). [PRLR] at 600 nM, 66.67 nM and 7.41 nM (3 point, 9-fold dilution series), fit to a 1:1 binding model (local Rmax, MT term included) using Biacore T200 Evaluation Software. Results are depicted in Table 14.

The Biacore data provides more detailed biochemical binding information. The lower affinity binding of the humanized antibodies to mouse PRLR are more accurately quantified with this assay.

Figure 10:
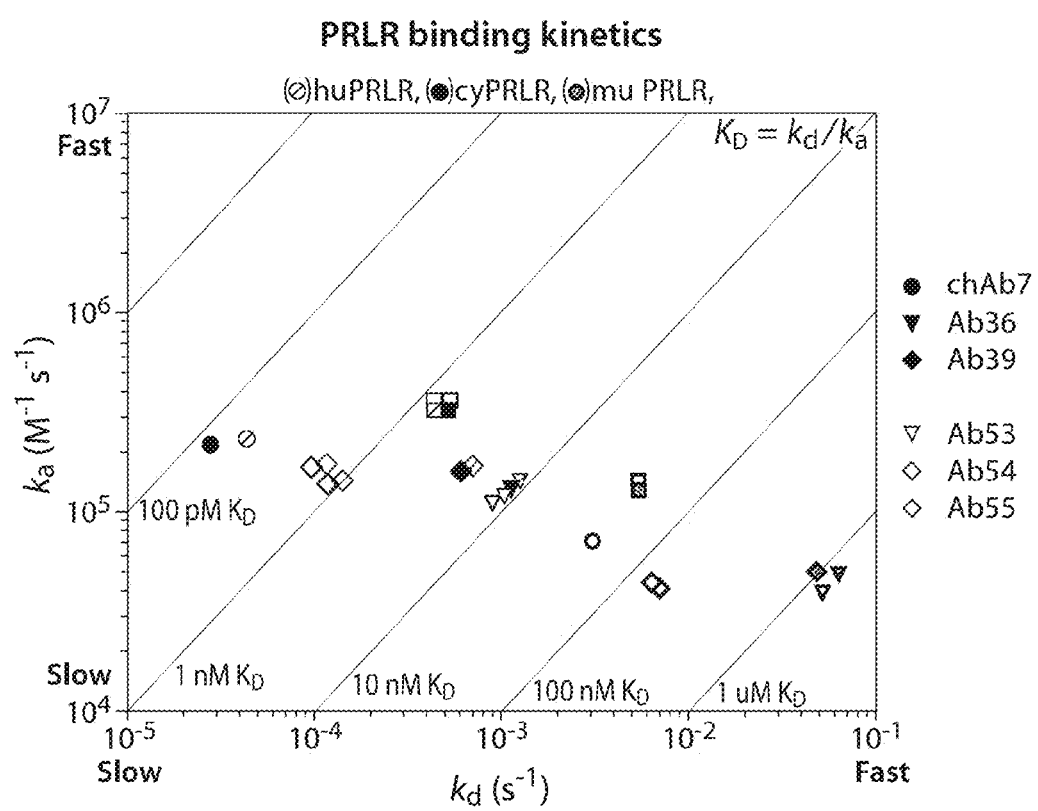
FIG. 10. Comparison of binding of certain anti-PRLR antibodies to huPRLR, cyPRLR and muPRLR as follows (see Example 10).
Figure 11:
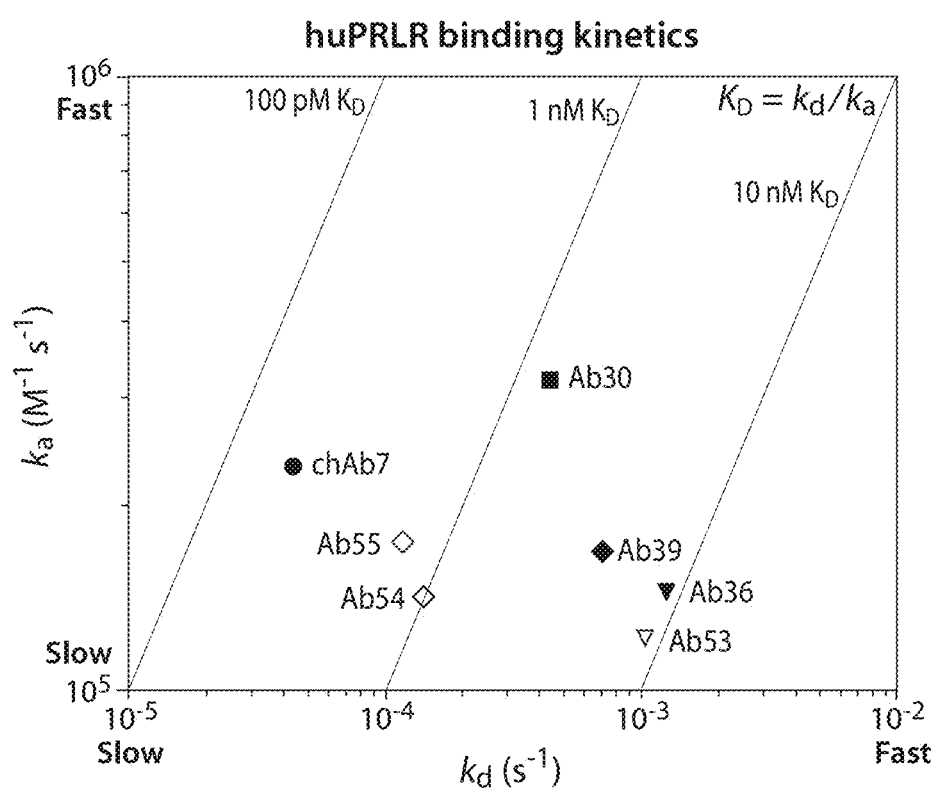
FIG. 11. Comparison of binding of certain anti-PRLR antibodies upon humanization from the chimeric antibody.

Analysis of the results in FIG. 11 demonstrate that chAb7 has a high affinity for human PRLR. Further, upon humanization of the chimeric antibody to make the humanized antibodies Ab36 and Ab39, the affinity decreases by ~45-fold and ~22-fold, respectively. The decreases in affinity are primarily due to changes in the $k_{off}$ rate. While back mutations performed on Ab36 (i.e., Ab53) did not improve the antibody affinity, back mutations performed on Ab39 (i.e., Ab54 and Ab55) increased the affinity to a level that was approximately 4-fold and 5-fold weaker than that observed with chAb7. Analysis of the results in FIG. 10 indicated that all the mAbs show significantly and proportionally weaker binding kinetics for murine PRLR.

TABLE 13

SUMMARY OF FINDINGS FROM EXAMPLES 2.1 (T47D pPRLR ELISA), 2.2 (Baf3-xPRLR and NB2-11 CELL PROLIFERATION ASSAYS), 2.3 ( ELISA BINDING ASSAY FOR ECD) & 2.4 (FACS BINDING ASSAY)

| Antibody | Isotype | Cell Phospho-ELISA T47D pPRLR IC50 (ug/mL) | Cell Proliferation Assay | | | | Binding ELISA | | | | FACS (GeoMean-neg) | | |
|---|---|---|---|---|---|---|---|---|---|---|---|---|---|
| | | | Baf3- hPRLR IC50 (ug/mL) | Baf3- cyPRLR IC50 (ug/mL) | Baf3- mPRLR IC50 (ug/mL) | Nb2-11 IC50 (ug/mL) | Human EC50 (pM) | Cyno EC50 (pM) | Rat EC50 (pM) | Mouse EC50 (pM) | T47D 10 ug/mL | Nb2-11 20 ug/mL | Baf3- mPRLR 10 ug/mL |
| Ab6 | G1 | 0.039 | 0.26 | 0.44 | >30 | >30 | 86 | >50000 | >50000 | >50000 | 1838 | 0 | 0 |
| Ab5 | G2a | 0.038 | 0.24 | 0.38 | 1.03 | 0.91 | 71 | 95 | 80 | 98 | 1607 | 90 | 166 |
| Ab8 | G2b | 0.219 | 1.15 | 1.64 | >30 | >30 | 98 | >50000 | 205 | 342 | 1532 | 17 | 1 |
| Ab7 | G1 | 0.080 | 0.28 | 0.30 | 3.55 | 4.42 | 98 | 202 | 135 | 143 | 2380 | 82 | 27 |
| Ab13 | G2a | 0.047 | 0.32 | 0.85 | 4.69 | 7.56 | 70 | 143 | 85 | 88 | 1499 | 60 | 143 |
| Ab9 | G2b | 0.072 | 0.51 | 6.40 | >30 | >30 | 72 | >50000 | >50000 | >50000 | 1871 | 0 | 1 |
| Ab10 | G2a | 0.362 | 3.14 | >10 | >30 | >30 | 147 | >50000 | 234 | 1137 | 2723 | 16 | 49 |
| Ab11 | G1 | 0.047 | 1.11 | 1.20 | 18.52 | >30 | 93 | 153 | 87 | 86 | 2220 | 94 | 25 |
| Ab12 | G2a | 0.538 | stimulatory | >30 | >30 | stimulatory | 69 | >40000 | 116 | 121 | 1680 | 17 | 90 |
| chAb6 | G1 | | 0.28 | 12.17 | no | no | 103 | 72 | >1000 | >10000 | | | |
| chAb5 | G1 | | 0.15 | 0.42 | 2.51 | 0.69 | 98 | 103 | 147 | 120 | | | |
| chAb8 | G1 | | 0.30 | 2.94 | no | no | 80 | 191 | 305 | 1017 | | | |
| chAb7 | G1 | | 1.2 | 1.9 | 3.6 | 16.8 | 151 | 118 | 157 | 184 | | | |
| chAb9 | G1 | | 0.20 | 10.44 | no | no | | | | | | | |
| chAb12 | G1 | | 10.74 | >10 | no | 41.37 | | | | | | | |
| Ab14 | G1 | | 0.30 | 1.15 | >30 | | 32.86 | 30.98 | >10000 | >10000 | | | |
| Ab15 | G1 | | 0.13 | 0.19 | >30 | | 78.06 | 55.05 | >10000 | >10000 | | | |
| Ab16 | G1 | | 0.46 | 1.73 | >30 | | 64.07 | 67.14 | >10000 | >10000 | | | |
| Ab17 | G1 | | 0.14 | 0.27 | >30 | | 76.58 | 78.79 | >10000 | >10000 | | | |
| Ab18 | G1 | | 0.15 | 0.40 | >30 | | 67.52 | 110.8 | >10000 | >10000 | | | |
| Ab19 | G1 | | 0.12 | 0.13 | >30 | | 61.36 | 57.55 | >10000 | >10000 | | | |
| Ab20 | G1 | | 0.20 | 0.50 | >30 | | 83.57 | 71.08 | >10000 | >10000 | | | |
| Ab21 | G1 | | 0.15 | 0.15 | >30 | | 72.76 | 53.57 | >10000 | >10000 | | | |
| Ab22 | G1 | | >30 | | | | >10000 | >10000 | >10000 | >10000 | | | |
| Ab23 | G1 | | >30 | | | | >10000 | >10000 | >10000 | >10000 | | | |
| Ab24 | G1 | | >30 | | | | >10000 | >10000 | >10000 | >10000 | | | |
| Ab25 | G1 | | >30 | | | | >10000 | >10000 | >10000 | >10000 | | | |
| Ab26 | G1 | | 0.23 | 0.25 | y* | | 198.9 | 151.3 | 163.7 | 201.3 | | | |
| Ab27 | G1 | | 0.16 | 0.22 | y | | 169.7 | 101.9 | 125.2 | 185.1 | | | |
| Ab28 | G1 | | 0.22 | 0.31 | y | | 196.8 | 96.5 | 416.2 | 291.6 | | | |
| Ab29 | G1 | | 0.15 | 0.23 | y | | 269.2 | 153.1 | 688.5 | 238.2 | | | |
| Ab30 | G1 | | 0.14 | 0.24 | y | | 220.5 | 100.1 | 423.1 | 197.5 | | | |
| Ab31 | G1 | | 0.17 | 0.39 | y | | 452.6 | 255.5 | 717.6 | 332.7 | | | |
| Ab32 | G1 | | >30 | | | | >10000 | >10000 | >10000 | >10000 | | | |
| Ab33 | G1 | | >30 | | | | >10000 | >10000 | >10000 | >10000 | | | |
| Ab34 | G1 | | >30 | | | | >10000 | >10000 | >10000 | >10000 | | | |
| Ab35 | G1 | | 0.38 | 0.65 | >30 | | 2495 | 320.4 | >10000 | >10000 | | | |
| Ab36 | G1 | | 0.28 | 0.41 | >30 | | 556.4 | 538 | >10000 | >10000 | | | |
| Ab37 | G1 | | 0.43 | 0.44 | >30 | | 183.7 | 185.8 | >10000 | >10000 | | | |
| Ab38 | G1 | | 0.42 | 0.25 | >30 | | 346.3 | 263.5 | >10000 | >10000 | | | |
| Ab39 | G1 | | 0.27 | 0.25 | >30 | | 180.3 | 459.8 | >10000 | >10000 | | | |
| Ab40 | G1 | | 0.40 | 0.32 | >30 | | 4405 | 862.3 | >10000 | >10000 | | | |
| Ab41 | G1 | | 4.38 | | | | >10000 | >10000 | >10000 | >10000 | | | |
| Ab42 | G1 | | 4.76 | | | | >10000 | >10000 | >10000 | >10000 | | | |
| Ab43 | G1 | | 6.75 | | | | >10000 | >10000 | >10000 | >10000 | | | |
| Ab44 | G1 | | 0.30 | 1.76 | >30 | | 43.45 | 94.52 | >10000 | >10000 | | | |
| Ab45 | G1 | | 0.31 | 2.24 | >30 | | 68.37 | 201 | >10000 | 977.5 | | | |
| Ab46 | G1 | | 0.30 | 1.72 | >30 | | 62.57 | 81.4 | >10000 | 568.2 | | | |
| Ab47 | G1 | | 0.40 | 3.01 | >30 | | 81.88 | 119.3 | >10000 | >10000 | | | |
| Ab48 | G1 | | 0.40 | 4.87 | >30 | | 74.65 | 236.2 | >10000 | >10000 | | | |
| Ab49 | G1 | | 0.37 | 3.49 | >30 | | 95.44 | 360.7 | >10000 | >10000 | | | |
| Ab50 | G1 | | 0.51 | 41.58 | >30 | | 109.1 | >10000 | >10000 | >10000 | | | |
| Ab51 | G1 | | 0.55 | 100.04 | >30 | | 287.4 | >10000 | >10000 | >10000 | | | |
| Ab52 | G1 | | 0.51 | 304.52 | >30 | | 91.32 | >10000 | >10000 | >10000 | | | |
| Ab53 | G1 | | 1.03 | | | | | | | | | | |
| Ab54 | G1 | | 0.77 | | | | | | | | | | |
| Ab55 | G1 | | 0.92 | | | | | | | | | | |
| LFA102 | G1 | 0.069 | 0.56 | >30 | >30 | 0.93 | 53 | 154 | 157 | | 1636 | 98 | 4 |

TABLE 14

SUMMARY OF FINDINGS FROM EXAMPLE 2.5 (BIACORE BINDING ASSAY)

| | | Biacore: binding to human PRLR | | | Biacore: binding to cyno PRLR | | | Biacore: binding to murine PRLR | | |
|---|---|---|---|---|---|---|---|---|---|---|
| | Isotype | $k_a$ (1/Ms) | $k_d$ (1/s) | $K_D$ (M) | $k_a$ (1/Ms) | $k_d$ (1/s) | $K_D$ (M) | $k_a$ (1/Ms) | $k_d$ (1/s) | $K_D$ (M) |
| Ab6 | G1 | 1.28 E+06 | 5.76 E−04 | 4.50 E−10 | 1.36 E+06 | 1.09 E−03 | 8.07 E−10 | 6.22 E+05 | 3.94 E−01 | 6.35 E−07 |
| Ab5 | G2a | 3.55 E+05 | 2.03 E−04 | 5.72 E−10 | 3.36 E+05 | 2.35 E−04 | 7.00 E−10 | 2.02 E+05 | 2.91 E−03 | 1.44 E−08 |
| Ab8 | G2b | 5.36 E+05 | 8.19 E−05 | 1.53 E−10 | 5.26 E+05 | 1.16 E−03 | 2.20 E−09 | 1.80 E+05 | 4.66 E−02 | 2.59 E−07 |
| Ab7 | G1 | 2.80 E+05 | 4.27 E−05 | 1.53 E−10 | 2.59 E+05 | 3.29 E−05 | 1.27 E−10 | 8.40 E+04 | 3.50 E−03 | 4.17 E−08 |
| Ab 13 | G2a | 4.33 E+05 | 4.31 E−04 | 9.97 E−10 | | | | | | |
| Ab9 | G2b | 5.77 E+05 | 1.31 E−04 | 2.26 E−10 | | | | | | |
| Ab10 | G2a | 1.61 E+05 | 2.28 E−04 | 1.41 E−09 | | | | | | |
| Ab11 | G1 | 3.05 E+05 | 2.11 E−02 | 6.92 E−08 | | | | | | |
| Ab12 | G2a | 2.82 E+05 | 1.86 E−03 | 6.60 E−09 | | | | | | |
| chAb6 | G1 | 1.14 E+06 | 5.36 E−04 | 4.69 E−10 | 1.30 E+06 | 1.03 E−03 | 7.94 E−10 | 5.91 E+05 | 3.60 E−01 | 6.08 E−07 |
| chAb5 | G1 | 3.56 E+05 | 1.99 E−04 | 5.58 E−10 | 3.33 E+05 | 2.23 E−04 | 6.71 E−10 | 2.00 E+05 | 2.77 E−03 | 1.38 E−08 |
| chAb8 | G1 | 4.96 E+05 | 9.10 E−05 | 1.83 E−10 | 5.14 E+05 | 1.77 E−03 | 3.44 E−09 | 1.85 E+05 | 5.38 E−02 | 2.91 E−07 |
| chAb7 | G1 | 2.48 E+05 | 4.46 E−05 | 1.80 E−10 | 2.35 E+05 | 3.61 E−05 | 1.54 E−10 | 7.95 E+04 | 3.57 E−03 | 4.49 E−08 |
| chAb9 | G1 | | | | | | | | | |
| chAb12 | G1 | | | | | | | | | |
| Ab14 | G1 | 1.10 E+06 | 4.58 E−03 | 4.16 E−09 | | | | | | |
| Ab15 | G1 | 1.16 E+06 | 9.72 E−04 | 8.37 E−10 | | | | | | |
| Ab16 | G1 | 1.39 E+06 | 5.62 E−03 | 4.05 E−09 | | | | | | |
| Ab17 | G1 | 1.25 E+06 | 1.32 E−03 | 1.06 E−09 | | | | | | |
| Ab18 | G1 | 1.06 E+06 | 1.71 E−03 | 1.62 E−09 | | | | | | |
| Ab19 | G1 | 9.85 E+05 | 4.03 E−04 | 4.09 E−10 | 1.05 E+06 | 7.28 E−04 | 6.91 E−10 | 4.09 E+05 | 2.52 E−01 | 6.16 E−07 |
| Ab20 | G1 | 1.04 E+06 | 2.08 E−03 | 2.00 E−09 | | | | ** | ** | 6.20 E−07 |
| Ab21 | G1 | 1.06 E+06 | 5.86 E−04 | 5.54 E−10 | | | | 5.00 E+05 | 2.60 E−01 | 5.30 E−07 |
| Ab22 | G1 | 4.03 E+05 | 1.67 E−01 | 4.16 E−07 | | | | | | |
| Ab23 | G1 | | | | | | | | | |
| Ab24 | G1 | | | | | | | | | |
| Ab25 | G1 | | | | | | | | | |
| Ab26 | G1 | | | | | | | | | |
| Ab27 | G1 | 3.56 E+05 | 4.43 E−04 | 1.25 E−09 | 3.33 E+05 | 5.20 E−04 | 1.56 E−09 | 1.34 E+05 | 5.12 E−03 | 3.83 E−08 |
| Ab28 | G1 | 3.44 E+05 | 5.33 E−04 | 1.55 E−09 | 3.15 E+05 | 6.19 E−04 | 1.97 E−09 | 1.17 E+05 | 6.06 E−03 | 5.20 E−08 |
| Ab29 | G1 | 3.13 E+05 | 5.60 E−04 | 1.79 E−09 | 3.01 E+05 | 6.75 E−04 | 2.24 E−09 | 1.20 E+05 | 6.34 E−03 | 5.30 E−08 |
| Ab30 | G1 | 3.39 E+05 | 4.37 E−04 | 1.29 E−09 | 3.30 E+05 | 5.23 E−04 | 1.59 E−09 | 1.40 E+05 | 5.60 E−03 | 4.00 E−08 |
| Ab31 | G1 | 3.22 E+05 | 5.37 E−04 | 1.67 E−09 | 3.10 E+05 | 6.43 E−04 | 2.08 E−09 | 1.22 E+05 | 6.82 E−03 | 5.57 E−08 |
| Ab32 | G1 | | | | | | | | | |
| Ab33 | G1 | | | | | | | | | |
| Ab34 | G1 | | | | | | | | | |
| Ab35 | G1 | 1.20 E+05 | 1.60 E−03 | 1.33 E−08 | 1.05 E+05 | 1.42 E−03 | 1.35 E−08 | 4.98 E+04 | 7.85 E−02 | 1.58 E−06 |
| Ab36 | G1 | 1.57 E+05 | 1.28 E−03 | 8.13 E−09 | 1.33 E+05 | 1.14 E−03 | 8.51 E−09 | 4.98 E+04 | 5.68 E−02 | 1.14 E−06 |
| Ab37 | G1 | 1.19 E+05 | 1.46 E−03 | 1.23 E−08 | 1.07 E+05 | 1.32 E−03 | 1.23 E−08 | 4.11 E+04 | 6.87 E−02 | 1.67 E−06 |
| Ab38 | G1 | 1.41 E+05 | 8.79 E−04 | 6.22 E−09 | 1.25 E+05 | 7.56 E−04 | 6.04 E−09 | 5.30 E+04 | 5.27 E−02 | 9.94 E−07 |
| Ab39 | G1 | 1.68 E+05 | 7.15 E−04 | 4.25 E−09 | 1.53 E+05 | 6.13 E−04 | 4.01 E−09 | 5.76 E+04 | 4.27 E−02 | 7.42 E−07 |
| Ab40 | G1 | 1.53 E+05 | 8.23 E−04 | 5.38 E−09 | 1.34 E+05 | 7.19 E−04 | 5.38 E−09 | 4.50 E+04 | 5.34 E−02 | 1.19 E−06 |
| Ab41 | G1 | | | | | | | | | |
| Ab42 | G1 | | | | | | | | | |
| Ab43 | G1 | | | | | | | | | |
| Ab44 | G1 | | | | | | | | | |
| Ab45 | G1 | | | | | | | | | |
| Ab46 | G1 | | | | | | | | | |
| Ab47 | G1 | | | | | | | | | |
| Ab48 | G1 | 5.46 E+05 | 9.84 E−05 | 1.80 E−10 | 5.76 E+05 | 5.63 E−03 | 9.77 E−09 | 2.17 E+05 | 9.83 E−02 | 4.53 E−07 |
| Ab49 | G1 | 5.58 E+05 | 1.20 E−04 | 2.14 E−10 | | | | | | |
| Ab50 | G1 | | | | | | | | | |
| Ab51 | G1 | | | | | | | | | |
| Ab52 | G1 | | | | | | | | | |
| Ab53 | G1 | 1.2 E+05 | 1.0 E−03 | 8.5 E−09 | 1.1 E+05 | 8.9 E−04 | 7.8 E−09 | 4.0 E+04 | 5.2 E−02 | 1.3 E−06 |
| Ab54 | G1 | 1.4 E+05 | 1.4 E−04 | 1.0 E−09 | 1.4 E+05 | 1.2 E−04 | 8.5 E−10 | 4.1 E+04 | 7.0 E−03 | 1.7 E−07 |
| Ab55 | G1 | 1.7 E+05 | 1.2 E−04 | 6.7 E−10 | 1.7 E+05 | 9.8 E−05 | 5.9 E−10 | 4.4 E+04 | 6.3 E−03 | 1.4 E−07 |
| LFA102 | | 5.6 E+05 | 7.3 E−04 | 1.3 E−09 | 8.8 E+05 | 9.5 E−03 | 1.1 E−08 | 6.2 E+05 | 1.6 E−02 | 2.6 E−08 |

Example 3

Xenograft Tumor Growth Inhibition Assay

The effect of PRLR antibodies on the growth of Nb2-11 rat lymphoma xenograft tumors was evaluated. One million cancer cells suspended in S-MEM media (no calcium, no glutamine, Life Technologies Corporation) containing Matrigel (phenol red free, Becton Dickinson Biosciences Discovery Labware) were inoculated subcutaneously into the right hind flank of female SCID-beige mice (Charles Rivers Labs, 10 per group) on study day 0. Administration (IP) of antibodies or vehicle (normal saline) was initiated at the time of size match on day 7. The tumors were measured by a pair of calipers twice a week starting at the time of size match and tumor volumes were calculated according to the formula V=L×W$^2$/2 (V: volume, mm$^3$; L: length, mm. W: width, mm). Tumor volume was measured for the duration of the experiment until the mean tumor volume in each group reached an endpoint of >1000 mm$^3$. Results are shown in FIG. 5 and Table 15.

TABLE 15

Summary of the effects of PRLR antibodies in Nb2-11 xenograft model

| Treatment | Dose route, regimen | % TGI[a] | % TGD[b] |
|---|---|---|---|
| Ab7 | 30 mg/kg IP, Q7Dx3 | 12 | 17 |
| Ab6 | 30 mg/kg IP, Q7Dx3 | −15 | 9 |
| Ab11 | 30 mg/kg IP, Q7Dx3 | −5 | 13 |
| Ab5 | 30 mg/kg IP, Q7Dx3 | 78*** | 84*** |
| Ab9 | 30 mg/kg IP, Q7Dx3 | 2 | 17 |

[a]Tumor growth inhibition, % TGI = 100 − mean tumor volume of treatment group/mean tumor volume of control group × 100. The p values (as indicated by asterisks) are derived from Student's T test comparison of treatment group vs. control group. Based on day 26. *p < 0.05, p < 0.01, *p < 0.001.
[b]Tumor growth delay, % TGD = (T − C)/C × 100, where T = median time to endpoint of treatment group and C = median time to endpoint of control group. The p values (as indicated by asterisks) derived from Kaplan Meier log-rank comparison of treatment group vs. treatment control group. Based on an endpoint of 1000 mm$^3$. *p < 0.05, p < 0.01, *p < 0.001.

Example 4

Anti-PRLR Epitope Grouping

The epitope groupings of the PRLR antibodies of the invention were determined using the pair-wise binding assay as follows.

Murine Antibodies: Ab5-Ab12

Figure 6:
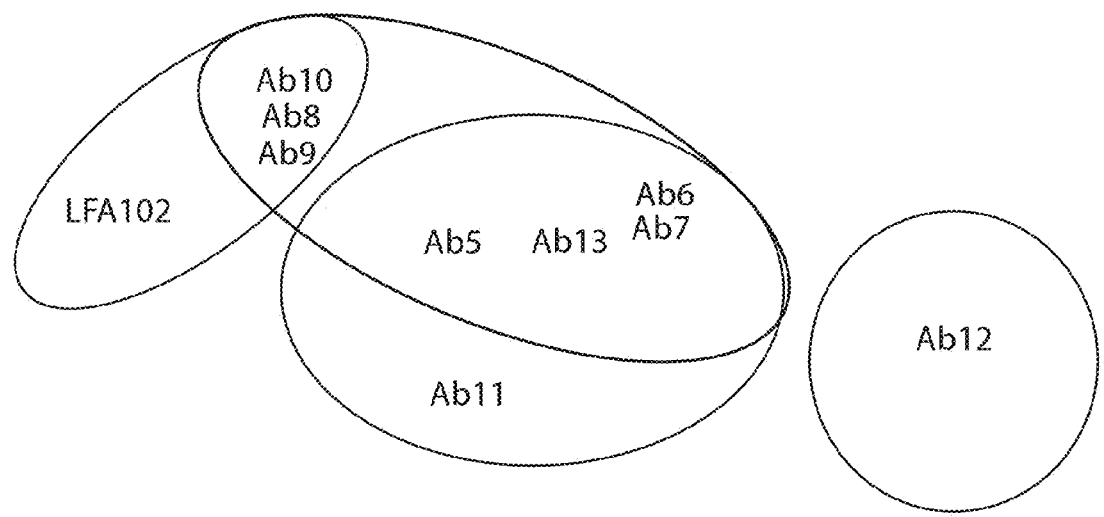
FIG. 6. PRLR antibody epitope grouping summary for murine antibodies Ab5, Ab6, Ab7, Ab8, Ab9, Ab10, Ab11 and Ab12, and for the LFA102 antibody (see Example 4).

Running buffer was HBS-EP+(10 mM Hepes, pH7.4, 150 mM NaCl, 3 mM EDTA, 0.05% surfactant). Assay was performed using Biacore T100 and CM5 sensor chips with anti-mouse IgG (Pierce) or anti-human IgG (Pierce) in each flow cell. A PRLR antibody was captured in a flow cell. The flow cell was then blocked by injection of a control antibody (50 μg/ml) prior to the injection of the antigen. A second PRLR antibody (10 μg/ml) was then injected. The binding response as a function of time was analyzed for each pairwise binding assay. Reciprocal binding assays were also performed. Results of assays performed with murine antibodies Ab5, Ab6, Ab7, Ab8, Ab9, Ab10, Ab11 and Ab12 are depicted in FIG. 6.

Chimeric and Humanized Antibodies

Running buffer was HBS-EP+ (10 mM Hepes, pH7.4, 150 mM NaCl, 3 mM EDTA, 0.05% surfactant). Assay was performed at 12° C. using Biacore T200 and CM5 sensor chips with anti-human IgG (Pierce) amine-coupled in all 4 flow cells to ~2000 RU.

Separate test mAbs were captured in flowcells 2, 3 & 4 (flowcell 1 was reference, no test mAb). All 4 flowcells were then blocked by injection with isotype control mAb at 50 ug/ml. All 4 flowcells were then injected with antigen or buffer only (buffer only is for double referencing, done for each mAb pair individually). All 4 flowcells were then injected with 2nd test mAb at 10 ug/ml. All 4 flowcells were then regenerated with glycine, pH1.5.

Figure 8:
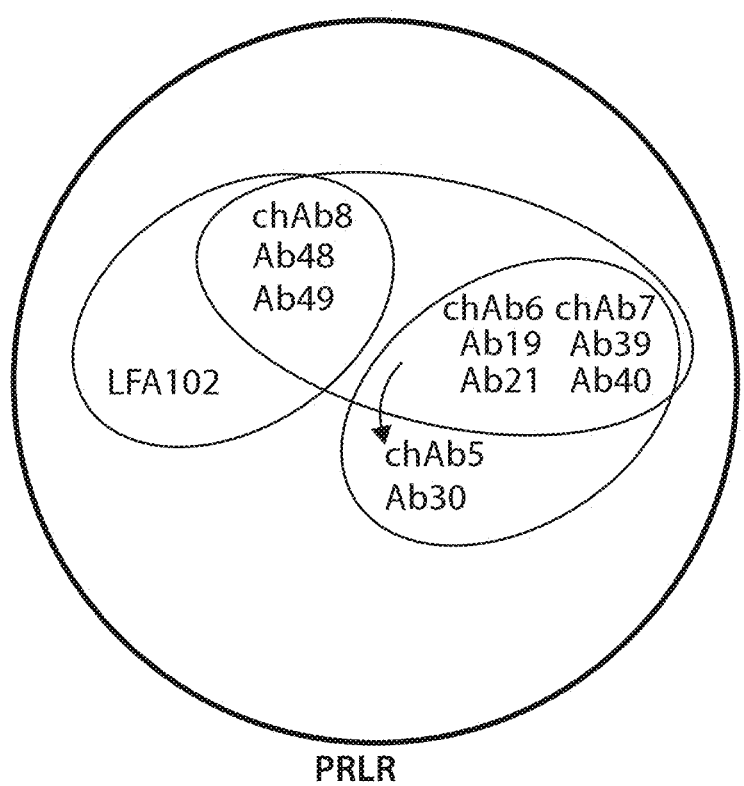
FIG. 8. PRLR antibody epitope grouping summary for chimeric and humanized antibodies chAb7, Ab39, Ab40, chAb5, Ab30, chAb6, Ab19, Ab21, chAb8, Ab48 and Ab49, and for the LFA102 antibody (see Example 4).

The binding response as a function of time was analyzed for each pairwise binding assay. Reciprocal binding assays were also performed. Results of simultaneous binding assays performed with chAb7, Ab39, Ab40, chAb5, Ab30, chAb6, Ab19, Ab21, chAb8, Ab48, Ab49 and LFA102 are depicted in FIG. 7 and FIG. 8.

These assays, performed using both chimeric and humanized antibodies, demonstrated that both the chimeric and the humanized antibodies recognized the same region of PRLR. FIG. 7 shows the results of an antibody binding assay performed to determine if the chimeric and humanized forms of each root mean antibody compete with each other for binding to PRLR. These results indicate that the chimeric and humanized forms of each root mean antibody do compete with each other, thus suggesting that the humanization of the chimeric antibody did not significantly change the core epitope for any given root mean antibody. In other words, chimeric engineering or humanization did not change the relative epitope grouping for most antibodies when compared to the epitope grouping of the parental mouse antibodies. However, there was a small shift in the epitope grouping for the Ab5 derived mAbs relative to the Ab8 derived mAbs when compared to the prior epitope grouping for the mouse mAbs. This difference is more likely to be due to steric differences between mouse and human frameworks as opposed to a change in the actual epitope. For similar results see Zettlitz, K. A., et al., *Mol Biotechnol* (2010) 46: 265-278.

Example 5

Crystallization of chAb6 (Fab)-PRLR Complex

Crystallization of the structure of the chAb6 Fab fragment-PRLR complex was performed and analyzed as follows.

Preparation and Purification of the chAb6 Fab Fragment:

The Fab fragment of chAb6 was prepared by papain cleavage of the parent mAb as detailed below. Papain was activated with 50 mM cysteine in PBS, pH 7.4 buffer. The mAb chAb6 in PBS, pH 7.4 buffer was mixed with papain at 1:77 weight ratio of papain to mAb and incubated for 1 h at 37° C. The reaction was quenched with 6.25 mM iodoacetamide. The mixture was purified on 8 ml Mab SelectSure resin (GE Healthcare) where the Fab fragment was collected as flow through. The flow through was concentrated using an Ultrafree-15 Biomax 30 kDa molecular weight cut-off (MWCO) centrifugal device (Millipore). The concentrated mixture was purified on a 2.6 cm×60 cm Sephacryl 200 HiPrep column (GE Healthcare), pre-equilibrated in 50 mM HEPES, 50 mM NaCl, pH 7.5 buffer. Fractions containing the Fab fragment (monitored by UV absorbance at 280 nm) were pooled and frozen at −80° C. Sample purity was assessed by analytical SEC, SDS-PAGE and mass spectrometry.

chAb6 Fab-PRLR Complex Preparation:

Recombinant human PRLR was expressed in a mammalian expression system and subsequently purified using techniques well known in the art. Recombinant human PRLR and the chAb6 Fab protein were mixed at a 1.15:1 molar ratio and incubated for 2 h at 22° C. The complex sample was loaded onto a 2.6 cm×60 cm Sephacryl 200 HiPrep column (GE Healthcare) pre-equilibrated in 50 mM HEPES, 50 mM NaCl, pH 7.5 buffer at 1 ml/min Fractions containing the complex (monitored by UV absorbance at 280 nm) were pooled and concentrated to 44 mg/ml using an Ultrafree-15 Biomax 30 kDa molecular weight cut-off (MWCO) centrifugal device (Millipore). Sample purity was assessed by analytical SEC and SDS-PAGE. Excess Fab-Complex protein was stored frozen at −80° C.

Crystallization of the chAb6 Fab-PRLR Complex:

The protein complex was delivered at 43.9 mg/ml in 50 mM HEPES pH 7.5, 50 mM NaCl and was used diluted to 30 mg/ml for crystallization trials. Crystals grew using the vapor diffusion technique at 17° C. The reservoir solution was 25% (w/v) PEG 3350, 0.1M Bis-Tris pH 5.5, 0.1M ammonium sulfate. Crystallization drops were made using a 1:1 ratio of protein and reservoir solution. The crystals were cryo-protected using 10% (v/v) propylene glycol. Diffraction data were collected under gaseous nitrogen at 100K at the Canadian Light Source (Saskatoon, Canada).

X-Ray Structure of the chAb6 Fab-PRLR Complex:

X-ray diffraction data extended to 1.93 Å resolution, and a full data set was processed with HKL2000 (HKL Research, Inc). The crystallographic space group is orthorhombic P212121 with unit cell parameters a=62 Å, b=83 Å, and c=135 Å. The statistics for the data set collected are provided in Table 16.

TABLE 16

X-RAY DIFFRACTION STATISTICS FOR chAb6 FAB-PRLR COMPLEX

| | |
|---|---|
| Resolution (Å) | 50-1.93 |
| Unique Reflections | 53,147 |
| Rmerge (%) | 9.9 |
| Completeness (%) | 99 |
| Multiplicity | 7.2 |

Structure Determination:

The crystal structure was determined by molecular replacement. Partial search model for the VhVl, ChCl, and PRLR portions were generated and sequentially placed using the program MOLREP (Vagin et al, 1997) in the CCP4 suite of programs (Winn et al. 2011). The asymmetric unit contains one molecular complex, and symmetry mates complete the crystalline lattice with intermolecular contacts. The coordinates were refined against the data using the program autoBUSTER (Global Phasing, Ltd) and iterative rounds of graphical analysis and rebuilding into electron density with the program COOT (Emsley et al, 2010). Statistics for the resulting structure are provided in Table 17:

TABLE 17

REFINEMENT STATISTICS FOR THE chAb6 FAB-PRLR COMPLEX

| | |
|---|---|
| Resolution (Å) | 50-1.93 |
| R/Rfree (%) | 20.2/23.6 |
| RMSDideal bonds (Å) | 0.010 |
| RMSDideal angles (°) | 1.11 |

Intermolecular contacts are observed between the PRLR extracellular domain and multiple chAb6 Fab CDRs. The contacts are comprised of critical hydrophobic and hydrophilic interactions and include bridging water molecules. These contacts directly engage CDR's H1, H2, H3, and L2 of SEQ ID Nos: 104 and 113. The contact area on the antigen covers an epitope surface at the intersection of the PRLR domains, comprising the topographical region defined by PRLR residues: E8, F10, C12, R25, E43, G44, I76, D91, E92, L93, Y94, V95, D96, Y99, I100, E145, F160, K185, D187, H188, Y190 and W191 of SEQ ID NO:2. The foregoing amino acid residues of PRLR are within 4 Å of the chAb6 Fab upon binding thereto.

Figure 9:
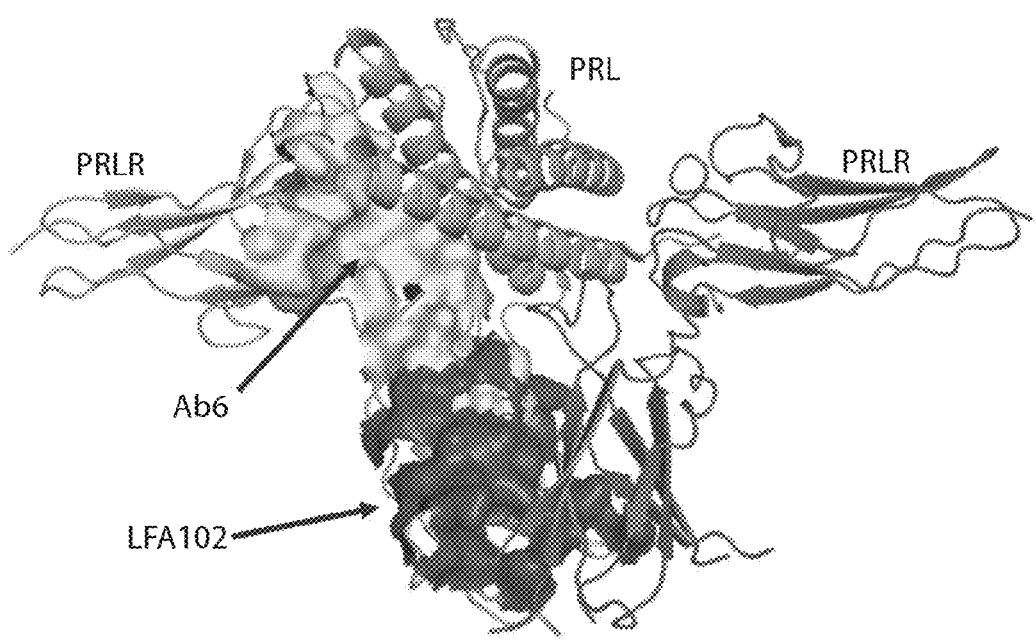
FIG. 9. Depiction of epitope surfaces for Ab6 and LFA102 mapped onto the structure of the PRL-PRLR ternary complex (see Example 5).

An illustration of the epitope surfaces mapped onto the structure of the PRL-PRLR ternary complex for Ab6 and LFA102 are shown in FIG. 9.

Example 6

Crystallization of chAb7 (Fab)-PRLR Complex

Crystallization of the structure of the chAb7 Fab fragment-PRLR complex was performed and analyzed as follows.

Preparation and Purification of the chAb7 Fab Fragment:

The Fab fragment of chAb7 was prepared by papain cleavage of the parent mAb as detailed below. Papain was activated with 50 mM cysteine in PBS, pH 7.4 buffer. The mAb chAb7 in PBS, pH 7.4 buffer was mixed with papain at 1:100 weight ratio of papain to mAb and incubated for 1 h at 37° C. The reaction was quenched with 6 mM iodoacetamide. The mixture was purified on 5 ml Mab SelectSure resin (GE Healthcare) where the Fab fragment was collected as flow through. The flow through was concentrated using an Ultrafree-15 Biomax 30 kDa molecular weight cut-off (MWCO) centrifugal device (Millipore). The concentrated mixture was purified on 2.6 cm×60 cm Sephacryl 200 HiPrep column (GE Healthcare) pre-equilibrated in 50 mM HEPES, 50 mM NaCl, pH 7.5 buffer. Fractions containing Fab fragment (monitored by UV absorbance at 280 nm) were pooled and frozen at −80° C. Sample purity was assessed by analytical SEC, SDS-PAGE and mass spectrometry.

chAb7 Fab-PRLR Complex Preparation:

Recombinant human PRLR was expressed in mammalian expression system and subsequently purified using techniques well known in the art. Recombinant human PRLR and the chAb7 Fab protein were mixed at a 2:1 molar ratio and incubated for 2 h at 4° C. The complex sample was loaded onto a 2.6 cm×60 cm Sephacryl 200 HiPrep column (GE Healthcare) pre-equilibrated in 50 mM HEPES, 50 mM NaCl, pH 7.5 buffer at 1 ml/min Fractions containing the complex (monitored by UV absorbance at 280 nm) were pooled and concentrated to 18 mg/ml using an Ultrafree-15 Biomax 30 kDa molecular weight cut-off (MWCO) centrifugal device (Millipore). Sample purity was assessed by analytical SEC and SDS-PAGE. Excess Fab-Complex protein was stored frozen at −80° C.

Crystallization of the chAb7 Fab-PRLR Complex:

The protein delivered at 17.6 mg/ml in 50 mM HEPES pH 7.5, 50 mM NaCl, 1 mM sodium azide and was used at the delivered concentration. Crystals grew using the vapor diffusion technique at 4° C. The reservoir solution was 22% (w/v) PEG 4000, 0.1M sodium acetate, 0.2M ammonium sulfate. Crystallization drops were made using a 1:1 ratio of protein and reservoir solution. The crystals were cryo protected using 15% (v/v) propylene glycol. Diffraction data were collected under gaseous nitrogen at 100K the 17ID line (IMCA-cat) at the Advanced Photon Source (Argonne, Ill.).

X-Ray Structure of the chAb7 Fab-PRLR Complex:

X-ray diffraction data extended to 2.0 Å resolution, and a full data set was processed with autoPROC (Global Phasing, Ltd). The crystal space group is monoclinic P21 with unit cell parameters a=99 Å, b=85 Å, c=101 Å, and beta=93°. The statistics for the data set collected are provided in Table 18.

TABLE 18

X-RAY DIFFRACTION STATISTICS FOR chAb7 FAB-PRLR COMPLEX

| | |
|---|---|
| Resolution (Å) | 49-2.0 |
| Unique Reflections | 103,942 |
| Rmerge (%) | 7.0 |
| Completeness (%) | 98 |
| Multiplicity | 3.4 |

Structure Determination:

The crystal structure was determined by molecular replacement. Partial search model for the VhVl, ChCl, and PRLR portions were generated and sequentially placed using the program MOLREP (Vagin et al, 1997) in the CCP4 suite of programs (Winn et al. 2011). The asymmetric unit contains 2 molecular complexes that are arranged similarly and pack with symmetry mates for complete crystalline lattice with intermolecular contacts. The coordinates were refined against the data using the program autoBUSTER (Global Phasing, Ltd) and iterative rounds of graphical analysis and rebuilding into electron density with the program COOT (Emsley et al, 2010). Statistics for the resulting structure are provided in Table 19:

TABLE 19

REFINEMENT STATISTICS FOR THE chAb7 FAB-PRLR COMPLEX

| | |
|---|---|
| Resolution (Å) | 20-2.0 |
| R/Rfree (%) | 18.4/21.6 |
| RMSDideal bonds (Å) | 0.010 |
| RMSDideal angles (°) | 1.12 |

PRLR/chAb7 Fab Complex Structure:

Intermolecular contacts are observed between the PRLR extracellular domain and multiple chAb7 Fab CDRs. The buried surface area of the receptor upon binding of antibody is 1198 Å$^2$. The contacts are comprised of critical hydrophobic and hydrophilic interactions and include bridging water molecules. These contacts directly engage CDR's H1, H2, H3, L1, and L2 of SEQ ID Nos: 105 and 114. The contact area on the antigen covers an epitope surface at the intersection of the PRLR domains, comprising the topographical region defined by PRLR residues: E8, I9, F10, K11, C12, R25, E43, G44, W72, T74, I76, D91, E92, L93, Y94, V95, D96, T98, Y99, I100, W139, L143, E145, F160, K185, D187, H188, Y190 and W191 of SEQ ID NO:2. The foregoing amino acid residues of PRLR are within 4 Å of the chAb7 Fab upon binding thereto.

The position of bound chAb7 to PRLR suggests that chAb7 would prevent prolactin binding to PRLR.

The findings of Examples 5 and 6 are consistent in demonstrating that chAb6 and chAb7 exhibit complementary interactions for roughly the same epitope. Conserved heavy chain features between the two antibodies suggest the importance of heavy chain interactions in PRLR binding.

Example 7

Crystallization of chAb8 (Fab)-PRLR Complexes

Crystallization of the structure of the chAb8 Fab fragment-PRLR complex was performed and analyzed as follows.

Preparation and Purification of the chAb8 Fab Fragment:

The Fab fragment of chAb8 was prepared by papain cleavage of the parent mAb as detailed below. Papain was activated with 50 mM cysteine in PBS, pH 7.4 buffer. The mAb chAb8 in PBS, pH 7.4 buffer was mixed with papain at 1:93 weight ratio of papain to mAb and incubated for 1 h at 37° C. The reaction was quenched with 5 mM iodoacetamide. The mixture was purified on 8 ml Mab SelectSure resin (GE Healthcare) where the Fab fragment was collected as flow through. The flow through was concentrated using an Ultrafree-15 Biomax 30 kDa molecular weight cut-off (MWCO) centrifugal device (Millipore). The concentrated mixture was purified on 2.6 cm×60 cm Sephacryl 200 HiPrep column (GE Healthcare) pre-equilibrated in 50 mM HEPES, 50 mM NaCl, pH 7.5 buffer. Fractions containing Fab fragment (monitored by UV absorbance at 280 nm) were pooled and frozen at −80° C. Sample purity was assessed by analytical SEC, SDS-PAGE and mass spectrometry.

chAb8 Fab-PRLR Complex Preparation:

Recombinant human PRLR was expressed in a mammalian expression system and subsequently purified using techniques well known in the art. Recombinant human PRLR and the chAb8 Fab protein were mixed at a 1.16:1 molar ratio and incubated for 2 h at 22° C. The complex sample was loaded onto a 2.6 cm×60 cm Sephacryl 200 HiPrep column (GE Healthcare) pre-equilibrated in 50 mM HEPES, 50 mM NaCl, pH 7.5 buffer at 1 ml/min Fractions containing the complex (monitored by UV absorbance at 280 nm) were pooled and concentrated to 38 mg/ml using an Ultrafree-15 Biomax 30 kDa molecular weight cut-off (MWCO) centrifugal device (Millipore). Sample purity was assessed by analytical SEC and SDS-PAGE. Excess Fab-Complex protein was stored frozen at −80° C.

Crystallization of the chAb8-PRLR Complex:

The protein complex was delivered at 38 mg/ml in 50 mM HEPES pH 7.5, 50 mM NaCl and was used diluted to 30 mg/ml for crystallization trials. Crystals grew using the vapor diffusion technique at 17° C. The reservoir solution was 20% (w/v) PEG 8000, 0.1M sodium cacodylate pH 5.5, 0.2 ammonium sulfate. Crystallization drops were made using a 1:1 ratio of protein and reservoir solution. The crystals were cryo-protected using 10% (v/v) propylene glycol. Diffraction data were collected under gaseous nitrogen at 100K at the Canadian Light Source (Saskatoon, Canada).

X-Ray Structure of the chAb8 Fab-PLR Complex:

X-ray diffraction data extended to 2.55 Å resolution, and a full data set was processed with HKL2000 (HKL Research, Inc). The crystallographic space group is orthorhombic P212121 with unit cell parameters a=55 Å, b=89 Å, and c=186 Å. The statistics for the data set collected are provided in Table 20.

TABLE 20

X-RAY DIFFRACTION STATISTICS FOR chAb8 FAB-PRLR COMPLEX

| | |
|---|---|
| Resolution (Å) | 50-2.55 |
| Unique Reflections | 30,353 |
| Rmerge (%) | 12.7 |
| Completeness (%) | 99 |
| Multiplicity | 7.2 |

Structure Determination:

The crystal structure was determined by molecular replacement. Partial search model for the VhVl, ChCl, and PRLR portions were generated and sequentially placed using the program MOLREP (Vagin et al, 1997) in the CCP4 suite of programs (Winn et al. 2011). The asymmetric unit contains one molecular complex, and symmetry mates complete the crystalline lattice with intermolecular contacts. The coordinates were refined against the data using the program autoBUSTER (Global Phasing, Ltd) and iterative rounds of graphical analysis and rebuilding into electron density with the program COOT (Emsley et al, 2010). Statistics for the resulting structure are provided in Table 21:

TABLE 21

REFINEMENT STATISTICS FOR THE chAb8 FAB-PRLR COMPLEX

| | |
|---|---|
| Resolution (Å) | 44-2.55 |
| R/Rfree (%) | 23.1/28.3 |
| RMSDideal bonds (Å) | 0.010 |
| RMSDideal angles (°) | 1.28 |

PRLR/chAb8 Fab Complex Structure:

Intermolecular contacts are observed between the PRLR extracellular domain and multiple chAb8 Fab CDRs. The contacts are comprised of critical hydrophobic and hydrophilic interactions and include bridging water molecules. These contacts directly engage CDR's H1, H2, H3, L1 and L3 of SEQ ID Nos: 106 and 115. The contact area on the antigen covers an epitope surface at the intersection of the PRLR domains, comprising the topographical region defined by PRLR residues: R25, T141, L143, E145, R147, E155, W156, E157, I158, H159, F160, A161, G162, Q163, Q164, F167, S171, R183, K185, D187, H188, W191, and W194 of SEQ ID NO:2. The foregoing amino acid residues of PRLR are within 4 Å of the chAb8 Fab upon binding thereto.

Example 8

Crystallization of chAb5 (Fab)

Crystallization of the structure of the chAb5 Fab fragment was performed and analyzed as follows.

Preparation and Purification of the chAb5 Fab Fragment:

The Fab fragment of chAb5 was prepared by papain cleavage of the parent mAb as detailed below. Papain was activated with 50 mM cysteine in PBS, pH 7.4 buffer. The mAb chAb5 in PBS, pH 7.4 buffer was mixed with papain at 1:100 weight ratio of papain to mAb and incubated for 1 h at 37° C. The reaction was quenched with 5.5 mM iodoacetamide. The mixture was purified on 5 ml Mab SelectSure resin (GE Healthcare) where the Fab fragment was collected as flow through. The flow through was concentrated using an Ultrafree-15 Biomax 30 kDa molecular weight cut-off (MWCO) centrifugal device (Millipore). The concentrated mixture was purified on 2.6 cm×60 cm Sephacryl 200 HiPrep column (GE Healthcare) pre-equilibrated in 50 mM HEPES, 50 mM NaCl, pH 7.5 buffer. Fractions containing Fab fragment (monitored by UV absorbance at 280 nm) were pooled and concentrated to 31.3 mg/ml using an Ultrafree-15 Biomax 30 kDa molecular weight cut-off (MWCO) centrifugal device (Millipore). Sample purity was assessed by analytical SEC, SDS-PAGE and mass spectrometry.

Crystallization of the chAb5:

The protein was delivered at 31.3 mg/mL in 50 mM HEPES pH 7.5, 50 mM NaCl, 1 mM sodium azide and was diluted to 20 mg/ml for crystallization trials using protein buffer. Crystals grew using the vapor diffusion technique at 4° C. The reservoir solution was 20% (w/v) PEG 3350, 0.2M sodium formate. Crystallization drops were made using a 1:1 ratio of protein and reservoir solution. The crystals were cryo-protected using 15% (v/v) propylene glycol. Diffraction data were collected under gaseous nitrogen at 100K the 17ID line (IMCA-CAT) at the Advanced Photon Source (Argonne, Ill.).

X-Ray Structure of the chAb5

X-ray diffraction data extended to 2.1 Å resolution, and a full data set was processed with autoPROC (Global Phasing, Ltd). The crystal space group is monoclinic P21 with unit cell parameters a=72 Å, b=66 Å, c=92 Å, and beta=96°. The statistics for the data set collected are provided in Table 22.

TABLE 22

X-RAY DIFFRACTION STATISTICS FOR chAb5 FAB

| Resolution (Å) | 66-2.1 |
|---|---|
| Unique Reflections | 51,329 |

TABLE 22-continued

X-RAY DIFFRACTION STATISTICS FOR chAb5 FAB

| Rmerge (%) | 10.5 |
|---|---|
| Completeness (%) | 99 |
| Multiplicity | 3.4 |

Structure Determination:

The crystal structure was determined by molecular replacement. Partial search models for the VhVl and ChCl portions were generated and sequentially placed using the program MOLREP (Vagin et al, 1997) in the CCP4 suite of programs (Winn et al. 2011). The asymmetric unit contains two (2) Fab molecules of similar conformation and pack with symmetry mates for complete crystalline lattice with intermolecular contacts. The coordinates were refined against the data using the program autoBUSTER (Global Phasing, Ltd) and iterative rounds of graphical analysis and rebuilding into electron density with the program COOT (Emsley et al, 2010). Statistics for the resulting structure are provided in Table 23:

TABLE 23

REFINEMENT STATISTICS FOR THE chAb5 FAB

| Resolution (Å) | 42-2.1 |
|---|---|
| R/Rfree (%) | 21.2/26.2 |
| RMSDideal bonds (Å) | 0.010 |
| RMSDideal angles (°) | 1.23 | chAb5 Fab Structure:

Overlay of the chAb5 with chAb7 Fab from the complex with PRLR reveals close structural alignment, yielding 0.67 Å RMSD for the aligned C-alpha coordinates of the VhVl domains. The comparison highlighted the expected aspect of very similar structural conformation for these closely related Fabs, and provided evidence for similar conformations at the locations of different amino acids. Inspection of the interface with PRLR for the aligned structures reveals no severe clashes with the conformation of chAb5.

An overlay of a model of chAb5 with chAb7, based on their respective crystal structures, suggests that the antibodies have few differences and share similar conformations. Based on the foregoing, chAb5 is expected to have a similar epitope as chAb7 with similar PRLR interactions.

Example 9

Crystallization of LFA-102-PRLR Complexes

Crystallization of the structure of the LFA102-PRLR complex was performed and analyzed as follows.

Preparation and Purification of the LFA-102 Fab Fragment:

The Fab fragment of LFA-102 was prepared by papain cleavage of the parent mAb as detailed below. Papain was activated with 50 mM cysteine in PBS, pH 7.4 buffer. mAb LFA-102 in PBS, pH 7.4 buffer was mixed with papain at 1:100 weight ratio of papain to mAb and incubated for 1 h at 37° C. The reaction was quenched with 5 mM iodoacetamide. The mixture was purified on 20 ml Mab SelectSure resin (GE Healthcare) where the Fab fragment was collected as flow through. The flow through was concentrated using an Ultrafree-15 Biomax 30 kDa molecular weight cut-off (MWCO) centrifugal device (Millipore). The concentrated mixture was purified on 2.6 cm×60 cm Sephacryl 300 HR column (GE Healthcare) pre-equilibrated in 50 mM HEPES, 50 mM NaCl, pH 7.5 buffer. Fractions containing Fab fragment (monitored by UV absorbance at 280 nm) were pooled and frozen at −80° C. Sample purity was assessed by analytical SEC, SDS-PAGE and mass spectrometry.

LFA-102 Fab-PRLR Complex Preparation:

Recombinant human PRLR was expressed in mammalian expression system and subsequently purified using techniques well known in the art. Recombinant human PRLR and LFA-102 Fab protein were mixed at a 1.1:1 molar ratio and incubated for 3 h at 4° C. The complex sample was loaded onto a 2.6 cm×60 cm Sephacryl 300 HR column (GE Healthcare) pre-equilibrated in 50 mM HEPES, 50 mM NaCl, pH 7.5 buffer at 1 ml/min Fractions containing the complex (monitored by UV absorbance at 280 nm) were pooled and concentrated to 18 mg/ml using an Ultrafree-15 Biomax 30 kDa molecular weight cut-off (MWCO) centrifugal device (Millipore). Sample purity was assessed by analytical SEC and SDS-PAGE. Excess Fab-Complex protein was stored frozen at −80° C.

Crystallization of the LFA-102 Fab-PRLR Complex:

The protein was delivered at 20.7 mg/ml in 50 mM HEPES pH 7.5, 50 mM NaCl, 1 mM sodium azide and was used at the delivered concentration. Crystals grew using the vapor diffusion technique at 4° C. with the reservoir being 45% (w/v) 2-methyl-2,4-pentanediol (MPD), 0.1M Tris-HCl pH 8.5, 0.1M ammonium dihydrogen phosphate. With these solution conditions no additional cryo-protectant was required so crystals were retrieved directly from the drop and cryo-cooled in liquid nitrogen. Diffraction data were collected under gaseous nitrogen at 100K the 17ID line (IMCA-cat) at the Advanced Photon Source (Argonne, Ill.).

X-Ray Structure of the LFA-102 Fab-PRLR Complex:

X-ray diffraction data extended to 2.25 Å resolution, and a full data set was processed with autoPROC (Global Phasing, Ltd). The crystallographic space group is monoclinic C2 with unit cell parameters a=98 Å, b=119 Å, c=81 Å, and beta=107°. The statistics for the data set collected are provided in Table 24.

TABLE 24

X-RAY DIFFRACTION STATISTICS FOR LFA-102 FAB-PRLR COMPLEX

| Resolution (Å) | 77-2.25 |
| --- | --- |
| Unique Reflections | 41,794 |
| Rmerge (%) | 3.9 |
| Completeness (%) | 99 |
| Multiplicity | 3.4 |

Structure Determination:

The crystal structure was determined by molecular replacement. Partial search model for the VhVl, ChCl, and PRLR portions were generated and sequentially placed using the program MOLREP (Vagin et al, 1997) in the CCP4 suite of programs (Winn et al. 2011). The asymmetric unit contains one molecular complex, and symmetry mates complete the crystalline lattice with intermolecular contacts. The coordinates were refined against the data using the program autoBUSTER (Global Phasing, Ltd) and iterative rounds of graphical analysis and rebuilding into electron density with the program COOT (Emsley et al, 2010). Statistics for the resulting structure are provided in Table 25:

TABLE 25

REFINEMENT STATISTICS FOR THE LFA-102 FAB-PRLR COMPLEX

| Resolution (Å) | 77-2.25 |
| --- | --- |
| R/Rfree (%) | 19.7/23.1 |
| RMSDideal bonds (Å) | 0.010 |
| RMSDideal angles (°) | 1.17 |

PRLR/chAb7 Fab Complex Structure:

Intermolecular contacts are between PRLR and LFA102 involve CDR's L1, L3, H2 and H3 of LFA102 (Seq ID Nos 156 and 157). The contact area on the antigen covers an epitope defined by PRLR residues: E145, E155, W156, E157, I158, H159, F160, A161, G162, Q164, L170 and S171 of SEQ ID NO:2. The foregoing amino acid residues of PRLR are within 4 Å of LFA102 upon binding thereto.

The position of bound LFA102 to PRLR suggests that LFA102 would inhibit PRLR dimerization, but appears to nearly allow simultaneous binding of prolactin to PRLR.

Example 10

Binding of Anti-PRLR Antibodies to cyPRLR and muPRLR

Assays were performed to assess the binding of certain anti-PRLR antibodies to cyPRLR and muPRLR as follows.

Running buffer was HBS-EP+ (10 mM Hepes, pH7.4, 150 mM NaCl, 3 mM EDTA, 0.05% P20). Assay was performed using Biacore T200 and CM5 sensor chips with anti-mouse Fc (Pierce 31170) or anti-human Fc (Pierce 31125), amine coupled in all 4 flow cells to ~8000.

mAb was captured in flow cells 2, 3 or 4. Antigen was injected (2 min at 80 µl/min). Concentrations were a 3 point, 9 fold dilution series from 500 nM-7.4 nM, and buffer only. Dissociation was monitored for 15 minutes. Regeneration was performed with 2 consecutive injections (60 and 10 sec at 60 µ/min) of 10 mM glycine, pH 1.5.

Results are depicted in FIG. 10. Cyno and human PRLR binding kinetics are virtually identical for the tested antibodies. However, each tested antibody shows significantly and proportionally weaker binding kinetics for muPRLR.

Sequence Listing

| Sequence Identifier | Protein | Sequence 123456789012345678901234567890123456789012 |
| --- | --- | --- |
| SEQ ID NO.: 1 | Human PRLR | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV |

Sequence Listing

| Sequence Identifier | Protein | Sequence<br>123456789012345678901234567890 12 |
|---|---|---|
| | | ALKGYSMVTCIFPPVPGPKIKGFDAHLLEKGK<br>SEELLSALGCQDFPPTSDYEDLLVEYLEVDDS<br>EDQHLMSVHSKEHPSQGMKPTYLDPDTDSGRG<br>SCDSPSLLSEKCEEPQANPSTFYDPEVIEKPE<br>NPETTHTWDPQCISMEGKIPYFHAGGSKCSTW<br>PLPQPSQHNPRSSYHNITDVCELAVGPAGAPA<br>TLLNEAGKDALKSSQTIKSREEGKATQQREVE<br>SFHSETDQDTPWLLPQEKTPFGSAKPLDYVEI<br>HKVNKDGALSLLPKQRENSGKPKKPGTPENNK<br>EYAKVSGVMDNNILVLVPDPHAKNVACFEESA<br>KEAPPSLEQNQAEKALANFTATSSKCRLQLGG<br>LDYLDPACFTHSFH |
| SEQ ID NO.: 2 | Human PRLR Extra-cellular Domain | QLPPGKPEIFKCRSPNKETFTCWWRPGTDGGL<br>PTNYSLTYHREGETLMHECPDYITGGPNSCHF<br>GKQYTSMWRTYIMMVNATNQMGSSFSDELYVD<br>VTYIVQPDPPLELAVEVKQPEDRKPYLWIKWS<br>PPTLIDLKTGWFTLLYEIRLKPEKAAEWEIHF<br>AGQQTEFKILSLHPGQKYLVQVRCKPDHGYWS<br>AWSPATFIQIPSDFTMN |
| SEQ ID NO.: 3 | Human PRLR Isoform 2 | MKENVASATVFTLLLFLNTCLLNVQPDPPLEL<br>AVEVKQPEDRKPYLWIKWSPPTLIDLKTGWFT<br>LLYEIRLKPEKAAEWEIHFAGQQTEFKILSLH<br>PGQKYLVQVRCKPDHGYWSAWSPATFIQIPSD<br>FTMNDTTVWISVAVLSAVICLIIVWAVALKGY<br>SMVTCIFPPVPGPKIKGFDAHLLEKGKSEELL<br>SALGCQDFPPTSDYEDLLVEYLEVDDSEDQHL<br>MSVHSKEHPSQGMKPTYLDPDTDSGRGSCDSP<br>SLLSEKCEEPQANPSTFYDPEVIEKPENPETT<br>HTWDPQCISMEGKIPYFHAGGSKCSTWPLPQP<br>SQHNPRSSYHNITDVCELAVGPAGAPATLLNE<br>AGKDALKSSQTIKSREEGKATQQREVESFHSE<br>TDQDTPWLLPQEKTPFGSAKPLDYVEIHKVNK<br>DGALSLLPKQRENSGKPKKPGTPENNKEYAKV<br>SGVMDNNILVLVPDPHAKNVACFEESAKEAPP<br>SLEQNQAEKALANFTATSSKCRLQLGGLDYLD<br>PACFTHSFH |
| SEQ ID NO.: 4 | Human PRLR Isoform 3 | MKENVASATVFTLLLFLNTCLLNGQLPPGKPE<br>IFKCRSPNKETFTCWWRPGTDGGLPTNYSLTY<br>HREGETLMHECPDYITGGPNSCHFGKQYTSMW<br>RTYIMMVNATNQMGSSFSDELYVDVTYIVQPD<br>PPLELAVEVKQPEDRKPYLWIKWSPPTLIDLK<br>TGWFTLLYEIRLKPEKAAEWEIHFAGQQTEFK<br>ILSLHPGQKYLVQVRCKPDHGYWSAWSPATFI<br>QIPSAW |
| SEQ ID NO.: 5 | Human PRLR Isoform 4 | MKENVASATVFTLLLFLNTCLLNGQLPPGKPE<br>IFKCRSPNKETFTCWWRPGTDGGLPTNYSLTY<br>HREGETLMHECPDYITGGPNSCHFGKQYTSMW<br>RTYIMMVNATNQMGSSFSDELYVDVTYIVQPD<br>PPLELAVEVKQPEDRKPYLWIKWSPPTLIDLK<br>TGWFTLLYEIRLKPEKAAEWEIHFAGQQTEFK<br>ILSLHPGQKYLVQVRCKPDHGYWSAWSPATFI<br>QIPSDFTMNDTTVWISVAVLSAVICLIIVWAV<br>ALKGYSMVTCIFPPVPGPKIKGFDAHLLEKGK<br>SEELLSALGCQDFPPTSDYEDLLVEYLEVDDS<br>EDQHLMSVHSKEHPSQGDPLMLGASHYKNLKS<br>YRPRKISSQGRLAVFTKATLTTVQ |
| SEQ ID NO.: 6 | Human PRLR Isoform 5 | MKENVASATVFTLLLFLNTCLLNGQLPPGKPE<br>IFKCRSPNKETFTCWWRPGTDGGLPTNYSLTY<br>HREGETLMHECPDYITGGPNSCHFGKQYTSMW<br>RTYIMMVNATNQMGSSFSDELYVDVTYIVQPD<br>PPLELAVEVKQPEDRKPYLWIKWSPPTLIDLK<br>TGWFTLLYEIRLKPEKAAEWEIHFAGQQTEFK<br>ILSLHPGQKYLVQVRCKPDHGYWSAWSPATFI<br>QIPSDFTMNDTTVWISVAVLSAVICLIIVWAV<br>ALKGYSMVTCIFPPVPGPKIKGFDAHLLEKGK<br>SEELLSALGCQDFPPTSDYEDLLVEYLEVDDS<br>EDQHLMSVHSKEHPSQEREQRQAQEARDS |

Sequence Listing

| Sequence Identifier | Protein | Sequence 1234567890123456789012345678901 2 |
|---|---|---|
| SEQ ID NO.: 7 | Human PRLR Isoform 6 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSDFTMNDTTVWISVAVLSAVICLIIVWAV ALKGYSMVTCIFPPVPGPKIKGFDAHLLEVTP |
| SEQ ID NO.: 8 | Human PRLR Isoform 7 | MKENVASATVFTLLLFLNTCLLNGQLPPGKPE IFKCRSPNKETFTCWWRPGTDGGLPTNYSLTY HREGETLMHECPDYITGGPNSCHFGKQYTSMW RTYIMMVNATNQMGSSFSDELYVDVTYIVQPD PPLELAVEVKQPEDRKPYLWIKWSPPTLIDLK TGWFTLLYEIRLKPEKAAEWEIHFAGQQTEFK ILSLHPGQKYLVQVRCKPDHGYWSAWSPATFI QIPSGDPLMLGASHYKNLKSYRPRKISSQGRL AVFTKATLTTVQ |
| SEQ ID NO.: 9 | Human PRLR Isoform 8 | MHECPDYITGGPNSCHFGKQYTSMWRTYIMMV NATNQMGSSFSDELYVDVTYIVQPDPPLELAV EVKQPEDRKPYLWIKWSPPTLIDLKTGWFTLL YEIRLKPEKAAEWEIHFAGQQTEFKILSLHPG QKYLVQVRCKPDHGYWSAWSPATFIQIPSDFT MNDTTVWISVAVLSAVICLIIVWAVALKGYSM VTCIFPPVPGPKIKGFDAHLLEVTP |
| SEQ ID NO.: 10 | Ig gamma-1 constant region | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| SEQ ID NO.: 11 | Ig gamma-1 constant region mutant | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| SEQ ID NO.: 12 | Ig Kappa constant region | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| SEQ ID NO.: 13 | Ig Lambda constant region | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |
| SEQ ID NO.: 14 | VH1-18 & JH6 FR1 21/28 & JH4 FR1 VH1-46 & JH6 FR1 | QVQLVQSGAEVKKPGASVKVSCKASGYTFT |
| SEQ ID NO.: 15 | VH1-18 & JH6 FR2 VH1-46 & JH6 FR2 | WVRQAPGQGLEWMG |

Sequence Listing

| Sequence Identifier | Protein | Sequence<br>123456789012345678901234567890 12 |
|---|---|---|
| SEQ ID NO.: 16 | VH1-18 & JH6 FR3 | RVTMTTDTSTSTAYMELRSLRSDDTAVYYCAR |
| SEQ ID NO.: 17 | VH1-18 & JH6 FR4<br>VH2-26 & JH6 FR4<br>VH1-46 & JH6 FR4 | WGQGTTVTVSS |
| SEQ ID NO.: 18 | 21/28 & JH4 FR2 | WVRQAPGQRLEWMG |
| SEQ ID NO.: 19 | 21/28 & JH4 FR3 | RVTITRDTSASTAYMELSSLRSEDTAVYYCAR |
| SEQ ID NO.: 20 | 21/28 & JH4 FR4<br>M60 & JH4 FR4 | WGQGTLVTVSS |
| SEQ ID NO.: 21 | VH2-26 & JH6 FR1 | QVTLKESGPVLVKPTETLTLTCTVSGFSLS |
| SEQ ID NO.: 22 | VH2-26 & JH6 FR2 | WIRQPPGKALEWLAH |
| SEQ ID NO.: 23 | VH2-26 & JH6 FR3 | RLTISKDTSKSQVVLTMTNMDPVDTATYYCAR |
| SEQ ID NO.: 24 | M60 & JH4 FR1 | QVTLRESGPALVKPTQTLTLTCTLYGFSLS |
| SEQ ID NO.: 25 | M60 & JH4 FR2 | WIRQPPGKALEWLA |
| SEQ ID NO.: 26 | M60 & JH4 FR3 | RLTISKDTSKNQVVLTMTNMDPVDTATYYCAR |
| SEQ ID NO.: 27 | VH1-46 & JH6 FR3 | RVTMTRDTSTSTVYMELSSLRSEDTAVYYCAR |
| SEQ ID NO.: 28 | A20 & JK4 FR1<br>III-3R & JK4 FR1 | DIQMTQSPSSLSASVGDRVTITC |
| SEQ ID NO.: 29 | A20 & JK4 FR2<br>III-3R & JK4 FR2 | WYQQKPGKVPKLLIY |
| SEQ ID NO.: 30 | A20 & JK4 FR3 | GVPSRFSGSGSGTDFTLTISSLQPEDVATYYC |
| SEQ ID NO.: 31 | A20 & JK4 FR4<br>III-3R & JK4 FR4<br>A1 & JK4 FR4 | FGGGTKVEIKR |
| SEQ ID NO.: 32 | III-3R & JK4 FR3 | GVPSRISGSGSGTDFTFTISSLQPEDIATYYC |
| SEQ ID NO.: 33 | A1 & JK4 FR1 | DVVMTQSPLSLPVTLGQPASISC |
| SEQ ID NO.: 34 | A1 & JK4 FR2 | WFQQRPGQSPRRLIY |

| | | Sequence Listing |
|---|---|---|
| Sequence Identifier | Protein | Sequence 123456789012345678901234567890123 |

SEQ ID NO.: 35  A1 & JK4 FR3  O1 & JK2 FR3  GVPDRFSGSGSGTDFTLKISRVEAEDVGVYYC

SEQ ID NO.: 36  O1 & JK2 FR1  DIVMTQTPLSLPVTPGEPASISC

SEQ ID NO.: 37  O1 & JK2 FR2  WYLQKPGQSPQLLIY

SEQ ID NO.: 38  O1 & JK2 FR4  FGQGTKLEIKR

SEQ ID NO.: 39  Ab1 VH.1z  QVQLVQSGAEVKKPGSSVKVSCKASGYTFTTY WMHWVRQAPGQGLEWMGEIDPSDSYSNYNQKF KDRVTITADKSTSTAYMELSSLRSEDTAVYYC ARNGGLGPAWFSYWGQGTLVTVSS

SEQ ID NO.: 40  Ab1 VH.1z CDRH1  Ab1 VH.1 CDRH1  Ab1 VH.1a CDRH1  GYTFTTYWMH

SEQ ID NO.: 41  Ab1 VH.1z CDRH2  Ab1 VH.1 CDRH2  Ab1 VH.1a CDRH2  EIDPSDSYSNYNQKFKD

SEQ ID NO.: 42  Ab1 VH.1z CDRH3  Ab1 VH.1 CDRH3  Ab1 VH.1a CDRH3  Ab1 VH.1b CDRH3  NGGLGPAWFSY

SEQ ID NO.: 43  Ab1 VH.1  EVQLVQSGAEVKKPGSSVKVSCKASGYTFTTY WMHWVRQAPGQGLEWMGEIDPSDSYSNYNQKF KDRVTITADKSTSTAYMELSSLRSEDTAVYYC ARNGGLGPAWFSYWGQGTLVTVSS

SEQ ID NO.: 44  Ab1 VH.1a  EVQLVQSGAEVKKPGSSVKVSCKASGYTFTTY WMHWVRQAPGQGLEWIGEIDPSDSYSNYNQKF KDRATLTVDKSTSTAYMELSSLRSEDTAVYYC ARNGGLGPAWFSYWGQGTLVTVSS

SEQ ID NO.: 45  Ab1 VH.1b  EVQLVQSGAEVKKPGSSVKVSCKASGGTFTTY WMHWVRQAPGQGLEWIGEIDPSDSYSNYAQKF QGRVTITVDKSTSTAYMELSSLRSEDTAVYYC ARNGGLGPAWFSYWGQGTLVTVSS

SEQ ID NO.: 46  Ab1 VH.1b CDRH1  GGTFTTYWMH

SEQ ID NO.: 47  Ab1 VH.1b CDRH2  EIDPSDSYSNYAQKF

Sequence Listing

| Sequence Identifier | Protein | Sequence<br>123456789012345678901234567890123456789012 |
|---|---|---|
| SEQ ID NO.: 48 | Ab1 VL.1 | DIQMTQSPSSVSASVGDRVTITCKASQYVGTA<br>VAWYQQKPGKAPKLLIYSASNRYTGVPSRFSG<br>SGSGTDFTLTISSLQPEDFATYYCQQYSSYPW<br>TFGGGTKVEIK |
| SEQ ID NO.: 49 | Ab1 VL.1 CDRL1<br>Ab1 VL.1a CDRL1<br>Ab1 VL.2 CDRL1<br>Ab1 VL.2a CDRL1 | KASQYVGTAVA |
| SEQ ID NO.: 50 | Ab1 VL.1 CDRL2<br>Ab1 VL.1a CDRL2<br>Ab1 VL.2 CDRL2<br>Ab1 VL.2a CDRL2 | SASNRYT |
| SEQ ID NO.: 51 | Ab1 VL.1 CDRL3<br>Ab1 VL.1a CDRL3<br>Ab1 VL.2 CDRL3<br>Ab1 VL.2a CDRL3 | QQYSSYPWT |
| SEQ ID NO.: 52 | Ab1 VL.1a | DIQMTQSPSSVSASVGDRVTITCKASQYVGTA<br>VAWYQQKPGKSPKLLIYSASNRYTGVPSRFSD<br>SGSGTDFTLTISSLQPEDFATY<u>F</u>CQQYSSYPW<br>TFGGGTKVEIK |
| SEQ ID NO.: 53 | Ab1 VL.2 | EIVMTQSPATLSVSPGERATLSCKASQYVGTA<br>VAWYQQKPGQAPRLLIYSASNRYTGIPARFSG<br>SGSGTEFTLTISSLQSEDFAVYYCQQYSSYPW<br>TFGGGTKVEIK |
| SEQ ID NO.: 54 | Ab1 VL.2a | EIVMTQSPATLSVSPGERATLSCKASQYVGTA<br>VAWYQQKPGQSPRLLIYSASNRYTGVPARFSD<br>SGSGTEFTLTISSLQSEDFAVY<u>F</u>CQQYSSYPW<br>TFGGGTKVEIK |
| SEQ ID NO.: 55 | Ab2 VH.1z | QVQLVQSGAEVKKPGSSVKVSCKASGYTFTSF<br>WMHWVRQAPGQGLEWMGVIDPSDTYTNYNQKF<br>KGRVTITADESTSTAYMELSSLRSEDTAVYYC<br>ARGDYSNWFTYWGQGTLVTVSS |
| SEQ ID NO.: 56 | Ab2 VH.1z CDRH1<br>Ab2 VH.1 CDRH1<br>Ab2 VH.1a CDRH1 | GYTFTSFWMH |
| SEQ ID NO.: 57 | Ab2 VH.1z CDRH2<br>Ab2 VH.1 CDRH2<br>Ab2 | VIDPSDTYTNYNQKFKG |

Sequence Listing

| Sequence Identifier | Protein | Sequence 123456789012345678901234567890123 |
|---|---|---|
| | VH.1a CDRH2 | |
| SEQ ID NO.: 58 | Ab2 VH.1z CDRH3 Ab2 VH.1 CDRH3 Ab2 VH.1a CDRH3 Ab2 VH.1b CDRH3 | GDYSNWFTY |
| SEQ ID NO.: 59 | Ab2 VH.1 | EVQLVQSGAEVKKPGSSVKVSCKASGYTFTSF WMHWVRQAPGQGLEWMGVIDPSDTYTNYNQKF KGRVTITADESTSTAYMELSSLRSEDTAVYYC ARGDYSNWFTYWGQGTLVTVSS |
| SEQ ID NO.: 60 | Ab2 VH.1a | EVQLVQSGAEVKKPGSSVKVSCKASGYTFTSF WMHWVRQAPGQGLEWIGVIDPSDTYTNYNQKF KGRATLTVDESSSTAYMELSSLRSEDTAVYYC ARGDYSNWFTYWGQGTLVTVSS |
| SEQ ID NO.: 61 | Ab2 VH.1b | EVQLVQSGAEVKKPGSSVKVSCKASGGTFTSF WMHWVRQAPGQGLEWIGVIDPSDTYTNYAQKF QGRVTITVDESTSTAYMELSSLRSEDTAVYYC ARGDYSNWFTYWGQGTLVTVSS |
| SEQ ID NO.: 62 | Ab2 VH.1b CDRH1 | GGTFTSFWMH |
| SEQ ID NO.: 63 | Ab2 VH.1b CDRH2 | VIDPSDTYTNYAQKFQG |
| SEQ ID NO.: 64 | Ab2 VL.1 | DIVMTQTPLSLSVTPGQPASISCRSSQRLVHS NGNTYLHWYLQKPGQSPQLLIYKVSNRFSGVP DRFSGSGSGTDFTLKISRVEAEDVGVYYCSQS THVPWTFGGGTKVEIK |
| SEQ ID NO.: 65 | Ab2 VL.1 CDRL1 Ab2 VL.1a CDRL1 Ab2 VL.1b CDRL1 | RSSQRLVHSNGNTYLH |
| SEQ ID NO.: 66 | Ab2 VL.1 CDRL2 Ab2 VL.1a CDRL2 Ab2 VL.1b CDRL2 | KVSNRFS |
| SEQ ID NO.: 67 | Ab2 VL.1 CDRL3 Ab2 VL.1a CDRL3 Ab2 VL.1b CDRL3 | SQSTHVPWT |

-continued

Sequence Listing

| Sequence Identifier | Protein | Sequence<br>123456789012345678901234567890123456789012 |
|---|---|---|
| SEQ ID NO.: 68 | Ab2 VL.1a | DVVMTQTPLSLSVTPGQPASISCRSSQRLVHS<br>NGNTYLHWYLQKPGQSPQLLIYKVSNRFSGVP<br>DRFSGSGSGTDFTLKISRVEAEDVGVYFCSQS<br>THVPWTFGGGTKVEIK |
| SEQ ID NO.: 69 | Ab2 VL.1b | DVVMTQTPLSLSVTPGQPASISCRSSQRLVHS<br>NGNTYLHWYLQKPGQSPQLLIYKVSNRFSGVP<br>DRFSGSGSGTDFTLKISRVEAEDVGVYFCSQS<br>THVPWTFGGGTKVEIK |
| SEQ ID NO.: 70 | Ab3 VH.1z | QVQLVQSGAEVKKPGASVKVSCKASGYTFTDY<br>NIHWVRQAPGQGLEWMGYIYPNNDGTYNQKF<br>KSRVTMTTDTSTSTAYMELRSLRSDDTAVYYC<br>ARGDGNYVGDMDYWGQGTTVTSS |
| SEQ ID NO.: 71 | Ab3 VH.1z CDRH1<br>Ab3 VH.1 CDRH1<br>Ab3 VH.1a CDRH1<br>Ab3 VH.1b CDRH1 | GYTFTDYNIH |
| SEQ ID NO.: 72 | Ab3 VH.1z CDRH2<br>Ab3 VH.1 CDRH2<br>Ab3 VH.1a CDRH2 | YIYPNNDGTYNQKFKS |
| SEQ ID NO.: 73 | Ab3 VH.1z CDRH3<br>Ab3 VH.1 CDRH3<br>Ab3 VH.1a CDRH3<br>Ab3 VH.1b CDRH3 | GDGNYVGDMDY |
| SEQ ID NO.: 74 | Ab3 VH.1 | EVQLVQSGAEVKKPGASVKVSCKASGYTFTDY<br>NIHWVRQAPGQGLEWMGYIYPNNDGTYNQKF<br>KSRVTMTTDTSTSTAYMELRSLRSDDTAVYYC<br>ARGDGNYVGDMDYWGQGTTVTSS |
| SEQ ID NO.: 75 | Ab3 VH.1a | EVQLVQSGAEVKKPGASVKVSCKASGYTFTDY<br>NIHWVRQAPGQGLEWIGYIYPNNDGTYNQKF<br>KSRATLTVDNSTSTAYMELRSLRSDDTAVYYC<br>ARGDGNYVGDMDYWGQGTTVTSS |
| SEQ ID NO.: 76 | Ab3 VH.1b | EVQLVQSGAEVKKPGASVKVSCKASGYTFTDY<br>NIHWVRQAPGQGLEWIGYIYPNNDGTYAQKL<br>QGRVTMTVDTSTSTAYMELRSLRSDDTAVYYC<br>ARGDGNYVGDMDYWGQGTTVTSS |
| SEQ ID NO.: 77 | Ab3 VH.1b CDRH2 | YIYPNNDGTYAQKLQG |
| SEQ ID NO.: 78 | Ab3 VL.1 | DIQMTQSPSSLSASVGDRVTITCRASENIYSY<br>LAWYQQKPGKAPKLLIYNAKTLAEGVPSRFSG<br>SGSGTDFTLTISSLQPEDFATYYCQHHYATPF<br>TFGQGTKLEIK |

Sequence Listing

| Sequence Identifier | Protein | Sequence<br>123456789012345678901234567890212 |
|---|---|---|
| SEQ ID NO.: 79 | Ab3 VL.1 CDRL1<br>Ab3 VL.1a CDRL1<br>Ab3 VL.1b CDRL1 | RASENIYSYLA |
| SEQ ID NO.: 80 | Ab3 VL.1 CDRL2<br>Ab3 VL.1a CDRL2<br>Ab3 VL.1b CDRL2 | NAKTLAE |
| SEQ ID NO.: 81 | Ab3 VL.1 CDRL3<br>Ab3 VL.1a CDRL3<br>Ab3 VL.1b CDRL3 | QHHYATPFT |
| SEQ ID NO.: 82 | Ab3 VL.1a | DIQMTQSPSSLSASVGDRVTITCRASENIYSY LAWYQQKPGKPPKLLVYNAKTLAEGVPSRFSG SGSGTDFTLTISSLQPEDFATYYCQHHYATPF TFGQGTKLEIK |
| SEQ ID NO.: 83 | Ab3 VL.1b | DIQMTQSPSSLSASVGDRVTITCRASENIYSY LAWYQQKPGKAPKLLVYNAKTLAEGVPSRFSG SGSGTDFTLTISSLQPEDFATYYCQHHYATPF TFGQGTKLEIK |
| SEQ ID NO.: 84 | Ab4 VH.1z | QVQLVQSGAEVKKPGSSVKVSCKASGYTFTSY WIHWVRQAPGQGLEWMGEIDPSDSYTNYNQKF KGRVTITADKSTSTAYMELSSLRSEDTAVYYC ARSFFTNWFAYWGQGTLVTVSS |
| SEQ ID NO.: 85 | Ab4 VH.1z CDRH1<br>Ab4 VH.1 CDRH1<br>Ab4 VH.1a CDRH1<br>Ab4 VH.1a.2 CDRH1<br>Ab4 VH.1a.3 CDRH1<br>Ab4 VH.1b.2 CDRH1 | GYTFTSYWIH |
| SEQ ID NO.: 86 | Ab4 VH.1z CDRH2<br>Ab4 VH.1 CDRH2<br>Ab4 VH.1a CDRH2<br>Ab4 VH.1a.2 CDRH2<br>Ab4v VH.1a.3 | EIDPSDSYTNYNQKFKG |

| Sequence Identifier | Protein | Sequence<br>123456789012345678901234567890ABC |
|---|---|---|
| | CDRH2<br>Ab4<br>VH.1b.2<br>CDRH2 | |
| SEQ ID NO.: 87 | Ab4 VH.1z CDRH3<br>Ab4 VH.1 CDRH3<br>Ab4 VH.1a CDRH3<br>Ab4 VH.1a.2 CDRH3<br>Ab4 VH.1a.3 CDRH3<br>Ab4 VH.1b CDRH3<br>Ab4 VH.1b.2 CDRH3 | SFFTNWFAY |
| SEQ ID NO.: 88 | Ab4 VH.1 | EVQLVQSGAEVKKPGSSVKVSCKASGYTFTSYWIHWVRQAPGQGLEWMGEIDPSDSYTNYNQKFKGRVTITADKSTSTAYMELSSLRSEDTAVYYCARSFFTNWFAYWGQGTLVTVSS |
| SEQ ID NO.: 89 | Ab4 VH.1a | EVQLVQSGAEVKKPGSSVKVSCKASGYTFTSYWIHWVRQAPGQGLEWIGEIDPSDSYTNYNQKFKGRATLTVDKSSSTAYMELSSLRSEDTAVYYCARSFFTNWFAYWGQGTLVTVSS |
| SEQ ID NO.: 90 | Ab4 VH.1b.2 | EVQLVQSGAEVKKPGSSVKVSCKASGYTFTSYWIHWVRQAPGQGLEWIGEIDPSDSYTNYNQKFKGRVTITVDKSTSTAYMELSSLRSEDTAVYYCARSFFTNWFAYWGQGTLVTVSS |
| SEQ ID NO.: 91 | Ab4 VL.1 | DIVMTQTPLSLSVTPGQPASISCRSSQSLVHSNGNTYLHWYLQKPGQSPQLLIYKVSNRFSGVPDRFSGSGSGTDFTLKISRVEAEDVGVYYCSQSTHVPFTFGGGTKVEIK |
| SEQ ID NO.: 92 | Ab4 VL.1 CDRH1<br>Ab4 VL.1a CDRH1<br>Ab4 VL.1b CDRH1 | RSSQSLVHSNGNTYLH |
| SEQ ID NO.: 93 | Ab4 VL.1 CDRH2<br>Ab4 VL.1a CDRH2<br>Ab4 VL.1b CDRH2 | KVSNRFS |
| SEQ ID NO.: 94 | Ab4 VL.1 CDRH3<br>Ab4 VL.1a CDRH3<br>Ab4 VL.1b CDRH3 | SQSTHVPFT |

-continued

Sequence Listing

| Sequence Identifier | Protein | Sequence<br>123456789012345678901234567890123 |
|---|---|---|
| SEQ ID NO.: 95 | Ab4 VL.1a | DVVMTQTPLSLSVTPGQPASISCRSSQSLVHS NGNTYLHWYLQKPGQSPQLLIYKVSNRFSGVP DRFSGSGSGTDFTLKISRVEAEDVGVYFCSQS THVPFTFGGGTKVEIK |
| SEQ ID NO.: 96 | Ab4 VL.1b | DVVMTQTPLSLSVTPGQPASISCRSSQSLVHS NGNTYLHWYLQKPGQSPQLLIYKVSNRFSGVP DRFSGSGSGTDFTLKISRVEAEDVGVYYCSQS THVPFTFGGGTKVEIK |

SEQ ID NO.: 97  CDR Region: CDRH1  Consensus sequence:

| 26 | 27 | 28 | 29 | 30 | 31 | 32 | 33 | 34 | 35 | 35a |
|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ |
| G | Y | T | F | T | S | Y | W | M | H | |
| | F | S | I | S | D | F | N | I | F | N |
| | | | | T | D | Y | A | | | |
| | | | | | | | W | | | |

SEQ ID NO.: 98  CDR Region: CDRH2  Consensus sequence:

| 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ | $X_{14}$ | $X_{15}$ | $X_{16}$ | $X_{17}$ |
| Y | I | D | P | S | D | G | Y | T | N | Y | N | Q | K | F | K | G |
| V | F | Y | N | Y | N | S | G | S | G | F | P | D | E | L | K | S |
| E | | S | | N | G | D | H | A | Y | | | P | T | V | | D |
| | | G | | | G | S | T | S | | | | | S | | | N |
| | | | | | | R | | | | | | | | | | |

SEQ ID NO.: 99  CDR Region: CDRH3  Consensus sequence:

| 95 | 96 | 97 | 98 | 99 | 100 | 100a | 100b | 100c | 100d | 100e | 101 | 102 |
|---|---|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ |
| G | D | G | S | Y | W | F | | | | | D | Y |
| S | F | F | N | N | V | G | D | M | A | M | T | |
| N | G | Y | T | G | P | A | W | F | | | A | |
| Q | L | W | L | I | G | Y | A | G | | | S | |
| | | | | G | M | Y | R | | | | G | |
| | | | | Y | | — | | | | | | |
| | | | | A | | | | | | | | |

SEQ ID NO.: 100  CDR Region: CDRL1Xi  Consensus sequence:

| 24 | 25 | 26 | 27 | 27a | 27b | 27c | 27d | 27e | 28 | 29 | 30 | 31 | 32 | 33 | 34 |
|---|---|---|---|---|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ | $X_{14}$ | $X_{15}$ | $X_{16}$ |
| R | A | S | Q | — | — | — | — | — | N | G | N | T | Y | L | H |
| K | S | | E | S | L | V | H | S | Y | I | Y | S | A | V | A |
| S | | | S | R | I | | | | — | V | G | | | M | T |
| | | | | | | | | | S | V | | | | | E |

SEQ ID NO.: 101  CDR Region: CDRL2  Consensus sequence:

| 50 | 51 | 52 | 53 | 54 | 55 | 56 |
|---|---|---|---|---|---|---|
| $X_1$ | $X_2$ | $X_3$ | $X_4$ | $X_5$ | $X_6$ | $X_7$ |
| K | A | S | N | R | F | S |
| N | V | K | T | L | A | E |
| S | T | | | | Y | T |
| L | | | | | | S |

SEQ ID NO.: 102  CDR Region: CDRL3  Consensus sequence:

| 89 | 90 | 91 | 92 | 93 | 94 | 95 | 95a | 96 | 97 |
|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ |
| Q | Q | S | S | H | V | P | — | F | T |
| S | H | H | T | S | T | | P | W | |
| F | | G | Y | A | Y | | | L | |
| | | Y | | G | | | | | |
| | | W | | V | | | | | |

| SEQ ID NO.: 103 | Murine Ab5 Variable Light Chain | DVVMTQTPLSLPVSLGDQASISCRSSQRLVHS NGNTYLHWYLQKPGQSPKLLIYKVSNRFSGVP DRFSGSGSGTDFTLKISRVEAEDLGVYFCSQS THVPWTFGGGTKLEIK |
| SEQ ID NO.: 104 | Murine Ab6 Variable Light Chain | DIVMTQSQKFMSTTVGDRVSITCKASQYVGTA VAWYQQKPGQSPKLLIYSASNRYTGVPDRFTD SGSGTDFTLTISNLQSEDLADYFCQQYSSYPW TFGGGTKLEIK |

| Sequence Identifier | Protein | Sequence 12345678901234567890123456789012 |
|---|---|---|
| SEQ ID NO.: 105 | Murine Ab7 Variable Light Chain | DVVMTQTPLSLPVSLGDQASISCRSSQSLVHS NGNTYLHWYLQKPGQSPKLLIYKVSNRFSGVP DRFSGSGSGTDFTLKINRVEAEDLGVYFCSQS THVPFTFGSGTKLEIK |
| SEQ ID NO.: 106 | Murine Ab8 Variable Light Chain | DIQMTQSPASLSASVGETVTITCRASENIYSY LAWYQQKQGKPPQLLVYNAKTLAEGVPSRFSG GGSGTQFSLKINSLQPEDFGSYYCQHHYATPF TFGSGTKLEIK |
| SEQ ID NO.: 107 | Murine Ab9 Variable Light Chain | DIQMTQSPASLSASVGETVTITCRASENIYSY LAWYQQKQGKSPQLLVYNAKTLAEGVPSRFSG SGSGTQFSLKINSLQPEDFGSYYCQHHSGTPF TFGSGTKLEIK |
| SEQ ID NO.: 108 | Murine Ab10 Variable Light Chain | DIQMTQSPASLSASVGETVTITCRASENIYSY LTWYQQKQGKSPQLLVYNAKTLAEGVPSRFSG SGSGTQFSLKINSLQPEDFGSYHCQHHSVTPL TFGAGTKLELK |
| SEQ ID NO.: 109 | Murine Ab11 Variable Light Chain | DVLMTQTPLSLPVSLGDQASISCRSSQSIVHS NGNTYLEWYLQKPGQSPKLLIYKVSNRFSGVP DRFSGSGSGTDFTLKISRVEAEDLGVYYCFQG SHVPFTFGSGTKLEIK |
| SEQ ID NO.: 110 | Murine Ab12 Variable Light Chain | QIVLTQSPGIMSASPGEKVTMTCSASSSVTYM YWYQQKPRSSPKPWIYLTSNLASGVPARFSGS GSGTSYSLTISSMEAEDGATYYCQQWSSTPPL TFGGGTKLELN |
| SEQ ID NO.: 111 | Murine Ab13 Variable Light Chain | DVVMTQTPFSLPVSLGDQASISCRSSQSLVHS NGNTYLHWYLQKPGQSPKLLIYKVSNRFSGVP DRFSGSGSGTDFTLKISRVEAEDLELYFCSQS THVPWTFGGGTKLEIK |
| SEQ ID NO.: 112 | Murine Ab5 Variable Heavy Chain | QVQLQQPGAELVRPGTSVKLSCKASGYTFTSF WMHWVKQRPGQGLEWIGVIDPSDTYTNYNQKF KGKATLTVDTSSSTAYMQLSSLTSEDSAVYYC ARGDYSNWFTYWGQGTLVTVSA |
| SEQ ID NO.: 113 | Murine Ab6 Variable Heavy Chain | QVQLQQPGAELVMPGSSVKLSCKASGYTFTTY WMHWVKQRPGQGLEWIGEIDPSDSYSNYNQKF KDKATLTVDKSSSTAYMQLSSLTSEDSAVYYC ARNGGLGPAWFSYWGQGTLVTVSA |
| SEQ ID NO.: 114 | Murine Ab7 Variable Heavy Chain | QVQLQQPGAELVMPGTSVKLSCKASGYTFTSY WIHWVKQRPGQGLEWIGEIDPSDSYTNYNQKF KGKATLTVDRSSSTAYMQLSSLTSEDSAVYYC GRSFFTNWFAYWGQGTLVTVSA |
| SEQ ID NO.: 115 | Murine Ab8 Variable Heavy Chain | EVQLQQSGPELVKPGASVKISCKASGYTFTDY NIHWVKQSHGKSLEWIGYIYPNNDGTGYNQKF KSKATLTVDNSSSTAYMEVRSLTSEDSAVYYC ARGDNYVGDMDYWGQGTSVTVSS |
| SEQ ID NO.: 116 | Murine Ab9 Variable Heavy Chain | EVQLQQSGPELVRPGASVKISCKASGYSFTDY NMHWVKQSHGKSLEWIGYIYPYNGGAGYNQKF KSKATMNVGISSSTAYMELRSLTSEDSAVYYC ARGDGNYVGDMDYWGQGTSVTVSS |

| Sequence Identifier | Protein | Sequence 123456789012345678901234567890012 |
|---|---|---|
| SEQ ID NO.: 117 | Murine Ab10 Variable Heavy Chain | EVQLHQSGPELVKPGASVKISCKASGYTFTDY NMHWMKQSHGKSLEWIGYFYPYNGGTYNQEF KNKATLTVDISSSTAYMELRRLTSEDSAVYYC ARGGWGIYYAMDYWGQGTSVTVSS |
| SEQ ID NO.: 118 | Murine Ab11 Variable Heavy Chain | EVKLVESGGGLVQPGGSLKLSCAASGFTFSDY YMFWVRQTPEKSLEWVAYISNGGGSTYYPDTV KGRFTISRDNAKNTLYLQMSRLKSEDTAMYYC SRQLFYYGSRGAMGYWGQGTSVTVSS |
| SEQ ID NO.: 119 | Murine Ab12 Variable Heavy Chain | DVQLQESGPGLVKPSQSLSLTCTVTGYSITSD YAWNWIRQFPGNKLEWMGYIGYSGRTSFNPSL KSRISITRDTSKNQFFLQLNSVTTEDTATYYC ARGGFAMDYWGQGTSVTVSS |
| SEQ ID NO.: 120 | Murine Ab13 Variable Heavy Chain | QVQLQQPGAELVRPGTSVKLSCKASGYTFTSF WMHWVKQRPGQGLEWIGVIDPSDSHTNYNQKF KGKATLTVNTSSSTAYMHLSSLTSEDSAVYYC ARGDYSNWFTYWGQGTLVTVSA |
| SEQ ID NO.: 121 | Ab4VH. 1a.2 | EVQLVQSGAEVKKPGSSVKVSCKASGYTFTSY WIHWVRQAPGQGLEWIGEIDPSDSYTNYNQKF KGRATLTVDRSSSTAYMELSSLRSEDTAVYYC GRSFFTNWFAYWGQGTLVTVSS |
| SEQ ID NO.: 122 | Ab4VH. 1a.3 | EVQLVQSGAEVKKPGSSVKVSCKASGYTFTSY WIHWVRQAPGQGLEWIGEIDPSDSYTNYNQKF KGRATLTVDKSSSTAYMELSSLRSEDTAVYYC GRSFFTNWFAYWGQGTLVTVSS |
| SEQ ID NO.: 123 | Ab4VH.1b | EVQLVQSGAEVKKPGSSVKVSCKASGGTFTSY WIHWVRQAPGQGLEWIGEIDPSDSYTNYAQKF QGRVTITVDKSTSTAYMELSSLRSEDTAVYYC ARSFFTNWFAYWGQGTLVTVSS |
| SEQ ID NO.: 124 | Ab1HC.1 | EVQLVQSGAEVKKPGSSVKVSCKASGYTFTTY WMHWVRQAPGQGLEWMGEIDPSDSYSNYNQKF KDRVTITADKSTSTAYMELSSLRSEDTAVYYC ARNGGLGPAWFSYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVMHEALHNHYTQKSLSLSP GK |
| SEQ ID NO.: 125 | Ab1LC.1 | DIQMTQSPSSVSASVGDRVTITCKASQYVGTA VAWYQQKPGKAPKLLIYSASNRYTGVPSRFSG SGSGTDFTLTISSLQPEDFATYYCQQYSSYPW TFGGGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO.: 126 | Ab1LC.1a | DIQMTQSPSSVSASVGDRVTITCKASQYVGTA VAWYQQKPGKSPKLLIYSASNRYTGVPSRFSD SGSGTDFTLTISSLQPEDFATYFCQQYSSYPW TFGGGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |

-continued

| Sequence Identifier | Protein | Sequence 12345678901234567890123456789012 |
|---|---|---|
| SEQ ID NO.: 127 | Ab1LC.2 | EIVMTQSPATLSVSPGERATLSCKASQYVGTA VAWYQQKPGQAPRLLIYSASNRYTGIPARFSG SGSGTEFTLTISSLQSEDFAVYYCQQYSSYPW TFGGGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO.: 128 | Ab1LC.2a | EIVMTQSPATLSVSPGERATLSCKASQYVGTA VAWYQQKPGQSPRLLIYSASNRYTGVPARFSD SGSGTEFTLTISSLQSEDFAVYFCQQYSSYPW TFGGGTKVEIKRTVAAPSVFIFPPSDEQLKSG TASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO.: 129 | Ab1HC.1a | EVQLVQSGAEVKKPGSSVKVSCKASGYTFTTY WMHWVRQAPGQGLEWIGEIDPSDSYSNYNQKF KDRATLTVDKSTSTAYMELSSLRSEDTAVYYC ARNGGLGPAWFSYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVMHEALHNHYTQKSLSLSP GK |
| SEQ ID NO.: 130 | Ab1HC.1b | EVQLVQSGAEVKKPGSSVKVSCKASGGTFTTY WMHWVRQAPGQGLEWIGEIDPSDSYSNYAQKF QGRVTITVDKSTSTAYMELSSLRSEDTAVYYC ARNGGLGPAWFSYWGQGTLVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPELLGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSREEMTKNQVSLTCLVKGFYPSDIAVEW ESNGQPENNYKTTPPVLDSDGSFFLYSKLTVD KSRWQQGNVFSCSVMHEALHNHYTQKSLSLSP GK |
| SEQ ID NO.: 131 | Ab2HC.1 | EVQLVQSGAEVKKPGSSVKVSCKASGYTFTSF WMHWVRQAPGQGLEWMGVIDPSDTYTNYNQKF KGRVTITADESTSTAYMELSSLRSEDTAVYYC ARGDYSNWFTYWGQGTLVTVSSASTKGPSVFP LAPSSKSTSGGTAALGCLVKDYFPEPVTVSWN SGALTSGVHTFPAVLQSSGLYSLSSVVTVPSS SLGTQTYICNVNHKPSNTKVDKKVEPKSCDKT HTCPPCPAPELLGGPSVFLFPPKPKDTLMISR TPEVTCVVVDVSHEDPEVKFNWYVDGVEVHNA KTKPREEQYNSTYRVVSVLTVLHQDWLNGKEY KCKVSNKALPAPIEKTISKAKGQPREPQVYTL PPSREEMTKNQVSLTCLVKGFYPSDIAVEWES NGQPENNYKTTPPVLDSDGSFFLYSKLTVDKS RWQQGNVFSCSVMHEALHNHYTQKSLSLSPGK |
| SEQ ID NO.: 132 | Ab2LC.1 | DIVMTQTPLSLSVTPGQPASISCRSSQRLVHS NGNTYLHWYLQKPGQSPQLLIYKVSNRFSGVP DRFSGSGSGTDFTLKISRVEAEDVGVYYCSQS THVPWTFGGGTKVEIKRTVAAPSVFIFPPSDE QLKSGTASVVCLLNNFYPREAKVQWKVDNALQ SGNSQESVTEQDSKDSTYSLSSTLTLSKADYE KHKVYACEVTHQGLSSPVTKSFNRGEC |

Sequence Listing

| Sequence Identifier | Protein | Sequence<br>123456789012345678901234567890212 |
|---|---|---|
| SEQ ID NO.: 133 | Ab2LC.1a | DVVMTQTPLSLSVTPGQPASISCRSSQRLVHS<br>NGNTYLHWYLQKPGQSPQLLIYKVSNRFSGVP<br>DRFSGSGSGTDFTLKISRVEAEDVGVYFCSQS<br>THVPWTFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| SEQ ID NO.: 134 | Ab2LC.1b | DVVMTQTPLSLSVTPGQPASISCRSSQRLVHS<br>NGNTYLHWYLQKPGQSPQLLIYKVSNRFSGVP<br>DRFSGSGSGTDFTLKISRVEAEDVGVYYCSQS<br>THVPWTFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| SEQ ID NO.: 135 | Ab2HC.1a | EVQLVQSGAEVKKPGSSVKVSCKASGYTFTSF<br>WMHWVRQAPGQGLEWIGVIDPSDTYTNYNQKF<br>KGRATLTVDESSSTAYMELSSLRSEDTAVYYC<br>ARGDYSNWFTYWGQGTLVTVSSASTKGPSVFP<br>LAPSSKSTSGGTAALGCLVKDYFPEPVTVSWN<br>SGALTSGVHTFPAVLQSSGLYSLSSVVTVPSS<br>SLGTQTYICNVNHKPSNTKVDKKVEPKSCDKT<br>HTCPPCPAPELLGGPSVFLFPPKPKDTLMISR<br>TPEVTCVVVDVSHEDPEVKFNWYVDGVEVHNA<br>KTKPREEQYNSTYRVVSVLTVLHQDWLNGKEY<br>KCKVSNKALPAPIEKTISKAKGQPREPQVYTL<br>PPSREEMTKNQVSLTCLVKGFYPSDIAVEWES<br>NGQPENNYKTTPPVLDSDGSFFLYSKLTVDKS<br>RWQQGNVFSCSVMHEALHNHYTQKSLSLSPGK |
| SEQ ID NO.: 136 | Ab2HC.1b | EVQLVQSGAEVKKPGSSVKVSCKASGGTFTSF<br>WMHWVRQAPGQGLEWIGVIDPSDTYTNYAQKF<br>QGRVTITVDESTSTAYMELSSLRSEDTAVYYC<br>ARGDYSNWFTYWGQGTLVTVSSASTKGPSVFP<br>LAPSSKSTSGGTAALGCLVKDYFPEPVTVSWN<br>SGALTSGVHTFPAVLQSSGLYSLSSVVTVPSS<br>SLGTQTYICNVNHKPSNTKVDKKVEPKSCDKT<br>HTCPPCPAPELLGGPSVFLFPPKPKDTLMISR<br>TPEVTCVVVDVSHEDPEVKFNWYVDGVEVHNA<br>KTKPREEQYNSTYRVVSVLTVLHQDWLNGKEY<br>KCKVSNKALPAPIEKTISKAKGQPREPQVYTL<br>PPSREEMTKNQVSLTCLVKGFYPSDIAVEWES<br>NGQPENNYKTTPPVLDSDGSFFLYSKLTVDKS<br>RWQQGNVFSCSVMHEALHNHYTQKSLSLSPGK |
| SEQ ID NO.: 137 | Ab4HC.1 | EVQLVQSGAEVKKPGSSVKVSCKASGYTFTSY<br>WIHWVRQAPGQGLEWMGEIDPSDSYTNYNQKF<br>KGRVTITADKSTSTAYMELSSLRSEDTAVYYC<br>ARSFFTNWFAYWGQGTLVTVSSASTKGPSVFP<br>LAPSSKSTSGGTAALGCLVKDYFPEPVTVSWN<br>SGALTSGVHTFPAVLQSSGLYSLSSVVTVPSS<br>SLGTQTYICNVNHKPSNTKVDKKVEPKSCDKT<br>HTCPPCPAPELLGGPSVFLFPPKPKDTLMISR<br>TPEVTCVVVDVSHEDPEVKFNWYVDGVEVHNA<br>KTKPREEQYNSTYRVVSVLTVLHQDWLNGKEY<br>KCKVSNKALPAPIEKTISKAKGQPREPQVYTL<br>PPSREEMTKNQVSLTCLVKGFYPSDIAVEWES<br>NGQPENNYKTTPPVLDSDGSFFLYSKLTVDKS<br>RWQQGNVFSCSVMHEALHNHYTQKSLSLSPGK |
| SEQ ID NO.: 138 | Ab4LC.1 | DIVMTQTPLSLSVTPGQPASISCRSSQSLVHS<br>NGNTYLHWYLQKPGQSPQLLIYKVSNRFSGVP<br>DRFSGSGSGTDFTLKISRVEAEDVGVYYCSQS<br>THVPFTFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| SEQ ID NO.: 139 | Ab4LC.1a | DVVMTQTPLSLSVTPGQPASISCRSSQSLVHS<br>NGNTYLHWYLQKPGQSPQLLIYKVSNRFSGVP<br>DRFSGSGSGTDFTLKISRVEAEDVGVYFCSQS |

| Sequence Identifier | Protein | Sequence |
|---|---|---|
| | | THVPFTFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| SEQ ID NO.: 140 | Ab4LC.1b | DVVMTQTPLSLSVTPGQPASISCRSSQSLVHS<br>NGNTYLHWYLQKPGQSPQLLIYKVSNRFSGVP<br>DRFSGSGSGTDFTLKISRVEAEDVGVYYCSQS<br>THVPFTFGGGTKVEIKRTVAAPSVFIFPPSDE<br>QLKSGTASVVCLLNNFYPREAKVQWKVDNALQ<br>SGNSQESVTEQDSKDSTYSLSSTLTLSKADYE<br>KHKVYACEVTHQGLSSPVTKSFNRGEC |
| SEQ ID NO.: 141 | Ab4HC.1a | EVQLVQSGAEVKKPGSSVKVSCKASGYTFTSY<br>WIHWVRQAPGQGLEWIGEIDPSDSYTNYNQKF<br>KGRATLTVDKSSSTAYMELSSLRSEDTAVYYC<br>ARSFFTNWFAYWGQGTLVTVSSASTKGPSVFP<br>LAPSSKSTSGGTAALGCLVKDYFPEPVTVSWN<br>SGALTSGVHTFPAVLQSSGLYSLSSVVTVPSS<br>SLGTQTYICNVNHKPSNTKVDKKVEPKSCDKT<br>HTCPPCPAPELLGGPSVFLFPPKPKDTLMISR<br>TPEVTCVVVDVSHEDPEVKFNWYVDGVEVHNA<br>KTKPREEQYNSTYRVVSVLTVLHQDWLNGKEY<br>KCKVSNKALPAPIEKTISKAKGQPREPQVYTL<br>PPSREEMTKNQVSLTCLVKGFYPSDIAVEWES<br>NGQPENNYKTTPPVLDSDGSFFLYSKLTVDKS<br>RWQQGNVFSCSVMHEALHNHYTQKSLSLSPGK |
| SEQ ID NO.: 142 | Ab4HC.1b | EVQLVQSGAEVKKPGSSVKVSCKASGGTFTSY<br>WIHWVRQAPGQGLEWIGEIDPSDSYTNYAQKF<br>QGRVTITVDKSTSTAYMELSSLRSEDTAVYYC<br>ARSFFTNWFAYWGQGTLVTVSSASTKGPSVFP<br>LAPSSKSTSGGTAALGCLVKDYFPEPVTVSWN<br>SGALTSGVHTFPAVLQSSGLYSLSSVVTVPSS<br>SLGTQTYICNVNHKPSNTKVDKKVEPKSCDKT<br>HTCPPCPAPELLGGPSVFLFPPKPKDTLMISR<br>TPEVTCVVVDVSHEDPEVKFNWYVDGVEVHNA<br>KTKPREEQYNSTYRVVSVLTVLHQDWLNGKEY<br>KCKVSNKALPAPIEKTISKAKGQPREPQVYTL<br>PPSREEMTKNQVSLTCLVKGFYPSDIAVEWES<br>NGQPENNYKTTPPVLDSDGSFFLYSKLTVDKS<br>RWQQGNVFSCSVMHEALHNHYTQKSLSLSPGK |
| SEQ ID NO.: 143 | Ab3HC.1 | EVQLVQSGAEVKKPGASVKVSCKASGYTFTDY<br>NIHWVRQAPGQGLEWMGYIYPNNDGTGYNQKF<br>KSRVTMTTDTSTSTAYMELRSLRSDDTAVYYC<br>ARGDNYVGDMDYWGQGTTVTVSSASTKGPSV<br>FPLAPSSKSTSGGTAALGCLVKDYFPEPVTVS<br>WNSGALTSGVHTFPAVLQSSGLYSLSSVVTVP<br>SSSLGTQTYICNVNHKPSNTKVDKKVEPKSCD<br>KTHTCPPCPAPELLGGPSVFLFPPKPKDTLMI<br>SRTPEVTCVVVDVSHEDPEVKFNWYVDGVEVH<br>NAKTKPREEQYNSTYRVVSVLTVLHQDWLNGK<br>EYKCKVSNKALPAPIEKTISKAKGQPREPQVY<br>TLPPSREEMTKNQVSLTCLVKGFYPSDIAVEW<br>ESNGQPENNYKTTPPVLDSDGSFFLYSKLTVD<br>KSRWQQGNVFSCSVMHEALHNHYTQKSLSLSP<br>GK |
| SEQ ID NO.: 144 | Ab3 LC.1 | DIQMTQSPSSLSASVGDRVTITCRASENIYSY<br>LAWYQQKPGKAPKLLIYNAKTLAEGVPSRFSG<br>SGSGTDFTLTISSLQPEDFATYYCQHHYATPF<br>TFGQGTKLEIKRTVAAPSVFIFPPSDEQLKSG<br>TASVVCLLNNFYPREAKVQWKVDNALQSGNSQ<br>ESVTEQDSKDSTYSLSSTLTLSKADYEKHKVY<br>ACEVTHQGLSSPVTKSFNRGEC |
| SEQ ID NO.: 145 | Ab3 LC.1a | DIQMTQSPSSLSASVGDRVTITCRASENIYSY<br>LAWYQQKPGKPPKLLVYNAKTLAEGVPSRFSG<br>SGSGTDFTLTISSLQPEDFATYYCQHHYATPF<br>TFGQGTKLEIKRTVAAPSVFIFPPSDEQLKSG<br>TASVVCLLNNFYPREAKVQWKVDNALQSGNSQ |

| Sequence Identifier | Protein | Sequence<br>123456789012345678901234567890012 |
|---|---|---|
| | | ESVTEQDSKDSTYSLSSTLTLSKADYEKHKVY<br>ACEVTHQGLSSPVTKSFNRGEC |
| SEQ ID NO.: 146 | Ab3 LC.1b | DIQMTQSPSSLSASVGDRVTITCRASENIYSY<br>LAWYQQKPGKAPKLLVYNAKTLAEGVPSRFSG<br>SGSGTDFTLTISSLQPEDFATYYCQHHYATPF<br>TFGQGTKLEIKRTVAAPSVFIFPPSDEQLKSG<br>TASVVCLLNNFYPREAKVQWKVDNALQSGNSQ<br>ESVTEQDSKDSTYSLSSTLTLSKADYEKHKVY<br>ACEVTHQGLSSPVTKSFNRGEC |
| SEQ ID NO.: 147 | Ab3 HC.1a | EVQLVQSGAEVKKPGASVKVSCKASGYTFTDY<br>NIHWVRQAPGQGLEWIGYIYPNNDGTYNQKF<br>KSRATLTVDNSTSTAYMELRSLRSDDTAVYYC<br>ARGDGNYVGDMDYWGQGTTVTVSSASTKGPSV<br>FPLAPSSKSTSGGTAALGCLVKDYFPEPVTVS<br>WNSGALTSGVHTFPAVLQSSGLYSLSSVVTVP<br>SSSLGTQTYICNVNHKPSNTKVDKKVEPKSCD<br>KTHTCPPCPAPELLGGPSVFLFPPKPKDTLMI<br>SRTPEVTCVVVDVSHEDPEVKFNWYVDGVEVH<br>NAKTKPREEQYNSTYRVVSVLTVLHQDWLNGK<br>EYKCKVSNKALPAPIEKTISKAKGQPREPQVY<br>TLPPSREEMTKNQVSLTCLVKGFYPSDIAVEW<br>ESNGQPENNYKTTPPVLDSDGSFFLYSKLTVD<br>KSRWQQGNVFSCSVMHEALHNHYTQKSLSLSP<br>GK |
| SEQ ID NO.: 148 | Ab3 HC.1b | EVQLVQSGAEVKKPGASVKVSCKASGYTFTDY<br>NIHWVRQAPGQGLEWIGYIYPNNDGTYAQKL<br>QGRVTMTVDTSTSTAYMELRSLRSDDTAVYYC<br>ARGDGNYVGDMDYWGQGTTVTVSSASTKGPSV<br>FPLAPSSKSTSGGTAALGCLVKDYFPEPVTVS<br>WNSGALTSGVHTFPAVLQSSGLYSLSSVVTVP<br>SSSLGTQTYICNVNHKPSNTKVDKKVEPKSCD<br>KTHTCPPCPAPELLGGPSVFLFPPKPKDTLMI<br>SRTPEVTCVVVDVSHEDPEVKFNWYVDGVEVH<br>NAKTKPREEQYNSTYRVVSVLTVLHQDWLNGK<br>EYKCKVSNKALPAPIEKTISKAKGQPREPQVY<br>TLPPSREEMTKNQVSLTCLVKGFYPSDIAVEW<br>ESNGQPENNYKTTPPVLDSDGSFFLYSKLTVD<br>KSRWQQGNVFSCSVMHEALHNHYTQKSLSLSP<br>GK |
| SEQ ID NO.: 149 | Ab4 VH.1b CDRH1 | GGTFTSYWIH |
| SEQ ID NO.: 150 | Ab4 VH.1b CDRH2 | EIDPSDSYTNYAQKFQG |

SEQ ID NO.: 151 CDR Region: CDRH1

Consensus sequence:

| 26 | 27 | 28 | 29 | 30 | 31 | 32 | 33 | 34 | 35 | 35a |
|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ |
| G | Y | T | F | T | S | Y | W | M | H | |
| | F | S | I | S | D | F | N | I | F | N |
| | G | | | | T | D | Y | A | W | |

SEQ ID NO.: 152 CDR Region: CDRH2

Consensus sequence:

| 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|
| $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ | $X_{14}$ | $X_{15}$ | $X_{16}$ | $X_{17}$ |
| Y | I | D | P | S | D | G | Y | T | N | Y | N | Q | K | F | K | G |
| V | F | Y | N | Y | N | S | G | S | G | F | P | D | E | L | Q | S |
| E | | S | | N | G | D | H | A | Y | | A | P | T | V | | D |
| | | G | | | G | S | T | | S | | | S | | | | N |
| | | | | | | R | | | | | | | | | | |

| SEQ ID NO.: 153 | Ab4 HC.1b.2 | EVQLVQSGAEVKKPGSSVKVSCKASGYTFTSYWIHW<br>VRQAPGQGLEWIGEIDPSDSYTNYNQKFKGRVTITV<br>DKSTSTAYMELSSLRSEDTAVYYCARSFFTNWFAYW<br>GQGTLVTVSSASTKGPSVFPLAPSSKSTSGGTAALG<br>CLVKDYFPEPVTVSWNSGALTSGVHTFPAVLQSSGL<br>YSLSSVVTVPSSSLGTQTYICNVNHKPSNTKVDKKV<br>EPKSCDKTHTCPPCPAPELLGGPSVFLFPPKPKDTL |

| Sequence Identifier | Protein | Sequence 123456789012345678901234567890012 |
|---|---|---|
| | | MISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSREEMT KNQVSLTCLVKGFYPSDIAVEWESNGQPENNYKTTP PVLDSDGSFFLYSKLTVDKSRWQQGNVFSCSVMHEA LHNHYTQKSLSLSPGK |
| SEQ ID NO.: 154 | Ab4 HC.1a.3 | EVQLVQSGAEVKKPGSSVKVSCKASGYTFTSYWIHW VRQAPGQGLEWIGEIDPSDSYTNYNQKFKGRATLTV DKSSSTAYMELSSLRSEDTAVYYCGRSFFTNWFAYW GQGTLVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSREEMT KNQVSLTCLVKGFYPSDIAVEWESNGQPENNYKTIP PVLDSDGSFFLYSKLTVDKSRWQQGNVFSCSVMHEA LHNHYTQKSLSLSPGK |
| SEQ ID NO.: 155 | Ab4 HC.1a.2 | EVQLVQSGAEVKKPGSSVKVSCKASGYTFTSYWIHW VRQAPGQGLEWIGEIDPSDSYTNYNQKFKGRATLTV DRSSSTAYMELSSLRSEDTAVYYCGRSFFTNWFAYW GQGTLVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPELLGGPSVFLFPPKPKDTL MISRTPEVTCVVVDVSHEDPEVKFNWYVDGVEVHNA KTKPREEQYNSTYRVVSVLTVLHQDWLNGKEYKCKV SNKALPAPIEKTISKAKGQPREPQVYTLPPSREEMT KNQVSLTCLVKGFYPSDIAVEWESNGQPENNYKTTP PVLDSDGSFFLYSKLTVDKSRWQQGNVFSCSVMHEA LHNHYTQKSLSLSPGK |
| SEQ ID NO.: 156 | LFA102 Heavy Chain | EVQLVESGGGLVQPGGSLRLSCAVSGFTFSSYGMSW VRQAPGKRLEWVATVSSGGTYTYYPDSVKGRFTISR DNSKNTLYLQMNSLRAEDTAMYYCARHGNYYATYY YAMDYWGQGTLVTVSSASTKGPSVFPLAPSSKSTSG GTAALGCLVKDYFPEPVTVSWNSGALTSGVHTFPAV LQSSGLYSLSSVVTVPSSSLGTQTYICNVNHKPSNT KVDKKVEPKSCDKTHTCPPCPAPELLGGPSVFLFPP KPKDTLMISRTPEVTCVVVDVSHEDPEVKFNWYVDG VEVHNAKTKPREEQYNSTYRVVSVLTVLHQDWLNGK EYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPGK |
| SEQ ID NO.: 157 | LFA102 Light Chain | DIVLTQSPDSLAVSLGERATINCKASKSVSTSGYTY MHWYQQKPGQPPKLLIYLASNRESGVPDRFSGSGSG TDFTLTISPVQAEDVATYYCQHSGELPPSFGQGTKL EIKRTVAAPSVFIFPPSDEQLKSGTASVVCLLNNFY PREAKVQWKVDNALQSGNSQESVTEQDSKDSTYSLS STLTLSKADYEKHKVYACEVTHQGLSSPVTKSFNRG EC |
| SEQ ID NO: 158 | III-3R & JK4 FR2 | WYQQKPGKAPKLLIY |
| SEQ ID NO: 159 | Histag | HHHHHH |

We claim:

1. A method for reducing human prolactin receptor (PRLR) activity in a human subject suffering from a cancer in which PRLR activity is detrimental, comprising administering an anti-PRLR antibody, or an antigen-binding fragment thereof, to the human subject, such that human PRLR activity in the human subject is reduced, wherein the antibody, or antigen-binding fragment thereof, comprises a heavy chain variable domain comprising the amino acid sequences of SEQ ID NO: 40, SEQ ID NO: 41, and SEQ ID NO: 42; and comprises a light chain variable domain comprising the amino acid sequences of SEQ ID NO: 49, SEQ ID NO: 50, and SEQ ID NO: 51.

2. A method for treating a human subject having a cancer in which PRLR activity is detrimental, said method comprising administering an anti-PRLR antibody, or an antigen-binding fragment thereof, to the human subject such that treatment is achieved, wherein the antibody, or antigen-binding fragment thereof, comprises a heavy chain variable domain comprising the amino acid sequences of SEQ ID NO: 40, SEQ ID NO: 41, and SEQ ID NO: 42; and comprises a light chain variable domain comprising the amino acid sequences of SEQ ID NO: 49, SEQ ID NO: 50, and SEQ ID NO: 51.

3. The method according to claim 2, wherein said antibody, or an antigen-binding fragment thereof, is administered to the subject by a mode selected from the group consisting of parenteral, subcutaneous, intramuscular intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

4. The method of claim 2, wherein the cancer is selected from the group consisting of melanoma, lymphoma, ovarian cancer, renal carcinoma, gastrointestinal cancer, colon cancer, lung cancer, and pancreatic cancer.

5. The method of claim 2, wherein the cancer is breast cancer.

6. The method of claim 2, wherein the cancer is prostate cancer.

7. The method of claim 2, wherein the cancer is endometrial cancer.

8. The method of claim 2, wherein the antibody, or antigen binding fragment thereof, is administered to the subject at a dose of 0.1-20 mg/kg.

9. The method of claim 2, wherein the antibody, or antigen binding fragment thereof, is administered to the subject at a dose of 1-10 mg/kg.

10. The method of claim 1, wherein the antibody, or antigen binding fragment thereof, comprises a light chain variable domain comprising the amino acid sequence set forth in SEQ ID NO: 52, and a heavy chain variable domain comprising the amino acid sequence set forth in SEQ ID NO: 44.

11. The method according to claim 1, wherein said antibody, or an antigen-binding fragment thereof, is administered to the subject by a mode selected from the group consisting of parenteral, subcutaneous, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

12. The method of claim 1, wherein the cancer is selected from the group consisting of melanoma, lymphoma, ovarian cancer, renal carcinoma, gastrointestinal cancer, colon cancer, lung cancer, and pancreatic cancer.

13. The method of claim 1, wherein the cancer is breast cancer.

14. The method of claim 1, wherein the cancer is prostate cancer.

15. The method of claim 1, wherein the cancer is endometrial cancer.

16. The method of claim 1, wherein the antibody, or antigen binding fragment thereof, is administered to the subject at a dose of 0.1-20 mg/kg.

17. The method of claim 1, wherein the antibody, or antigen binding fragment thereof, is administered to the subject at a dose of 1-10 mg/kg.

18. A method for treating a human subject having a cancer in which PRLR activity is detrimental comprising administering an anti-PRLR antibody, or antigen binding fragment thereof, to the human subject, wherein the antibody, or antigen binding fragment thereof, comprises a light chain variable domain comprising the amino acid sequence set forth in SEQ ID NO: 52, and a heavy chain variable domain comprising the amino acid sequence set forth in SEQ ID NO: 44.

19. The method of claim 18, wherein the antibody, or antigen binding fragment thereof, comprises a light chain comprising the amino acid sequence of SEQ ID NO:126.

20. The method of claim 18, wherein the antibody, or antigen binding fragment thereof, comprises a heavy chain comprising the amino acid sequence of SEQ ID NO:129.

21. The method of claim 20, wherein the antibody, or antigen binding fragment thereof, comprises a light chain comprising the amino acid sequence of SEQ ID NO:126.

22. The method according to claim 18, wherein said antibody, or an antigen-binding fragment thereof, is administered to the subject by a mode selected from the group consisting of parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

23. The method of claim 18, wherein the cancer is selected from the group consisting of melanoma, lymphoma, ovarian cancer, renal carcinoma, gastrointestinal cancer, colon cancer, lung cancer, and pancreatic cancer.

24. The method of claim 18, wherein the cancer is breast cancer.

25. The method of claim 18, wherein the cancer is prostate cancer.

26. The method of claim 18, wherein the cancer is endometrial cancer.

27. The method of claim 18, wherein the antibody, or antigen binding fragment thereof, is administered to the subject at a dose of 0.1-20 mg/kg.

28. The method of claim 18, wherein the antibody, or antigen binding fragment thereof, is administered to the subject at a dose of 1-10 mg/kg.

29. A method for treating a human subject having a cancer in which PRLR activity is detrimental, said method comprising administering an anti-PRLR antibody, or antigen binding fragment thereof, to the human subject, wherein the antibody, or antigen binding fragment thereof, is an IgG antibody, comprises a light chain variable domain comprising the amino acid sequence set forth in SEQ ID NO: 52, and comprises a heavy chain variable domain comprising the amino acid sequence set forth in SEQ ID NO: 44.

30. The method of claim 29, wherein the antibody, or antigen binding fragment thereof, comprises a light chain comprising the amino acid sequence of SEQ ID NO:126.

31. The method of claim 29, wherein the antibody, or antigen binding fragment thereof, comprises a heavy chain comprising the amino acid sequence of SEQ ID NO:129.

32. The method of claim 31, wherein the antibody, or antigen binding fragment thereof, comprises a light chain comprising the amino acid sequence of SEQ ID NO:126.

33. The method according to claim 29, wherein said antibody, or an antigen-binding fragment thereof, is administered to the subject by a mode selected from the group consisting of parenteral, subcutaneous, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

34. The method of claim 29, wherein the cancer is breast cancer.

35. The method of claim 29, wherein the cancer is selected from the group consisting of melanoma, lymphoma, ovarian cancer, renal carcinoma, gastrointestinal cancer, colon cancer, lung cancer, and pancreatic cancer.

36. The method of claim 29, wherein the cancer is prostate cancer.

37. The method of claim 29, wherein the cancer is endometrial cancer.

38. The method of claim 29, wherein the antibody, or antigen binding fragment thereof, is administered to the subject at a dose of 0.1-20 mg/kg.

39. The method of claim 29, wherein the antibody, or antigen binding fragment thereof, is administered to the subject at a dose of 1-10 mg/kg.

40. A method of inhibiting tumor growth in a human subject having a tumor, comprising administering an anti-PRLR antibody, or an antigen-binding fragment thereof, to the human subject, such that tumor growth is inhibited,
wherein the tumor expresses PRLR, and
wherein the antibody, or antigen-binding fragment thereof, comprises a heavy chain variable domain comprising the amino acid sequences of SEQ ID NO: 40, SEQ ID NO: 41, and SEQ ID NO: 42; and comprises a light chain variable domain comprising the amino acid sequences of SEQ ID NO: 49, SEQ ID NO: 50, and SEQ ID NO: 51.

41. The method of claim 40, wherein the antibody, or antigen binding fragment thereof, comprises a light chain variable domain comprising the amino acid sequence set forth in SEQ ID NO: 52, and a heavy chain variable domain comprising the amino acid sequence set forth in SEQ ID NO: 44.

42. The method of claim 40, wherein antibody, or antigen binding fragment thereof, is administered intravenously.

43. The method of claim 40, wherein the tumor is a breast tumor.

44. The method of claim 40, wherein the tumor is a prostate tumor.

45. The method of claim 40, wherein the tumor is an endometrial tumor.

46. The method of claim 40, wherein the antibody, or antigen binding fragment thereof, is administered to the subject at a dose of 0.1-20 mg/kg.

47. The method of claim 40, wherein said antibody, or an antigen-binding fragment thereof, is intravenously administered to the subject.

48. The method of claim 1, wherein said antibody, or an antigen-binding fragment thereof, is intravenously administered to the subject.

49. The method of claim 2, wherein said antibody, or an antigen-binding fragment thereof, is intravenously administered to the subject.

50. The method of claim 29, wherein said antibody, or an antigen-binding fragment thereof, is intravenously administered to the subject.

* * * * *

UNITED STATES PATENT AND TRADEMARK OFFICE
CERTIFICATE OF CORRECTION

PATENT NO. : 9,725,515 B2
APPLICATION NO. : 14/138906
DATED : August 8, 2017
INVENTOR(S) : Anderson et al.

Page 1 of 2

It is certified that error appears in the above-identified patent and that said Letters Patent is hereby corrected as shown below:

In the Specification

In the Description, Column No: 42, Table: 5, SEQ ID NO. 39, "NQKFKDRVTITADSKTSTAYMELSSLRSED" to read as --NQKFKDRVTITADKSTSTAYMELSSLRSED--

In the Description, Column No: 43, Table: 5, SEQ ID NO. 45, "TYWMHWVRQAPGQLGEWIGEIDPSDSYSNY" to read as --TYWMHWVRQAPGQGLEWIGEIDPSDSYSNY--

In the Description, Column No: 43, Table: 5, SEQ ID NO. 49, "KASWYVGTAVA" to read as --KASQYVGTAVA--

In the Description, Column No: 45, Table: 5, SEQ ID NO. 55, "QVLQVQSGAEVKKPGSSVKVSCKASGYTFT" to read as --QVQLVQSGAEVKKPGSSVKVSCKASGYTFT--

In the Description, Column No: 45, Table: 5, SEQ ID NO. 55, "TAVYYCARGDYSNWFTYWGQGLTVTVSS" to read as --TAVYYCARGDYSNWFTYWGQGTLVTVSS--

In the Description, Column No: 45, Table: 5, SEQ ID NO. 60, "EVLQVQSGAEVKKPGSSVKVSCKASGYTFT" to read --EVQLVQSGAEVKKPGSSVKVSCKASGYTFT--

In the Description, Column No: 51, Table: 5, SEQ ID NO. 89, "WYWIHWVRQAPGQGLEWIGEIDPSDSYTNY" to read as --SYWIHWVRQAPGQGLEWIGEIDPSDSYTNY--

Signed and Sealed this
Twenty-fourth Day of September, 2019

Andrei Iancu
*Director of the United States Patent and Trademark Office*

CERTIFICATE OF CORRECTION (continued)
U.S. Pat. No. 9,725,515 B2

In the Description, Column No: 51, Table: 5, SEQ ID NO. 85, "GYFTFSYWIH" to read as --GYTFTSYWIH--

In the Description, Column No: 51, Table: 5, SEQ ID NO. 123, "AQKFKGRVTITVDKSTSTAYMELSSLRSED" to read as --AQKFQGRVTITVDKSTSTAYMELSSLRSED--

In the Description, Column No: 51, Table: 5, "SEQ ID NO. 159" to read as --SEQ ID NO. 150--

In the Description, Column No: 53, Table: 5, "NQKFKGRVTITVDKSTSTAYMWLSSLRSED" to read as --NQKFKGRVTITVDKSTSTAYMELSSLRSED--

SEQUENCE LISTING

<160> NUMBER OF SEQ ID NOS: 159

<210> SEQ ID NO 1
<211> LENGTH: 622

```
<212> TYPE: PRT
<213> ORGANISM: Homo sapiens

<400> SEQUENCE: 1

Met Lys Glu Asn Val Ala Ser Ala Thr Val Phe Thr Leu Leu Leu Phe
 1               5                  10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
    370                 375                 380

Asn Pro Glu Thr Thr His Thr Trp Asp Pro Gln Cys Ile Ser Met Glu
385                 390                 395                 400
```

```
Gly Lys Ile Pro Tyr Phe His Ala Gly Gly Lys Cys Ser Thr Trp
            405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
            435                 440                 445

Thr Leu Leu Asn Glu Ala Gly Lys Asp Ala Leu Lys Ser Ser Gln Thr
            450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
            515                 520                 525

Glu Asn Ser Gly Lys Pro Lys Lys Pro Gly Thr Pro Glu Asn Asn Lys
            530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
                580                 585                 590

Ala Asn Phe Thr Ala Thr Ser Ser Lys Cys Arg Leu Gln Leu Gly Gly
                595                 600                 605

Leu Asp Tyr Leu Asp Pro Ala Cys Phe Thr His Ser Phe His
610                 615                 620

<210> SEQ ID NO 2
<211> LENGTH: 209
<212> TYPE: PRT
<213> ORGANISM: Homo sapiens

<400> SEQUENCE: 2

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
                20                  25                  30

Pro Thr Asn Tyr Ser Leu Thr Tyr His Arg Glu Gly Glu Thr Leu Met
            35                  40                  45

His Glu Cys Pro Asp Tyr Ile Thr Gly Gly Pro Asn Ser Cys His Phe
        50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Ile His Phe
```

```
                145                 150                 155                 160
Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
                180                 185                 190

Ala Trp Ser Pro Ala Thr Phe Ile Gln Ile Pro Ser Asp Phe Thr Met
                195                 200                 205

Asn

<210> SEQ ID NO 3
<211> LENGTH: 521
<212> TYPE: PRT
<213> ORGANISM: Homo sapiens

<400> SEQUENCE: 3

Met Lys Glu Asn Val Ala Ser Ala Thr Val Phe Thr Leu Leu Leu Phe
1               5                   10                  15

Leu Asn Thr Cys Leu Leu Asn Val Gln Pro Asp Pro Pro Leu Glu Leu
                20                  25                  30

Ala Val Glu Val Lys Gln Pro Glu Asp Arg Lys Pro Tyr Leu Trp Ile
            35                  40                  45

Lys Trp Ser Pro Pro Thr Leu Ile Asp Leu Lys Thr Gly Trp Phe Thr
        50                  55                  60

Leu Leu Tyr Glu Ile Arg Leu Lys Pro Glu Lys Ala Ala Glu Trp Glu
65                  70                  75                  80

Ile His Phe Ala Gly Gln Gln Thr Glu Phe Lys Ile Leu Ser Leu His
                85                  90                  95

Pro Gly Gln Lys Tyr Leu Val Gln Val Arg Cys Lys Pro Asp His Gly
                100                 105                 110

Tyr Trp Ser Ala Trp Ser Pro Ala Thr Phe Ile Gln Ile Pro Ser Asp
            115                 120                 125

Phe Thr Met Asn Asp Thr Thr Val Trp Ile Ser Val Ala Val Leu Ser
        130                 135                 140

Ala Val Ile Cys Leu Ile Ile Val Trp Ala Val Ala Leu Lys Gly Tyr
145                 150                 155                 160

Ser Met Val Thr Cys Ile Phe Pro Pro Val Pro Gly Pro Lys Ile Lys
                165                 170                 175

Gly Phe Asp Ala His Leu Leu Glu Lys Gly Lys Ser Glu Glu Leu Leu
                180                 185                 190

Ser Ala Leu Gly Cys Gln Asp Phe Pro Pro Thr Ser Asp Tyr Glu Asp
            195                 200                 205

Leu Leu Val Glu Tyr Leu Glu Val Asp Asp Ser Glu Asp Gln His Leu
        210                 215                 220

Met Ser Val His Ser Lys Glu His Pro Ser Gln Gly Met Lys Pro Thr
225                 230                 235                 240

Tyr Leu Asp Pro Asp Thr Asp Ser Gly Arg Gly Ser Cys Asp Ser Pro
                245                 250                 255

Ser Leu Leu Ser Glu Lys Cys Glu Glu Pro Gln Ala Asn Pro Ser Thr
                260                 265                 270

Phe Tyr Asp Pro Glu Val Ile Glu Lys Pro Glu Asn Pro Glu Thr Thr
            275                 280                 285

His Thr Trp Asp Pro Gln Cys Ile Ser Met Glu Gly Lys Ile Pro Tyr
        290                 295                 300

Phe His Ala Gly Gly Ser Lys Cys Ser Thr Trp Pro Leu Pro Gln Pro
```

-continued

```
                305                 310                 315                 320
        Ser Gln His Asn Pro Arg Ser Ser Tyr His Asn Ile Thr Asp Val Cys
                        325                 330                 335

Glu Leu Ala Val Gly Pro Ala Gly Ala Pro Ala Thr Leu Leu Asn Glu
                        340                 345                 350

Ala Gly Lys Asp Ala Leu Lys Ser Ser Gln Thr Ile Lys Ser Arg Glu
                        355                 360                 365

Glu Gly Lys Ala Thr Gln Gln Arg Glu Val Glu Ser Phe His Ser Glu
                        370                 375                 380

Thr Asp Gln Asp Thr Pro Trp Leu Leu Pro Gln Glu Lys Thr Pro Phe
        385                 390                 395                 400

Gly Ser Ala Lys Pro Leu Asp Tyr Val Glu Ile His Lys Val Asn Lys
                        405                 410                 415

Asp Gly Ala Leu Ser Leu Leu Pro Lys Gln Arg Glu Asn Ser Gly Lys
                        420                 425                 430

Pro Lys Lys Pro Gly Thr Pro Glu Asn Asn Lys Glu Tyr Ala Lys Val
                        435                 440                 445

Ser Gly Val Met Asp Asn Asn Ile Leu Val Leu Val Pro Asp Pro His
                        450                 455                 460

Ala Lys Asn Val Ala Cys Phe Glu Glu Ser Ala Lys Glu Ala Pro Pro
        465                 470                 475                 480

Ser Leu Glu Gln Asn Gln Ala Glu Lys Ala Leu Ala Asn Phe Thr Ala
                        485                 490                 495

Thr Ser Ser Lys Cys Arg Leu Gln Leu Gly Gly Leu Asp Tyr Leu Asp
                        500                 505                 510

Pro Ala Cys Phe Thr His Ser Phe His
                        515                 520

<210> SEQ ID NO 4
<211> LENGTH: 230
<212> TYPE: PRT
<213> ORGANISM: Homo sapiens

<400> SEQUENCE: 4

Met Lys Glu Asn Val Ala Ser Ala Thr Val Phe Thr Leu Leu Leu Phe
        1               5                   10                  15

Leu Asn Thr Cys Leu Leu Asn Gly Gln Leu Pro Pro Gly Lys Pro Glu
                        20                  25                  30

Ile Phe Lys Cys Arg Ser Pro Asn Lys Glu Thr Phe Thr Cys Trp Trp
                        35                  40                  45

Arg Pro Gly Thr Asp Gly Gly Leu Pro Thr Asn Tyr Ser Leu Thr Tyr
                        50                  55                  60

His Arg Glu Gly Glu Thr Leu Met His Glu Cys Pro Asp Tyr Ile Thr
        65                  70                  75                  80

Gly Gly Pro Asn Ser Cys His Phe Gly Lys Gln Tyr Thr Ser Met Trp
                        85                  90                  95

Arg Thr Tyr Ile Met Met Val Asn Ala Thr Asn Gln Met Gly Ser Ser
                        100                 105                 110

Phe Ser Asp Glu Leu Tyr Val Asp Val Thr Tyr Ile Val Gln Pro Asp
                        115                 120                 125

Pro Pro Leu Glu Leu Ala Val Glu Val Lys Gln Pro Glu Asp Arg Lys
                        130                 135                 140

Pro Tyr Leu Trp Ile Lys Trp Ser Pro Pro Thr Leu Ile Asp Leu Lys
        145                 150                 155                 160
```

```
Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Ala Trp
225                 230

<210> SEQ ID NO 5
<211> LENGTH: 376
<212> TYPE: PRT
<213> ORGANISM: Homo sapiens

<400> SEQUENCE: 5

Met Lys Glu Asn Val Ala Ser Ala Thr Val Phe Thr Leu Leu Leu Phe
 1               5                  10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300
```

```
Ser Asp Tyr Glu Asp Leu Leu Val Glu Tyr Leu Val Asp Ser
305                 310                 315                 320

Glu Asp Gln His Leu Met Ser Val His Ser Lys Glu His Pro Ser Gln
            325                 330                 335

Gly Asp Pro Leu Met Leu Gly Ala Ser His Tyr Lys Asn Leu Lys Ser
            340                 345                 350

Tyr Arg Pro Arg Lys Ile Ser Ser Gln Gly Arg Leu Ala Val Phe Thr
            355                 360                 365

Lys Ala Thr Leu Thr Thr Val Gln
            370                 375

<210> SEQ ID NO 6
<211> LENGTH: 349
<212> TYPE: PRT
<213> ORGANISM: Homo sapiens

<400> SEQUENCE: 6

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
        50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
```

```
                290                 295                 300
Ser Asp Tyr Glu Asp Leu Leu Val Glu Tyr Leu Glu Val Asp Ser
305                 310                 315                 320

Glu Asp Gln His Leu Met Ser Val His Ser Lys Glu His Pro Ser Gln
                325                 330                 335

Glu Arg Glu Gln Arg Gln Ala Gln Glu Ala Arg Asp Ser
            340                 345
```

<210> SEQ ID NO 7
<211> LENGTH: 288
<212> TYPE: PRT
<213> ORGANISM: Homo sapiens

<400> SEQUENCE: 7

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Val Thr Pro
        275                 280                 285
```

<210> SEQ ID NO 8
<211> LENGTH: 268
<212> TYPE: PRT
<213> ORGANISM: Homo sapiens -continued

<400> SEQUENCE: 8

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Gly Asp Pro Leu Met Leu Gly Ala Ser His Tyr Lys
225                 230                 235                 240

Asn Leu Lys Ser Tyr Arg Pro Arg Lys Ile Ser Ser Gln Gly Arg Leu
                245                 250                 255

Ala Val Phe Thr Lys Ala Thr Leu Thr Thr Val Gln
            260                 265
```

<210> SEQ ID NO 9
<211> LENGTH: 217
<212> TYPE: PRT
<213> ORGANISM: Homo sapiens

<400> SEQUENCE: 9

```
Met His Glu Cys Pro Asp Tyr Ile Thr Gly Gly Pro Asn Ser Cys His
1               5                   10                  15

Phe Gly Lys Gln Tyr Thr Ser Met Trp Arg Thr Tyr Ile Met Met Val
            20                  25                  30

Asn Ala Thr Asn Gln Met Gly Ser Ser Phe Ser Asp Glu Leu Tyr Val
        35                  40                  45

Asp Val Thr Tyr Ile Val Gln Pro Asp Pro Pro Leu Glu Leu Ala Val
    50                  55                  60

Glu Val Lys Gln Pro Glu Asp Arg Lys Pro Tyr Leu Trp Ile Lys Trp
65                  70                  75                  80

Ser Pro Pro Thr Leu Ile Asp Leu Lys Thr Gly Trp Phe Thr Leu Leu
                85                  90                  95
```

-continued

```
Tyr Glu Ile Arg Leu Lys Pro Glu Lys Ala Ala Glu Trp Glu Ile His
            100                 105                 110

Phe Ala Gly Gln Gln Thr Glu Phe Lys Ile Leu Ser Leu His Pro Gly
        115                 120                 125

Gln Lys Tyr Leu Val Gln Val Arg Cys Lys Pro Asp His Gly Tyr Trp
    130                 135                 140

Ser Ala Trp Ser Pro Ala Thr Phe Ile Gln Ile Pro Ser Asp Phe Thr
145                 150                 155                 160

Met Asn Asp Thr Thr Val Trp Ile Ser Val Ala Val Leu Ser Ala Val
                165                 170                 175

Ile Cys Leu Ile Ile Val Trp Ala Val Ala Leu Lys Gly Tyr Ser Met
            180                 185                 190

Val Thr Cys Ile Phe Pro Pro Val Pro Gly Pro Lys Ile Lys Gly Phe
        195                 200                 205

Asp Ala His Leu Leu Glu Val Thr Pro
    210                 215

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 106
<212> TYPE: PRT
<213> ORGANISM: Homo sapiens

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 13
<211> LENGTH: 105
<212> TYPE: PRT
<213> ORGANISM: Homo sapiens

<400> SEQUENCE: 13

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
                100                 105

<210> SEQ ID NO 14
<211> LENGTH: 30
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
                20                  25                  30
```

<210> SEQ ID NO 15
<211> LENGTH: 14
<212> TYPE: PRT
<213> ORGANISM: Homo sapiens

<400> SEQUENCE: 15

Trp Val Arg Gln Ala Pro Gly Gln Gly Leu Glu Trp Met Gly
1               5                   10

<210> SEQ ID NO 16
<211> LENGTH: 32
<212> TYPE: PRT
<213> ORGANISM: Homo sapiens

<400> SEQUENCE: 16

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 17
<211> LENGTH: 11
<212> TYPE: PRT
<213> ORGANISM: Homo sapiens

<400> SEQUENCE: 17

Trp Gly Gln Gly Thr Thr Val Thr Val Ser Ser
1               5                   10

<210> SEQ ID NO 18
<211> LENGTH: 14
<212> TYPE: PRT
<213> ORGANISM: Homo sapiens

<400> SEQUENCE: 18

Trp Val Arg Gln Ala Pro Gly Gln Arg Leu Glu Trp Met Gly
1               5                   10

<210> SEQ ID NO 19
<211> LENGTH: 32
<212> TYPE: PRT
<213> ORGANISM: Homo sapiens

<400> SEQUENCE: 19

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 20
<211> LENGTH: 11
<212> TYPE: PRT
<213> ORGANISM: Homo sapiens

<400> SEQUENCE: 20

Trp Gly Gln Gly Thr Leu Val Thr Val Ser Ser
1               5                   10

<210> SEQ ID NO 21
<211> LENGTH: 30
<212> TYPE: PRT
<213> ORGANISM: Homo sapiens

```
<400> SEQUENCE: 21

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 22
<211> LENGTH: 15
<212> TYPE: PRT
<213> ORGANISM: Homo sapiens

<400> SEQUENCE: 22

Trp Ile Arg Gln Pro Pro Gly Lys Ala Leu Glu Trp Leu Ala His
1               5                   10                  15

<210> SEQ ID NO 23
<211> LENGTH: 32
<212> TYPE: PRT
<213> ORGANISM: Homo sapiens

<400> SEQUENCE: 23

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 24
<211> LENGTH: 30
<212> TYPE: PRT
<213> ORGANISM: Homo sapiens

<400> SEQUENCE: 24

Gln Val Thr Leu Arg Glu Ser Gly Pro Ala Leu Val Lys Pro Thr Gln
1               5                   10                  15

Thr Leu Thr Leu Thr Cys Thr Leu Tyr Gly Phe Ser Leu Ser
            20                  25                  30

<210> SEQ ID NO 25
<211> LENGTH: 14
<212> TYPE: PRT
<213> ORGANISM: Homo sapiens

<400> SEQUENCE: 25

Trp Ile Arg Gln Pro Pro Gly Lys Ala Leu Glu Trp Leu Ala
1               5                   10

<210> SEQ ID NO 26
<211> LENGTH: 32
<212> TYPE: PRT
<213> ORGANISM: Homo sapiens

<400> SEQUENCE: 26

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 27
<211> LENGTH: 32
<212> TYPE: PRT
<213> ORGANISM: Homo sapiens

<400> SEQUENCE: 27
```

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 28
<211> LENGTH: 23
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 29
<211> LENGTH: 15
<212> TYPE: PRT
<213> ORGANISM: Homo sapiens

<400> SEQUENCE: 29

Trp Tyr Gln Gln Lys Pro Gly Lys Val Pro Lys Leu Leu Ile Tyr
1               5                   10                  15

<210> SEQ ID NO 30
<211> LENGTH: 32
<212> TYPE: PRT
<213> ORGANISM: Homo sapiens

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 31
<211> LENGTH: 11
<212> TYPE: PRT
<213> ORGANISM: Homo sapiens

<400> SEQUENCE: 31

Phe Gly Gly Gly Thr Lys Val Glu Ile Lys Arg
1               5                   10

<210> SEQ ID NO 32
<211> LENGTH: 32
<212> TYPE: PRT
<213> ORGANISM: Homo sapiens

<400> SEQUENCE: 32

Gly Val Pro Ser Arg Ile Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 33
<211> LENGTH: 23
<212> TYPE: PRT
<213> ORGANISM: Homo sapiens

<400> SEQUENCE: 33

-continued

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 34
<211> LENGTH: 15
<212> TYPE: PRT
<213> ORGANISM: Homo sapiens

<400> SEQUENCE: 34

Trp Phe Gln Gln Arg Pro Gly Gln Ser Pro Arg Arg Leu Ile Tyr
1               5                   10                  15

<210> SEQ ID NO 35
<211> LENGTH: 32
<212> TYPE: PRT
<213> ORGANISM: Homo sapiens

<400> SEQUENCE: 35

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 36
<211> LENGTH: 23
<212> TYPE: PRT
<213> ORGANISM: Homo sapiens

<400> SEQUENCE: 36

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 37
<211> LENGTH: 15
<212> TYPE: PRT
<213> ORGANISM: Homo sapiens

<400> SEQUENCE: 37

Trp Tyr Leu Gln Lys Pro Gly Gln Ser Pro Gln Leu Leu Ile Tyr
1               5                   10                  15

<210> SEQ ID NO 38
<211> LENGTH: 11
<212> TYPE: PRT
<213> ORGANISM: Homo sapiens

<400> SEQUENCE: 38

Phe Gly Gln Gly Thr Lys Leu Glu Ile Lys Arg
1               5                   10

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ser

```
                1               5                   10                  15
            Ser Val Lys Val Ser Cys Lys Ala Ser Gly Tyr Thr Phe Thr Thr Tyr
                            20                  25                  30
            Trp Met His Trp Val Arg Gln Ala Pro Gly Gln Gly Leu Glu Trp Met
                            35                  40                  45
            Gly Glu Ile Asp Pro Ser Asp Ser Tyr Ser Asn Tyr Asn Gln Lys Phe
                        50                  55                  60
            Lys Asp Arg Val Thr Ile Thr Ala Asp Lys Ser Thr Ser Thr Ala Tyr
             65                 70                  75                  80
            Met Glu Leu Ser Ser Leu Arg Ser Glu Asp Thr Ala Val Tyr Tyr Cys
                            85                  90                  95
            Ala Arg Asn Gly Gly Leu Gly Pro Ala Trp Phe Ser Tyr Trp Gly Gln
                        100                 105                 110
            Gly Thr Leu Val Thr Val Ser Ser
                        115                 120

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Tyr Thr Phe Thr Thr Tyr Trp Met His
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ile Asp Pro Ser Asp Ser Tyr Ser Asn Tyr Asn Gln Lys Phe Lys
1               5                   10                  15
Asp

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Gly Gly Leu Gly Pro Ala Trp Phe Ser Tyr
1               5                   10

<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Gln Ser Gly Ala Glu Val Lys Lys Pro Gly Ser
```

```
1               5                   10                  15
Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asp Pro Ser Asp Ser Tyr Ser Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Ala Gln Lys Phe
```

```
                 50                  55                  60
Gln Gly Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Gly Gly Leu Gly Pro Ala Trp Phe Ser Tyr Trp Gly Gln
                100                 105                 110

Gly Thr Leu Val Thr Val Ser Ser
            115                 120

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Thr Phe Thr Thr Tyr Trp Met His
 1               5                  10

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ile Asp Pro Ser Asp Ser Tyr Ser Asn Tyr Ala Gln Lys Phe
 1               5                  10                  15

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Gln Met Thr Gln Ser Pro Ser Ser Val Ser Ala Ser Val Gly
 1               5                  10                  15

Asp Arg Val Thr Ile Thr Cys Lys Ala Ser Gln Tyr Val Gly Thr Ala
                 20                  25                  30

Val Ala Trp Tyr Gln Gln Lys Pro Gly Lys Ala Pro Lys Leu Leu Ile
             35                  40                  45

Tyr Ser Ala Ser Asn Arg Tyr Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Ser Tyr Pro Trp
                 85                  90                  95

Thr Phe Gly Gly Gly Thr Lys Val Glu Ile Lys
            100                 105

<210> SEQ ID NO 49
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 49

Lys Ala Ser Gln Tyr Val Gly Thr Ala Val Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ala Ser Asn Arg Tyr Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Ser Ser Tyr Pro Trp Thr
1               5

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Tyr Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Ser Arg Phe Ser Asp
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Trp
                85                  90                  95

Thr Phe Gly Gly Gly Thr Lys Val Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Tyr Val Gly Thr Ala
            20                  25                  30

Val Ala Trp Tyr Gln Gln Lys Pro Gly Gln Ala Pro Arg Leu Leu Ile
        35                  40                  45

Tyr Ser Ala Ser Asn Arg Tyr Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Ser Tyr Pro Trp
                85                  90                  95

Thr Phe Gly Gly Gly Thr Lys Val Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Tyr Val Gly Thr Ala
            20                  25                  30

Val Ala Trp Tyr Gln Gln Lys Pro Gly Gln Ser Pro Arg Leu Leu Ile
        35                  40                  45

Tyr Ser Ala Ser Asn Arg Tyr Thr Gly Val Pro Ala Arg Phe Ser Asp
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Trp
                85                  90                  95

Thr Phe Gly Gly Gly Thr Lys Val Glu Ile Lys
            100                 105

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Val Ile Asp Pro Ser Asp Thr Tyr Thr Asn Tyr Asn Gln Lys Phe
    50                  55                  60

Lys Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                 85                  90                  95

Ala Arg Gly Asp Tyr Ser Asn Trp Phe Thr Tyr Trp Gly Gln Gly Thr
            100                 105                 110

Leu Val Thr Val Ser Ser
        115

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Tyr Thr Phe Thr Ser Phe Trp Met His
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Ile Asp Pro Ser Asp Thr Tyr Thr Asn Tyr Asn Gln Lys Phe Lys
1               5                   10                  15

Gly

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Asp Tyr Ser Asn Trp Phe Thr Tyr
1               5

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Val Ile Asp Pro Ser Asp Thr Tyr Thr Asn Tyr Asn Gln Lys Phe
    50                  55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Ile
        35                  40                  45

Gly Val Ile Asp Pro Ser Asp Thr Tyr Thr Asn Tyr Asn Gln Lys Phe
    50                  55                  60

Lys Gly Arg Ala Thr Leu Thr Val Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Phe
            20                  25                  30

Trp Met His Trp Val Arg Gln Ala Pro Gly Gln Gly Leu Glu Trp Ile
        35                  40                  45

Gly Val Ile Asp Pro Ser Asp Thr Tyr Thr Asn Tyr Ala Gln Lys Phe
    50                  55                  60

Gln Gly Arg Val Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ser
        115
```

```
<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Thr Phe Thr Ser Phe Trp Met His
1               5                   10

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Ile Asp Pro Ser Asp Thr Tyr Thr Asn Tyr Ala Gln Lys Phe Gln
1               5                   10                  15

Gly

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Ser Ser Gln Arg Leu Val His Ser Asn Gly Asn Thr Tyr Leu His
1               5                   10                  15

<210> SEQ ID NO 66
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Val Ser Asn Arg Phe Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gln Ser Thr His Val Pro Trp Thr
1               5

<210> SEQ ID NO 68
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Val Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
```

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gly Gly Thr Lys Val Glu Ile Lys
            100                 105                 110

<210> SEQ ID NO 70
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Met
             35                  40                  45

Gly Tyr Ile Tyr Pro Asn Asn Asp Gly Thr Gly Tyr Asn Gln Lys Phe
 50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asp Gly Asn Tyr Val Gly Asp Met Asp Tyr Trp Gly Gln
            100                 105                 110

Gly Thr Thr Val Thr Val Ser Ser
            115                 120

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Tyr Thr Phe Thr Asp Tyr Asn Ile His
 1               5                  10

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Ile Tyr Pro Asn Asn Asp Gly Thr Gly Tyr Asn Gln Lys Phe Lys
 1               5                  10                  15

Ser

<210> SEQ ID NO 73
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Asp Gly Asn Tyr Val Gly Asp Met Asp Tyr
1               5                   10

<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Met
        35                  40                  45

Gly Tyr Ile Tyr Pro Asn Asn Asp Gly Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser
        115                 120

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Asn Gln Lys Phe
    50                  55                  60

Lys Ser Arg Ala Thr Leu Thr Val Asp Asn Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser
```

```
                    115                 120

<210> SEQ ID NO 76
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Ala Gln Lys Leu
    50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser
        115                 120

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Ile Tyr Pro Asn Asn Asp Gly Thr Gly Tyr Ala Gln Lys Leu Gln
1               5                   10                  15

Gly

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys
            100                 105

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ala Ser Glu Asn Ile Tyr Ser Tyr Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Ala Lys Thr Leu Ala Glu
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln His His Tyr Ala Thr Pro Phe Thr
1               5

<210> SEQ ID NO 82
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Pro Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys
            100                 105
```

```
<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys
            100                 105

<210> SEQ ID NO 84
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser
        115

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

```
Gly Tyr Thr Phe Thr Ser Tyr Trp Ile His
1               5                   10
```

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Glu Ile Asp Pro Ser Asp Ser Tyr Thr Asn Tyr Asn Gln Lys Phe Lys
1               5                   10                  15

Gly
```

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Ser Phe Phe Thr Asn Trp Phe Ala Tyr
1               5
```

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Met
            35                  40                  45

Gly Glu Ile Asp Pro Ser Asp Ser Tyr Thr Asn Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser
        115
```

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser
        115
```

<210> SEQ ID NO 90
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser
        115
```

<210> SEQ ID NO 91
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Val Glu Ile Lys
            100                 105                 110
```

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Arg Ser Ser Gln Ser Leu Val His Ser Asn Gly Asn Thr Tyr Leu His
1               5                   10                  15
```

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Lys Val Ser Asn Arg Phe Ser
1               5
```

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Ser Gln Ser Thr His Val Pro Phe Thr
1               5
```

<210> SEQ ID NO 95
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Phe Cys Ser Gln Ser
            85                  90                  95

Thr His Val Pro Phe Thr Phe Gly Gly Gly Thr Lys Val Glu Ile Lys
            100                 105                 110

<210> SEQ ID NO 96
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Phe Thr Phe Gly Gly Gly Thr Lys Val Glu Ile Lys
            100                 105                 110

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (4)..(4)
<223> OTHER INFORMATION: Phe or Ile
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (6)..(6)
<223> OTHER INFORMATION: Ser, Asp or Thr
<220> FEATURE:
<221> NAME/KEY: MOD_RES
<222> LOCATION: (7)..(7)
<223> OTHER INFORMATION: Tyr, Phe or Asp
<220> FEATURE:
<221> NAME/KEY: MOD_RES
<222> LOCATION: (8)..(8)
<223> OTHER INFORMATION: Trp, Asn or Tyr
<220> FEATURE:
<221> NAME/KEY: MOD_RES
<222> LOCATION: (9)..(9)
<223> OTHER INFORMATION: Met, Ile or Ala

```
<220> FEATURE:
<221> NAME/KEY: MOD_RES
<222> LOCATION: (10)..(10)
<223> OTHER INFORMATION: His, Phe or Trp
<220> FEATURE:
<221> NAME/KEY: MOD_RES
<222> LOCATION: (11)..(11)
<223> OTHER INFORMATION: May or may not be present

<400> SEQUENCE: 97

Gly Xaa Xaa Xaa Xaa Xaa Xaa Xaa Xaa Asn
1               5                   10

<210> SEQ ID NO 98
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Val or Glu
<220> FEATURE:
<221> NAME/KEY: MOD_RES
<222> LOCATION: (2)..(2)
<223> OTHER INFORMATION: Ile or Phe
<220> FEATURE:
<221> NAME/KEY: MOD_RES
<222> LOCATION: (3)..(3)
<223> OTHER INFORMATION: Asp, Tyr, Ser or Gly
<220> FEATURE:
<221> NAME/KEY: MOD_RES
<222> LOCATION: (4)..(4)
<223> OTHER INFORMATION: Pro, Asn or not present
<220> FEATURE:
<221> NAME/KEY: MOD_RES
<222> LOCATION: (5)..(5)
<223> OTHER INFORMATION: Ser, Tyr, Asn or Gly
<220> FEATURE:
<221> NAME/KEY: MOD_RES
<222> LOCATION: (6)..(6)
<223> OTHER INFORMATION: Asp, Asn, Gly or Ser
<220> FEATURE:
<221> NAME/KEY: MOD_RES
<222> LOCATION: (7)..(7)
<223> OTHER INFORMATION: Gly, Ser, Asp or Thr
<220> FEATURE:
<221> NAME/KEY: MOD_RES
<222> LOCATION: (8)..(8)
<223> OTHER INFORMATION: Tyr, Gly, His, Ser or Arg
<220> FEATURE:
<221> NAME/KEY: MOD_RES
<222> LOCATION: (9)..(9)
<223> OTHER INFORMATION: Thr, Ser or Ala
<220> FEATURE:
<221> NAME/KEY: MOD_RES
<222> LOCATION: (10)..(10)
<223> OTHER INFORMATION: Asn, Gly, Tyr or Ser
<220> FEATURE:
<221> NAME/KEY: MOD_RES
<222> LOCATION: (11)..(11)
<223> OTHER INFORMATION: Tyr or Phe
<220> FEATURE:
<221> NAME/KEY: MOD_RES
<222> LOCATION: (12)..(12)
<223> OTHER INFORMATION: Asn or Pro
<220> FEATURE:
<221> NAME/KEY: MOD_RES
<222> LOCATION: (13)..(13)
<223> OTHER INFORMATION: Gln, Asp or Pro
<220> FEATURE:
<221> NAME/KEY: MOD_RES
<222> LOCATION: (14)..(14)
<223> OTHER INFORMATION: Lys, Glu, Thr or Ser
<220> FEATURE:
```

```
<221> NAME/KEY: MOD_RES
<222> LOCATION: (15)..(15)
<223> OTHER INFORMATION: Phe, Leu or Val
<220> FEATURE:
<221> NAME/KEY: MOD_RES
<222> LOCATION: (17)..(17)
<223> OTHER INFORMATION: Gly, Ser, Asp or Asn

<400> SEQUENCE: 98

Xaa Xaa Xaa Xaa Xaa Xaa Xaa Xaa Xaa Xaa Xaa Xaa Xaa Xaa Xaa Lys
1               5                   10                  15

Xaa

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Ser, Asn or Gln
<220> FEATURE:
<221> NAME/KEY: MOD_RES
<222> LOCATION: (2)..(2)
<223> OTHER INFORMATION: Asp, Phe, Gly or Leu
<220> FEATURE:
<221> NAME/KEY: MOD_RES
<222> LOCATION: (3)..(3)
<223> OTHER INFORMATION: Gly, Phe, Tyr or Trp
<220> FEATURE:
<221> NAME/KEY: MOD_RES
<222> LOCATION: (4)..(4)
<223> OTHER INFORMATION: Ser, Asn, Thr, Leu, Gly, Tyr or Ala
<220> FEATURE:
<221> NAME/KEY: MOD_RES
<222> LOCATION: (5)..(5)
<223> OTHER INFORMATION: Tyr, Asn, Gly, Ile or Met
<220> FEATURE:
<221> NAME/KEY: MOD_RES
<222> LOCATION: (6)..(6)
<223> OTHER INFORMATION: Trp, Val, Pro, Gly, Tyr or not present
<220> FEATURE:
<221> NAME/KEY: MOD_RES
<222> LOCATION: (7)..(7)
<223> OTHER INFORMATION: Phe, Gly, Ala, Tyr, Ser or not present
<220> FEATURE:
<221> NAME/KEY: MOD_RES
<222> LOCATION: (8)..(8)
<223> OTHER INFORMATION: Asp, Trp, Ala, Arg or not present
<220> FEATURE:
<221> NAME/KEY: MOD_RES
<222> LOCATION: (9)..(9)
<223> OTHER INFORMATION: Met, Phe, Gly or not present
<220> FEATURE:
<221> NAME/KEY: MOD_RES
<222> LOCATION: (10)..(11)
<223> OTHER INFORMATION: May or may not be present
<220> FEATURE:
<221> NAME/KEY: MOD_RES
<222> LOCATION: (12)..(12)
<223> OTHER INFORMATION: Asp, Thr, Ala, Ser or Gly

<400> SEQUENCE: 99

Xaa Xaa Xaa Xaa Xaa Xaa Xaa Xaa Xaa Ala Met Xaa Tyr
1               5                   10

<210> SEQ ID NO 100
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg, Lys or Ser
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (4)..(4)
<223> OTHER INFORMATION: Gln, Glu or Ser
<220> FEATURE:
<221> NAME/KEY: MOD_RES
<222> LOCATION: (5)..(5)
<223> OTHER INFORMATION: Ser, Arg or not present
<220> FEATURE:
<221> NAME/KEY: MOD_RES
<222> LOCATION: (6)..(6)
<223> OTHER INFORMATION: Leu, Ile or not present
<220> FEATURE:
<221> NAME/KEY: MOD_RES
<222> LOCATION: (7)..(9)
<223> OTHER INFORMATION: May or may not be present
<220> FEATURE:
<221> NAME/KEY: MOD_RES
<222> LOCATION: (10)..(10)
<223> OTHER INFORMATION: Asn, Tyr or not present
<220> FEATURE:
<221> NAME/KEY: MOD_RES
<222> LOCATION: (11)..(11)
<223> OTHER INFORMATION: Gly, Ile, Val or Ser
<220> FEATURE:
<221> NAME/KEY: MOD_RES
<222> LOCATION: (12)..(12)
<223> OTHER INFORMATION: Asn, Tyr, Gly or Val
<220> FEATURE:
<221> NAME/KEY: MOD_RES
<222> LOCATION: (13)..(13)
<223> OTHER INFORMATION: Thr or Ser
<220> FEATURE:
<221> NAME/KEY: MOD_RES
<222> LOCATION: (14)..(14)
<223> OTHER INFORMATION: Tyr or Ala
<220> FEATURE:
<221> NAME/KEY: MOD_RES
<222> LOCATION: (15)..(15)
<223> OTHER INFORMATION: Leu, Val or Met
<220> FEATURE:
<221> NAME/KEY: MOD_RES
<222> LOCATION: (16)..(16)
<223> OTHER INFORMATION: His, Ala, Thr or Glu

<400> SEQUENCE: 100

Xaa Xaa Ser Xaa Xaa Xaa Val His Ser Xaa Xaa Xaa Xaa Xaa Xaa Xaa
1               5                   10                  15

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Asn, Ser or Leu
<220> FEATURE:
<221> NAME/KEY: MOD_RES
<222> LOCATION: (2)..(2)
<223> OTHER INFORMATION: Ala, Val or Thr
<220> FEATURE:
<221> NAME/KEY: MOD_RES
<222> LOCATION: (3)..(3)
```

```
<223> OTHER INFORMATION: Ser or Lys
<220> FEATURE:
<221> NAME/KEY: MOD_RES
<222> LOCATION: (4)..(4)
<223> OTHER INFORMATION: Asn or Thr
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Phe, Ala or Tyr
<220> FEATURE:
<221> NAME/KEY: MOD_RES
<222> LOCATION: (7)..(7)
<223> OTHER INFORMATION: Ser, Glu, Thr or Ser

<400> SEQUENCE: 101

Xaa Xaa Xaa Xaa Xaa Xaa Xaa
1               5

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ser or Phe
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (3)..(3)
<223> OTHER INFORMATION: Ser, His, Gly, Tyr or Trp
<220> FEATURE:
<221> NAME/KEY: MOD_RES
<222> LOCATION: (4)..(4)
<223> OTHER INFORMATION: Ser, Thr or Tyr
<220> FEATURE:
<221> NAME/KEY: MOD_RES
<222> LOCATION: (5)..(5)
<223> OTHER INFORMATION: His, Ser, Ala, Gly or Val
<220> FEATURE:
<221> NAME/KEY: MOD_RES
<222> LOCATION: (6)..(6)
<223> OTHER INFORMATION: Val, Thr or Tyr
<220> FEATURE:
<221> NAME/KEY: MOD_RES
<222> LOCATION: (8)..(8)
<223> OTHER INFORMATION: May or may not be present
<220> FEATURE:
<221> NAME/KEY: MOD_RES
<222> LOCATION: (9)..(9)
<223> OTHER INFORMATION: Phe, Trp or Leu

<400> SEQUENCE: 102

Xaa Xaa Xaa Xaa Xaa Xaa Pro Pro Xaa Thr
1               5                   10

<210> SEQ ID NO 103
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103
```

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Val Met Thr Gln Ser Gln Lys Phe Met Ser Thr Thr Val Gly
1               5                   10                  15

Asp Arg Val Ser Ile Thr Cys Lys Ala Ser Gln Tyr Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Asp
    50                  55                  60

Ser Gly Ser Gly Thr Asp Phe Thr Leu Thr Ile Ser Asn Leu Gln Ser
65                  70                  75                  80

Glu Asp Leu Ala Asp Tyr Phe Cys Gln Gln Tyr Ser Ser Tyr Pro Trp
                85                  90                  95

Thr Phe Gly Gly Gly Thr Lys Leu Glu Ile Lys
            100                 105

<210> SEQ ID NO 105
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

-continued

Asn Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Pro Pro Gln Leu Leu Val
        35                  40                  45

Tyr Asn Ala Lys Thr Leu Ala Glu Gly Val Pro Ser Arg Phe Ser Gly
50                  55                  60

Gly Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Ala Thr Pro Phe
                85                  90                  95

Thr Phe Gly Ser Gly Thr Lys Leu Glu Ile Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Ser Gly Thr Pro Phe
                85                  90                  95

Thr Phe Gly Ser Gly Thr Lys Leu Glu Ile Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 108

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr His Cys Gln His Ser Val Thr Pro Leu
                85                  90                  95

Thr Phe Gly Ala Gly Thr Lys Leu Glu Leu Lys
            100                 105

<210> SEQ ID NO 109
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Ile Val Leu Thr Gln Ser Pro Gly Ile Met Ser Ala Ser Pro Gly
1               5                   10                  15

Glu Lys Val Thr Met Thr Cys Ser Ala Ser Ser Ser Val Thr Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Gly Ala Thr Tyr Tyr Cys Gln Gln Trp Ser Ser Thr Pro Pro Leu
                85                  90                  95

Thr Phe Gly Gly Gly Thr Lys Leu Glu Leu Asn
            100                 105

<210> SEQ ID NO 111
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Val Val Met Thr Gln Thr Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Glu Leu Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 112
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Phe
            20                  25                  30

Trp Met His Trp Val Lys Gln Arg Pro Gly Gln Gly Leu Glu Trp Ile
        35                  40                  45

Gly Val Ile Asp Pro Ser Asp Thr Tyr Thr Asn Tyr Asn Gln Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ala
            115

<210> SEQ ID NO 113
<211> LENGTH: 120

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Gln Gln Pro Gly Ala Glu Leu Val Met Pro Gly Ser
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Ser Asn Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ala
        115                 120

<210> SEQ ID NO 114
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Gln Gln Pro Gly Ala Glu Leu Val Met Pro Gly Thr
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Arg Ser Ser Thr Ala Tyr
65                  70                  75                  80

Met Gln Leu Ser Ser Leu Thr Ser Glu Asp Ser Ala Val Tyr Tyr Cys
                85                  90                  95

Gly Arg Ser Phe Phe Thr Asn Trp Phe Ala Tyr Trp Gly Gln Gly Thr
            100                 105                 110

Leu Val Thr Val Ser Ala
        115

<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Gln Gln Ser Gly Pro Glu Leu Val Lys Pro Gly Ala

```
1               5                   10                  15
Ser Val Lys Ile Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
            35                  40                  45

Gly Tyr Ile Tyr Pro Asn Asn Asp Gly Thr Gly Tyr Asn Gln Lys Phe
        50                  55                  60

Lys Ser Lys Ala Thr Leu Thr Val Asp Asn Ser Ser Thr Ala Tyr
65                  70                  75                  80

Met Glu Val Arg Ser Leu Thr Ser Glu Asp Ser Ala Val Tyr Tyr Cys
            85                  90                  95

Ala Arg Gly Asp Gly Asn Tyr Val Gly Asp Met Asp Tyr Trp Gly Gln
                100                 105                 110

Gly Thr Ser Val Thr Val Ser Ser
        115                 120

<210> SEQ ID NO 116
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Gln Gln Ser Gly Pro Glu Leu Val Arg Pro Gly Ala
1               5                   10                  15

Ser Val Lys Ile Ser Cys Lys Ala Ser Gly Tyr Ser Phe Thr Asp Tyr
            20                  25                  30

Asn Met His Trp Val Lys Gln Ser His Gly Lys Ser Leu Glu Trp Ile
            35                  40                  45

Gly Tyr Ile Tyr Pro Tyr Asn Gly Gly Ala Gly Tyr Asn Gln Lys Phe
        50                  55                  60

Lys Ser Lys Ala Thr Met Asn Val Gly Ile Ser Ser Ser Thr Ala Tyr
65                  70                  75                  80

Met Glu Leu Arg Ser Leu Thr Ser Glu Asp Ser Ala Val Tyr Tyr Cys
            85                  90                  95

Ala Arg Gly Asp Gly Asn Tyr Val Gly Asp Met Asp Tyr Trp Gly Gln
                100                 105                 110

Gly Thr Ser Val Thr Val Ser Ser
        115                 120

<210> SEQ ID NO 117
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu His Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Met Lys Gln Ser His Gly Lys Ser Leu Glu Trp Ile
            35                  40                  45

Gly Tyr Phe Tyr Pro Tyr Asn Gly Gly Thr Gly Tyr Asn Gln Glu Phe
```

```
            50                  55                  60
Lys Asn Lys Ala Thr Leu Thr Val Asp Ile Ser Ser Ser Thr Ala Tyr
 65                  70                  75                  80

Met Glu Leu Arg Arg Leu Thr Ser Glu Asp Ser Ala Val Tyr Tyr Cys
                 85                  90                  95

Ala Arg Gly Gly Trp Gly Ile Tyr Tyr Ala Met Asp Tyr Trp Gly Gln
            100                 105                 110

Gly Thr Ser Val Thr Val Ser Ser
            115                 120

<210> SEQ ID NO 118
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Tyr
            20                  25                  30

Tyr Met Phe Trp Val Arg Gln Thr Pro Glu Lys Ser Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ser Arg Gln Leu Phe Tyr Tyr Gly Ser Arg Gly Ala Met Gly Tyr Trp
            100                 105                 110

Gly Gln Gly Thr Ser Val Thr Val Ser Ser
            115                 120

<210> SEQ ID NO 119
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Val Gln Leu Gln Glu Ser Gly Pro Gly Leu Val Lys Pro Ser Gln
 1               5                  10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Gly Tyr Ser Gly Arg Thr Ser Phe Asn Pro Ser Leu
    50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Thr Glu Asp Thr Ala Thr Tyr Tyr Cys
                 85                  90                  95

Ala Arg Gly Gly Phe Ala Met Asp Tyr Trp Gly Gln Gly Thr Ser Val
```

```
                        100                 105                 110

Thr Val Ser Ser
            115

<210> SEQ ID NO 120
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Phe
            20                  25                  30

Trp Met His Trp Val Lys Gln Arg Pro Gly Gln Gly Leu Glu Trp Ile
        35                  40                  45

Gly Val Ile Asp Pro Ser Asp Ser His Thr Asn Tyr Asn Gln Lys Phe
    50                  55                  60

Lys Gly Lys Ala Thr Leu Thr Val Asn Thr Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ala
            115

<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Arg Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Phe Phe Thr Asn Trp Phe Ala Tyr Trp Gly Gln Gly Thr
            100                 105                 110

Leu Val Thr Val Ser Ser
            115

<210> SEQ ID NO 122
<211> LENGTH: 118
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Phe Phe Thr Asn Trp Phe Ala Tyr Trp Gly Gln Gly Thr
            100                 105                 110

Leu Val Thr Val Ser Ser
        115

<210> SEQ ID NO 123
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Ala Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser
        115

<210> SEQ ID NO 124
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Thr Phe Thr Thr Tyr
            20                  25                  30
Trp Met His Trp Val Arg Gln Ala Pro Gly Gln Gly Leu Glu Trp Met
            35                  40                  45
Gly Glu Ile Asp Pro Ser Asp Ser Tyr Ser Asn Tyr Asn Gln Lys Phe
50                  55                  60
Lys Asp Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Asn Gly Gly Leu Gly Pro Ala Trp Phe Ser Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
            435                 440                 445

Gly Lys
    450

<210> SEQ ID NO 125
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Tyr Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 126
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Tyr Val Gly Thr Ala
            20                  25                  30

Val Ala Trp Tyr Gln Gln Lys Pro Gly Lys Ser Pro Lys Leu Leu Ile
        35                  40                  45
```

-continued

```
Tyr Ser Ala Ser Asn Arg Tyr Thr Gly Val Pro Ser Arg Phe Ser Asp
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Ser Ser Tyr Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 127
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Ile Val Met Thr Gln Ser Pro Ala Thr Leu Ser Val Ser Pro Gly
 1                5                  10                  15

Glu Arg Ala Thr Leu Ser Cys Lys Ala Ser Gln Tyr Val Gly Thr Ala
                 20                  25                  30

Val Ala Trp Tyr Gln Gln Lys Pro Gly Gln Ala Pro Arg Leu Leu Ile
             35                  40                  45

Tyr Ser Ala Ser Asn Arg Tyr Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ser Ser Tyr Pro Trp
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Tyr Val Gly Thr Ala
            20                  25                  30

Val Ala Trp Tyr Gln Gln Lys Pro Gly Gln Ser Pro Arg Leu Leu Ile
        35                  40                  45

Tyr Ser Ala Ser Asn Arg Tyr Thr Gly Val Pro Ala Arg Phe Ser Asp
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Ser Ser Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45
```

```
Gly Glu Ile Asp Pro Ser Asp Ser Tyr Ser Asn Tyr Asn Gln Lys Phe
    50                  55                  60

Lys Asp Arg Ala Thr Leu Thr Val Asp Lys Ser Thr Ser Thr Ala Tyr
 65              70                  75                  80

Met Glu Leu Ser Ser Leu Arg Ser Glu Asp Thr Ala Val Tyr Tyr Cys
                 85                  90                  95

Ala Arg Asn Gly Gly Leu Gly Pro Ala Trp Phe Ser Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145             150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225             230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305             310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385             390                 395                 400

Leu Asp Ser Asp Gly Ser Phe Phe Leu Tyr Ser Lys Leu Thr Val Asp
             405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Lys
    450
```

<210> SEQ ID NO 130
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Ala Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 131
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Val Ile Asp Pro Ser Asp Thr Tyr Thr Asn Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 132
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Asp Ile Val Met Thr Gln Thr Pro Leu Ser Leu Ser Val Thr Pro Gly
1               5                   10                  15
Gln Pro Ala Ser Ile Ser Cys Arg Ser Ser Gln Arg Leu Val His Ser
                20                  25                  30
Asn Gly Asn Thr Tyr Leu His Trp Tyr Leu Gln Lys Pro Gly Gln Ser
                35                  40                  45
Pro Gln Leu Leu Ile Tyr Lys Val Ser Asn Arg Phe Ser Gly Val Pro
            50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Ser
                85                  90                  95
Thr His Val Pro Trp Thr Phe Gly Gly Gly Thr Lys Val Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 133
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 134
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Arg Leu Val His Ser
            20                  25                  30
```

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 135
<211> LENGTH: 448
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 135

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Ile
        35                  40                  45

Gly Val Ile Asp Pro Ser Asp Thr Tyr Thr Asn Tyr Asn Gln Lys Phe
 50                  55                  60

Lys Gly Arg Ala Thr Leu Thr Val Asp Glu Ser Ser Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Asp Tyr Ser Asn Trp Phe Thr Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 136
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Phe
            20                  25                  30

Trp Met His Trp Val Arg Gln Ala Pro Gly Gln Gly Leu Glu Trp Ile
        35                  40                  45

Gly Val Ile Asp Pro Ser Asp Thr Tyr Thr Asn Tyr Ala Gln Lys Phe
    50                  55                  60

Gln Gly Arg Val Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
```

85                  90                  95
Ala Arg Gly Asp Tyr Ser Asn Trp Phe Thr Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 137
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

-continued

```
Glu Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Ser Tyr
            20                  25                  30
Trp Ile His Trp Val Arg Gln Ala Pro Gly Gln Gly Leu Glu Trp Met
        35                  40                  45
Gly Glu Ile Asp Pro Ser Asp Ser Tyr Thr Asn Tyr Asn Gln Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Phe Phe Thr Asn Trp Phe Ala Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
```

<210> SEQ ID NO 138
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 138

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 139
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 139

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro

```
                    50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 140
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Val Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 141
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

```
Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 142
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Ser Tyr
            20                  25                  30

Trp Ile His Trp Val Arg Gln Ala Pro Gly Gln Gly Leu Glu Trp Ile
            35                  40                  45

Gly Glu Ile Asp Pro Ser Asp Ser Tyr Thr Asn Tyr Ala Gln Lys Phe
        50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
```

```
                  245                 250                 255
Thr Pro Glu Val Thr Cys Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 143
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Ile His Trp Val Arg Gln Ala Pro Gly Gln Gly Leu Glu Trp Met
        35                  40                  45
Gly Tyr Ile Tyr Pro Asn Asn Asp Gly Thr Gly Tyr Asn Gln Lys Phe
    50                  55                  60
Lys Ser Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Asp Gly Asn Tyr Val Gly Asp Met Asp Tyr Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 144
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Glu Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 145
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Pro Pro Lys Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

```
                    195                 200                 205

Phe Asn Arg Gly Glu Cys
    210

<210> SEQ ID NO 146
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Asn Gln Lys Phe
```

```
            50                  55                  60
Lys Ser Arg Ala Thr Leu Thr Val Asp Asn Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asp Gly Asn Tyr Val Gly Asp Met Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 148
```

```
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Ile
            35                  40                  45

Gly Tyr Ile Tyr Pro Asn Asn Asp Gly Thr Gly Tyr Ala Gln Lys Leu
    50                  55                  60

Gln Gly Arg Val Thr Met Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
                     370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Thr Phe Thr Ser Tyr Trp Ile His
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Glu Ile Asp Pro Ser Asp Ser Tyr Thr Asn Tyr Ala Gln Lys Phe Gln
1               5                   10                  15
Gly

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Phe or Gly
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (4)..(4)
<223> OTHER INFORMATION: Phe or Ile
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (6)..(6)
<223> OTHER INFORMATION: Ser, Asp or Thr
<220> FEATURE:
<221> NAME/KEY: MOD_RES
<222> LOCATION: (7)..(7)
<223> OTHER INFORMATION: Tyr, Phe or Asp
```

```
<220> FEATURE:
<221> NAME/KEY: MOD_RES
<222> LOCATION: (8)..(8)
<223> OTHER INFORMATION: Trp, Asn or Tyr
<220> FEATURE:
<221> NAME/KEY: MOD_RES
<222> LOCATION: (9)..(9)
<223> OTHER INFORMATION: Met, Ile or Ala
<220> FEATURE:
<221> NAME/KEY: MOD_RES
<222> LOCATION: (10)..(10)
<223> OTHER INFORMATION: His, Phe or Trp
<220> FEATURE:
<221> NAME/KEY: MOD_RES
<222> LOCATION: (11)..(11)
<223> OTHER INFORMATION: May or may not be present

<400> SEQUENCE: 151

Gly Xaa Xaa Xaa Xaa Xaa Xaa Xaa Xaa Asn
1               5                   10

<210> SEQ ID NO 152
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Val or Glu
<220> FEATURE:
<221> NAME/KEY: MOD_RES
<222> LOCATION: (2)..(2)
<223> OTHER INFORMATION: Ile or Phe
<220> FEATURE:
<221> NAME/KEY: MOD_RES
<222> LOCATION: (3)..(3)
<223> OTHER INFORMATION: Asp, Tyr, Ser or Gly
<220> FEATURE:
<221> NAME/KEY: MOD_RES
<222> LOCATION: (4)..(4)
<223> OTHER INFORMATION: Pro, Asn or not present
<220> FEATURE:
<221> NAME/KEY: MOD_RES
<222> LOCATION: (5)..(5)
<223> OTHER INFORMATION: Ser, Tyr, Asn or Gly
<220> FEATURE:
<221> NAME/KEY: MOD_RES
<222> LOCATION: (6)..(6)
<223> OTHER INFORMATION: Asp, Asn, Gly or Ser
<220> FEATURE:
<221> NAME/KEY: MOD_RES
<222> LOCATION: (7)..(7)
<223> OTHER INFORMATION: Gly, Ser, Asp or Thr
<220> FEATURE:
<221> NAME/KEY: MOD_RES
<222> LOCATION: (8)..(8)
<223> OTHER INFORMATION: Tyr, Gly, His, Ser or Arg
<220> FEATURE:
<221> NAME/KEY: MOD_RES
<222> LOCATION: (9)..(9)
<223> OTHER INFORMATION: Thr, Ser or Ala
<220> FEATURE:
<221> NAME/KEY: MOD_RES
<222> LOCATION: (10)..(10)
<223> OTHER INFORMATION: Asn, Gly, Tyr or Ser
<220> FEATURE:
<221> NAME/KEY: MOD_RES
<222> LOCATION: (11)..(11)
<223> OTHER INFORMATION: Tyr or Phe
<220> FEATURE:
<221> NAME/KEY: MOD_RES
<222> LOCATION: (12)..(12)
<223> OTHER INFORMATION: Asn, Pro or Ala
<220> FEATURE:
```

```
<221> NAME/KEY: MOD_RES
<222> LOCATION: (13)..(13)
<223> OTHER INFORMATION: Gln, Asp or Pro
<220> FEATURE:
<221> NAME/KEY: MOD_RES
<222> LOCATION: (14)..(14)
<223> OTHER INFORMATION: Lys, Glu, Thr or Ser
<220> FEATURE:
<221> NAME/KEY: MOD_RES
<222> LOCATION: (15)..(15)
<223> OTHER INFORMATION: Phe, Leu or Val
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
<223> OTHER INFORMATION: Gly, Ser, Asp or Asn

<400> SEQUENCE: 152

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 153
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Ile
            35                  40                  45

Gly Glu Ile Asp Pro Ser Asp Ser Tyr Thr Asn Tyr Asn Gln Lys Phe
        50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Phe Thr Asn Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 154
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Arg Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Phe Phe Thr Asn Trp Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly

```
                130                 135                 140
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 155
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Ile
                35                  40                  45
```

```
Gly Glu Ile Asp Pro Ser Asp Ser Tyr Thr Asn Tyr Asn Gln Lys Phe
 50                  55                  60

Lys Gly Arg Ala Thr Leu Thr Val Asp Arg Ser Ser Thr Ala Tyr
 65                  70                  75                  80

Met Glu Leu Ser Ser Leu Arg Ser Glu Asp Thr Ala Val Tyr Tyr Cys
                 85                  90                  95

Gly Arg Ser Phe Phe Thr Asn Trp Phe Ala Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 156
<211> LENGTH: 454
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 156

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Gly Met Ser Trp Val Arg Gln Ala Pro Gly Lys Arg Leu Glu Trp Val
        35                  40                  45

Ala Thr Val Ser Ser Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg His Arg Gly Asn Tyr Tyr Ala Thr Tyr Tyr Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 157
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Val Leu Thr Gln Ser Pro Asp Ser Leu Ala Val Ser Leu Gly
1               5                   10                  15

Glu Arg Ala Thr Ile Asn Cys Lys Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Pro Val Gln Ala Glu Asp Val Ala Thr Tyr Tyr Cys Gln His Ser Gly
                85                  90                  95

Glu Leu Pro Pro Ser Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 158
<211> LENGTH: 15
<212> TYPE: PRT
<213> ORGANISM: Homo sapiens

<400> SEQUENCE: 158

Trp Tyr Gln Gln Lys Pro Gly Lys Ala Pro Lys Leu Leu Ile Tyr
1               5                   10                  15
```

```
<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 159

His His His His His His
1               5
```